(12) United States Patent
Degnan et al.

(10) Patent No.: US 8,383,821 B2
(45) Date of Patent: Feb. 26, 2013

(54) NK-1 AND SEROTONIN TRANSPORTER INHIBITORS

(75) Inventors: Andrew P. Degnan, Rocky Hill, CT (US); Kevin W. Gillman, Madison, CT (US); Derek J. Denhart, Durham, CT (US); Jonathan L. Ditta, Meriden, CT (US); Ramkumar Rajamani, Middletown, CT (US); Ying Han, Cheshire, CT (US); George O. Tora, Langhorne, PA (US)

(73) Assignee: Bristol-Meyers Squibb Company, Princeton, NJ (US)

( * ) Notice: Subject to any disclaimer, the term of this patent is extended or adjusted under 35 U.S.C. 154(b) by 460 days.

(21) Appl. No.: 12/618,025

(22) Filed: Nov. 13, 2009

(65) Prior Publication Data

US 2010/0087434 A1    Apr. 8, 2010

Related U.S. Application Data

(63) Continuation of application No. 11/734,809, filed on Apr. 13, 2007, now abandoned.

(60) Provisional application No. 60/792,604, filed on Apr. 17, 2006.

(51) Int. Cl.
*A61K 31/4523* (2006.01)
*C07D 403/14* (2006.01)

(52) U.S. Cl. ........ 546/194; 546/207; 546/208; 546/211; 546/209; 546/213; 546/214; 514/318; 514/323; 514/326

(58) Field of Classification Search .................. None
See application file for complete search history.

(56) References Cited

U.S. PATENT DOCUMENTS

| | | | |
|---|---|---|---|
| 5,620,989 | A | 4/1997 | Harrison et al. |
| 5,760,018 | A | 6/1998 | Baker et al. |
| 7,098,203 | B2 | 8/2006 | Wu et al. |
| 7,138,423 | B2 | 11/2006 | Wu et al. |
| 7,276,631 | B2 | 10/2007 | Wu et al. |
| 7,494,986 | B2 | 2/2009 | Wu et al. |

FOREIGN PATENT DOCUMENTS

| | | |
|---|---|---|
| EP | 0 337 167 | 10/1989 |
| WO | WO 03/078376 | 9/2003 |
| WO | WO 2004/004722 | 1/2004 |
| WO | WO 2004/022539 | 3/2004 |

OTHER PUBLICATIONS

Kenakin "The ligand paradox between affinity and efficacy: can you be there and not make a difference?" TRENDS in Pharmacological Sciences 2002, 23, 275-280.*
Hafizi et. al. "Neurokinin-1 receptor antagonists as novel antidepressants: trials and tribulations" British Journal of Psychiatry 2007, 191, 282-284.*
McLean, S. Current Pharmaceutical Design 2005, 11, 1529.*
Barrett, D.G. et al., "Novel, potent $P^2$-$P^3$ pyrrolidine derivatives of ketoamide-based cathepsin K inhibitors", Bioorganic & Medicinal Chemistry Letters, vol. 16, pp. 1735-1739 (2006).
Gentsch, C. et al., "Anxiolytic effect of NKP608, a NK1-receptor antagonist, in the social investigation test in gerbils", Behavioural Brain Research, vol. 133, pp. 363-368 (2002).
Jefferson, E.A. et al., "Optimizing the antibacterial activity of a lead structure discovered by 'SAR by MS' technology", Bioorganic & Medicinal Chemistry Letters, vol. 14, pp. 5257-5261 (2004).
Kramer, M.S. et al., "Distinct Mechanism for Antidepressant Activity by Blockade of Central Substance P Receptors", Science, vol. 281, pp. 1640-1645 (1998).
Lee, K. et al., "Structural Modification of an Orally Active Thrombin Inhibitor, LB30057: Replacement of the D-Pocket-binding Naphthyl Moiety", Bioorganic & Medicinal Chemistry, vol. 6, pp. 869-876 (1998).
Li, B. et al., "*N*-(Arylacetyl)-biphenylalanines as Potent VLA-4 Antagonists", Bioorganic & Medicinal Chemistry Letters, vol. 12, pp. 2141-2144 (2002).
Malamas, M.S. et al., "Novel Benzofuran and Benzothiophene Biphenyls as Inhibitors of Protein Tyrosine Phosphatase 1B with Antihyperglycemic Properties", Journal of Medicinal Chemistry, vol. 43, No. 7, pp. 1293-1310 (2000).
Nakamura, T. et al., "Imidazole derivatives as new potent and selective 20-HETE synthase inhibitors", Bioorganic & Medicinal Chemistry Letters, vol. 14, pp. 333-336 (2004).
Papp, M. et al., "The NK1-receptor antagonist NKP608 has an antidepressant-like effect in the chronic mild stress model of depression in rats", Behavioural Brain Research, vol. 115, pp. 19-23 (2000).
Patani, G.A. et al., "Bioisosterism: A Rational Approach in Drug Design", Chemical Reviews, vol. 96, No. 8, pp. 3147-3176 (1996).
Rosen, T.J. et al., "Synthesis and Structure-Activity Relationships of CP-122,721, a Second-Generation NK-1 Receptor Antagonist", Bioorganic & Medicinal Chemistry Letters, vol. 8, pp. 281-284 (1998).
Singh, C. et al., "Geraniol-Derived 1,2,4-Trioxanes with Potent In-Vivo Antimalarial Activity", Bioorganic & Medicinal Chemistry Letters, vol. 13, pp. 3447-3450 (2003).
Stevenson, G.I. et al., "4,4-Disubstituted Piperidine High-Affinity $NK_1$ Antagonists: Structure-Activity Relationships and in Vivo Activity", Journal of Medicinal Chemistry, vol. 41, No. 23, pp. 4623-4635 (1998).

(Continued)

*Primary Examiner* — David K O'Dell
(74) *Attorney, Agent, or Firm* — James Epperson

(57) ABSTRACT

The invention encompasses compounds of Formula I, including pharmaceutically acceptable salts, their pharmaceutical compositions, and their use in treating disorders associated with an excess or imbalance of tachykinins or serotonin or both.

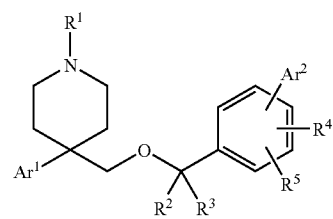

9 Claims, No Drawings

OTHER PUBLICATIONS

Stevenson, G.I. et al., "4,4-Disubstituted Piperidines: A New Class of $NK_1$ Antagonist", Journal of Medicinal Chemistry, vol. 38, No. 8, pp. 1264-1266 (1995).

Su, B. et al., "Lead optimization of 7-benzyloxy 2-(4'-pyridylmethyl)thio isoflavone aromatase inhibitors", Bioorganic & Medicinal Chemistry, vol. 13, pp. 6571-6577 (2005).

Varty, G.B. et al., "The Gerbil Elevated Plus-maze II: Anxiolytic-like Effects of Selective Neurokinin NK1 Receptor Antagonists", Neuropsychopharmacology, vol. 27, No. 3, pp. 371-379 (2002).

Wermuth, C.G., Chapter 13: "Molecular Variations Based on Isosteric Replacements", The Practice of Medicinal Chemistry, pp. 203-237, Academic Press Limited, publ. (1996).

Yamazaki, K. et al., "Synthesis of potent and selective inhibitors of *Candida albicans* N-myristoyltransferase based on the benzothiazole structure", Bioorganic & Medicinal Chemistry, vol. 13, pp. 2509-2522 (2005).

* cited by examiner

NK-1 AND SEROTONIN TRANSPORTER INHIBITORS

CROSS REFERENCE TO RELATED APPLICATIONS

This application is a continuation of U.S. nonprovisional application Ser. No. 11/734,809, filed Apr. 13, 2007 and claims the benefit of U.S. provisional application No. 60/792,604, filed Apr. 17, 2006.

BACKGROUND OF THE INVENTION

Tachykinins are a group of naturally occurring peptides found widely distributed throughout mammals, both within the central nervous system and in the peripheral nervous and circulatory systems. The three known mammalian tachykinins are Neurokinin-1 (NK-1, substance P), Neurokinin A, and Neurokinin B. These compounds act as neurotransmitters and immunomodulators and may contribute to the pathophysiology of a wide variety of human diseases.

Receptors for tachykinins have been identified and include neurokinin-1 (NK-1 or Substance P-preferring), NK-2 (Neurokinin A-preferring) and NK-3 (Neurokinin B-preferring). NK-1 receptor antagonists are being developed for the treatment of physiological conditions associated with an excess or imbalance of tachykinins, particularly substance P. Such conditions include affective disorders such as anxiety, depression, obsessive compulsive disorder, bulimia, and panic disorder. See Gentsch et al. *Behav. Brain Res.* 2002, 133, 363; Varty et al. *Neuropsychopharmacology* 2002, 27, 371; Papp et al. *Behav. Brain Res.* 2000, 115, 19; Kramer et al. *Science* 1998, 281, 1640; and Rosen et al. *Bioorg. Med. Chem. Lett.* 1998, 8, 281.

NK-1 antagonists are believed to modulate 5-HT function via noradrenergic pathways and have been shown to attenuate presynaptic 5-HT$_{1A}$ receptor function. Thus, the combination of serotonin reuptake inhibition with NK-1 antagonism may lead to new classes of drugs with improved characteristics.

DESCRIPTION OF THE INVENTION

The invention encompasses compounds of Formula I, including pharmaceutically acceptable salts, pharmaceutical compositions, and their use in treating disorders related to levels of tachykinins or serotonin or both.

One aspect of the invention are compounds of Formula I

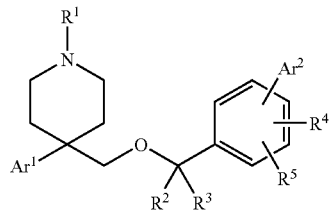

where:
$R^1$ is hydrogen, alkyl, cycloalkyl, or benzyl;
$R^2$ is hydrogen or alkyl;
$R^3$ is hydrogen or alkyl;
$R^4$ is hydrogen, alkyl, haloalkyl, hydroxy, alkoxy, haloalkoxy, cyano, or $COR^6$;
$R^5$ is hydrogen, alkyl, haloalkyl, hydroxy, alkoxy, haloalkoxy, cyano, or $COR^6$;
$R^6$ is hydroxy, alkoxy, benzyloxy, amino, alkylamino, dialkylamino, pyrrolidinyl, piperidinyl, piperazinyl, N-alkylpiperazinyl, or morpholinyl;
$Ar^1$ is phenyl or pyridinyl, and is substituted with 0-2 substituents selected from the group consisting of halo, alkyl, haloalkyl, cyano, phenyl and furanyl;
$Ar^2$ is phenyl substituted with 1-5 substituents or is naphthyl substituted with 0-3 substituents where the substituents are selected from the group consisting of halo, alkyl, cycloalkyl, haloalkyl, hydroxyalkyl, alkoxyalkyl, hydroxy, alkoxy, haloalkoxy, benzyloxy, alkylthio, cyano, nitro, amino, alkylamino, dialkylamino, (alkylcarbonyl)amino, (alkoxycarbonyl)amino(benzyloxycarbonyl)amino, carboxy, alkoxycarbonyl, benzyloxycarbonyl, alkylSO$_2$, phenyl, phenoxy, acetyl, and formyl;
or $Ar^2$ is furanyl, thienyl, pyrrolyl, isoxazolyl, isothiazolyl, pyrazolyl, oxazolyl, thiazolyl, imidazolyl, oxadiazolyl, thiadiazolyl, triazolyl, tetrazolyl, pyridinyl, pyridazinyl, pyrimidinyl, pyrazinyl, triazinyl, quinolinyl, or isoquinolinyl, and is substituted with 0-3 substituents selected from the group consisting of amino, alkylamino, dialkylamino, oxo, halo, alkyl, haloalkyl, alkoxy, alkylthio, haloalkoxy, cyano, nitro, pyrrolidinyl, piperidinyl, piperazinyl, N-alkylpiperazinyl, and morpholinyl;
or $Ar^2$ is benzodioxolyl, dibenzofuranyl, thianthrenyl, or trimethylenedioxybenzen-yl;
or a pharmaceutically acceptable salt thereof.

Another aspect of the invention are compounds of Formula I where
$R^1$ is hydrogen or alkyl;
$R^4$ is hydrogen, alkyl, haloalkyl, alkoxy, haloalkoxy, or cyano;
$R^5$ is hydrogen, alkyl, haloalkyl, alkoxy, haloalkoxy, or cyano;
$Ar^1$ is phenyl substituted with 0-2 substituents selected from the group consisting of halo, alkyl, haloalkyl, and cyano;
$Ar^2$ is phenyl substituted with 1-3 substituents or is naphthyl substituted with 0-3 substituents where the substituents are selected from the group consisting of halo, alkyl, haloalkyl, hydroxyalkyl, hydroxy, alkoxy, alkoxyalkyl, haloalkoxy, alkylthio, cyano, nitro, amino, alkylamino, dialkylamino, phenyl, phenoxy, acetyl, and formyl;
or $Ar^2$ is furanyl, thienyl, pyrrolyl, isoxazolyl, isothiazolyl, pyrazolyl, oxazolyl, thiazolyl, imidazolyl, oxadiazolyl, thiadiazolyl, triazolyl, tetrazolyl, pyridinyl, pyridazinyl, pyrimidinyl, triazinyl, quinolinyl, or isoquinolinyl, and is substituted with 0-3 substituents selected from the group consisting of amino, alkylamino, dialkylamino, oxo, halo, alkyl, haloalkyl, alkoxy, alkylthio, haloalkoxy, cyano, nitro, pyrrolidinyl, piperidinyl, piperazinyl, N-alkylpiperazinyl, or morpholinyl;
or $Ar^2$ is benzodioxolyl, dibenzofuranyl or thianthrenyl.

Another aspect of the invention are compounds of Formula I where $R^1$ is hydrogen.

Another aspect of the invention are compounds of Formula I where $R^2$ and $R^3$ are hydrogen.

Another aspect of the invention are compounds of Formula I where $R^2$ is methyl and $R^3$ is hydrogen.

Another aspect of the invention are compounds of Formula I where $Ar^1$ is phenyl.

Another aspect of the invention are compounds of Formula I where $Ar^2$ is phenyl substituted with 1-5 substituents or is naphthyl substituted with 0-3 substituents where the substituents are selected from the group consisting of halo, alkyl, cycloalkyl, haloalkyl, hydroxyalkyl, alkoxyalkyl, hydroxy, alkoxy, haloalkoxy, benzyloxy, alkylthio, cyano, nitro, amino, alkylamino, dialkylamino, (alkylcarbonyl)amino, (alkoxycarbonyl)amino(benzyloxycarbonyl)amino, carboxy, alkoxycarbonyl, benzyloxycarbonyl, alkylSO$_2$, phenyl, phenoxy, acetyl, and formyl.

Another aspect of the invention are compounds of Formula I where Ar$^2$ is phenyl substituted with 1-3 substituents or is naphthyl substituted with 0-3 substituents where the substituents are selected from the group consisting of halo, alkyl, haloalkyl, hydroxyalkyl, hydroxy, alkoxy, alkoxyalkyl, haloalkoxy, alkylthio, cyano, nitro, amino, alkylamino, dialkylamino, phenyl, phenoxy, acetyl, and formyl.

Another aspect of the invention are compounds of Formula I where Ar$^2$ is furanyl, thienyl, pyrrolyl, isoxazolyl, isothiazolyl, pyrazolyl, oxazolyl, thiazolyl, imidazolyl, oxadiazolyl, thiadiazolyl, triazolyl, tetrazolyl, pyridinyl, pyridazinyl, pyrimidinyl, pyrazinyl, triazinyl, quinolinyl, or isoquinolinyl, and is substituted with 0-3 substituents selected from the group consisting of amino, alkylamino, dialkylamino, oxo, halo, alkyl, haloalkyl, alkoxy, alkylthio, haloalkoxy, cyano, nitro, pyrrolidinyl, piperidinyl, piperazinyl, N-alkylpiperazinyl, and morpholinyl.

Another aspect of the invention are compounds of Formula I where Ar$^2$ is furanyl, thienyl, pyrrolyl, isoxazolyl, isothiazolyl, pyrazolyl, oxazolyl, thiazolyl, imidazolyl, oxadiazolyl, thiadiazolyl, triazolyl, tetrazolyl, pyridinyl, pyridazinyl, pyrimidinyl, triazinyl, quinolinyl, or isoquinolinyl, and is substituted with 0-3 substituents selected from the group consisting of amino, alkylamino, dialkylamino, oxo, halo, alkyl, haloalkyl, alkoxy, alkylthio, haloalkoxy, cyano, nitro, pyrrolidinyl, piperidinyl, piperazinyl, N-alkylpiperazinyl, or morpholinyl.

Another aspect of the invention are compounds of Formula I where Ar$^2$ is furanyl, thienyl, pyrazolyl, thiazolyl, imidazolyl, tetrazolyl, pyridinyl, pyrimidinyl, quinolinyl, or isoquinolinyl and is substituted with 0-3 substituents selected from the group consisting of halo, alkyl, haloalkyl, alkoxy, haloalkoxy, or cyano.

Any scope of any substituent, including R$^1$, R$^2$, R$^3$, R$^4$, R$^5$, R$^6$, Ar$^1$, or Ar$^2$, can be used independently with the scope of any other instance of a substituent.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Haloalkyl" and "haloalkoxy" include all halogenated isomers from monohalo substituted alkyl to perhalo substituted alkyl. "Aryl" includes carbocyclic and heterocyclic aromatic substituents. Parenthetic and multiparenthetic terms are intended to clarify bonding relationships to those skilled in the art. For example, a term such as ((R)alkyl) means an alkyl substituent further substituted with the substituent R.

Trimethylenedioxybenzen-yl Means

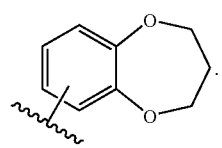

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some Formula I compounds contain at least one asymmetric carbon atom, an example of which is shown below. The invention includes all stereoisomeric forms of the compounds, both mixtures and separated isomers. Mixtures of stereoisomers can be separated into individual isomers by methods known in the art.

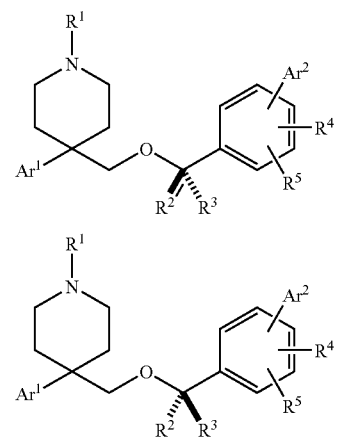

Synthetic Methods

Compounds of Formula I can be made according to methods known in the art and those illustrated in the schemes below and in the specific embodiments section. The schemes encompass reasonable variations known in the art. The variables describing general structural formulas and features in the synthetic schemes are distinct from and should not be confused with the variables in the claims or the rest of the specification. These variables are meant only to illustrate how to make some of the compounds of this invention.

Scheme 1.

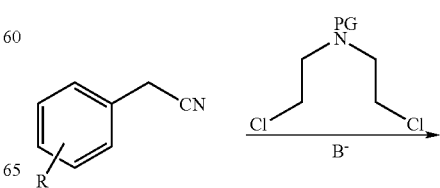

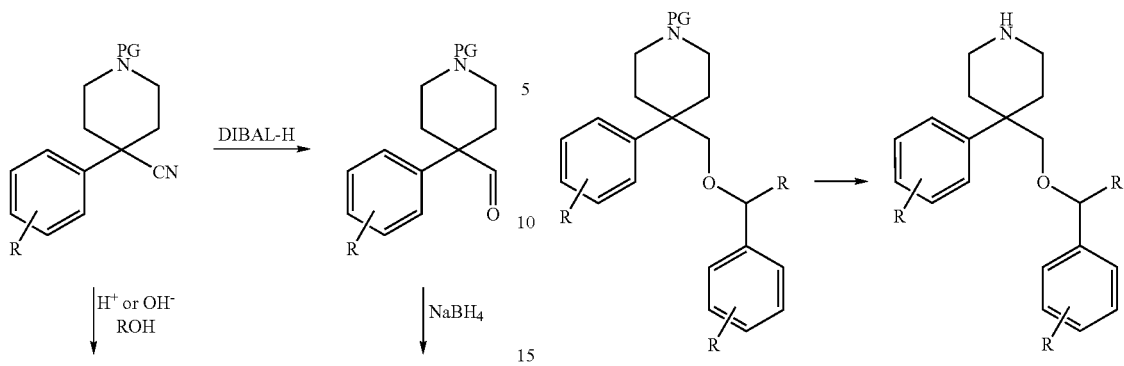
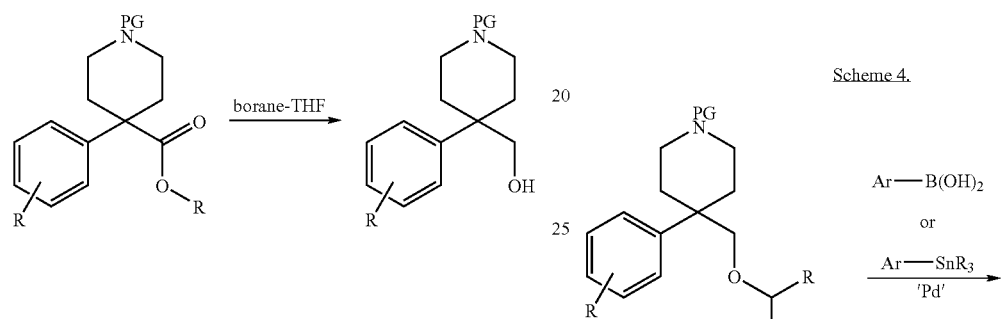
Scheme 2.
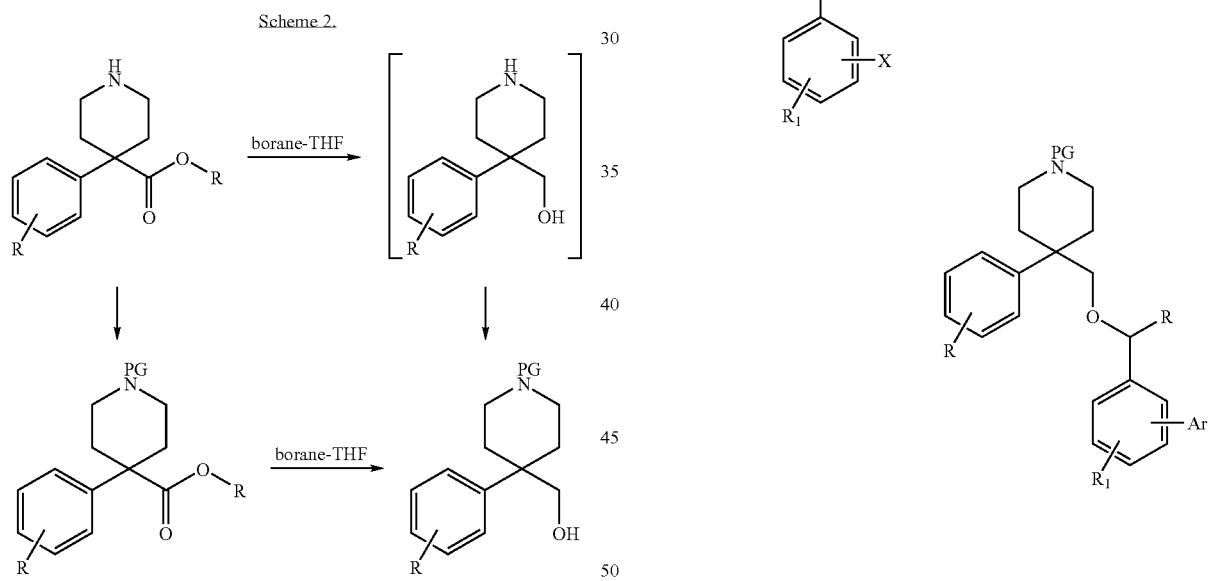
Scheme 4.
Scheme 3.
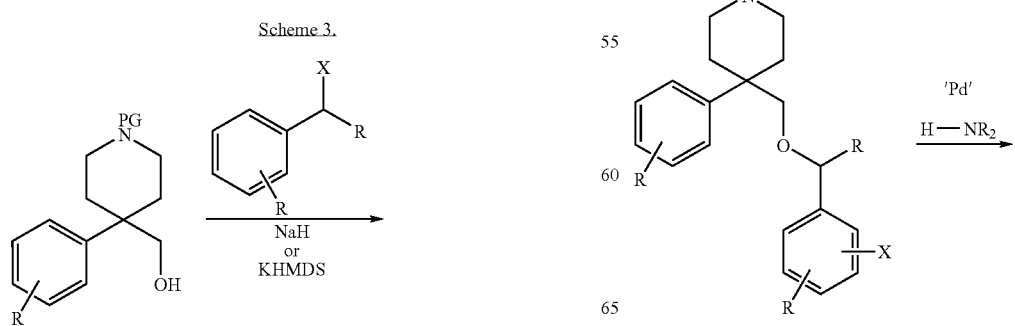
Scheme 5.

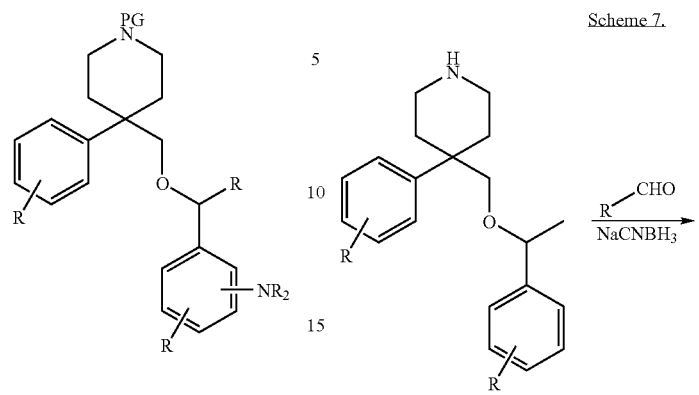
Scheme 6.
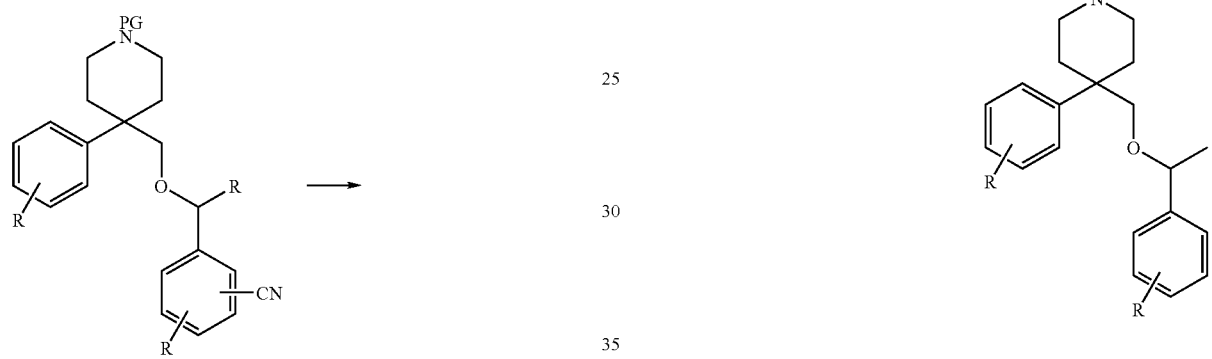
Scheme 7.
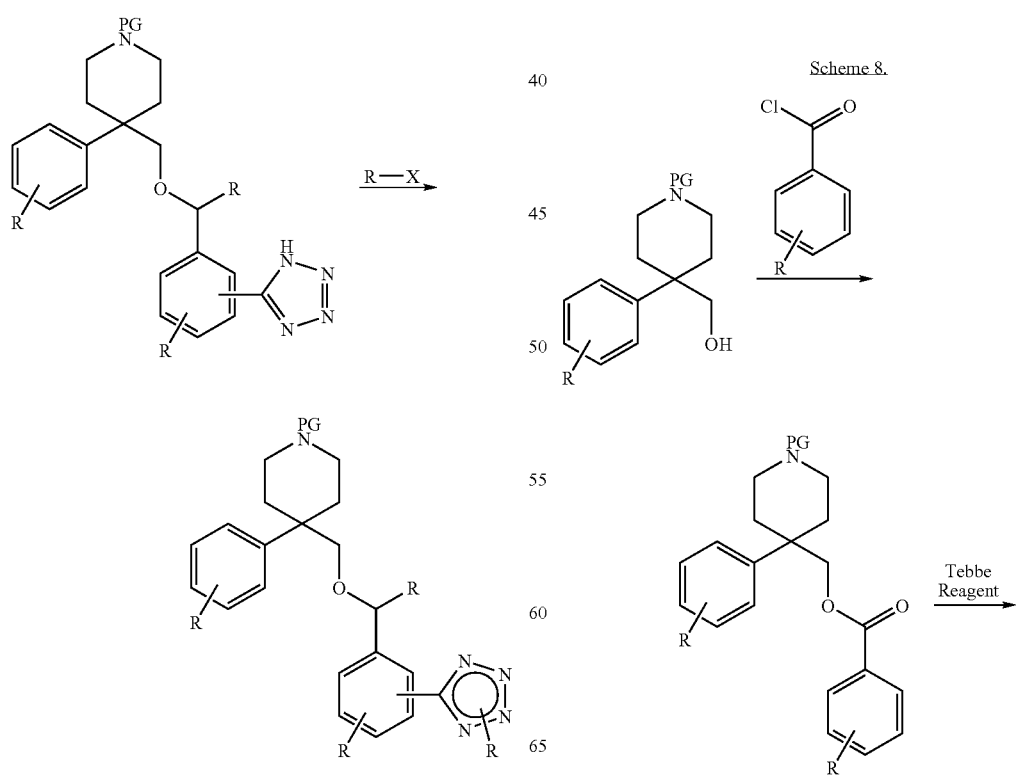
Scheme 8.

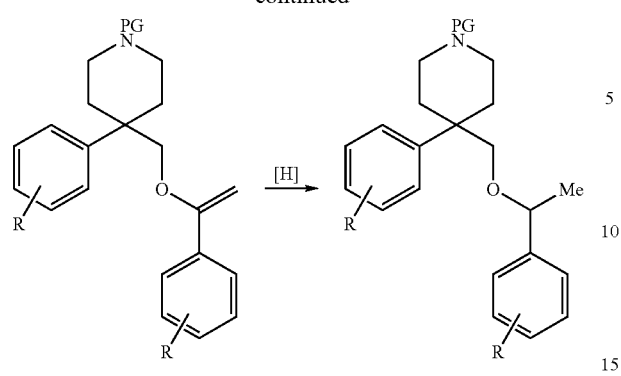
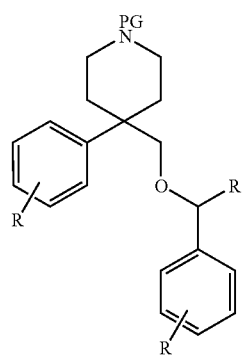
Scheme 9.
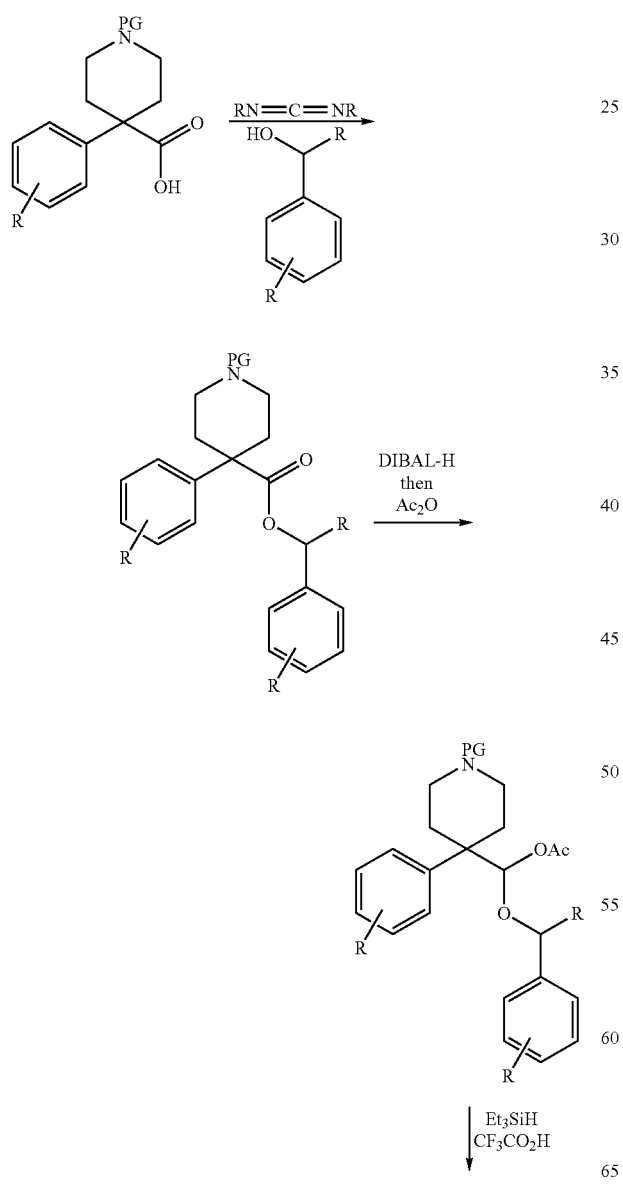
Scheme 10.
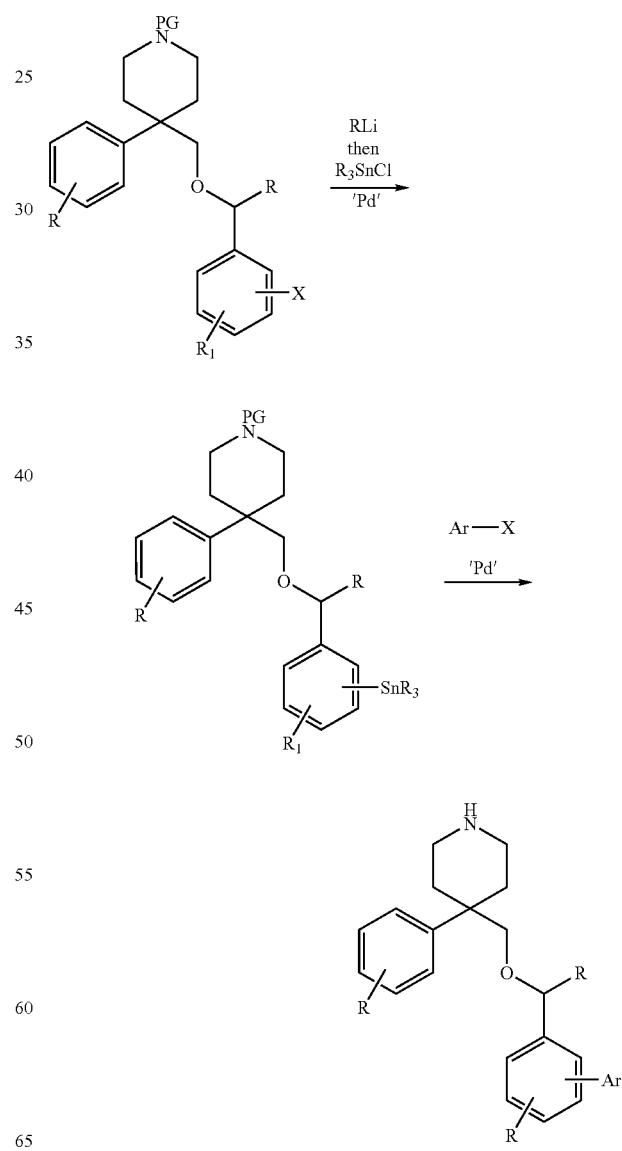

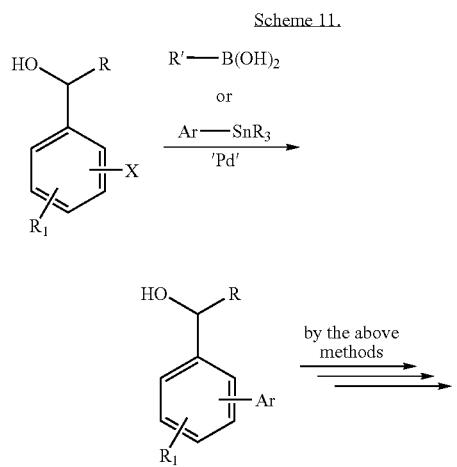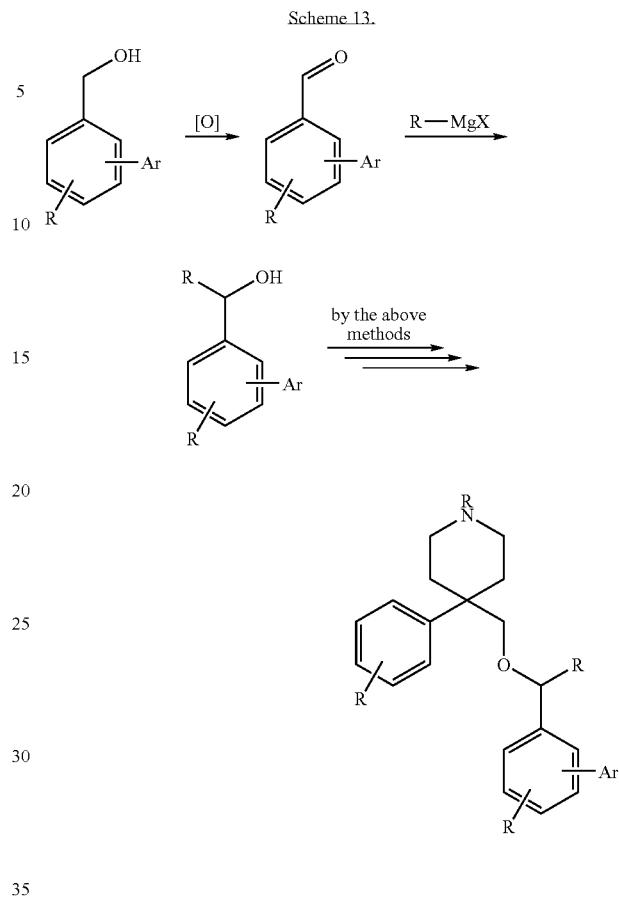

-continued

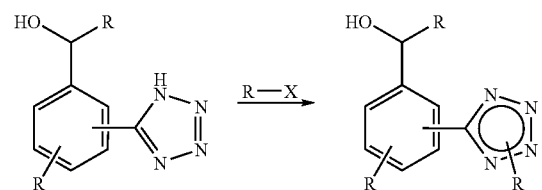

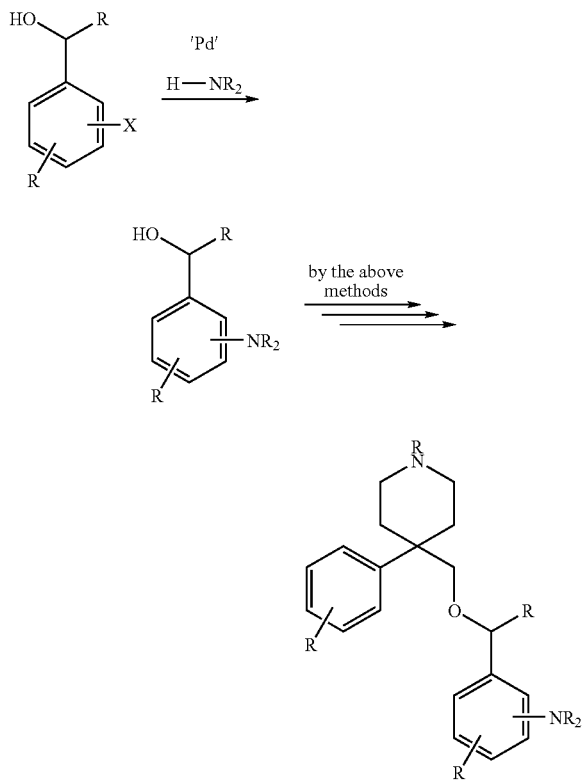

Biological Methods

NK-1 Binding assay. U373 cells, a human glioblastoma-astrocytoma cell line that endogenously expresses the neurokinin-1 (NK-1) receptor, were grown in a monolayer culture at 37° C. in 5% $CO_2$ and fed with Minimum Essential Medium (MEM) supplemented with 10% fetal bovine serum. Membranes were prepared as follows: Cells were washed twice with ice-cold phosphate-buffered saline (pH 7.4) and then incubated for 5-10 minutes with ice-cold 10 mM Tris buffer (pH 7.4) containing 5 mM EDTA. Cells were removed from plates, homogenized, and centrifuged at 32,000×g for 20 minutes. The resulting supernatant was discarded, and the pellet resuspended by homogenization in 50 mM Tris buffer (pH 7.4) containing 1 mM EDTA and centrifuged at 32,000×g for 20 minutes. The resulting supernatant was discarded, and the pellet resuspended by homogenization in NK-1 binding assay buffer (50 mM Tris-HCL (pH 7.4), 3 mM $MnCl_2$, 200 μg/ml BSA, 5 μg/ml chymostatin, 40 μg/ml bacitracin and 4 μg/ml leupeptin).

On the day of an experiment the membrane preparation was thawed, homogenized and diluted with NK-1 binding assay buffer to the appropriate concentration. Competition binding assays were performed in 96 well plate format by incubating membranes (5-10 μg/well) with Bolton Hunter labeled [$^{125}$I] Substance P, at a concentration of 200 nM, and concentrations of drugs ranging from 10000 to 0.01 nM. Samples were incubated for 30 min at 20° C. then filtered through GF/B glass fiber filters (pretreated with 1% polyethyleneimine and 0.3% Triton X-100) using a Brandel cell harvester. The filters were then washed with 10 ml ice cold 50 mM Tris-HCL (pH 7.4) containing 3 mM $MgCl_2$. Non-specific was defined in the presence of 2 μM L-733,060 (a nonpeptide NK-1 antagonist). The amount of radioligand bound in the presence and absence of competitor was analyzed by plotting (−) log drug concentration versus the amount of radioligand specifically bound. The midpoint of the displacement curve ($IC_{50}$, nM), signifies the potency. Ki values can be calculated using the method of Cheng and Prusoff (Cheng and Prusoff, *Biochemical Pharmacology*, Vol 22, pp. 3099-3108, Pergamon Press (1973)).

Serotonin transporter binding assay. HEK-293 cells that stably express human serotonin transporters (HEK-hSERT cells) were grown at 37° C. in 5% $CO_2$ as a monolayer in medium consisting of EMEM supplemented with 10% fetal bovine serum and G418 sulfate (500 μg/ml). To prepare membranes for radioligand binding experiments, cells were rinsed twice with phosphate-buffered saline (138 mM NaCl, 4.1 mM KCl, 5.1 mM $Na_2PO_4$, 1.5 mM $KH_2PO_4$, 11.1 mM glucose, pH 7.4). Cells were transferred from plates to polypropylene tubes (16×100 mm), centrifuged at 1,200×g for 5 min and were frozen at −80° C. until assay. Following centrifugation, pellets were resuspended by homogenization in buffer consisting of 50 mM Tris (pH 7.7 at 25° C.), 120 mM NaCl and 5 mM KCl and then centrifuged at 32,000×g for 10 min. Following centrifugation, supernatants were discarded and pellets were resuspended in buffer consisting of 50 mM Tris (pH 7.4 at 25° C.), 150 mM NaCl and 5 mM KCl. Membrane homogenates (200 μl/plate) were incubated with 1 nM [$^3$H]-citalopram (specific activity=85 Ci/mmol) and increasing concentrations of test compounds for 1 hr at 25° C. in a total volume of 250 μl. The assay buffer consisted of 50 mM Tris (pH 7.4 at 25° C.), 120 mM NaCl and 5 mM KCl (pH 7.4 with conc. HCl). Plates were incubated for 1 hr at 25° C., then filtered through 0.5% PEI treated Whatman GF/B filters using a Brandel cell harvester. Filters were washed three times with 3 ml of ice-cold tris wash buffer. Non-specific binding was defined with 10 μM fluoxetine. Amount of radioligand bound in the presence and absence of competitor was analyzed by plotting (−) log drug concentration versus the amount of radioligand specifically bound. The midpoint of the displacement curve ($IC_{50}$, nM), signifies the potency. Ki values can be calculated using the method of Cheng and Prusoff (Cheng and Prusoff, *Biochemical Pharmacology*, Vol 22, pp. 3099-3108, Pergamon Press (1973)). NK-1 and serotonin transporter binding results are shown in Tables 1 and 2.

TABLE 1
| Structure | NK-1 IC$_{50}$ (nM) | SERT IC$_{50}$ (nM) |
| --- | --- | --- |
| 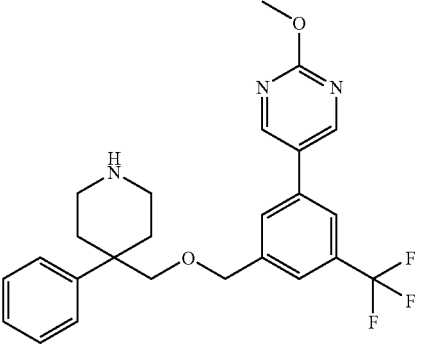 [SMILES: COc1ncc(-c2cc(COCC3(c4ccccc4)CCNCC3)cc(C(F)(F)F)c2)cn1] | A | A |
| 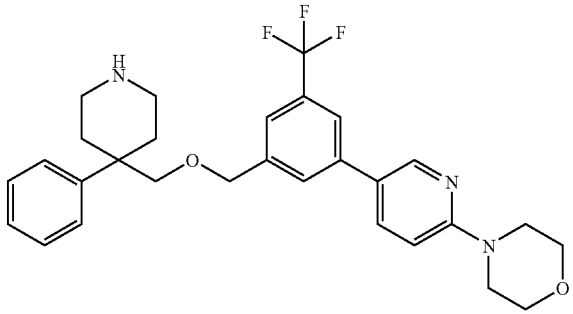 [SMILES: FC(F)(F)c1cc(COCC2(c3ccccc3)CCNCC2)cc(-c2ccc(N3CCOCC3)nc2)c1] | C | A |
| 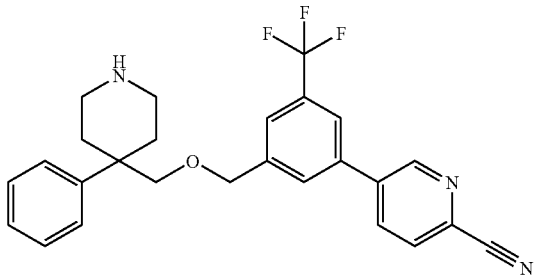 [SMILES: N#Cc1ccc(-c2cc(COCC3(c4ccccc4)CCNCC3)cc(C(F)(F)F)c2)cn1] | A | A |
| 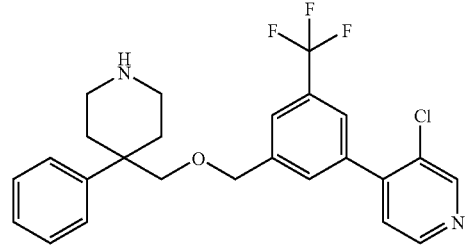 [SMILES: FC(F)(F)c1cc(COCC2(c3ccccc3)CCNCC2)cc(-c2ccncc2Cl)c1] | A | A |
| 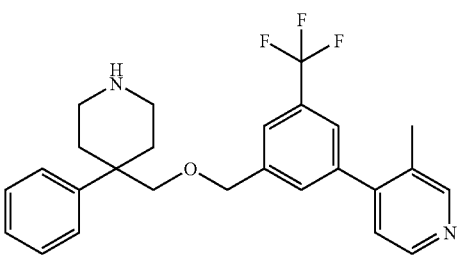 [SMILES: Cc1cnccc1-c1cc(COCC2(c3ccccc3)CCNCC2)cc(C(F)(F)F)c1] | A | A |

TABLE 1-continued

| Structure | NK-1 IC$_{50}$ (nM) | SERT IC$_{50}$ (nM) |
|---|---|---|
| (structure) | A | A |
| (structure) | A | A |
| (structure) | A | A |
| (structure) | C | B |
| (structure) | A | A |

TABLE 1-continued

| Structure | NK-1 IC$_{50}$ (nM) | SERT IC$_{50}$ (nM) |
|---|---|---|
|  | B | A |
|  | C | A |
|  | C | B |
| 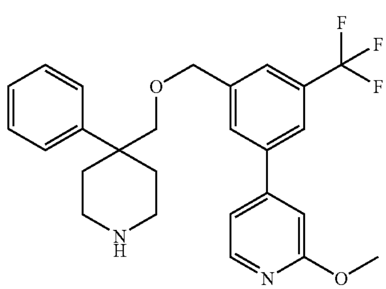 [SMILES: COc1cc(-c2cc(COCC3(c4ccccc4)CCNCC3)cc(C(F)(F)F)c2)ccn1] | A | A |
|  | B | A |

TABLE 1-continued

| Structure | NK-1 IC$_{50}$ (nM) | SERT IC$_{50}$ (nM) |
|---|---|---|
| | B | A |
| | A | A |
| | B | A |
| | A | A |

TABLE 1-continued

| Structure | NK-1 IC$_{50}$ (nM) | SERT IC$_{50}$ (nM) |
|---|---|---|
| | A | A |
| | A | A |
| | A | A |
| 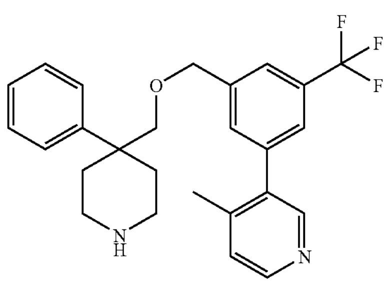 | C | A |
| | A | A |

TABLE 1-continued

| Structure | NK-1 IC$_{50}$ (nM) | SERT IC$_{50}$ (nM) |
|---|---|---|
| | A | A |
| | A | A |
| 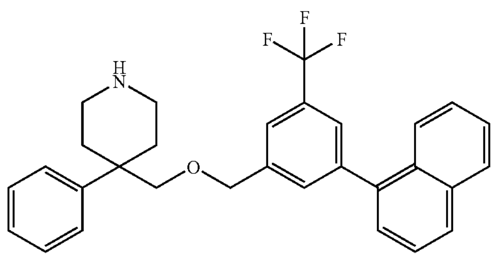 [SMILES: FC(F)(F)c1cc(COCC2(c3ccccc3)CCNCC2)cc(-c2cccc3ccccc23)c1] | C | B |
| | A | A |
| | A | A |
| | A | A |

TABLE 1-continued

| Structure | NK-1 IC$_{50}$ (nM) | SERT IC$_{50}$ (nM) |
|---|---|---|
| | A | A |
| | A | A |
| | A | A |
| | B | B |
| | B | A |

TABLE 1-continued

| Structure | NK-1 IC$_{50}$ (nM) | SERT IC$_{50}$ (nM) |
|---|---|---|
| | C | C |
| | B | A |
| 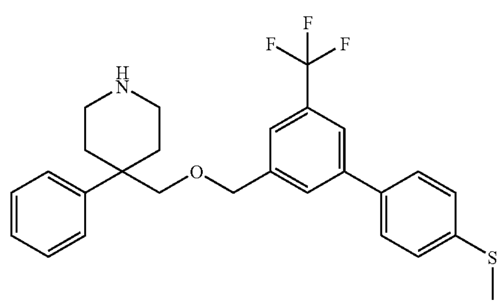 [SMILES: CSc1ccc(-c2cc(COCC3(c4ccccc4)CCNCC3)cc(C(F)(F)F)c2)cc1] | A | A |
| | B | A |
| | C | B |

TABLE 1-continued

| Structure | NK-1 IC$_{50}$ (nM) | SERT IC$_{50}$ (nM) |
| --- | --- | --- |
| 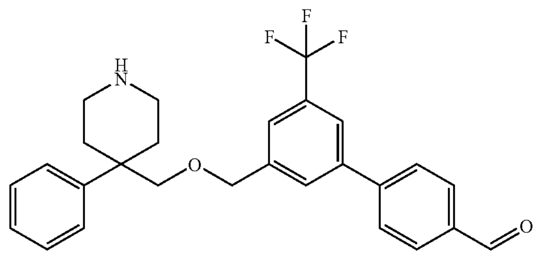 [SMILES: O=Cc1ccc(-c2cc(COCC3(c4ccccc4)CCNCC3)cc(C(F)(F)F)c2)cc1] | — | — |
| | A | A |
| 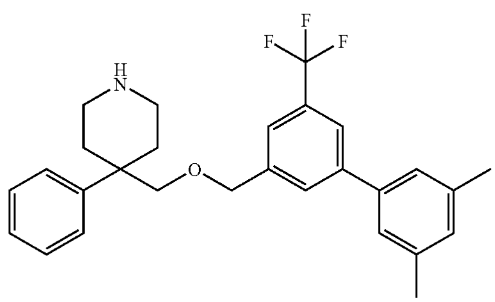 [SMILES: Cc1cc(C)cc(-c2cc(COCC3(c4ccccc4)CCNCC3)cc(C(F)(F)F)c2)c1] | C | A |
| | A | A |
| | A | A |

TABLE 1-continued

| Structure | NK-1 IC$_{50}$ (nM) | SERT IC$_{50}$ (nM) |
|---|---|---|
| | B | B |
| | B | A |
| | A | A |
| | A | A |
| | A | A |

TABLE 1-continued
| Structure | NK-1 IC$_{50}$ (nM) | SERT IC$_{50}$ (nM) |
|---|---|---|
| 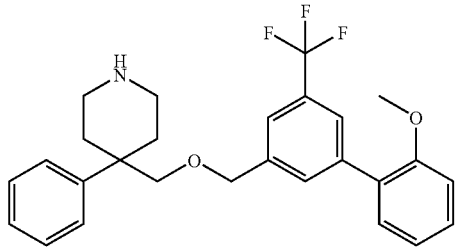 [SMILES: COc1ccccc1-c1cc(COCC2(c3ccccc3)CCNCC2)cc(C(F)(F)F)c1] | A | A |
| 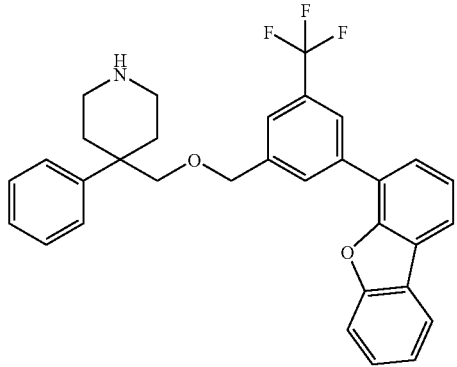 [SMILES: FC(F)(F)c1cc(COCC2(c3ccccc3)CCNCC2)cc(-c2cccc3c2oc2ccccc23)c1] | C | A |
| 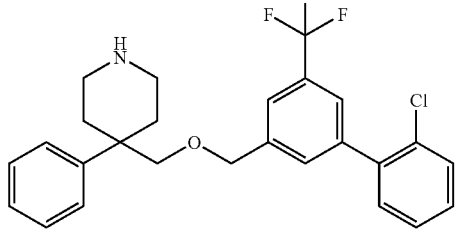 | A | A |
| 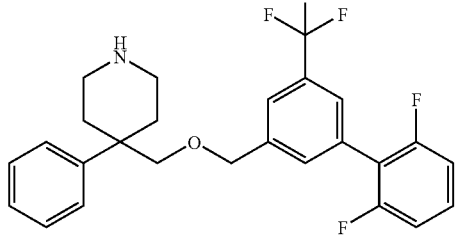 | A | A |
| 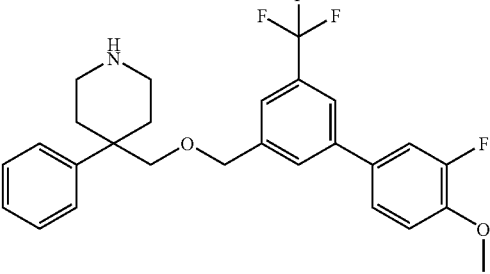 | A | A |

TABLE 1-continued

| Structure | NK-1 IC$_{50}$ (nM) | SERT IC$_{50}$ (nM) |
|---|---|---|
| | A | A |
| 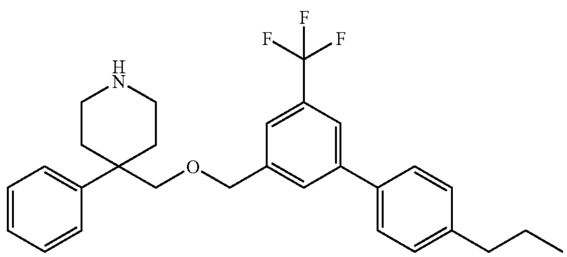 [SMILES: CCCc1ccc(-c2cc(COCC3(c4ccccc4)CCNCC3)cc(C(F)(F)F)c2)cc1] | — | — |
| | A | B |
| 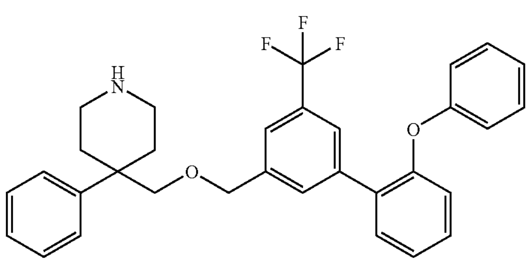 [SMILES: FC(F)(F)c1cc(COCC2(c3ccccc3)CCNCC2)cc(-c2ccccc2Oc2ccccc2)c1] | C | B |
| 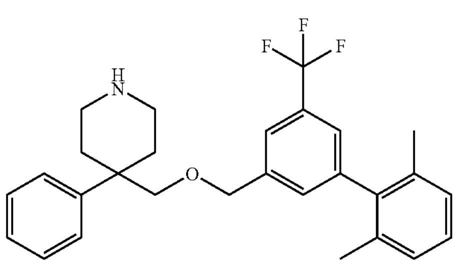 | B | B |

TABLE 1-continued

| Structure | NK-1 IC$_{50}$ (nM) | SERT IC$_{50}$ (nM) |
|---|---|---|
| | A | A |
| 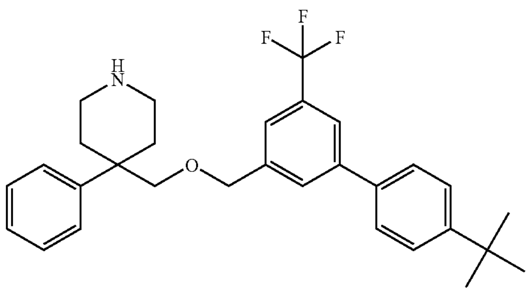 [SMILES: CC(C)(C)c1ccc(-c2cc(COCC3(c4ccccc4)CCNCC3)cc(C(F)(F)F)c2)cc1] | C | C |
| | A | A |
| | A | A |
| | A | A |

TABLE 1-continued

| Structure | NK-1 IC$_{50}$ (nM) | SERT IC$_{50}$ (nM) |
|---|---|---|
| | A | A |
| | A | A |
| | B | A |
| | B | A |
| 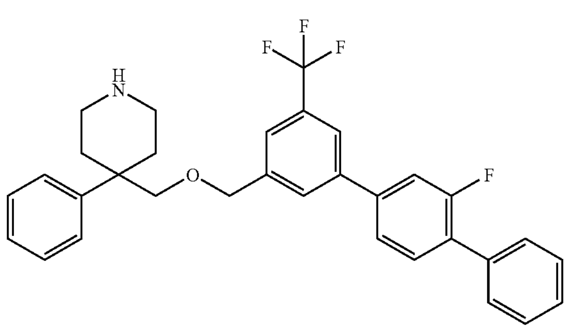 [SMILES: Fc1cc(-c2cc(COCC3(c4ccccc4)CCNCC3)cc(C(F)(F)F)c2)ccc1-c1ccccc1] | C | A |

TABLE 1-continued

| Structure | NK-1 IC$_{50}$ (nM) | SERT IC$_{50}$ (nM) |
|---|---|---|
| 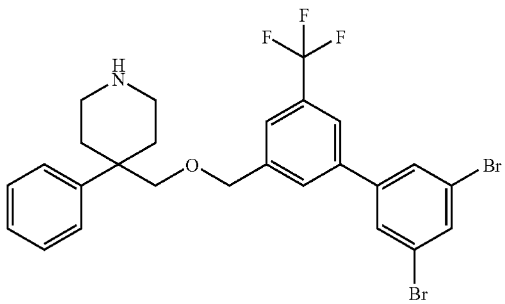 [SMILES: FC(F)(F)c1cc(COCC2(c3ccccc3)CCNCC2)cc(-c2cc(Br)cc(Br)c2)c1] | — | — |
| | B | B |
| | B | A |
| | B | A |
| | B | B |

TABLE 1-continued

| Structure | NK-1 IC$_{50}$ (nM) | SERT IC$_{50}$ (nM) |
|---|---|---|
| 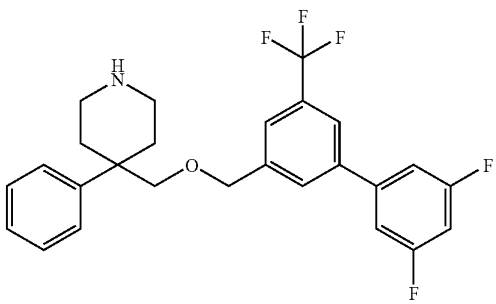 [SMILES: Fc1cc(F)cc(-c2cc(COCC3(c4ccccc4)CCNCC3)cc(C(F)(F)F)c2)c1] | A | A |
| 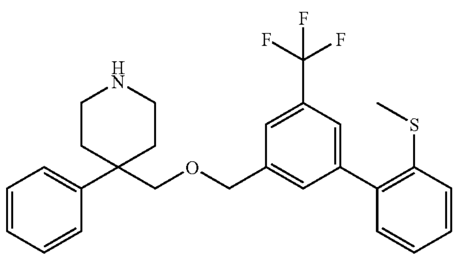 | B | A |
| | C | C |
| | C | A |
| | C | A |

TABLE 1-continued
| Structure | NK-1 IC$_{50}$ (nM) | SERT IC$_{50}$ (nM) |
|---|---|---|
| 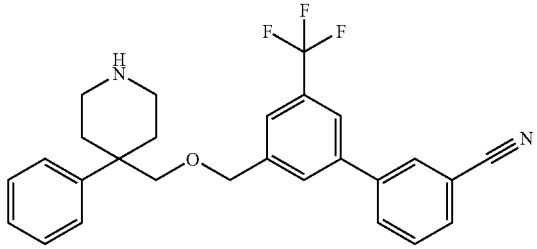 [SMILES: N#Cc1cccc(-c2cc(COCC3(c4ccccc4)CCNCC3)cc(C(F)(F)F)c2)c1] | A | A |
| 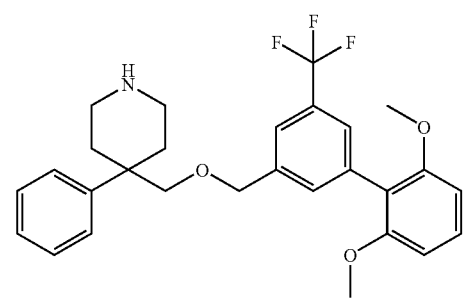 [SMILES: COc1cccc(OC)c1-c1cc(COCC2(c3ccccc3)CCNCC2)cc(C(F)(F)F)c1] | A | A |
| 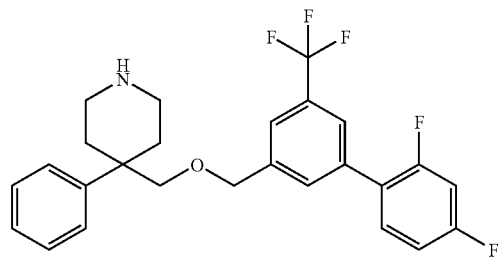 [SMILES: Fc1ccc(-c2cc(COCC3(c4ccccc4)CCNCC3)cc(C(F)(F)F)c2)c(F)c1] | A | A |
| 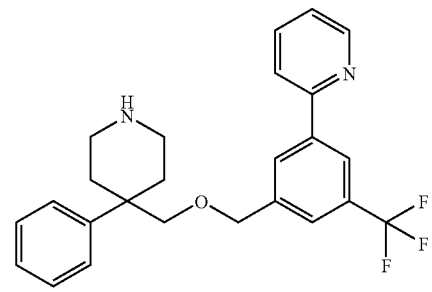 [SMILES: FC(F)(F)c1cc(COCC2(c3ccccc3)CCNCC2)cc(-c2ccccn2)c1] | A | A |
| 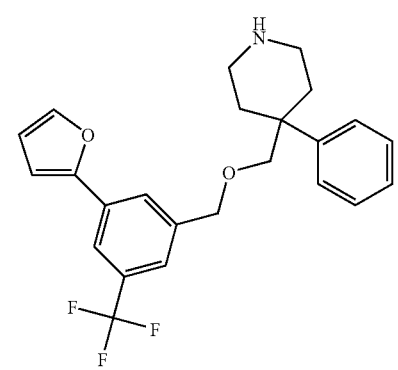 [SMILES: FC(F)(F)c1cc(COCC2(c3ccccc3)CCNCC2)cc(-c2ccco2)c1] | A | A |

TABLE 1-continued

| Structure | NK-1 IC$_{50}$ (nM) | SERT IC$_{50}$ (nM) |
|---|---|---|
| 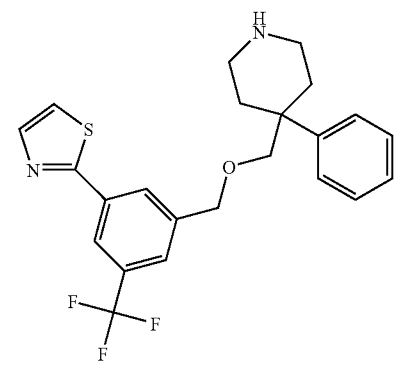 [SMILES: FC(F)(F)c1cc(COCC2(c3ccccc3)CCNCC2)cc(-c2nccs2)c1] | A | A |
| | B | A |
| 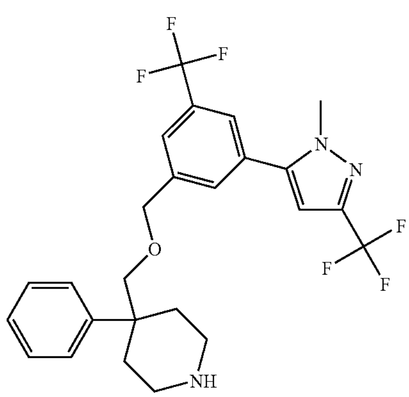 [SMILES: Cn1nc(C(F)(F)F)cc1-c1cc(COCC2(c3ccccc3)CCNCC2)cc(C(F)(F)F)c1] | C | A |
| | B | A |

TABLE 1-continued
| Structure | NK-1 IC$_{50}$ (nM) | SERT IC$_{50}$ (nM) |
|---|---|---|
| 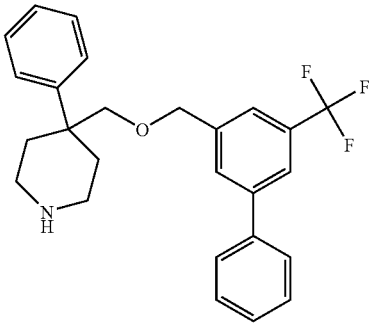 [SMILES: FC(F)(F)c1cc(COCC2(c3ccccc3)CCNCC2)cc(-c2ccccc2)c1] | A | A |
| 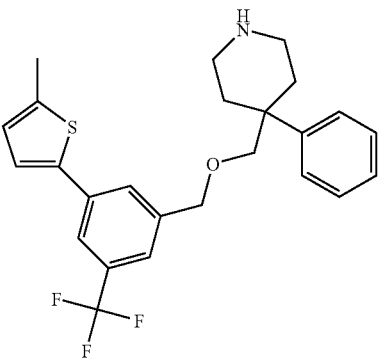 [SMILES: Cc1ccc(-c2cc(COCC3(c4ccccc4)CCNCC3)cc(C(F)(F)F)c2)s1] | A | A |
| 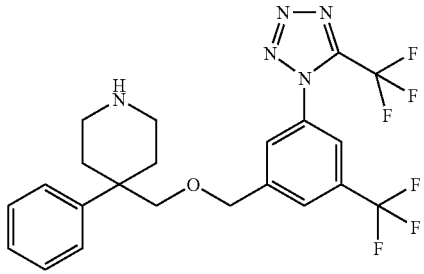 [SMILES: FC(F)(F)c1cc(COCC2(c3ccccc3)CCNCC2)cc(-n2nnnc2C(F)(F)F)c1] | C | A |
| 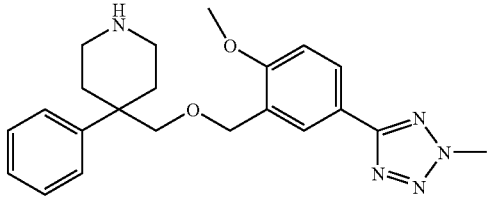 [SMILES: COc1ccc(-c2nnn(C)n2)cc1COCC1(c2ccccc2)CCNCC1] | C | B |
| 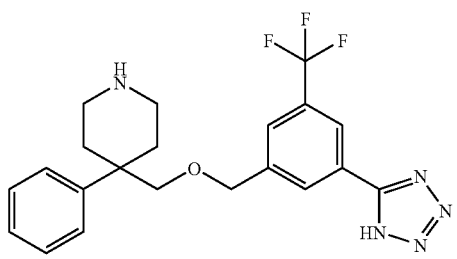 [SMILES: FC(F)(F)c1cc(COCC2(c3ccccc3)CCNCC2)cc(-c2nnn[nH]2)c1] | B | A |

TABLE 1-continued

| Structure | NK-1 IC$_{50}$ (nM) | SERT IC$_{50}$ (nM) |
|---|---|---|
| | A | A |
| | A | A |
| 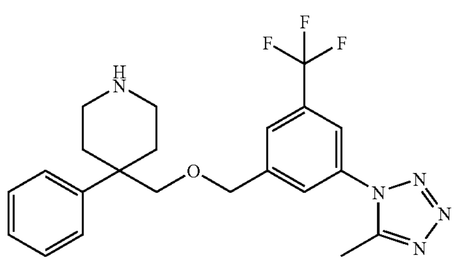 [SMILES: Cc1nnnn1-c1cc(COCC2(c3ccccc3)CCNCC2)cc(C(F)(F)F)c1] | B | A |
| | A | A |
| 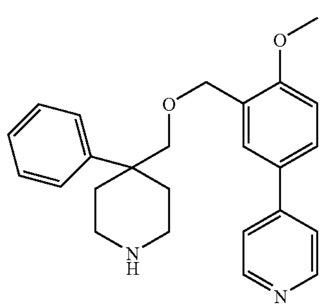 [SMILES: COc1ccc(-c2ccncc2)cc1COCC1(c2ccccc2)CCNCC1] | C | A |

TABLE 1-continued

| Structure | NK-1 IC$_{50}$ (nM) | SERT IC$_{50}$ (nM) |
|---|---|---|
| 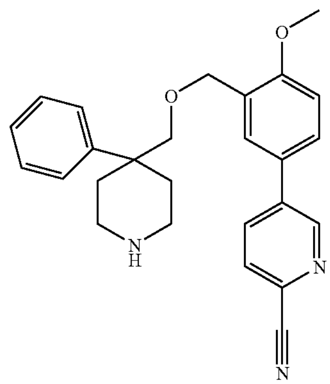 [SMILES: COc1ccc(-c2ccc(C#N)nc2)cc1COCC1(c2ccccc2)CCNCC1] | B | A |
| | A | A |
| | A | A |
| | A | A |

TABLE 1-continued

| Structure | NK-1 IC$_{50}$ (nM) | SERT IC$_{50}$ (nM) |
|---|---|---|
| | A | A |
| | A | A |
| | A | A |
| | A | A |

TABLE 1-continued
| Structure | NK-1 IC$_{50}$ (nM) | SERT IC$_{50}$ (nM) |
|---|---|---|
| 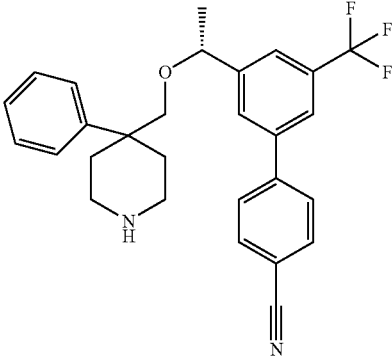 [SMILES: CC(OCC1(c2ccccc2)CCNCC1)c1cc(-c2ccc(C#N)cc2)cc(C(F)(F)F)c1] | A | A |
| 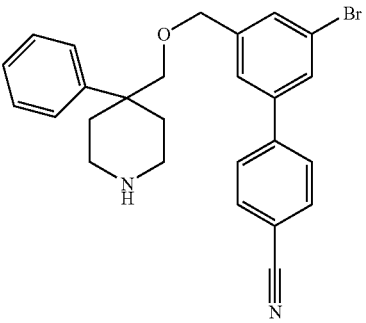 [SMILES: N#Cc1ccc(-c2cc(Br)cc(COCC3(c4ccccc4)CCNCC3)c2)cc1] | A | A |
Values:
A = 0.01-100 nM;
B = 100-300 nM;
C > 300 nM.
TABLE 2
| Structure | NK-1 IC$_{50}$ (nM) | SERT IC$_{50}$ (nM) |
|---|---|---|
| 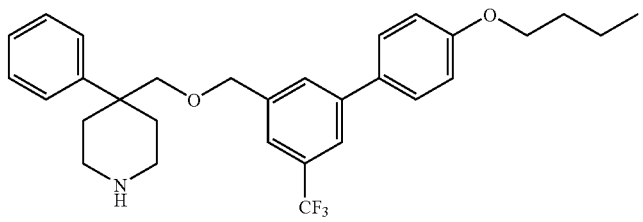 [SMILES: CCCCOc1ccc(-c2cc(COCC3(c4ccccc4)CCNCC3)cc(C(F)(F)F)c2)cc1] | A | A |
| 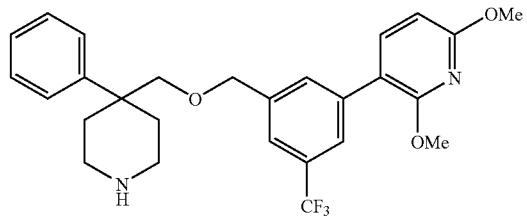 [SMILES: COc1ccc(-c2cc(COCC3(c4ccccc4)CCNCC3)cc(C(F)(F)F)c2)c(OC)n1] | A | A |

TABLE 2-continued
| Structure | NK-1 IC$_{50}$ (nM) | SERT IC$_{50}$ (nM) |
|---|---|---|
| 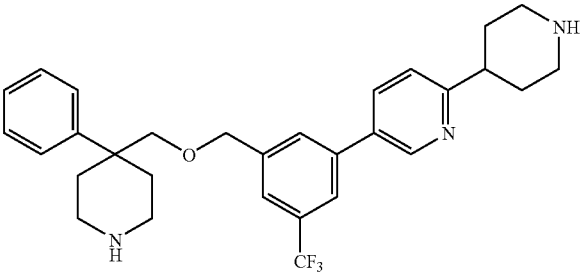 [SMILES: FC(F)(F)c1cc(COCC2(c3ccccc3)CCNCC2)cc(-c2ccc(C3CCNCC3)nc2)c1] | C | A |
| 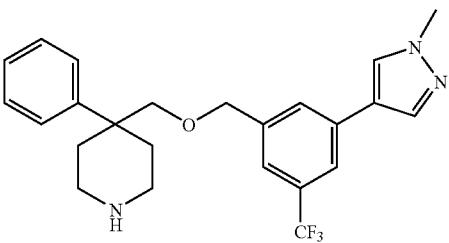 [SMILES: Cn1cc(-c2cc(COCC3(c4ccccc4)CCNCC3)cc(C(F)(F)F)c2)cn1] | A | A |
| 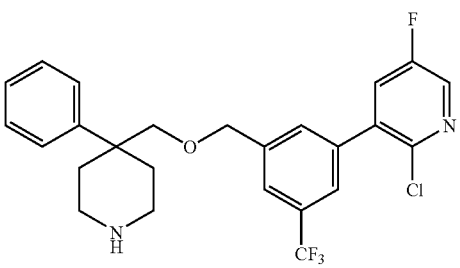 [SMILES: Fc1cnc(Cl)c(-c2cc(COCC3(c4ccccc4)CCNCC3)cc(C(F)(F)F)c2)c1] | B | A |
| 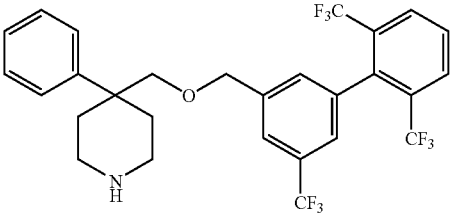 [SMILES: FC(F)(F)c1cc(COCC2(c3ccccc3)CCNCC2)cc(-c2c(C(F)(F)F)cccc2C(F)(F)F)c1] | A | A |
| 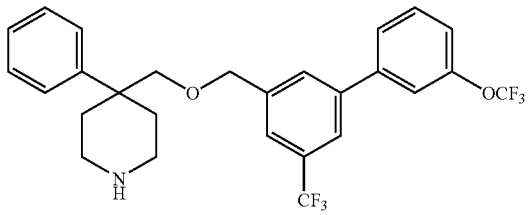 [SMILES: FC(F)(F)Oc1cccc(-c2cc(COCC3(c4ccccc4)CCNCC3)cc(C(F)(F)F)c2)c1] | C | A |
| 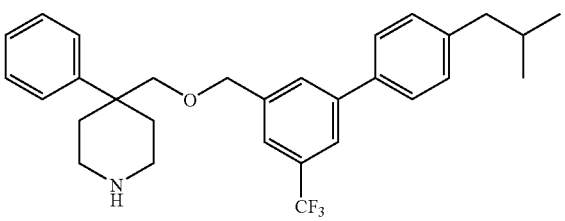 [SMILES: CC(C)Cc1ccc(-c2cc(COCC3(c4ccccc4)CCNCC3)cc(C(F)(F)F)c2)cc1] | C | B |

TABLE 2-continued
| Structure | NK-1 IC$_{50}$ (nM) | SERT IC$_{50}$ (nM) |
|---|---|---|
| 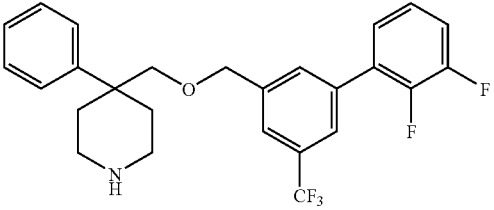 [SMILES: Fc1cccc(-c2cc(COCC3(c4ccccc4)CCNCC3)cc(C(F)(F)F)c2)c1F] | A | A |
| 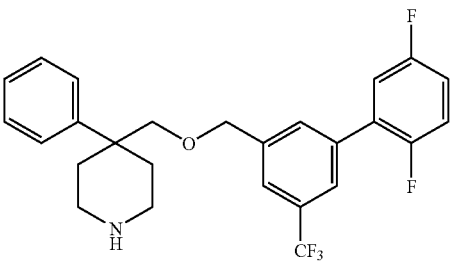 | A | A |
| 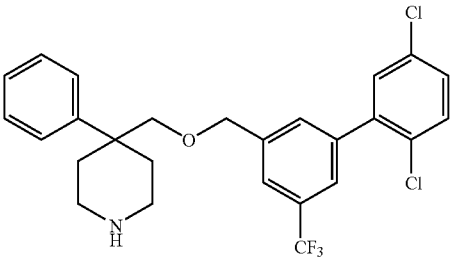 [SMILES: FC(F)(F)c1cc(COCC2(c3ccccc3)CCNCC2)cc(-c2cc(Cl)ccc2Cl)c1] | C | A |
| 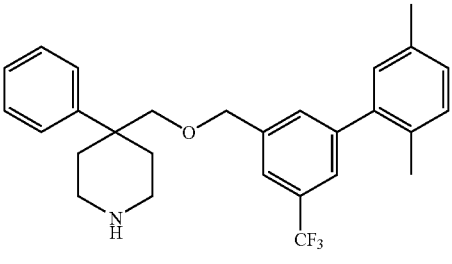 [SMILES: Cc1ccc(C)c(-c2cc(COCC3(c4ccccc4)CCNCC3)cc(C(F)(F)F)c2)c1] | C | A |
| 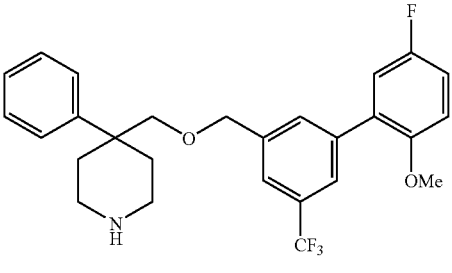 [SMILES: COc1ccc(F)cc1-c1cc(COCC2(c3ccccc3)CCNCC2)cc(C(F)(F)F)c1] | B | A |
| 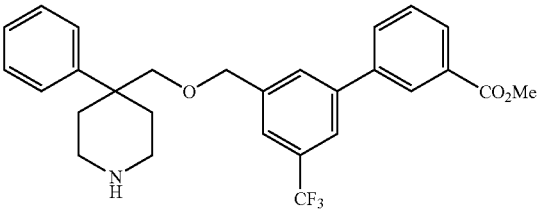 [SMILES: COC(=O)c1cccc(-c2cc(COCC3(c4ccccc4)CCNCC3)cc(C(F)(F)F)c2)c1] | B | A |

TABLE 2-continued

| Structure | NK-1 IC$_{50}$ (nM) | SERT IC$_{50}$ (nM) |
|---|---|---|
| (4-phenylpiperidin-4-yl)methoxymethyl-3-CF$_3$-biphenyl-3'-CO$_2$iPr | C | B |
| (4-phenylpiperidin-4-yl)methoxymethyl-3-CF$_3$-biphenyl-4'-NHC(O)OBn | A | A |
| (4-phenylpiperidin-4-yl)methoxymethyl-3-CF$_3$-biphenyl-3'-OBn | A | A |
| (4-phenylpiperidin-4-yl)methoxymethyl-3-CF$_3$-biphenyl-3',4',5'-trifluoro | A | A |
| (4-phenylpiperidin-4-yl)methoxymethyl-3-CF$_3$-biphenyl-4'-SO$_2$Et | B | A |
| (4-phenylpiperidin-4-yl)methoxymethyl-3-CF$_3$-biphenyl-3'-OMe-4'-OH | A | A |

TABLE 2-continued

| Structure | NK-1 IC$_{50}$ (nM) | SERT IC$_{50}$ (nM) |
|---|---|---|
| | A | A |
| | C | A |
| | A | A |
| 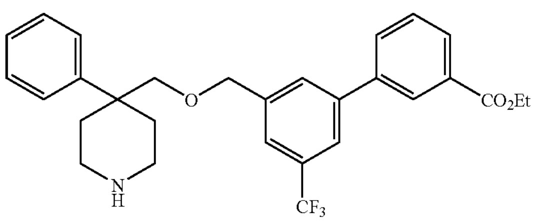 [SMILES: CCOC(=O)c1cccc(-c2cc(COCC3(c4ccccc4)CCNCC3)cc(C(F)(F)F)c2)c1] | B | A |
| | C | A |
| | A | A |

TABLE 2-continued

| Structure | NK-1 IC$_{50}$ (nM) | SERT IC$_{50}$ (nM) |
|---|---|---|
| (4-phenylpiperidin-4-yl)methoxymethyl-3-CF$_3$-5-(4-NHAc-phenyl)benzene | A | A |
| (4-phenylpiperidin-4-yl)methoxymethyl-3-CF$_3$-5-(2-CO$_2$Et-phenyl)benzene | C | B |
| (4-phenylpiperidin-4-yl)methoxymethyl-3-CF$_3$-5-(4-CO$_2$Et-2-NO$_2$-phenyl)benzene | | |
| (4-phenylpiperidin-4-yl)methoxymethyl-3-CF$_3$-5-(2-OMe-5-Me-phenyl)benzene | C | A |
| (4-phenylpiperidin-4-yl)methoxymethyl-3-CF$_3$-5-(3-CO$_2$Me-5-NO$_2$-phenyl)benzene | C | A |
| (4-phenylpiperidin-4-yl)methoxymethyl-3-CF$_3$-5-(4-CO$_2$iPr-phenyl)benzene | A | A |

TABLE 2-continued

| Structure | NK-1 IC$_{50}$ (nM) | SERT IC$_{50}$ (nM) |
|---|---|---|
| | B | B |
| | C | A |
| | B | A |
| | B | B |
| | C | B |
| 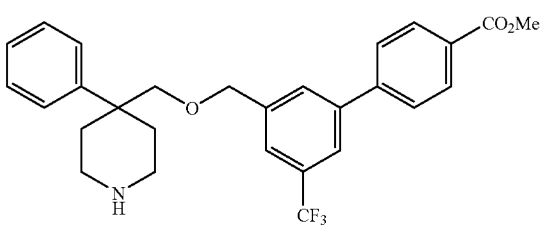 [SMILES: COC(=O)c1ccc(-c2cc(COCC3(c4ccccc4)CCNCC3)cc(C(F)(F)F)c2)cc1] | A | A |
| | C | B |

TABLE 2-continued
| Structure | NK-1 IC$_{50}$ (nM) | SERT IC$_{50}$ (nM) |
| --- | --- | --- |
| 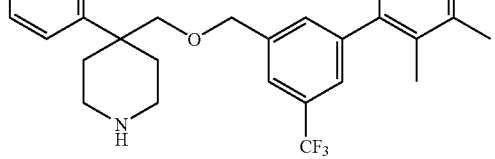 | B | A |
| 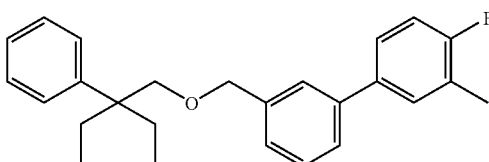 | A | A |
| 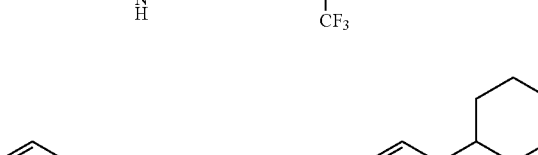 | C | B |
| 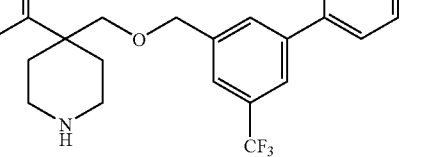 | C | A |
| 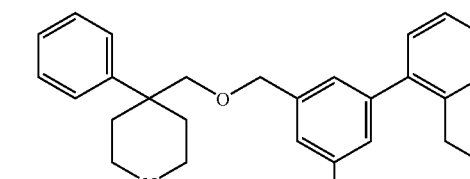 | C | A |
| 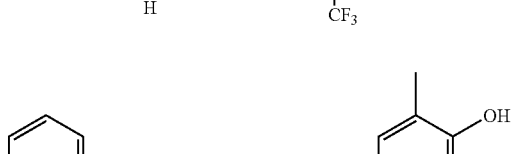 | A | A |

TABLE 2-continued
| Structure | NK-1 IC$_{50}$ (nM) | SERT IC$_{50}$ (nM) |
|---|---|---|
| 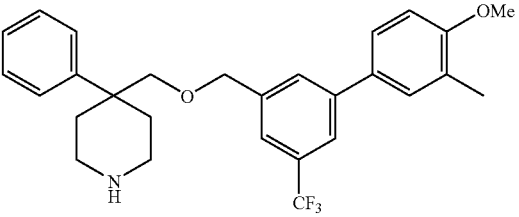 [SMILES: COc1ccc(-c2cc(COCC3(c4ccccc4)CCNCC3)cc(C(F)(F)F)c2)cc1C] | A | A |
| 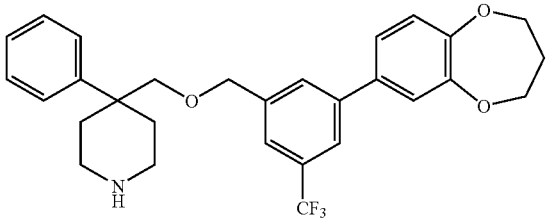 [SMILES: FC(F)(F)c1cc(COCC2(c3ccccc3)CCNCC2)cc(-c2ccc3c(c2)OCCCO3)c1] | | |
| 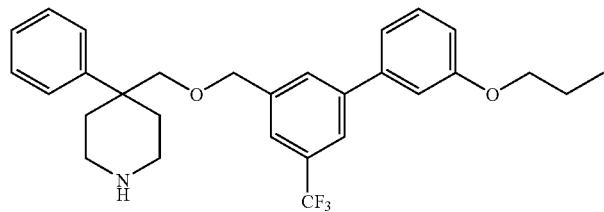 [SMILES: CCCOc1cccc(-c2cc(COCC3(c4ccccc4)CCNCC3)cc(C(F)(F)F)c2)c1] | C | B |
| 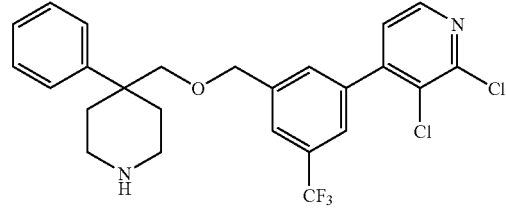 [SMILES: FC(F)(F)c1cc(COCC2(c3ccccc3)CCNCC2)cc(-c2ccnc(Cl)c2Cl)c1] | | |
| 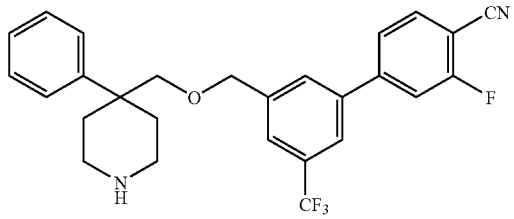 | A | A |
| 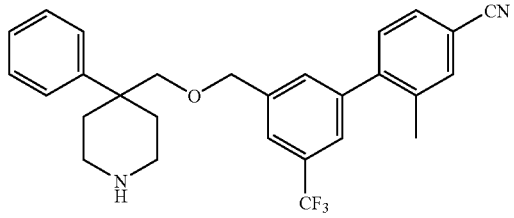 [SMILES: Cc1cc(C#N)ccc1-c1cc(COCC2(c3ccccc3)CCNCC2)cc(C(F)(F)F)c1] | A | A |

TABLE 2-continued
| Structure | NK-1 IC$_{50}$ (nM) | SERT IC$_{50}$ (nM) |
|---|---|---|
| 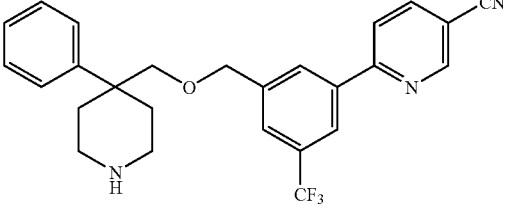 | A | A |
| 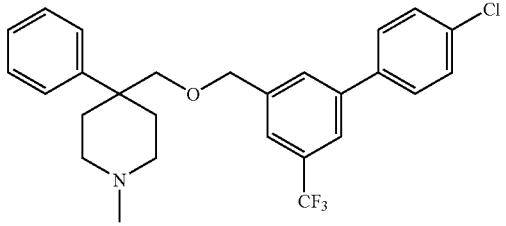 [SMILES: CN1CCC(COCc2cc(-c3ccc(Cl)cc3)cc(C(F)(F)F)c2)(c2ccccc2)CC1] | A | A |
| 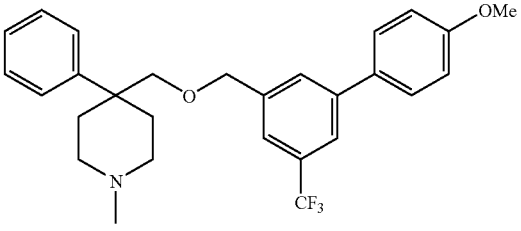 [SMILES: COc1ccc(-c2cc(COCC3(c4ccccc4)CCN(C)CC3)cc(C(F)(F)F)c2)cc1] | A | A |
| 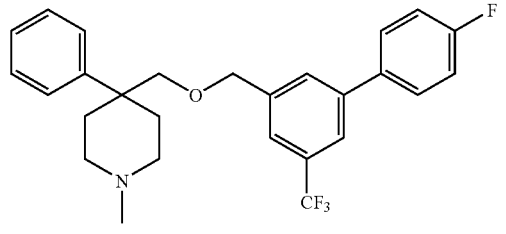 [SMILES: CN1CCC(COCc2cc(-c3ccc(F)cc3)cc(C(F)(F)F)c2)(c2ccccc2)CC1] | A | A |
| 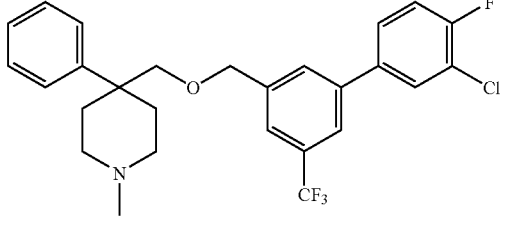 | A | A |
| 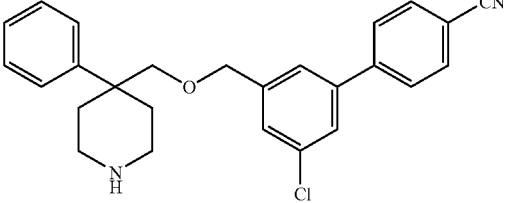 | A | A |

TABLE 2-continued

| Structure | NK-1 IC$_{50}$ (nM) | SERT IC$_{50}$ (nM) |
|---|---|---|
| | A | A |
| | A | A |
| | A | A |
| | A | A |
| | A | B |
| | A | A |

TABLE 2-continued

| Structure | NK-1 IC$_{50}$ (nM) | SERT IC$_{50}$ (nM) |
| --- | --- | --- |
| 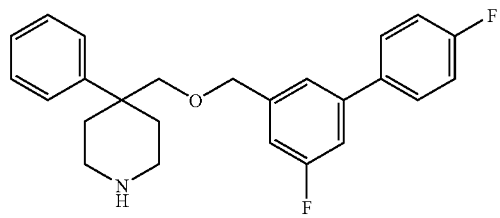 [SMILES: Fc1ccc(-c2cc(F)cc(COCC3(c4ccccc4)CCNCC3)c2)cc1] | C | A |
| | A | A |
| 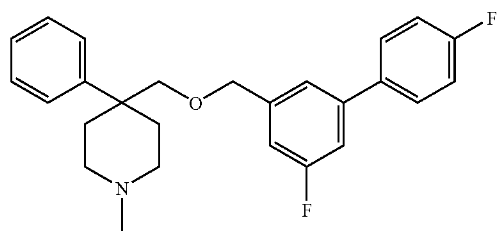 [SMILES: CN1CCC(COCc2cc(F)cc(-c3ccc(F)cc3)c2)(c2ccccc2)CC1] | B | A |
| | A | A |
| | A | A |
| | A | A |

TABLE 2-continued

| Structure | NK-1 IC$_{50}$ (nM) | SERT IC$_{50}$ (nM) |
|---|---|---|
| (structure: 4-phenyl-1-ethylpiperidine-CH$_2$-O-CH$_2$-[3-CF$_3$-5-(4-cyanophenyl)phenyl]) | A | C |
| (structure: 4-phenyl-1-benzylpiperidine-CH$_2$-O-CH$_2$-[3-CF$_3$-5-(4-cyanophenyl)phenyl]) | A | C |
| (structure: 4-phenyl-1-isopropylpiperidine-CH$_2$-O-CH$_2$-[3-CF$_3$-5-(4-cyanophenyl)phenyl]) | A | C |
| (structure: 4-phenylpiperidine-CH$_2$-O-CH(CH$_3$)-[3-Cl-5-(4-cyanophenyl)phenyl]) | A | A |
| (structure: 4-phenylpiperidine-CH$_2$-O-CH$_2$-[3-methyl-5-(4-cyanophenyl)phenyl]) | A | A |
| (structure: 4-phenylpiperidine-CH$_2$-O-CH$_2$-[3-CONMe$_2$-5-(4-cyanophenyl)phenyl]) | C | A |

TABLE 2-continued

| Structure | NK-1 IC$_{50}$ (nM) | SERT IC$_{50}$ (nM) |
|---|---|---|
| | C | A |
| | C | A |
| | C | A |
| | A | A |
| | C | A |
| | A | A |

TABLE 2-continued
| Structure | NK-1 IC$_{50}$ (nM) | SERT IC$_{50}$ (nM) |
|---|---|---|
| 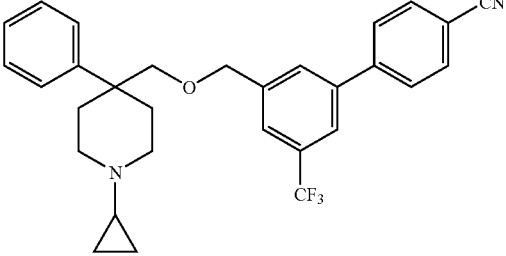 | A | C |
| 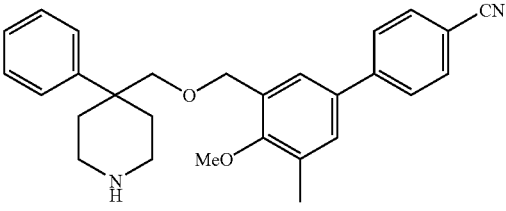 [SMILES: COc1c(C)cc(-c2ccc(C#N)cc2)cc1COCC1(c2ccccc2)CCNCC1] | A | A |
| 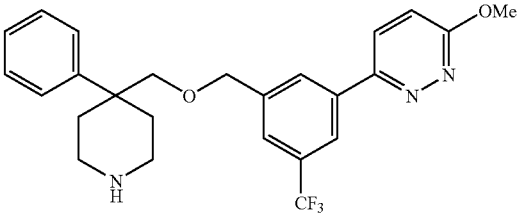 [SMILES: COc1ccc(-c2cc(COCC3(c4ccccc4)CCNCC3)cc(C(F)(F)F)c2)nn1] | A | A |
| 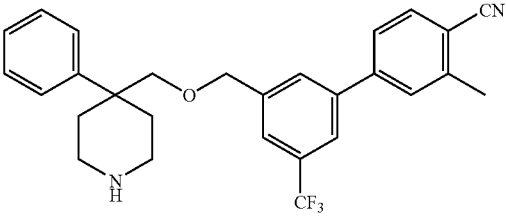 [SMILES: Cc1cc(-c2cc(COCC3(c4ccccc4)CCNCC3)cc(C(F)(F)F)c2)ccc1C#N] | A | A |
| 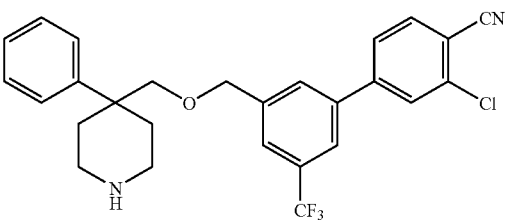 [SMILES: N#Cc1ccc(-c2cc(COCC3(c4ccccc4)CCNCC3)cc(C(F)(F)F)c2)cc1Cl] | A | A |
| 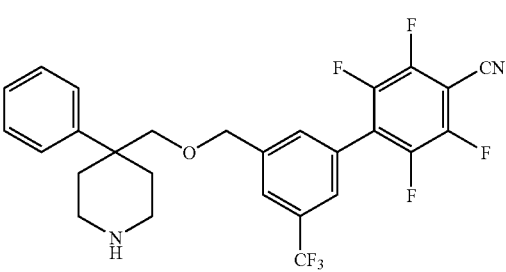 | A | A |

TABLE 2-continued
| Structure | NK-1 IC$_{50}$ (nM) | SERT IC$_{50}$ (nM) |
|---|---|---|
| 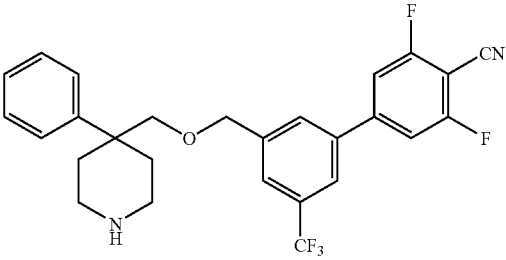 [SMILES: N#Cc1c(F)cc(-c2cc(COCC3(c4ccccc4)CCNCC3)cc(C(F)(F)F)c2)cc1F] | A | A |
| 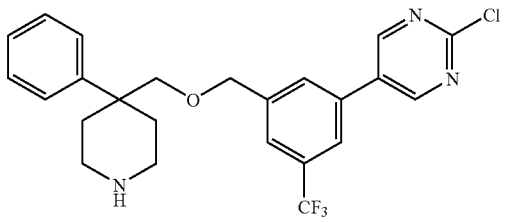 [SMILES: FC(F)(F)c1cc(COCC2(c3ccccc3)CCNCC2)cc(-c2cnc(Cl)nc2)c1] | A | A |
| 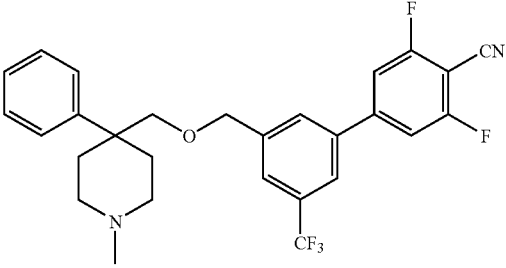 [SMILES: CN1CCC(COCc2cc(-c3cc(F)c(C#N)c(F)c3)cc(C(F)(F)F)c2)(c2ccccc2)CC1] | A | A |
| 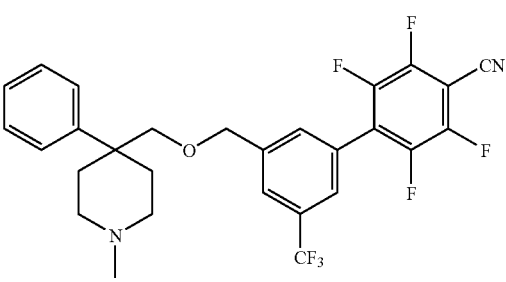 [SMILES: CN1CCC(COCc2cc(-c3c(F)c(F)c(C#N)c(F)c3F)cc(C(F)(F)F)c2)(c2ccccc2)CC1] | A | A |
| 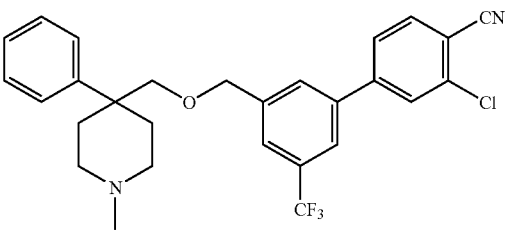 [SMILES: CN1CCC(COCc2cc(-c3ccc(C#N)c(Cl)c3)cc(C(F)(F)F)c2)(c2ccccc2)CC1] | A | A |
| 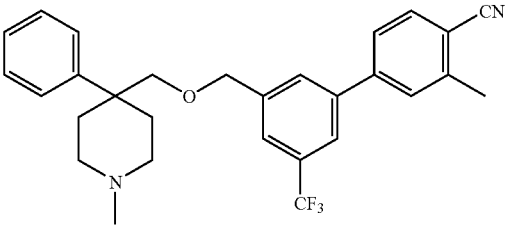 [SMILES: Cc1cc(-c2cc(COCC3(c4ccccc4)CCN(C)CC3)cc(C(F)(F)F)c2)ccc1C#N] | A | A |

TABLE 2-continued
| Structure | NK-1 IC$_{50}$ (nM) | SERT IC$_{50}$ (nM) |
|---|---|---|
| 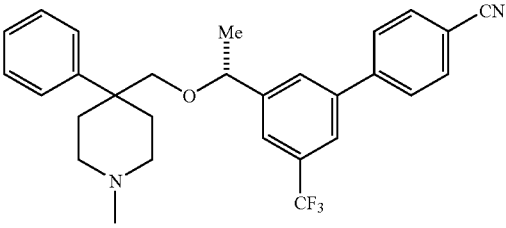 [SMILES: C[C@@H](OCC1(c2ccccc2)CCN(C)CC1)c1cc(-c2ccc(C#N)cc2)cc(C(F)(F)F)c1] | A | A |
| 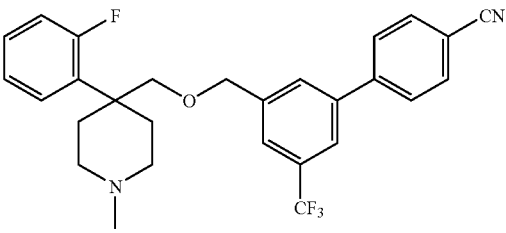 [SMILES: CN1CCC(COCc2cc(-c3ccc(C#N)cc3)cc(C(F)(F)F)c2)(c2ccccc2F)CC1] | A | A |
| 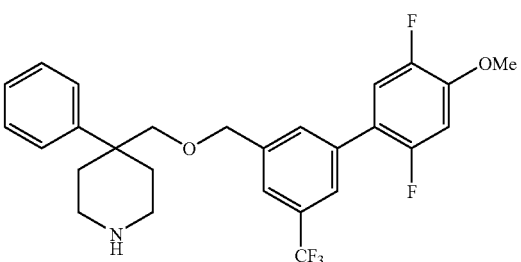 | A | A |
| 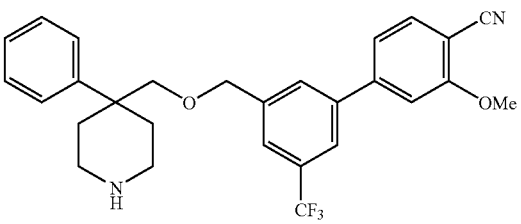 [SMILES: COc1cc(-c2cc(COCC3(c4ccccc4)CCNCC3)cc(C(F)(F)F)c2)ccc1C#N] | A | A |
| 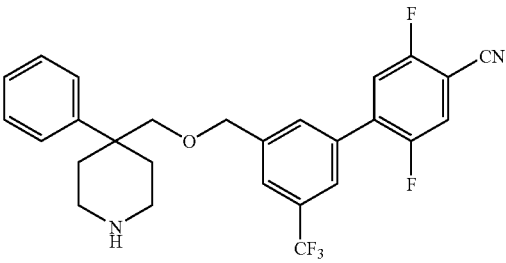 [SMILES: N#Cc1cc(F)c(-c2cc(COCC3(c4ccccc4)CCNCC3)cc(C(F)(F)F)c2)cc1F] | A | A |
| 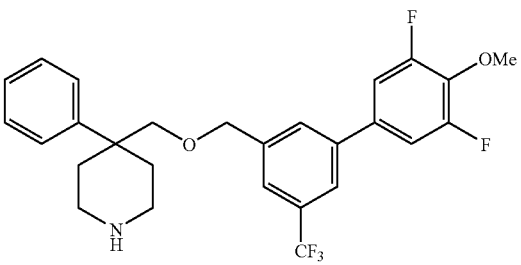 [SMILES: COc1c(F)cc(-c2cc(COCC3(c4ccccc4)CCNCC3)cc(C(F)(F)F)c2)cc1F] | A | A |

TABLE 2-continued
| Structure | NK-1 IC$_{50}$ (nM) | SERT IC$_{50}$ (nM) |
|---|---|---|
| 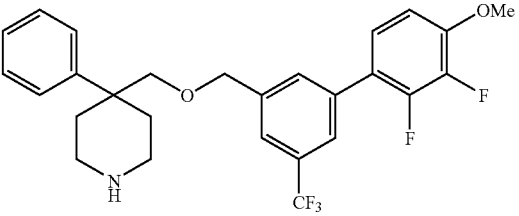 [SMILES: COc1ccc(-c2cc(COCC3(c4ccccc4)CCNCC3)cc(C(F)(F)F)c2)c(F)c1F] | A | A |
| 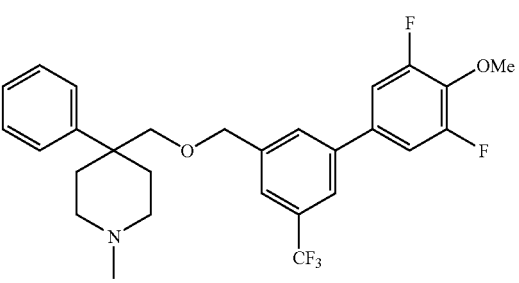 [SMILES: COc1c(F)cc(-c2cc(COCC3(c4ccccc4)CCN(C)CC3)cc(C(F)(F)F)c2)cc1F] | A | A |
| 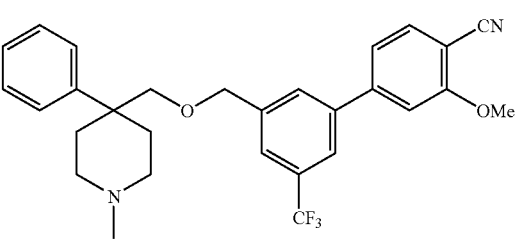 [SMILES: COc1cc(-c2cc(COCC3(c4ccccc4)CCN(C)CC3)cc(C(F)(F)F)c2)ccc1C#N] | A | A |
| 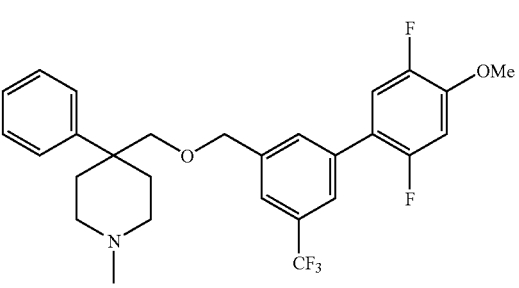 [SMILES: COc1cc(F)c(-c2cc(COCC3(c4ccccc4)CCN(C)CC3)cc(C(F)(F)F)c2)cc1F] | A | A |
| 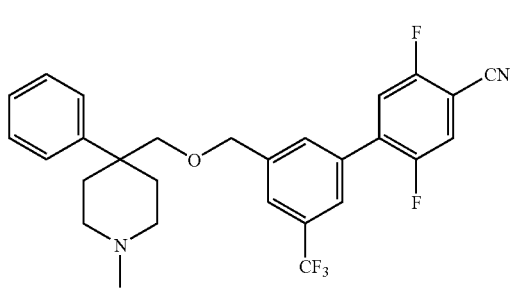 [SMILES: CN1CCC(COCc2cc(-c3cc(F)c(C#N)cc3F)cc(C(F)(F)F)c2)(c2ccccc2)CC1] | A | A |
| 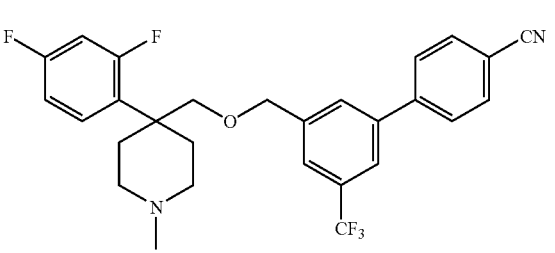 [SMILES: CN1CCC(COCc2cc(-c3ccc(C#N)cc3)cc(C(F)(F)F)c2)(c2ccc(F)cc2F)CC1] | A | A |

TABLE 2-continued
| Structure | NK-1 IC$_{50}$ (nM) | SERT IC$_{50}$ (nM) |
|---|---|---|
| 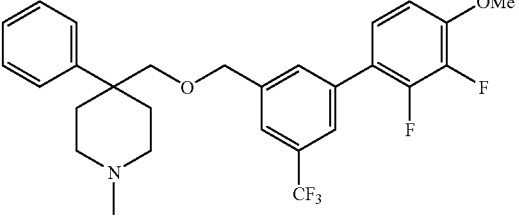 | A | A |
| 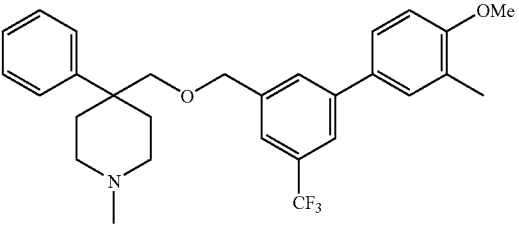 [SMILES: COc1ccc(-c2cc(COCC3(c4ccccc4)CCN(C)CC3)cc(C(F)(F)F)c2)cc1C] | A | A |
| 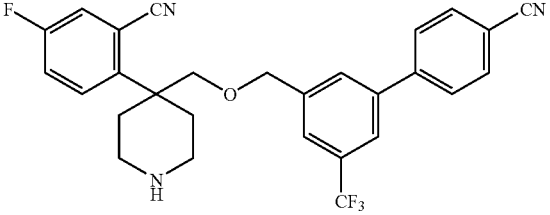 [SMILES: N#Cc1ccc(-c2cc(COCC3(c4ccc(F)cc4C#N)CCNCC3)cc(C(F)(F)F)c2)cc1] | A | A |
| 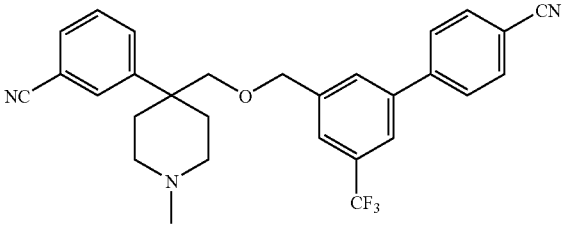 | A | A |
| 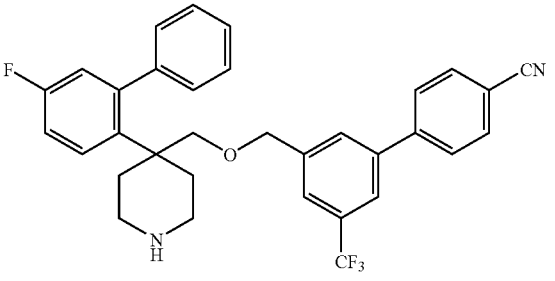 [SMILES: N#Cc1ccc(-c2cc(COCC3(c4ccc(F)cc4-c4ccccc4)CCNCC3)cc(C(F)(F)F)c2)cc1] | A | B |
| 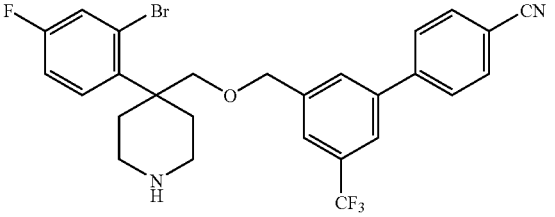 [SMILES: N#Cc1ccc(-c2cc(COCC3(c4ccc(F)cc4Br)CCNCC3)cc(C(F)(F)F)c2)cc1] | A | A |

TABLE 2-continued

| Structure | NK-1 IC$_{50}$ (nM) | SERT IC$_{50}$ (nM) |
|---|---|---|
| | A | A |
| | A | A |
| | A | A |
| | A | A |
| | A | A |
| | A | A |

TABLE 2-continued

| Structure | NK-1 IC$_{50}$ (nM) | SERT IC$_{50}$ (nM) |
|---|---|---|
| (4-bromophenyl piperidine, CH$_2$OCH$_2$, 3-CF$_3$-5-(4-cyanophenyl)phenyl) | A | A |
| (3-bromophenyl piperidine, CH$_2$OCH$_2$, 3-CF$_3$-5-(4-cyanophenyl)phenyl) | A | A |
| (4-cyanophenyl N-methylpiperidine, CH$_2$OCH$_2$, 3-CF$_3$-5-(4-cyanophenyl)phenyl) | A | A |
| (3-chlorophenyl N-methylpiperidine, CH$_2$OCH$_2$, 3-CF$_3$-5-(4-cyanophenyl)phenyl) | A | A |
| (3-trifluoromethylphenyl N-methylpiperidine, CH$_2$OCH$_2$, 3-CF$_3$-5-(4-cyanophenyl)phenyl) | A | A |
| (3-pyridyl N-methylpiperidine, CH$_2$OCH$_2$, 3-CF$_3$-5-(4-cyano-3-methylphenyl)phenyl) | A | A |

TABLE 2-continued

| Structure | NK-1 IC$_{50}$ (nM) | SERT IC$_{50}$ (nM) |
|---|---|---|
| [structure] | A | A |
| [structure] | A | B |
| [structure] | A | A |

Values:
A = 0.01-100 nM;
B = 100-300 nM;
C > 300 nM.

Pharmaceutical Composition and Methods of Use

The compounds of Formula I demonstrate inhibition of neurokinin-1 or serotonin reuptake or both. Inhibition of these receptors correlates with efficacy for affective disorders such as anxiety, depression, obsessive compulsive disorder, bulimia, and panic disorder. As such, the compounds of Formula I can be useful for the treatment of these disorders and other aspects of the invention are compositions and methods of using the compounds to treat these conditions and other conditions associated with aberrant levels of tachykinins or serotonin or both.

The compounds of this invention are generally given as pharmaceutical compositions comprised of a therapeutically effective amount of a compound of Formula I, or a pharmaceutically acceptable salt, and a pharmaceutically acceptable carrier and may contain conventional excipients. A therapeutically effective amount is the amount needed to provide a meaningful patient benefit as determined by practitioners in that art. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques and conventional excipients (such as binding and wetting agents) and vehicles (such as water and alcohols).

Solid compositions are normally formulated in dosage units providing from about 1 to about 1000 mg of the active ingredient per dose. Some examples of solid dosage units are 1 mg, 10 mg, 100 mg, 250 mg, 500 mg, and 1000 mg. Liquid compositions are generally in a unit dosage range of 1-100 mg/mL. Some examples of liquid dosage units are 1 mg/mL, 10 mg/mL, 25 mg/mL, 50 mg/mL, and 100 mg/mL. Generally, the dosage unit will be in a unit range similar to agents of that class used clinically, for example fluoxetine.

The invention encompasses all conventional modes of administration; oral and parenteral methods are preferred. Generally, the dosing regimen will be similar to agents of that class used clinically, for example fluoxetine. Typically, the daily dose will be 0.01-100 mg/kg body weight daily. Generally, more compound is required orally and less parenterally. The specific dosing regime, however, should be determined by a physician using sound medical judgement.

Tachykinin and serotonin modulators are associated with depression. Accordingly, another aspect of the invention are methods for treating depressive disorders including Major Depressive Disorders (MDD), bipolar depression, unipolar depression, single or recurrent major depressive episodes, recurrent brief depression, catatonic features, melancholic features including feeding disorders, such as anorexia, weight loss, atypical features, anxious depression, or postpartum onset. Other central nervous system disorders encompassed within the term MDD include neurotic depression, post-traumatic stress disorders (PTSD) and social phobia, with early or late onset dementia of the Alzheimer's type, with depressed mood, vascular dementia with depressed mood, mood disorders and tolerance induced by drugs such as alcohol, amphetamines, cocaine, inhalants, opioids, sedatives, anxiolytics and other substances, schizoaffective disorder of the depressed type, and adjustment disorder with depressed mood.

Tachykinin and serotonin modulators are also associated with the treatment or prevention of schizophrenic disorders. Accordingly, another aspect of the invention are methods for treating schizophrenic disorders including paranoid schizophrenia, disorganized schizophrenia, catatonic schizophrenia, undifferentiated schizophrenia, residual schizophrenia.

Tachykinin and serotonin modulators are also associated with the treatment or prevention of anxiety. Accordingly, another aspect of the invention are methods for treating anxiety disorders including panic disorders, agoraphobia, phobias, obsessive-compulsive disorder, stress disorders including post-traumatic stress disorders, generalized anxiety disorders, acute stress disorders and mixed anxiety-depression disorders.

Tachykinin and serotonin modulators are also associated with the treatment or prevention of cognitive disorders. Accordingly, another aspect of the invention are methods for treating cognitive disorders including dementia, and amnesia disorders. Tachykinin and serotonin modulators are also associated with the treatment or prevention of memory and cognition in healthy humans.

Tachykinin and serotonin modulators are also associated with use as analgesics. Accordingly, another aspect of the invention are methods for treating pain, including the treatment of traumatic pain such as postoperative pain, chronic pain such as arthritic pain such as occurring in osteo-, rheumatoid or psoriatic arthritis, neuropathic pain such as postherpetic neuralgia, trigeminal neuralgia, segmental or intercostal neuralgia, fibromyalgia, peripheral neuropathy, diabetic neuropathy, chemotherapy-induced neuropathy, AIDS-related neuropathy, various forms of headache such as migraine, acute or chronic tension headache, cluster headaches, maxillary sinus pain, cancer pain, pain of bodily origin, gastrointestinal pain, sport's injury pain, dysmennorrhoea, menstrual pain, meningitis, musculoskeletal pain, low back pain e.g. spinal stenosis, prolapsed disc, sciatica, angina, ankylosing spondylitis, gout, burns, scar pain, itch and thalamic pain such as post stroke thalamic pain.

Tachykinin and serotonin modulators are also associated with the treatment or prevention of sleep disorders. Accordingly, another aspect of the invention are methods for treating sleep disorders including insomnia, sleep apnea, narcolepsy, and circadian rhymic disorders.

Tachykinin and serotonin modulators are also associated with the treatment or prevention of inflammation. Accordingly, another aspect of the invention are methods for treating inflammation, including the treatment of inflammation in asthma, influenza and chronic bronchitis, in the treatment of inflammatory diseases of the gastrointestinal tract such as Crohn's disease, ulcerative colitis, inflammatory bowel disease and non-steroidal anti-inflammatory drug induced damage, inflammatory diseases of the skin such as herpes and eczema, inflammatory diseases of the bladder such as cystitis and urge incontinence, and eye and dental inflammation.

Tachykinin and serotonin modulators are also associated with the treatment or prevention of allergic disorders. Accordingly, another aspect of the invention are methods for treating allergic disorders, in particular allergic disorders of the skin such as urticaria, and allergic disorders of the airways such as rhinitis.

Tachykinin and serotonin modulators are also associated with the treatment or prevention of emesis, nausea, retching and vomiting. Accordingly, another aspect of the invention are methods for treating these disorders.

Tachykinin and serotonin modulators are also associated with the treatment or prevention of premenstrual dysphoric disorder (PMDD), in chronic fatigue syndrome and multiple sclerosis. Accordingly, another aspect of the invention are methods for treating these disorders.

DESCRIPTION OF SPECIFIC EMBODIMENTS

The following experimental procedures describe the synthesis of some Formula I compounds. Standard chemistry conventions are used in the text unless otherwise noted. The experimental encompass reasonable variations known in the art. Method A involves the use of a Suzuki coupling. Method B involves the use of a Stille coupling. Method D involves reductive amination. The following HPLC conditions were used in the preparing the compounds below. HPLC method 1: Xterra C18 2.0×50 mm, A=95% $H_2O$/5% ACN, B=95% ACN/5% $H_2O$, Modifier 10 mM $NH_4OAC$, 1 mL/min, 0.00 min=10% B, 2.00 min=100% B; HPLC method 2: Xterra C18 2.0×50 mm, A=95% $H_2O$/5% ACN, B=95% ACN/5% $H_2O$, Modifier 10 mM $NH_4OAC$, Flow rate=1 mL/min, 0.00 min=10% B, 0.80 min=60% B, 1.99 min=95% B, 2.00 min=100% B (1.5 mL/min); HPLC method 3: Phenomenex C18 4.6×50 mm, 10% MeOH/90% $H_2O$/0.1% TFA→90% MeOH/10% $H_2O$/0.1% TFA, Gradient time=4 min., Flow rate=4 mL/min; HPLC method 4: Phenomenex C18 4.6×50 mm, A=95% $H_2O$/5% ACN, B=95% ACN/5% $H_2O$, Modifier 10 mM $NH_4OAc$, 0.00 min=10% B, 3.5 min=95% B, Flow rate=1.5 mL/min; HPLC method 5: Phenomenex Luna 3.0× 50 mm, A=90% $H_2O$/10% MeOH, B=90% MeOH/10% $H_2O$, Modifier 0.1% TFA, 0.00 min=0% B, 4.0 min=100% B, Flow rate=4 mL/min; HPLC method 6: Xterra C18 2.1×50 mm, A=95% $H_2O$/5% ACN, B=95% ACN/5% $H_2O$, Modifier 10 mM $NH_4OAc$, 0.00 min=0% B, 0.80 min=80% B, 2.00 min=100% B, Flow rate=1.0 mL/min.

Intermediate 1

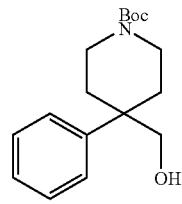

tert-Butyl 4-(hydroxymethyl)-4-phenylpiperidine-1-carboxylate. 4-Phenyl-4-piperidinecarboxylic acid p-methylbenzenesulfonate (19.0 g, 50.3 mmol) was suspended in dry tetrahydrofuran (100 mL) and cooled to 0° C. To this was added borane tetrahydrofuran complex (1 M in THF, 100 mL, 100 mmol) cautiously over 15 min and the reaction mixture allowed to warm to room temperature overnight. The reaction mixture was cooled to 0° C., treated with di-tert-butyl carbonate (15.0 g, 218 mmol) and 10 N sodium hydroxide (12 mL), stirred at 0° C., and at room temperature overnight. The reaction mixture was diluted with ethyl acetate, washed with water (2×), brine (2×), dried over sodium sulfate and concentrated. The crude product was triturated with 10% ethyl acetate/hexanes solution to afford 9.2 g (63%) of the title compound. $^1$H-NMR ($CD_3OD$, 300 MHz) δ 7.35-7.43 (m, 4H), 7.24-7.26 (m, 1H), 3.78-3.85 (m, 2H), 3.49 (s, 2H), 2.97 (m, 2H), 2.17-2.21 (m, 2H), 1.77-1.87 (m, 2H), 1.46 (s, 9H). Mass spec.: 292.17 (MH)+.

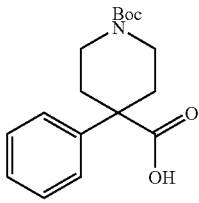

Intermediate 2

1-(tert-Butoxycarbonyl)-4-phenylpiperidine-4-carboxylic acid. To a suspension of 4-phenyl-4-piperidinecarboxylic acid p-methylbenzenesulfonate (100 g, 265 mmol) and triethylamine (111 mL, 795 mmol) in tetrahydrofuran (1200 mL) was added di-tert-butyl dicarbonate (63.6 g, 291 mmol). The reaction was slowly heated to a gentle reflux and held there for 1 h. After one hour, gas evolution had ended and the reaction had become a clear solution. The reaction was cooled to room temperature and concentrated to remove most of the tetrahydrofuran. The residue was dissolved in water/ether and the aqueous made very basic by the addition of 10 M sodium hydroxide (50 mL). The aqueous was washed with ether (2×) which was discarded. The aqueous was transferred to an erlenmeyer flask and made acidic (ca. pH 5) by addition of acetic acid to give a white precipitate. The precipitate was collected by filtration and air dried overnight to give a white powder. The last traces of water were removed under high vacuum to give the product (78.9 g, 258 mmol, 98% yield). $^1$H-NMR (CD$_3$OD, 500 MHz) δ 10.5 (bs, 1H), 7.39 (m, 2H), 7.33 (m, 2H), 7.26 (m, 1H), 3.90 (bs, 2H), 3.08, (bs, 2H), 2.48 (d, J=13.4 Hz, 2H), 1.85 (m, 2H), 1.44 (s, 9H); $^{13}$C NMR (126 MHz, CDCl$_3$) δ ppm 179.6, 155.0, 141.6, 128.8, 127.6, 126.1, 79.9, 49.3, 41.7, 33.4, 28.5. Mass spec.: 328.12 (MNa)+.

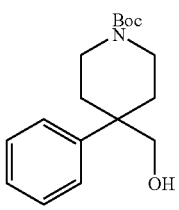

Intermediate 3 tert-Butyl 4-(hydroxymethyl)-4-phenylpiperidine-1-carboxylate. To a suspension of 1-(tert-butoxycarbonyl)-4-phenylpiperidine-4-carboxylic acid (40 g, 131 mmol) in tetrahydrofuran (131 mL) at room temperature was added borane tetrahydrofuran complex (1 M in tetrahydrofuran, 131 mL, 131 mmol). There was effervescence and the substrate quickly went into solution. The reaction was stirred at room temperature for 3 days. The reaction was cooled to 0° C. and quenched by the cautious addition of 1 M sodium hydroxide. The reaction was diluted with ether, washed with water (2×), then brine, dried over magnesium sulfate, and concentrated. Trituration with 10% EtOAc/Hex (300 mL) gave a white powder which was collected by filtration to give 36.9 g (97%). $^1$H-NMR (CD$_3$OD, 300 MHz) δ 7.35-7.43 (m, 4H), 7.24-7.26 (m, 1H), 3.78-3.85 (m, 2H), 3.49 (s, 2H), 2.97 (m, 2H), 2.17-2.21 (m, 2H), 1.77-1.87 (m, 2H), 1.46 (s, 9H). Mass spec.: 292.17 (MH)+.

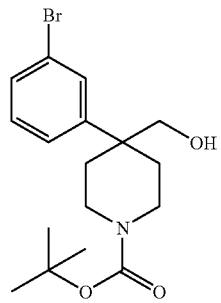

Intermediate 4 tert-Butyl 4-(3-bromophenyl)-4-(hydroxymethyl)piperidine-1-carboxylate. $^1$H-NMR (CDCl$_3$, 500 MHz) δ ppm 7.47 (s, 1H), 7.39 (m, 1H), 7.27 (m, 2H), 3.72 (m, 2H), 3.55 (s, 2H), 3.06 (m, 2H), 2.05 (m, 2H), 1.76 (m, 2H), 1.42 (s, 9H). Mass spec.: 370.12 (MH)+.

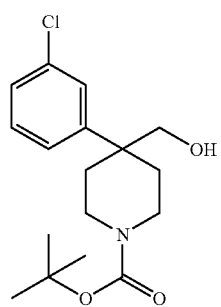

Intermediate 5 tert-Butyl 4-(3-chlorophenyl)-4-(hydroxymethyl)piperidine-1-carboxylate. $^1$H-NMR (CDCl$_3$, 500 MHz) δ ppm 7.30 (m, 2H), 7.23 (m, 2H), 3.72 (m, 2H), 3.53 (s, 2H), 2.08 (m, 2H), 1.76 (m, 2H), 1.41 (s, 9H). Mass spec.: 326.16 (MH)+.

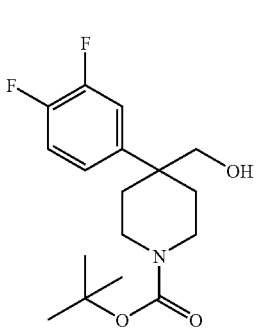

Intermediate 6 tert-Butyl 4-(3,4-difluorophenyl)-4-(hydroxymethyl)piperidine-1-carboxylate. $^1$H-NMR (CDCl$_3$, 500 MHz) δ ppm 7.10-7.18 (m, 2H), 7.05 (m, 1H), 3.68-3.73 (m, 2H), 3.54 (m, 2H), 3.01-3.08 (m, 2H), 2.08 (m, 2H), 1.74-1.79 (m, 2H), 1.42 (s, 9H).

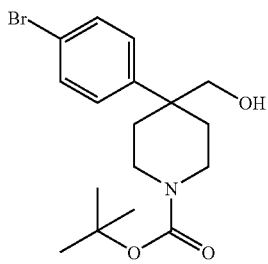

Intermediate 7 tert-Butyl 4-(4-bromophenyl)-4-(hydroxymethyl)piperidine-1-carboxylate. ¹H-NMR (CDCl₃, 500 MHz) δ ppm 7.50 (m, 2H), 7.21 (m, 2H), 3.70 (m, 2H), 3.53 (s, 2H), 3.02 (m, 2H), 2.10 (m, 2H), 1.75 (m, 2H), 1.42 (s, 9H). Mass spec.: 370.15 (MH)⁺.

Intermediate 8

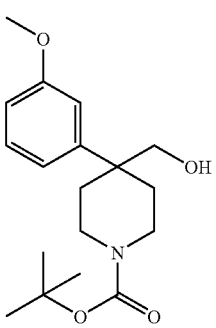

tert-Butyl 4-(hydroxymethyl)-4-(3-(trifluoromethyl)phenyl)piperidine-1-carboxylate. ¹H-NMR (CDCl₃, 500 MHz) δ ppm 7.49-7.57 (m, 4H), 3.71-3.75 (m, 2H), 3.59 (s, 2H), 3.01-3.10 (m, 2H), 2.15 (m, 2H), 1.85 (m, 2H), 1.42 (s, 9H). Mass spec.: 360.26 (MH)⁺.

Intermediate 9 tert-Butyl 4-(hydroxymethyl)-4-(3-methoxyphenyl)piperidine-1-carboxylate. ¹H-NMR (CDCl₃, 500 MHz) δ ppm 7.31 (m, 1H), 6.87-6.93 (m, 1H), 6.88 (s, 1H), 6.80 (m, 1H), 3.80 (s, 3H), 3.72-3.78 (m, 2H), 3.53 (d, J=6.41 Hz, 2H), 3.05 (t, J=11.14 Hz, 2H), 2.14 (d, J=14.04 Hz, 2H), 1.73 (ddd, J=14.11, 10.30, 3.97 Hz, 2H), 1.42 (s, 9H). Mass spec.: 322.22 (MH)⁺.

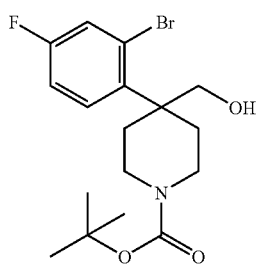

Intermediate 10 tert-Butyl 4-(2-bromo-4-fluorophenyl)-4-(hydroxymethyl)piperidine-1-carboxylate. ¹H-NMR (CDCl₃, 500 MHz) δ ppm 7.33-7.40 (m, 2H), 7.00-7.06 (m, 1H), 4.04 (d, J=6.3 Hz, 2H), 3.59 (m, 2H), 3.19-3.26 (m, 2H), 2.45-2.49 (m, 2H), 1.95-2.02 (m, 2H), 1.43 (s, 9H). Mass spec.: 390.15 (MH)⁺.

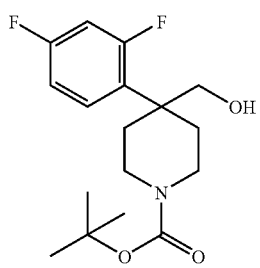

Intermediate 11 tert-Butyl 4-(2,4-difluorophenyl)-4-(hydroxymethyl)piperidine-1-carboxylate. ¹H-NMR (CDCl₃, 400 MHz) δ ppm 7.22 (m, 1H), 6.85 (m, 1H), 6.77 (m, 1H), 3.70 (s, 2H), 3.67 (m, 2H), 3.08 (m, 2H), 2.21 (m, 2H), 1.78 (m, 2H), 1.64 (m, 1H), 1.41 (s, 9H). Mass spec.: 328.27 (MH)⁺.

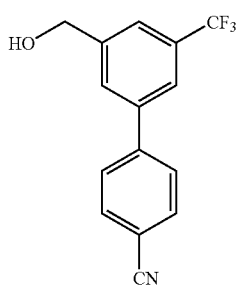

Intermediate 12

3'-(hydroxymethyl)-5'-(trifluoromethyl)biphenyl-4-carbonitrile. A solution of (3-bromo-5-(trifluoromethyl)phenyl)methanol (3.0 g, 11.8 mmol), 4-cyanophenyl boronic acid (5.2 g, 35 mmol), tetrakis(triphenylphosphine) palladium(0) (2.7 g, 2.4 mmol), and aqueous potassium hydroxide (41 mL, 1N, 41 mmol) in THF (80 mL) was degassed with nitrogen for 10 minutes and then heated at 120° C. for 18 hours. The reaction was cooled to ambient temperature and poured into water (100 mL), then was diluted with ethyl acetate (100 mL) and the layers were separated. The aqueous layer was extracted with ethyl acetate (2×20 mL) and the combined organic layers were dried with MgSO₄ and evaporated. The residue was purified by chromatography on SiO₂ with a gradient of ethyl acetate/hexanes of 5%-40%. The product 3'-(hydroxymethyl)-5'-(trifluoromethyl)biphenyl-4-carbonitrile (1.66 g, 51%) was obtained as a white solid. ¹H-NMR (CDCl$_3$, 400 MHz) δ 7.65-7.80 (m, 7H), 4.85 (s, 2H), 1.90 (bs, 1H). Mass spec.: 278.2 (M+H).

Intermediate 13

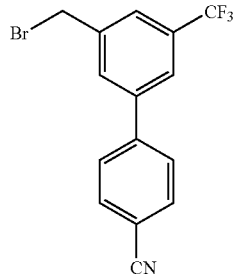

3'-(bromomethyl)-5'-(trifluoromethyl)biphenyl-4-carbonitrile. N-bromosuccinimide (2.24 g, 12.6 mmol) was added to a 0° C. solution of 3'-(hydroxymethyl)-5'-(trifluoromethyl)biphenyl-4-carbonitrile (1.66 g, 6.0 mmol) and triphenylphosphine (3.14 g, 12.0 mmol) in THF (100 mL). The reaction was warmed to ambient temperature and stirred for 18 hours. The solvent was evaporated and the residue was purified by chromatography on SiO$_2$ with a gradient of ethyl acetate/hexanes of 5% to 40%. The product 3'-(bromomethyl)-5'-(trifluoromethyl)biphenyl-4-carbonitrile (1.30 g, 64%) was obtained as a white solid. $^1$H-NMR (CDCl$_3$, 400 MHz) δ 7.65-7.80 (m, 7H), 4.56 (s, 2H).

Intermediate 14

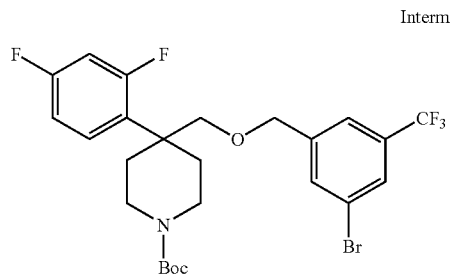

tert-Butyl 4-((3-bromo-5-(trifluoromethyl)benzyloxy)methyl)-4-(2,4-difluorophenyl)piperidine-1-carboxylate. tert-Butyl 4-(2,4-difluorophenyl)-4-(hydroxymethyl)piperidine-1-carboxylate (220 mg, 0.67 mmol) and 1-Bromo-3-(bromomethyl)-5-(trifluoromethyl)benzene (450 mg, 1.41 mmol) were combined in tetrahydrofuran (2 mL) and cooled to 0° C. The reaction was treated with sodium tert-butoxide (75 mg, 0.355 mmol) and stirred at 0° C. for 20 min. The reaction was treated with another aliquot of sodium tert-butoxide (75 mg, 0.355 mmol), allowed to warm to room temperature, and stirred for 30 min. The reaction was diluted with 10% sodium bicarbonate and extracted with ethyl acetate (2×). The organic layers were pooled together, washed with brine (1×), dried over sodium sulfate, and concentrated. Column chromatography on silica gel (0%→25% ethyl acetate/hexanes) gave 200 mg (50%). Mass spec.: 586.04 (MH)$^+$ LC t$_r$=2.552 min. (Phenomenex-Luna 4.6×50 mm S10, 10% MeOH/90% H$_2$O/0.1% TFA→90% MeOH/10% H$_2$O/0.1% TFA Gradient Time=2 min, Flow rate=4 mL/min).

Intermediate 15

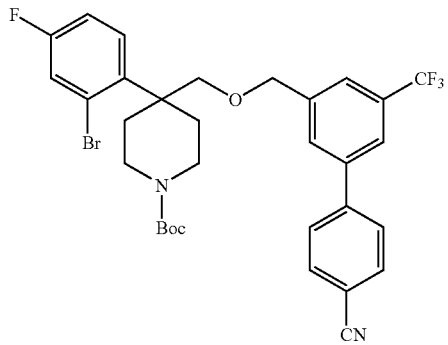

tert-butyl 4-(2-bromo-4-fluorophenyl)-4-(((4'-cyano-5-(trifluoromethyl)biphenyl-3-yl)methoxy)methyl)piperidine-1-carboxylate. Potassium tert-butoxide (266 mg, 2.37 mmol) was added to a 0° C. solution of tert-butyl 4-(2-bromo-4-fluorophenyl)-4-(hydroxymethyl)piperidine-1-carboxylate (460 mg, 1.18 mmol) and 3'-(bromomethyl)-5'-(trifluoromethyl)biphenyl-4-carbonitrile (524 mg, 1.54 mmol) in THF (10 mL) and was allowed to warm to ambient temperature and stir for 24 hours. The solvent was evaporated and the residue was purified by chromatography on SiO$_2$ with a gradient of ethyl acetate/hexanes from 5% to 40%. The product tert-butyl 4-(2-bromo-4-fluorophenyl)-4-(((4'-cyano-5-(trifluoromethyl)biphenyl-3-yl)methoxy)methyl)piperidine-1-carboxylate (520 mg, 68%) was isolated as a clear syrup. $^1$H-NMR (CDCl$_3$, 400 MHz) δ 7.75 (d, J=8.3 Hz, 2H), 7.67 (s, 1H), 7.58 (d, J=8.3 Hz, 2H), 7.36 (m, 3H), 7.22 (m, 1H), 6.99 (m, 1H), 4.49 (s, 2H), 3.94 (s, 2H), 3.57 (m, 1H), 3.24 (m 1H), 2.48 (m, 2H), 2.05 (m, 2H), 1.42 (s, 9H). Mass spec.: 647.2 (M+H).

Intermediate 16

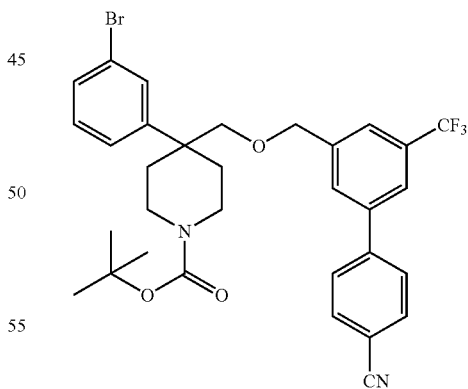

tert-Butyl 4-(3-bromophenyl)-4-(((4'-cyano-5-(trifluoromethyl)biphenyl-3-yl)methoxy)methyl)piperidine-1-carboxylate. $^1$H-NMR (CDCl$_3$, 500 MHz) δ ppm 7.75 (m, 2H), 7.67 (br s, 1H), 7.60 (m, 2H), 7.48 (m, 1H), 7.41 (m, 2H), 7.31 (m, 1H), 7.28 (m, 1H), 7.18 (m, 1H), 4.45 (m, 2H), 3.72 (m, 2H), 3.45 (m, 2H), 3.04 (m, 2H), 2.13 (m, 2H), 1.85 (m, 2H), 1.42 (s, 9H). Mass spec.: 629.22 (MH)$^+$.

Intermediate 17

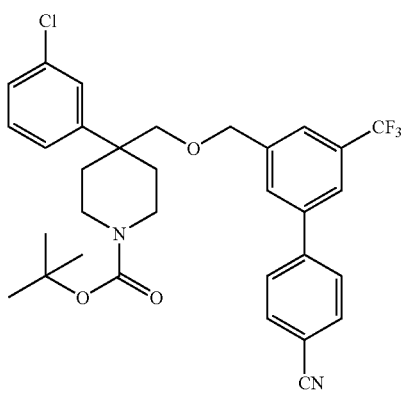

tert-Butyl 4-(3-chlorophenyl)-4-(((4'-cyano-5-(trifluoromethyl)biphenyl-3-yl)methoxy)methyl)piperidine-1-carboxylate. $^1$H-NMR (CDCl$_3$, 500 MHz) δ ppm 7.74 (m, 2H), 7.66 (s, 1H), 7.61 (s, 1H), 7.44 (s, 1H), 7.37 (s, 1H), 7.18-7.29 (m, 4H), 7.17 (m, 1H), 4.47 (s, 2H), 3.73 (m, 2H), 3.43 (s, 2H), 3.03 (m, 2H), 2.16 (m, 2H), 1.85 (m, 2H), 1.42 (s, 9H). Mass spec.: 585.27 (MH)$^+$.

Intermediate 18 tert-Butyl 4-(((4'-cyano-5-(trifluoromethyl)biphenyl-3-yl)methoxy)methyl)-4-(3,4-difluorophenyl)piperidine-1-carboxylate. $^1$H-NMR (CDCl$_3$, 500 MHz) δ ppm 7.75 (m, 2H), 7.68 (s, 1H), 7.59 (m, 2H), 7.42 (s, 1H), 7.38 (s, 1H), 7.01-7.19 (m, 3H), 4.47 (s, 2H), 3.69 (m, 2H), 3.42 (s, 2H), 3.05 (m, 2H), 2.07 (m, 2H), 1.83 (m, 2H), 1.42 (s, 9H).

Intermediate 19 tert-Butyl 4-(4-bromophenyl)-4-(((4'-cyano-5-(trifluoromethyl)biphenyl-3-yl)methoxy)methyl)piperidine-1-carboxylate. $^1$H-NMR (CDCl$_3$, 500 MHz) δ ppm 7.78 (m, 2H), 7.68 (s, 1H), 7.59 (m, 2H), 7.43 (m, 4H), 7.23 (m, 2H), 4.46 (s, 2H), 3.72 (m, 2H), 3.43 (s, 2H), 3.02 (s, 2H), 2.14 (m, 2H), 1.83 (m, 2H), 1.42 (s, 9H). Mass spec.: 653.06 (MNa)$^+$.

Intermediate 20

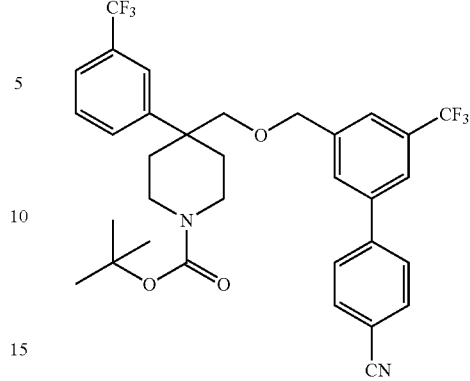

tert-Butyl 4-(((4'-cyano-5-(trifluoromethyl)biphenyl-3-yl)methoxy)methyl)-4-(3-(trifluoromethyl)phenyl)piperidine-1-carboxylate. $^1$H-NMR (CDCl$_3$, 500 MHz) δ ppm 7.74 (m, 2H), 7.68 (s, 1H), 7.51-7.59 (m, 4H), 7.36-7.45 (m, 4H), 4.46 (s, 2H), 3.70 (m, 2H), 3.47 (s, 2H), 3.03-3.09 (m, 2H), 2.18 (m, 2H), 1.87-1.92 (m, 2H), 1.42 (s, 9H). Mass spec.: 619.27 (MH)$^+$.

Intermediate 21

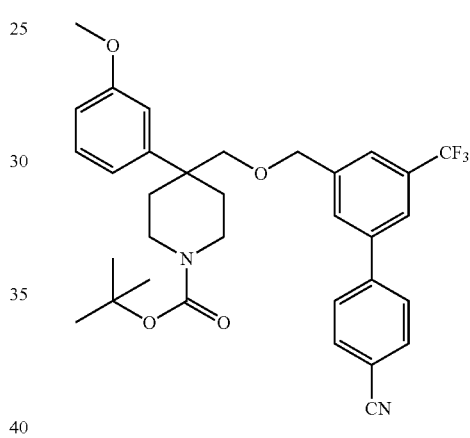

tert-Butyl 4-(((4'-cyano-5-(trifluoromethyl)biphenyl-3-yl)methoxy)methyl)-4-(3-methoxyphenyl)piperidine-1-carboxylate. $^1$H-NMR (CDCl$_3$, 500 MHz) δ ppm 7.74-7.76 (m, 2H), 7.67 (s, 1H), 7.59-7.62 (m, 2H), 7.47 (s, 1H), 7.41 (s, 1H), 7.22-7.26 (m, 1H), 6.92-6.95 (m, 1H), 6.90 (m, 1H), 6.73-6.76 (m, 1H), 4.45 (s, 2H), 3.70-3.78 (m, 2H), 3.75 (s, 3H), 3.44 (s, 2H), 3.02 (m, 2H), 2.14-2.19 (m, 2H), 1.80-1.88 (m, 2H), 1.41 (s, 9H). Mass spec.: 581.14 (MH)$^+$.

Intermediate 22

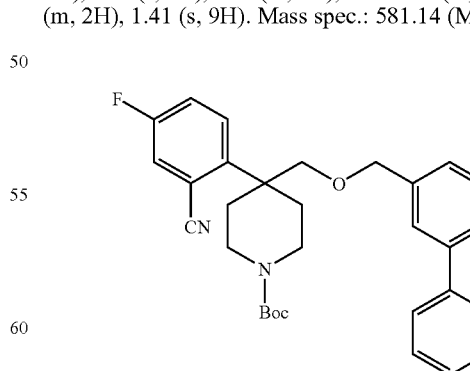

tert-butyl 4-(2-cyano-4-fluorophenyl)-4-(((4'-cyano-5-(trifluoromethyl)biphenyl-3-yl)methoxy)methyl)piperidine-1-carboxylate. A mixture of tert-butyl 4-(2-bromo-4-fluorophenyl)-4-(((4'-cyano-5-(trifluoromethyl)biphenyl-3-yl)methoxy)methyl)piperidine-1-carboxylate (50 mg, 0.077 mmol), Zinc cyanide (13.60 mg, 0.116 mmol), and tetrakis(triphenylphosphine)palladium(0) (8.92 mg, 7.72 μmol) were placed in a sealable vessel and degassed with nitrogen for 5 min. The vessel was then sealed and heated at 120° C. for 3 h. The reaction was poured into brine (20 mL) and extracted with ethyl acetate (4×5 mL). The combined organic layers were dried (MgSO₄) and evaporated to dryness. The resulting residue was purified by chromatography on SiO₂ with a ethyl acetate/hexanes gradient from 12% to 100%. The product tert-butyl 4-(2-cyano-4-fluorophenyl)-4-(((4'-cyano-5-(trifluoromethyl)biphenyl-3-yl)methoxy)methyl)piperidine-1-carboxylate (39 mg, 85%) was obtained as a clear oil. ¹H-NMR (CDCl₃, 400 MHz) δ 7.75 (d, J=8.7 Hz, 2H), 7.68 (s, 1H), 7.61 (d, J=8.4 Hz, 2H), 7.45 (m, 1H), 7.40 (s, 1H), 7.22-7.32 (m, 3H), 4.51 (s, 2H), 3.86 (s, 2H), 3.59 (m, 1H), 3.28 (m, 2H), 2.47 (m, 2H), 2.10 (m, 2H), 1.42 (s, 9H). Mass spec.: 594.3 (M+H).

Intermediate 23

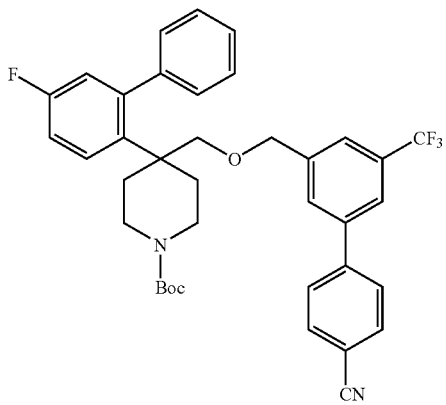

tert-butyl 4-(((4'-cyano-5-(trifluoromethyl)biphenyl-3-yl)methoxy)methyl)-4-(5-fluorobiphenyl-2-yl)piperidine-1-carboxylate. A mixture of tert-butyl 4-(2-bromo-4-fluorophenyl)-4-(((4'-cyano-5-(trifluoromethyl)biphenyl-3-yl)methoxy)methyl)piperidine-1-carboxylate (100 mg, 0.15 mmol), phenyl boronic acid (19 mg, 0.15 mmol), potassium carbonate (43 mg, 0.31 mmol) and tetrakis(triphenylphosphine)palladium(0) (18 mg, 0.15 mmol) were placed in a sealable vessel and degassed with nitrogen for 5 min. The vessel was then sealed and heated at 120° C. for 3 h. The reaction was poured into brine (20 mL) and extracted with ethyl acetate (4×5 mL). The combined organic layers were dried (MgSO₄) and evaporated to dryness. The resulting residue was purified by chromatography on SiO₂ with a ethyl acetate/hexanes gradient from 12% to 100%. The product tert-butyl 4-(((4'-cyano-5-(trifluoromethyl)biphenyl-3-yl)methoxy)methyl)-4-(5-fluorobiphenyl-2-yl)piperidine-1-carboxylate (39 mg, 39%) was isolated as a clear oil. ¹H-NMR (CDCl₃, 400 MHz) δ 7.68-7.76 (m, 3H), 7.55 (d, J=8.4 Hz, 2H), 7.44 (m, 3H), 7.18-7.28 (m, 3H), 7.03 (m, 1H), 6.94 m, 2H), 6.67 (m, 1H), 4.52 (s, 2H), 3.52 (m, 2H), 3.47 (s, 2H), 2.90 (m, 2H), 1.91 (m, 2H), 1.45 (m, 2H), 1.38 (s, 9H). Mass spec.: 645.2 (M+H).

Intermediate 24

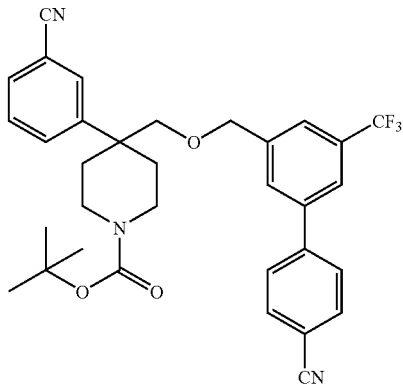

tert-Butyl 4-(((4'-cyano-5-(trifluoromethyl)biphenyl-3-yl)methoxy)methyl)-4-(3-cyanophenyl)piperidine-1-carboxylate. A mixture of tert-Butyl 4-(3-bromophenyl)-4-(((4'-cyano-5-(trifluoromethyl)biphenyl-3-yl)methoxy)methyl)piperidine-1-carboxylate (150 mg, 0.238 mmol), zinc cyanide (33.6 mg, 0.286 mmol), palladium tetrakis triphenylphosphine (27.5 mg, 0.024 mmol), and dimethylformamide (1 mL) was charged to a conical vial and purged with nitrogen for 5 minutes. The vial was sealed and heated at 120° C. for 2 hours and then held at room temperature overnight. The resulting mixture was filtered through a syringe tip filter and applied directly to a silica gel column. Gradient elution with 5-40% ethyl acetate/hexanes afforded the product as a clear oil (83 mg, 61%). ¹H-NMR (CDCl₃, 500 MHz) δ ppm 7.76 (m, 2H), 7.68 (s, 1H), 7.56-7.64 (m, 4H), 7.45-7.49 (m, 1H), 7.38-7.43 (m, 2H), 7.34 (s, 1H), 3.69 (m, 2H), 3.45 (s, 2H), 3.05 (m, 2H), 2.10 (m, 2H), 1.88 (m, 2H), 1.42 (s, 9H). Mass spec.: 576.17 (MH)⁺.

Intermediate 25

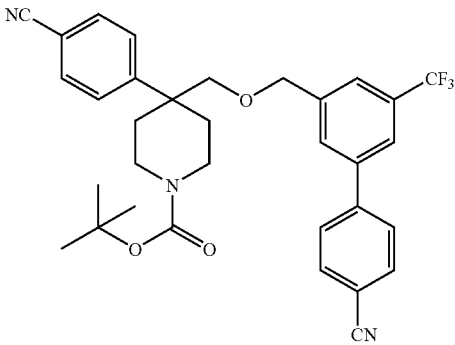

tert-Butyl 4-(((4'-cyano-5-(trifluoromethyl)biphenyl-3-yl)methoxy)methyl)-4-(4-cyanophenyl)piperidine-1-carboxylate. ¹H-NMR (CDCl₃, 500 MHz) δ ppm 7.77 (m, 2H), 7.68 (s, 1H), 7.58-7.63 (m, 4H), 7.46 (m, 2H), 7.43 (s, 1H), 7.35 (s, 1H), 4.46 (s, 2H), 3.68 (m, 2H), 3.47 (s, 2H), 3.05 (m, 2H), 2.17 (m, 2H), 1.85-1.92 (m, 2H), 1.42 (s, 9H). Mass spec.: 576.16 (MH)⁺.

Intermediate 26

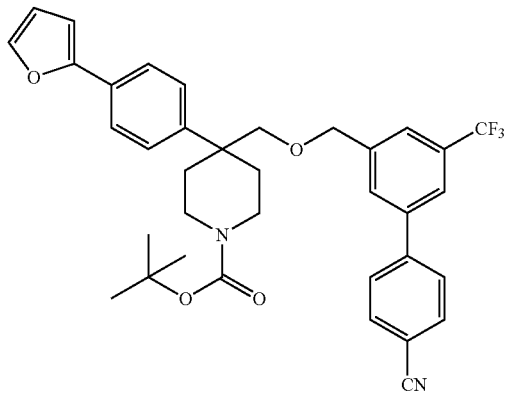

tert-Butyl 4-(((4'-cyano-5-(trifluoromethyl)biphenyl-3-yl)methoxy)methyl)-4-(4-(furan-2-yl)phenyl)piperidine-1-carboxylate. A solution of tert-butyl 4-(4-bromophenyl)-4-(((4'-cyano-5-(trifluoromethyl)biphenyl-3-yl)methoxy)methyl) piperidine-1-carboxylate (175 mg, 0.278 mmol), 2-(tributylstannyl)furan (109 mg, 0.306 mmol), and toluene (1.5 ml) in a conical reaction vial was purged with nitrogen for 10 minutes. Palladium tetrakistriphenylphosphine (321 mg, 0.278 mmol) was added. The vial was sealed and heated 120° C. overnight. The resulting mixture was cooled to room temperature and partitioned between ethyl acetate and brine. The organics were dried over sodium sulfate, filtered, and concentrated to a light amber oil. Silica gel column chromatography (5-40% ethyl acetate/hexanes) afforded the product as a colorless oil (130 mg, 72%). $^1$H-NMR (CDCl$_3$, 500 MHz) δ ppm 7.64 (s, 1H), 7.57-7.60 (m, 4H), 7.49 (m, 3H), 7.41 (s, 1H), 7.32-7.37 (m, 3H), 6.61 (m, 1H), 6.51 (m, 1H), 4.47 (s, 2H), 3.74 (br m, 2H), 3.46 (s, 2H), 3.04 (m, 2H), 2.22 (m, 2H), 1.83 (m, 2H), 1.42 (s, 9H). Mass spec.: 617.25 (MH)$^+$.

Intermediate 27

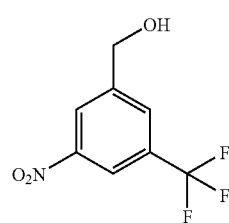

(3-Nitro-5-(trifluoromethyl)phenyl)methanol. 3-Nitro-5-(trifluoromethyl)benzoic acid (5.0 g, 21.2 mmol) was combined with tetrahydrofuran (43 mL) and cooled to 0° C. To this solution was added a 1 M borane tetrahydrofuran complex (42 mL, 42 mmol) cautiously over 15 min and the reaction mixture allowed to warm to room temperature overnight. The mixture was cooled to 0° C., treated with excess methanol and concentrated in vacuo to afford 4.0 g (85%) which was used without further purification. $^1$H-NMR (CDCl$_3$, 300 MHz) δ 8.39 (s, 1H), 8.35 (s, 1H), 7.94 (s, 1H), 4.87 (s, 2H).

Intermediate 28

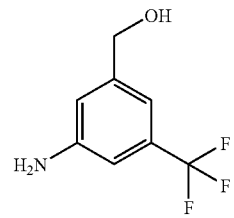

(3-Amino-5-(trifluoromethyl)phenyl)methanol. (3-Nitro-5-(trifluoromethyl)phenyl)methanol (2.6 g, 11.6 mmol) in methanol (30 mL) was flushed with nitrogen, and treated with palladium (10% on charcoal, 260 mg). The flask was flushed with hydrogen and allowed to stir under an atmosphere of hydrogen overnight. The reaction was flushed with nitrogen, filtered through celite, and concentrated. Column chromatography on silica gel (50% ethyl acetate/hexanes) afforded 1.9 g (85%). $^1$H-NMR (CDCl$_3$, 500 MHz) δ 6.95 (s, 1H), 6.80 (s, 1H), 6.79 (s, 1H), 4.61 (s, 2H). Mass spec.: 192.15 (MH)$^+$.

Intermediate 29

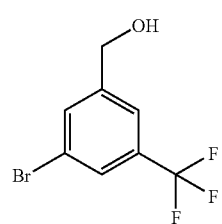

(3-Bromo-5-(trifluoromethyl)phenyl)methanol. (3-Amino-5-(trifluoromethyl)phenyl)methanol (1.6 g, 8.4 mmol) in dry acetonitrile (10 mL) was added dropwise to a solution of copper (II) bromide (2.24 g, 10.0 mmol) and tert-butyl nitrite (1.48 mL, 12.0 mmol) in acetonitrile (20 mL) at 65° C. After stirring for 30 min at 65° C., the reaction mixture was cooled to room temperature, poured into a 1 N hydrochloric acid solution, and extracted with ethyl acetate (2×). The organic layers were pooled together, washed with brine (2×), dried over sodium sulfate, and concentrated. Column chromatography on silica gel (20% ethyl acetate/hexanes) afforded 1.48 g (69%). $^1$H-NMR (CDCl$_3$, 500 MHz) δ 7.71 (s, 1H), 7.68 (s, 1H), 7.55 (s, 1H), 4.75 (s, 2H).

Intermediate 30

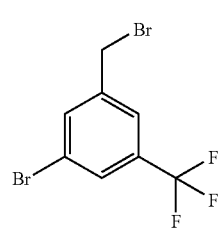

1-Bromo-3-(bromomethyl)-5-(trifluoromethyl)benzene. (3-Bromo-5-(trifluoromethyl)phenyl)methanol (1.6 g, 6.3 mmol) and triphenylphosphine (3.3 g, 12.6 mmol) were combined in tetrahydrofuran (30 mL) and cooled to 0° C. N-Bromosuccinimide (2.4 g, 13.2 mmol) was introduced in portions and the reaction allowed to warm to room temperature. After 16 h, the reaction mixture was diluted with ethyl acetate, washed with concentrated sodium bicarbonate (2×), brine (2×), dried over sodium sulfate, and concentrated. Column chromatography on silica gel (100% hexanes) gave 1.53 g (76%) as a light brown oil. ¹H-NMR (CDCl₃, 500 MHz) δ 7.73 (s, 1H), 7.70 (s, 1H), 7.58 (s, 1H), 4.44 (s, 2H).

Intermediate 31

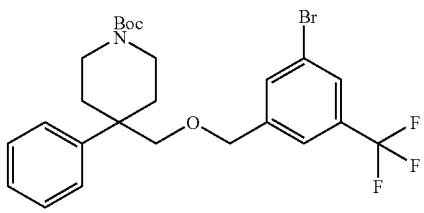

tert-Butyl 4-((3-bromo-5-(trifluoromethyl)benzyloxy)methyl)-4-phenylpiperidine-1-carboxylate. 1-Bromo-3-(bromomethyl)-5-(trifluoromethyl)benzene (1.0 g, 3.14 mmol) and tert-butyl 4-(hydroxymethyl)-4-phenylpiperidine-1-carboxylate (0.70 g, 2.4 mmol) were combined in dimethylformamide (8 mL) and cooled to 0° C. The reaction was treated with sodium hydride (115 mg, 4.8 mmol), stirred at 0° C. for 1 h, and at room temperature for 30 min. The reaction mixture was diluted with water and extracted with ethyl acetate (2×). The organic layers were pooled together, washed with brine (2×), dried over sodium sulfate, and concentrated. Column chromatography on silica gel (20% ethyl acetate/hexanes) gave 1.6 g (96%). ¹H-NMR (CDCl₃, 500 MHz) δ 7.61 (s, 1H), 7.39 (s, 1H), 7.34-7.37 (m, 4H), 7.25-7.28 (m, 2H), 4.35 (s, 2H), 3.75-3.77 (m, 2H), 3.41 (s, 2H), 3.01-3.06 (m, 2H), 2.19-2.22 (m, 2H), 1.83-1.89 (m, 2H), 1.44 (s, 9H). Mass spec.: 530.21 (MH)⁺.

Intermediate 32

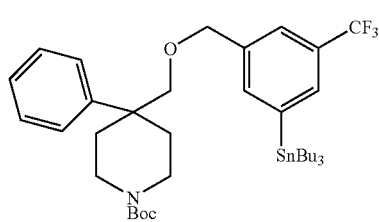

tert-Butyl 4-phenyl-4-((3-(tributylstannyl)-5-(trifluoromethyl)benzyloxy)methyl)piperidine-1-carboxylate. To a solution of tert-butyl 4-((3-bromo-5-(trifluoromethyl)benzyloxy)methyl)-4-phenylpiperidine-1-carboxylate (5.5 g, 10.4 mmol) in tetrahydrofuran (60 mL) at −78° C. was added n-butyllithium (1.6 M in hexane, 7.48 mL, 12.0 mmol) dropwise. The reaction was stirred at −78° C. for 20 min and treated with tributyltin chloride (3.25 mL, 12.0 mmol). The reaction was allowed to gradually warm to room temperature in the dewar over several hours. The reaction was poured into pentane, washed with water (2×), then brine, dried over magnesium sulfate, and concentrated. Column chromatography (5%→8% ethyl acetate/hexanes) gave 6.1 g (79%) as a colorless oil. ¹H-NMR (CDCl₃, 500 MHz) δ 7.56 (s, 1H), 7.44 (s, 1H), 7.37 (m, 5H), 7.24 (m, 1H), 4.38 (s, 2H), 3.74 (m, 2H), 3.43 (s, 2H), 3.06 (m, 2H), 2.20 (m, 2H), 1.90 (m, 2H), 1.54 (m, 6H), 1.44 (s, 9H), 1.34 (m, 6H), 1.09 (m, 6H), 0.90 (m, 9H); ¹³C NMR (126 MHz, CDCl₃) δ ppm 155.1143.6, 142.9, 138.4, 138.3, 131.7 (q, J=3.8 Hz), 130.0 (q, J=32 Hz), 128.5, 127.3, 126.5, 124.6 (q, J=273 Hz), 123.7 (q, J=3.8 Hz), 79.6, 79.3, 72.9, 41.7, 40.2 (br), 32.1, 29.1, 28.6, 27.3, 13.7, 9.8.

Intermediate 33

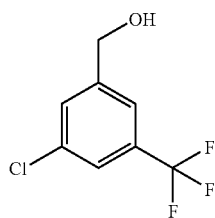

(3-Chloro-5-(trifluoromethyl)phenyl)methanol. (3-Amino-5-(trifluoromethyl)phenyl)methanol (1.0 g, 5.23 mmol) in dry acetonitrile (6 mL) was added dropwise to a solution of copper (II) chloride (0.83 g, 6.2 mmol) and tert-butyl nitrite (0.9 mL, 7.5 mmol) in acetonitrile (6 mL) at 65° C. After 30 min at 65° C., the reaction mixture was cooled to room temperature, poured into a 1 N hydrochloric acid solution, and extracted with ethyl acetate (2×). The organic layers were pooled together, washed with brine (2×), dried over sodium sulfate, and concentrated. Column chromatography on silica gel (30% ethyl acetate/hexanes) afforded 0.8 g (73%). ¹H-NMR (CDCl₃, 500 MHz) δ 7.54 (s, 1H), 7.52 (s, 1H), 7.50 (s, 1H), 4.74 (s, 2H).

Intermediate 34

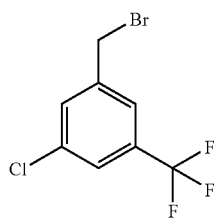

1-(Bromomethyl)-3-chloro-5-(trifluoromethyl)benzene. (3-Chloro-5-(trifluoromethyl)phenyl)methanol (0.78 g, 3.7 mmol) and triphenylphosphine (1.94 g, 7.4 mmol) were combined in tetrahydrofuran (18 mL) and cooled to 0° C. N-Bromosuccinimide (1.4 g, 7.8 mmol) was introduced in portions and the reaction allowed to warm to room temperature. After 16 h, the reaction mixture was diluted with ethyl acetate, washed with concentrated sodium bicarbonate (2×), brine (2×), dried over sodium sulfate, and concentrated. Column chromatography on silica gel (10% ethyl acetate/hexanes) gave 0.94 g (92%). ¹H-NMR (CDCl₃, 300 MHz) δ 7.55 (s, 1H), 7.52 (s, 1H), 7.51 (s, 1H), 4.42 (s, 2H).

Intermediate 35

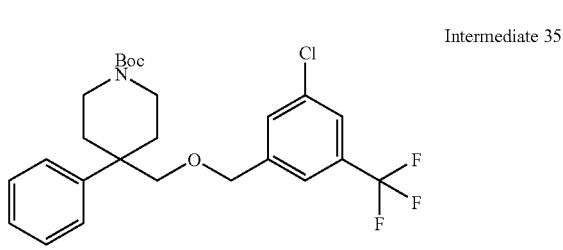 [SMILES: CC(C)(C)OC(=O)N1CCC(COCc2cc(Cl)cc(C(F)(F)F)c2)(c2ccccc2)CC1]

tert-Butyl 4-O-chloro-5-(trifluoromethyl)benzyloxy)methyl)-4-phenylpiperidine-1-carboxylate. 1-(Bromomethyl)-3-chloro-5-(trifluoromethyl)benzene (0.94 g, 3.4 mmol) and tert-butyl 4-(hydroxymethyl)-4-phenylpiperidine-1-carboxylate (1.0 g, 3.4 mmol) were combined in dimethylformamide (8 mL) and cooled to 0° C. The reaction was treated with sodium hydride (95 mg, 3.7 mmol), stirred at 0° C. for 1 h, and at room temperature overnight. The reaction mixture was diluted with water and extracted with ethyl acetate (2×). The organic layers were pooled together, washed with brine (2×), dried over sodium sulfate, and concentrated. Column chromatography on silica gel (20% ethyl acetate/hexanes) gave 0.78 g (52%). LC/MS (HPLC method 3): $t_R$=3.65 min, 484.20 (MH)$^+$.

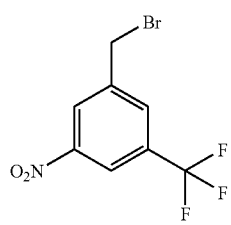

Intermediate 36

1-(Bromomethyl)-3-nitro-5-(trifluoromethyl)benzene. (3-Nitro-5-(trifluoromethyl)phenyl)methanol (0.5 g, 2.26 mmol) and triphenylphosphine (1.19 g, 4.5 mmol) were combined in tetrahydrofuran (15 mL) and cooled to 0° C. N-Bromosuccinimide (0.8 g, 4.8 mmol) was introduced in portions and the reaction allowed to warm to room temperature. After 16 h, the reaction mixture was diluted with ethyl acetate, washed with concentrated sodium bicarbonate (2×), brine (2×), dried over sodium sulfate, and concentrated. Column chromatography on silica gel (10% ethyl acetate/hexanes) gave 0.58 g (91%). $^1$H-NMR (CDCl$_3$, 500 MHz) δ 8.42 (s, 1H), 8.39 (s, 1H), 7.97 (s, 1H), 4.90 (s, 2H).

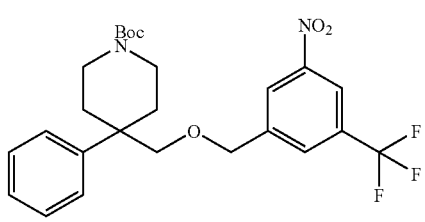

Intermediate 37 tert-Butyl 4-O-nitro-5-(trifluoromethyl)benzyloxy)methyl)-4-phenylpiperidine-1-carboxylate. 1-(Bromomethyl)-3-nitro-5-(trifluoromethyl)benzene (150 mg, 0.53 mmol) and tert-butyl 4-(hydroxymethyl)-4-phenylpiperidine-1-carboxylate (142 mg, 0.49 mmol) were combined in dimethylformamide (3 mL) and cooled to 0° C. The reaction was treated with sodium hydride (14 mg, 0.53 mmol), stirred at 0° C. for 1 h, and at room temperature overnight. The reaction mixture was diluted with water and extracted with ethyl acetate (2×). The organic layers were pooled together, washed with brine (2×), dried over sodium sulfate, and concentrated. Column chromatography on silica gel (10% ethyl acetate/hexanes) gave 138 mg (53%). LC/MS (HPLC method 3): $t_R$=3.42 min, 495.18 (MH)$^+$.

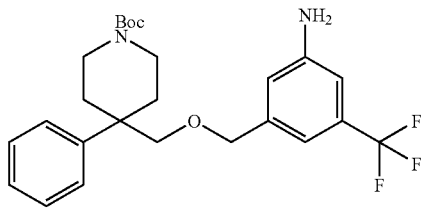

Intermediate 38 tert-Butyl 4-((3-amino-5-(trifluoromethyl)benzyloxy)methyl)-4-phenylpiperidine-1-carboxylate. tert-Butyl 4-((3-nitro-5-(trifluoromethyl)benzyloxy)methyl)-4-phenylpiperidine-1-carboxylate (118 mg, 0.24 mmol) in methanol (2.5 mL) was flushed with nitrogen, and treated with palladium (10% on charcoal, 12 mg). The flask was flushed with hydrogen and allowed to stir under an atmosphere of hydrogen overnight. The reaction was flushed with nitrogen, filtered through celite, and concentrated to afford 90 mg (80%). LC/MS (HPLC method 3): $t_R$=3.10 min, 465.22 (MH)$^+$.

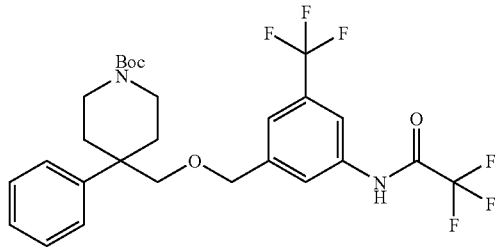

Intermediate 39 tert-Butyl 4-phenyl-4-((3-(2,2,2-trifluoroacetamido)-5-(trifluoromethyl)benzyloxy)methyl)piperidine-1-carboxylate. tert-Butyl 4-((3-amino-5-(trifluoromethyl)benzyloxy)methyl)-4-phenylpiperidine-1-carboxylate (90 mg, 0.19 mmol) and triethylamine (52.0 µL, 0.37 mmol) were combined in methylene chloride (2 mL) and cooled to 0° C. The reaction was treated with trifluoroacetic anhydride (33.0 µL, 0.23 mmol), stirred at 0° C. for 2 h, and at room temperature overnight. The reaction was cooled to 0° C., quenched by addition of a few drops of methanol and concentrated. Flash chromatography on silica gel (40% ethyl acetate/hexanes) gave 106 mg (98%). LC/MS (HPLC method 3): $t_R$=3.38 min, 561.18 (MH)$^+$.

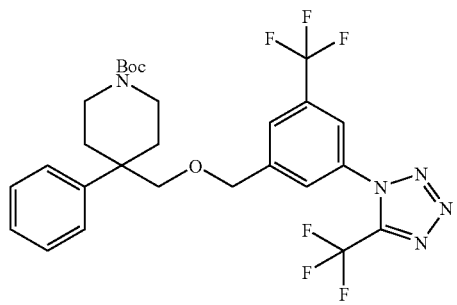

Intermediate 40 tert-Butyl 4-phenyl-4-((3-(trifluoromethyl)-5-(5-(trifluoromethyl)-1H-tetrazol-1-yl)benzyloxy)methyl)piperidine-1- carboxylate. tert-Butyl 4-phenyl-4-((3-(2,2,2-trifluoroacetamido)-5-(trifluoromethyl)benzyloxy)methyl)piperidine-1-carboxylate (100 mg, 0.18 mmol) in carbon tetrachloride (3 mL) was treated with triphenylphosphine (117 mg, 0.45 mmol) and heated at reflux overnight. After cooling to room temperature, the reaction was concentrated and the residue dissolved in dimethylformamide (2 mL). The mixture was treated with sodium azide (25 mg, 0.37 mmol) and stirred at room temperature for 5 h. The solvents were evaporated and the crude product purified by flash chromatography on silica gel (30% ethyl acetate/hexanes) to afford 46 mg (45%). $^1$H-NMR (CDCl$_3$, 500 MHz) δ 7.61 (s, 1H), 7.59 (s, 1H), 7.30-7.32 (m, 2H), 7.23-7.26 (m, 2H), 7.12 (s, 1H), 7.05-7.08 (m, 1H), 4.51 (s, 2H), 3.74 (m, 2H), 3.46 (s, 2H), 2.99-3.03 (m, 2H), 2.21-2.24 (m, 2H), 1.79-1.84 (m, 2H), 1.42 (s, 9H). Mass spec.: 608.16 (MNa)$^+$.

Intermediate 41

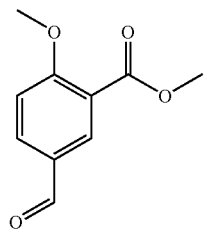

Methyl 5-formyl-2-methoxybenzoate. 5-Formyl salicylic acid (2.0 g, 12.0 mmol), methyl iodide (1.5 mL, 25 mmol) and potassium carbonate (3.06 g, 22.2 mmol) were combined in dimethylformamide (15 mL). After stirring at room temperature for 16 h, the solvent was removed in vacuo and the crude product dissolved in ethyl acetate, washed with water (2×), brine (2×), dried over sodium sulfate, concentrated, and purified by column chromatography to afford 1.85 g (79%). $^1$H-NMR (CDCl$_3$, 500 MHz) δ 9.91 (s, 1H), 8.31 (d, J=2.1 Hz, 1H), 8.02 (dd, J=8.5, 2.5 Hz, 1H), 7.11 (d, J=8.6 Hz, 1H), 3.99 (s, 3H), 3.91 (s, 3H). Mass spec.: 195.05 (MH)$^+$.

Intermediate 42

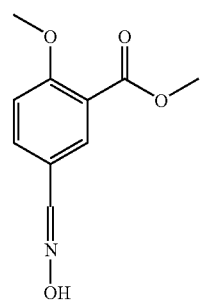

Methyl 5-((hydroxyimino)methyl)-2-methoxybenzoate. Methyl 5-formyl-2-methoxybenzoate 1.0 g, 5.15 mmol), hydroxylamine hydrochloride (1.8 g, 25.75 mmol) and sodium acetate (2.1 g, 25.75 mmol) were combined in a ethanol/water mixture (1:1, 40 mL) and stirred at 50° C. for 1 h. After cooling to room temperature, the reaction mixture was poured in to ice water and extracted with methylene chloride (2×). The combined organic layers were washed with brine (2×), dried over sodium sulfate and concentrated to afford 1.04 g (97%) which was used without purification. LC/MS (HPLC method 3): t$_R$=1.63 min, 210.06 (MH)$^+$.

Intermediate 43

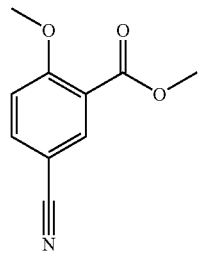

Methyl 5-cyano-2-methoxybenzoate. Methyl 5-((hydroxyimino)methyl)-2-methoxybenzoate (1.04 g, 4.94 mmol) was dissolved in methylene chloride (25 mL) and cooled to 0° C. The reaction was treated with thionyl chloride (0.59 mL, 8.1 mmol) and stirred at 0° C. for 2 h. After warming to room temperature, the reaction was diluted with methylene chloride, washed with saturated sodium bicarbonate (2×), brine (2×), dried over sodium sulfate, and concentrated to afford 0.87 g (92%) which was used without further purification. $^1$H-NMR (CDCl$_3$, 500 MHz) δ 8.09 (d, J=2.1 Hz, 1H), 7.75 (dd, J=8.9, 2.1 Hz, 1H), 7.05 (d, J=8.9 Hz, 1H), 3.96 (s, 3H), 3.90 (s, 3H). Mass spec.: 192.02 (MH)$^+$.

Intermediate 44

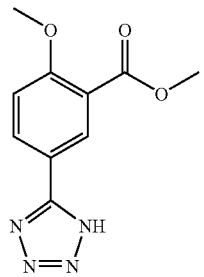

Methyl 2-methoxy-5-(1H-tetrazol-5-yl)benzoate. A stirred solution of methyl 5-cyano-2-methoxybenzoate (0.87 g, 4.5 mmol) in toluene (4 mL) was treated with azidotrimethyltin (1.85 g, 9.0 mmol) and heated at reflux overnight. After cooling to room temperature, the solvents were evaporated. The crude product was dissolved in ethyl acetate, washed with brine (2×), dried over sodium sulfate, and concentrated. Column chromatography on silica gel (5% methanol/methylene chloride) afforded 0.78 g (75%). LC/MS (HPLC method 3): t$_R$=1.66 min, 235.05 (MH)$^+$.

Intermediate 45

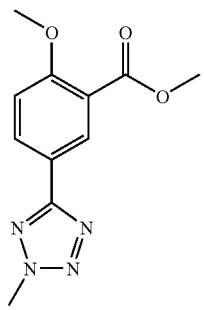

Methyl 2-methoxy-5-(2-methyl-2H-tetrazol-5-yl)benzoate. Methyl 2-methoxy-5-(1H-tetrazol-5-yl)benzoate (0.78 g, 3.33 mmol) methyl iodide (0.21 mL, 3.33 mmol) and potassium carbonate (0.46 g, 3.33 mmol) were combined in acetone (8 mL) and heated at reflux overnight. After cooling to room temperature, the mixture was filtered and concentrated. Flash chromatography on silica gel afforded 170 mg (21%). LC/MS (HPLC method 3): $t_R$=2.01 min, 249.09 (MH)$^+$ Intermediate 46

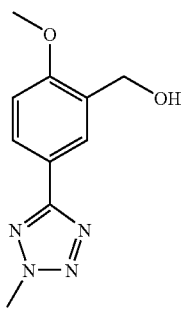

(2-Methoxy-5-(2-methyl-2H-tetrazol-5-yl)phenyl)methanol. Methyl 2-methoxy-5-(2-methyl-2H-tetrazol-5-yl)benzoate (130 mg, 0.52 mmol) was dissolved in methylene chloride (2 mL), cooled to −78° C. and treated with diisobutylaluminum hydride (1 M in methylene chloride, 1.5 mL, 1.5 mmol). After stirring at −78° C. for 1 h the reaction was quenched by a few drops of methanol (until no bubbling was observed) followed by addition of excess saturated sodium potassium tartarate (2 mL). The reaction was stirred at room temperature overnight, the layers were separated and the organic layer washed with brine (2×), dried over sodium sulfate and concentrated to afford 100 mg (86%). LC/MS (HPLC method 3): $t_R$=1.68 min, 221.11 (MH)$^+$ Intermediate 47

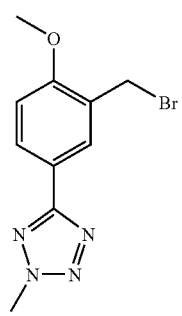

5-(3-(Bromomethyl)-4-methoxyphenyl)-2-methyl-2H-tetrazole. (2-Methoxy-5-(2-methyl-2H-tetrazol-5-yl)phenyl)methanol (100 mg, 0.45 mmol) and triphenylphosphine (238 mg, 0.9 mmol) were combined in methylene chloride (3 mL) and cooled to 0° C. N-Bromosuccinimide (170 mg, 0.95 mmol) was introduced in portions and the reaction allowed to warm to room temperature. After 16 h, the reaction mixture was diluted with methylene chloride and washed with concentrated sodium bicarbonate (2×), brine (2×), dried over sodium sulfate, and concentrated. Column chromatography on silica gel (30% ethyl acetate/hexanes) gave 80 mg (63%) of the desired material. LC/MS (HPLC method 3): $t_R$=2.69 min, 285.02 (MH)$^+$.

Intermediate 48

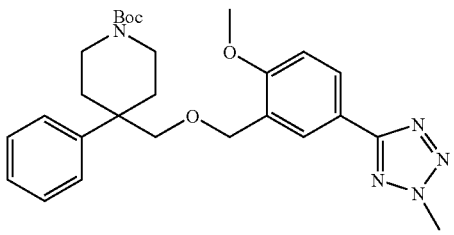

tert-Butyl 4-((2-methoxy-5-(2-methyl-2H-tetrazol-5-yl)benzyloxy)methyl)-4-phenylpiperidine-1-carboxylate. 5-(3-(Bromomethyl)-4-methoxyphenyl)-2-methyl-2H-tetrazole (35.0 mg, 0.12 mmol) and tert-butyl 4-(hydroxymethyl)-4-phenylpiperidine-1-carboxylate (40.0 mg, 0.14 mmol) were combined in dimethylformamide (1 mL) and cooled to 0° C. The reaction was treated with sodium hydride (3.2 mg, 0.14 mmol), stirred at 0° C. for 1 h, and at room temperature overnight. The solvents were removed in vacuo and the crude product purified by column chromatography on silica gel (30% ethyl acetate/hexanes) to afford 30 mg (50%). LC/MS (HPLC method 3): $t_R$=3.29 min, 494.25 (MH)$^+$.

Intermediate 49

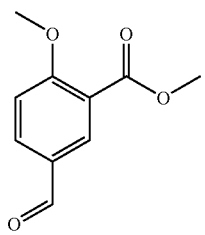

Methyl 5-formyl-2-methoxybenzoate. 5-Formyl salicylic acid (2.0 g, 12.0 mmol), methyl iodide (1.5 mL, 25 mmol) and potassium carbonate (3.06 g, 22.2 mmol) were combined in dimethylformamide (15 mL). After stirring at room temperature for 16 h, the solvent was removed in vacuo and the crude product dissolved in ethyl acetate, washed with water (2×), brine (2×), dried over sodium sulfate, concentrated, and purified by column chromatography to afford 1.85 g (79%). $^1$H-NMR (CDCl$_3$, 500 MHz) δ 9.91 (s, 1H), 8.31 (d, J=2.1 Hz, 1H), 8.02 (dd, J=8.5, 2.5 Hz, 1H), 7.11 (d, J=8.6 Hz, 1H), 3.99 (s, 3H), 3.91 (s, 3H). Mass spec.: 195.05 (MH)$^+$.

Intermediate 50

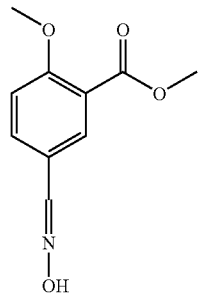

Methyl 5-((hydroxyimino)methyl)-2-methoxybenzoate. Methyl 5-formyl-2-methoxybenzoate 1.0 g, 5.15 mmol), hydroxylamine hydrochloride (1.8 g, 25.75 mmol) and sodium acetate (2.1 g, 25.75 mmol) were combined in a ethanol/water mixture (1:1, 40 mL) and stirred at 50° C. for 1 h. After cooling to room temperature, the reaction mixture was poured in to ice water and extracted with methylene chloride (2×). The combined organic layers were washed with brine (2×), dried over sodium sulfate and concentrated to afford 1.04 g (97%) which was used without purification. LC/MS (HPLC method 3): $t_R$=1.63 min, 210.06 (MH)$^+$.

Intermediate 51

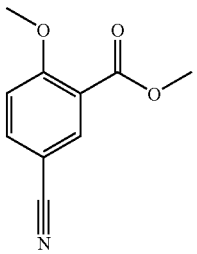

Methyl 5-cyano-2-methoxybenzoate. Methyl 5-((hydroxyimino)methyl)-2-methoxybenzoate (1.04 g, 4.94 mmol) was dissolved in methylene chloride (25 mL) and cooled to 0° C. The reaction was treated with thionyl chloride (0.59 mL, 8.1 mmol) and stirred at 0° C. for 2 h. After warming to room temperature, the reaction was diluted with methylene chloride, washed with saturated sodium bicarbonate (2×), brine (2×), dried over sodium sulfate, and concentrated to afford 0.87 g (92%) which was used without further purification. $^1$H-NMR (CDCl$_3$, 500 MHz) δ 8.09 (d, J=2.1 Hz, 1H), 7.75 (dd, J=8.9, 2.1 Hz, 1H), 7.05 (d, J=8.9 Hz, 1H), 3.96 (s, 3H), 3.90 (s, 3H). Mass spec.: 192.02 (MH)$^+$.

Intermediate 52

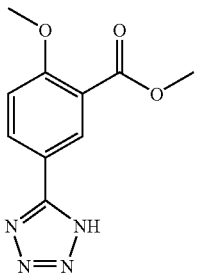

Methyl 2-methoxy-5-(1H-tetrazol-5-yl)benzoate. A stirred solution of methyl 5-cyano-2-methoxybenzoate (0.87 g, 4.5 mmol) in toluene (4 mL) was treated with azidotrimethyltin (1.85 g, 9.0 mmol) and heated at reflux overnight. After cooling to room temperature, the solvents were evaporated. The crude product was dissolved in ethyl acetate, washed with brine (2×), dried over sodium sulfate, and concentrated. Column chromatography on silica gel (5% methanol/methylene chloride) afforded 0.78 g (75%). LC/MS (HPLC method 3): $t_R$=1.66 min, 235.05 (MH)$^+$.

Intermediate 53

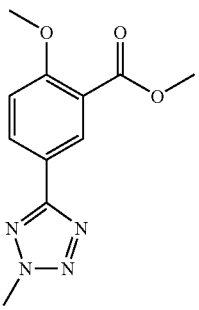

Methyl 2-methoxy-5-(2-methyl-2H-tetrazol-5-yl)benzoate. Methyl 2-methoxy-5-(1H-tetrazol-5-yl)benzoate (0.78 g, 3.33 mmol) methyl iodide (0.21 mL, 3.33 mmol) and potassium carbonate (0.46 g, 3.33 mmol) were combined in acetone (8 mL) and heated at reflux overnight. After cooling to room temperature, the mixture was filtered and concentrated. Flash chromatography on silica gel afforded 170 mg (21%). LC/MS (HPLC method 3): $t_R$=2.01 min, 249.09 (MH)$^+$ Intermediate 54

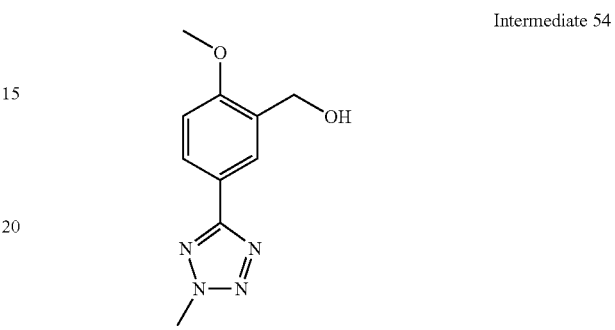

(2-Methoxy-5-(2-methyl-2H-tetrazol-5-yl)phenyl)methanol. Methyl 2-methoxy-5-(2-methyl-2H-tetrazol-5-yl)benzoate (130 mg, 0.52 mmol) was dissolved in methylene chloride (2 mL), cooled to −78° C. and treated with diisobutylaluminum hydride (1 M in methylene chloride, 1.5 mL, 1.5 mmol). After stirring at −78° C. for 1 h the reaction was quenched by a few drops of methanol (until no bubbling was observed) followed by addition of excess saturated sodium potassium tartarate (2 mL). The reaction was stirred at room temperature overnight, the layers were separated and the organic layer washed with brine (2×), dried over sodium sulfate and concentrated to afford 100 mg (86%). LC/MS (HPLC method 3): $t_R$=1.68 min, 221.11 (MH)$^+$ Intermediate 55

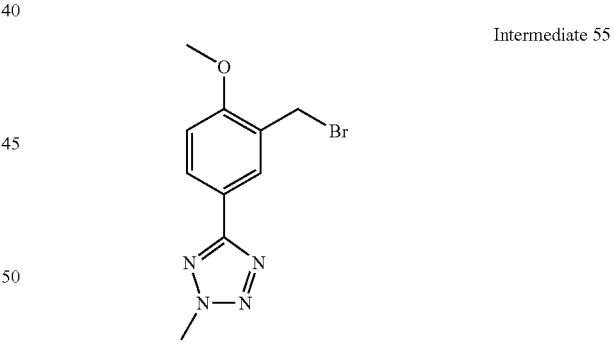

5-(3-(Bromomethyl)-4-methoxyphenyl)-2-methyl-2H-tetrazole. (2-Methoxy-5-(2-methyl-2H-tetrazol-5-yl)phenyl)methanol (100 mg, 0.45 mmol) and triphenylphosphine (238 mg, 0.9 mmol) were combined in methylene chloride (3 mL) and cooled to 0° C. N-Bromosuccinimide (170 mg, 0.95 mmol) was introduced in portions and the reaction allowed to warm to room temperature. After 16 h, the reaction mixture was diluted with methylene chloride and washed with concentrated sodium bicarbonate (2×), brine (2×), dried over sodium sulfate, and concentrated. Column chromatography on silica gel (30% ethyl acetate/hexanes) gave 80 mg (63%) of the desired material. LC/MS (HPLC method 3): $t_R$=2.69 min, 285.02 (MH)$^+$.

Intermediate 56

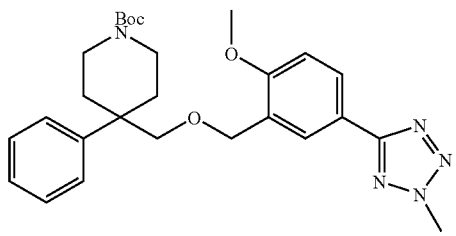

tert-Butyl 4-((2-methoxy-5-(2-methyl-2H-tetrazol-5-yl) benzyloxy)methyl)-4-phenylpiperidine-1-carboxylate. 5-(3-(Bromomethyl)-4-methoxyphenyl)-2-methyl-2H-tetrazole (35.0 mg, 0.12 mmol) and tert-butyl 4-(hydroxymethyl)-4-phenylpiperidine-1-carboxylate (40.0 mg, 0.14 mmol) were combined in dimethylformamide (1 mL) and cooled to 0° C. The reaction was treated with sodium hydride (3.2 mg, 0.14 mmol), stirred at 0° C. for 1 h, and at room temperature overnight. The solvents were removed in vacuo and the crude product purified by column chromatography on silica gel (30% ethyl acetate/hexanes) to afford 30 mg (50%). LC/MS (HPLC method 3): $t_R$=3.29 min, 494.25 (MH)$^+$.

Intermediate 57

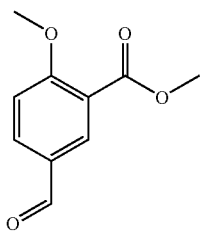

Methyl 5-formyl-2-methoxybenzoate. 5-Formyl salicylic acid (2.0 g, 12.0 mmol), methyl iodide (1.5 mL, 25 mmol) and potassium carbonate (3.06 g, 22.2 mmol) were combined in dimethylformamide (15 mL). After stirring at room temperature for 16 h, the solvent was removed in vacuo and the crude product dissolved in ethyl acetate, washed with water (2×), brine (2×), dried over sodium sulfate, concentrated, and purified by column chromatography to afford 1.85 g (79%). $^1$H-NMR (CDCl$_3$, 500 MHz) δ 9.91 (s, 1H), 8.31 (d, J=2.1 Hz, 1H), 8.02 (dd, J=8.5, 2.5 Hz, 1H), 7.11 (d, J=8.6 Hz, 1H), 3.99 (s, 3H), 3.91 (s, 3H). Mass spec.: 195.05 (MH)$^+$.

Intermediate 58

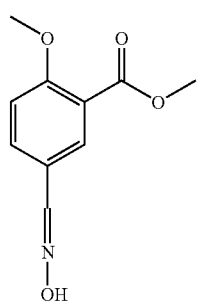

Methyl 5-((hydroxyimino)methyl)-2-methoxybenzoate. Methyl 5-formyl-2-methoxybenzoate 1.0 g, 5.15 mmol), hydroxylamine hydrochloride (1.8 g, 25.75 mmol) and sodium acetate (2.1 g, 25.75 mmol) were combined in a ethanol/water mixture (1:1, 40 mL) and stirred at 50° C. for 1 h. After cooling to room temperature, the reaction mixture was poured in to ice water and extracted with methylene chloride (2×). The combined organic layers were washed with brine (2×), dried over sodium sulfate and concentrated to afford 1.04 g (97%) which was used without purification. LC/MS (HPLC method 3): $t_R$=1.63 min, 210.06 (MH)$^+$.

Intermediate 59

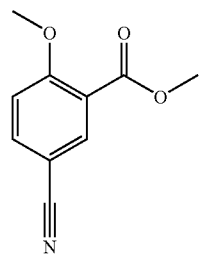

Methyl 5-cyano-2-methoxybenzoate. Methyl 5-((hydroxyimino)methyl)-2-methoxybenzoate (1.04 g, 4.94 mmol) was dissolved in methylene chloride (25 mL) and cooled to 0° C. The reaction was treated with thionyl chloride (0.59 mL, 8.1 mmol) and stirred at 0° C. for 2 h. After warming to room temperature, the reaction was diluted with methylene chloride, washed with saturated sodium bicarbonate (2×), brine (2×), dried over sodium sulfate, and concentrated to afford 0.87 g (92%) which was used without further purification. $^1$H-NMR (CDCl$_3$, 500 MHz) δ 8.09 (d, J=2.1 Hz, 1H), 7.75 (dd, J=8.9, 2.1 Hz, 1H), 7.05 (d, J=8.9 Hz, 1H), 3.96 (s, 3H), 3.90 (s, 3H). Mass spec.: 192.02 (MH)$^+$.

Intermediate 60

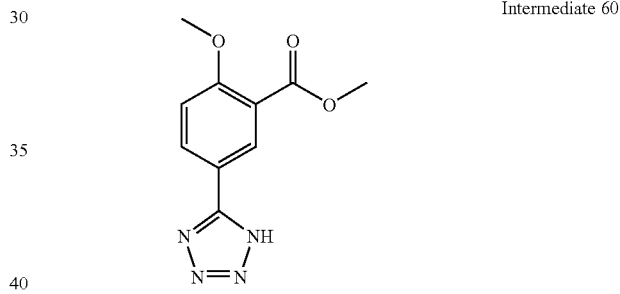

Methyl 2-methoxy-5-(1H-tetrazol-5-yl)benzoate. A stirred solution of methyl 5-cyano-2-methoxybenzoate (0.87 g, 4.5 mmol) in toluene (4 mL) was treated with azidotrimethyltin (1.85 g, 9.0 mmol) and heated at reflux overnight. After cooling to room temperature, the solvents were evaporated. The crude product was dissolved in ethyl acetate, washed with brine (2×), dried over sodium sulfate, and concentrated. Column chromatography on silica gel (5% methanol/methylene chloride) afforded 0.78 g (75%). LC/MS (HPLC method 3): $t_R$=1.66 min, 235.05 (MH)$^+$.

Intermediate 61

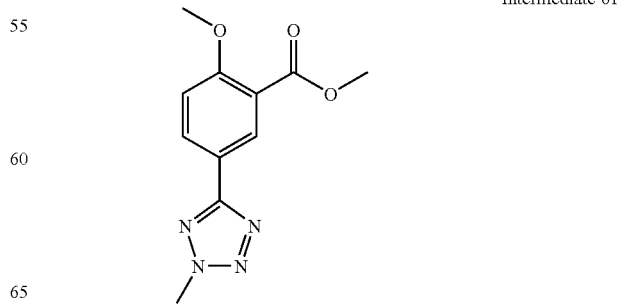

Methyl 2-methoxy-5-(2-methyl-2H-tetrazol-5-yl)benzoate. Methyl 2-methoxy-5-(1H-tetrazol-5-yl)benzoate (0.78 g, 3.33 mmol) methyl iodide (0.21 mL, 3.33 mmol) and potassium carbonate (0.46 g, 3.33 mmol) were combined in acetone (8 mL) and heated at reflux overnight. After cooling to room temperature, the mixture was filtered and concentrated. Flash chromatography on silica gel afforded 170 mg (21%). LC/MS (HPLC method 3): $t_R$=2.01 min, 249.09 (MH)$^+$ Intermediate 62

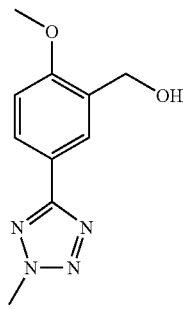

(2-Methoxy-5-(2-methyl-2H-tetrazol-5-yl)phenyl)methanol. Methyl 2-methoxy-5-(2-methyl-2H-tetrazol-5-yl)benzoate (130 mg, 0.52 mmol) was dissolved in methylene chloride (2 mL), cooled to −78° C. and treated with diisobutylaluminum hydride (1 M in methylene chloride, 1.5 mL, 1.5 mmol). After stirring at −78° C. for 1 h the reaction was quenched by a few drops of methanol (until no bubbling was observed) followed by addition of excess saturated sodium potassium tartarate (2 mL). The reaction was stirred at room temperature overnight, the layers were separated and the organic layer washed with brine (2×), dried over sodium sulfate and concentrated to afford 100 mg (86%). LC/MS (HPLC method 3): $t_R$=1.68 min, 221.11 (MH)$^+$ Intermediate 63

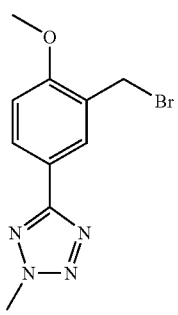

5-(3-(Bromomethyl)-4-methoxyphenyl)-2-methyl-2H-tetrazole. (2-Methoxy-5-(2-methyl-2H-tetrazol-5-yl)phenyl)methanol (100 mg, 0.45 mmol) and triphenylphosphine (238 mg, 0.9 mmol) were combined in methylene chloride (3 mL) and cooled to 0° C. N-Bromosuccinimide (170 mg, 0.95 mmol) was introduced in portions and the reaction allowed to warm to room temperature. After 16 h, the reaction mixture was diluted with methylene chloride and washed with concentrated sodium bicarbonate (2×), brine (2×), dried over sodium sulfate, and concentrated. Column chromatography on silica gel (30% ethyl acetate/hexanes) gave 80 mg (63%) of the desired material. LC/MS (HPLC method 3): $t_R$=2.69 min, 285.02 (MH)$^+$.

Intermediate 64

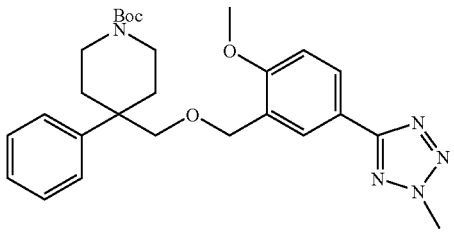

tert-Butyl 4-((2-methoxy-5-(2-methyl-2H-tetrazol-5-yl)benzyloxy)methyl)-4-phenylpiperidine-1-carboxylate. 5-(3-(Bromomethyl)-4-methoxyphenyl)-2-methyl-2H-tetrazole (35.0 mg, 0.12 mmol) and tert-butyl 4-(hydroxymethyl)-4-phenylpiperidine-1-carboxylate (40.0 mg, 0.14 mmol) were combined in dimethylformamide (1 mL) and cooled to 0° C. The reaction was treated with sodium hydride (3.2 mg, 0.14 mmol), stirred at 0° C. for 1 h, and at room temperature overnight. The solvents were removed in vacuo and the crude product purified by column chromatography on silica gel (30% ethyl acetate/hexanes) to afford 30 mg (50%). LC/MS (HPLC method 3): $t_R$=3.29 min, 494.25 (MH)$^+$.

Intermediate 65

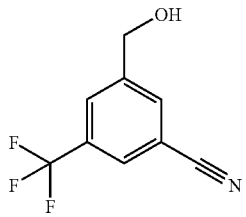

3-(Hydroxymethyl)-5-(trifluoromethyl)benzonitrile. (3-Bromo-5-(trifluoromethyl)phenyl)methanol (1.4 g, 5.5 mmol), tetrakis(triphenylphosphine) palladium(0) (0.64, 0.55 mmol) and zinc cyanide (388 mg, 3.31 mmol) were combined in dimethylformamide (6 mL). The reaction mixture degassed repeatedly using the freeze-thaw method. After warming to room temperature, the reaction was heated at 90° C. for 1 h, cooled to room temperature and concentrated. The crude product was dissolved in ethyl acetate, washed with water (2×), 1 N hydrochloric acid (2×), brine (2×), dried over sodium sulfate, and concentrated. Flash chromatography on silica gel gave 0.37 g (33%). LC/MS (HPLC method 3): $t_R$=2.06 min, 202.02 (MH)$^+$.

Intermediate 66

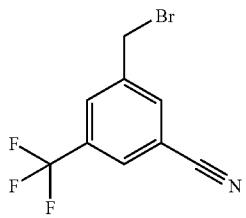

3-(Bromomethyl)-5-(trifluoromethyl)benzonitrile. 3-(Hydroxymethyl)-5-(trifluoromethyl)benzonitrile (0.33 mg, 1.64 mmol) and triphenylphosphine (0.86 g, 3.28 mmol) were combined in methylene chloride (6 mL) and cooled to 0° C. N-Bromosuccinimide (0.61 mg, 3.43 mmol) was introduced in portions and the reaction allowed to warm to room temperature. After 16 h, the reaction mixture was diluted with methylene chloride, washed with concentrated sodium bicarbonate (2×), brine (2×), dried over sodium sulfate, and concentrated. Column chromatography on silica gel (20% ethyl acetate/hexanes) gave 0.36 g (83%). $^1$H-NMR (CDCl$_3$, 500 MHz) δ 7.97 (s, 2H), 7.84 (s, 1H), 4.50 (s, 2H).

Intermediate 67

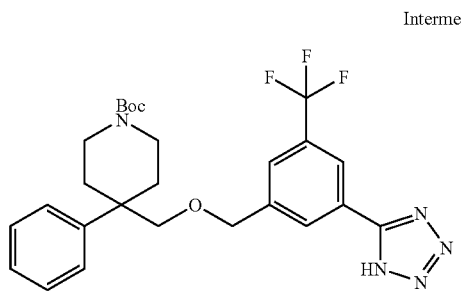

tert-Butyl 4-((3-(1H-tetrazol-5-yl)-5-(trifluoromethyl) benzyloxy)methyl)-4-phenylpiperidine-1-carboxylate. 3-(Bromomethyl)-5-(trifluoromethyl)benzonitrile (0.35 g, 1.32 mmol) and tert-butyl 4-(hydroxymethyl)-4-phenylpiperidine-1-carboxylate (0.35 g, 1.2 mmol) were combined in tetrahydrofuran (4 mL) and cooled to 0° C. The reaction was treated with sodium hydride (33.2 mg, 1.32 mmol), stirred at 0° C. for 1 h, and at room temperature overnight. The reaction mixture was diluted with water and extracted with ethyl acetate (2×). The organic layers were pooled together, washed with brine (2×), dried over sodium sulfate, and concentrated to afford a crude product which was dissolved in toluene (2.0), treated with azidotrimethylin (104 mg, 0.5 mmol) and heated at reflux overnight. After cooling to room temperature, the solvents were evaporated. The crude mixture was dissolved in methylene chloride, washed with water (2×), brine (2×), dried over sodium sulfate and concentrated. Flash chromatography on silica gel afforded 102 mg (12%, 2 steps). LC/MS (HPLC method 3): $t_R$=3.25 min, 518.29 (MH)$^+$.

Intermediates 68 and 69

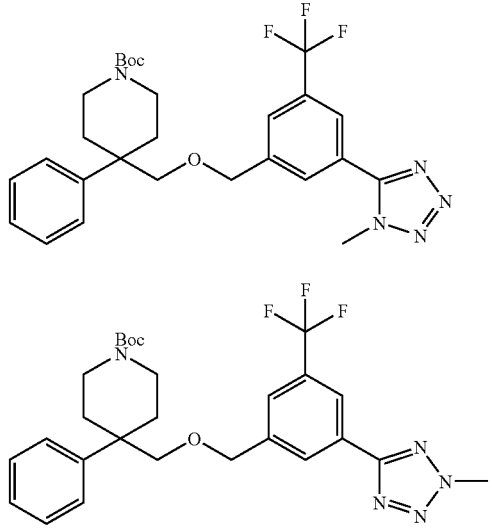

tert-Butyl 443-(1-methyl-1H-tetrazol-5-yl)-5-(trifluoromethyl)benzyloxy)methyl)-4-phenylpiperidine-1-carboxylate and tert-Butyl 4-((3-(2-methyl-2H-tetrazol-5-yl)-5-(trifluoromethyl)benzyloxy)methyl)-4-phenylpiperidine-1-carboxylate. tert-Butyl 4-((3-(1H-tetrazol-5-yl)-5-(trifluoromethyl)benzyloxy)methyl)-4-phenylpiperidine-1-carboxylate (80 mg, 0.15 mmol) methyl iodide (10.0 μL, 0.15 mmol) and potassium carbonate (21.0 mg, 0.15 mmol) were combined in acetone (1.5 mL) and heated at reflux overnight. After cooling to room temperature, the mixture was filtered and concentrated. Flash chromatography on silica gel (20% ethyl acetate/hexanes) afforded tert-Butyl 4-((3-(1-methyl-1H-tetrazol-5-yl)-5-(trifluoromethyl)benzyloxy)methyl)-4-phenylpiperidine-1-carboxylate (7.0 mg, 9%) and tert-Butyl 443-(2-methyl-2H-tetrazol-5-yl)-5-(trifluoromethyl)benzyloxy)methyl)-4-phenylpiperidine-1-carboxylate (48 mg, 60%). Retention time: 4.75 min and 5.20 min. (Phenomenex C18 4.6×50 mm, 10% MeOH/90% H$_2$O/0.1% TFA→90% MeOH/10% H$_2$O/0.1% TFA, Gradient time=6 min., Flow rate=4 mL/min.): Mass spec.: 532.31 (MH)$^+$ and 532.31 (MH)$^+$ respectively.

Intermediate 70

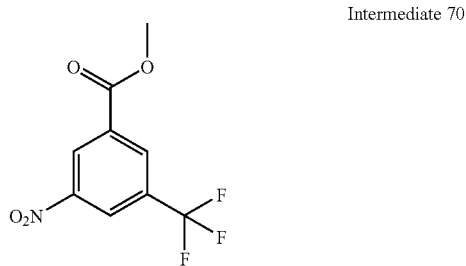 [SMILES: COC(=O)c1cc([N+](=O)[O-])cc(C(F)(F)F)c1]

Methyl 3-nitro-5-(trifluoromethyl)benzoate. 3-Nitro-5-(trifluoromethyl)benzoic acid (25.0 g, 106.3 mmol) was dissolved in methanol (60 mL) which was bubbled with hydrochloric acid gas for 1 h. The reaction was allowed to stir at room temperature overnight and concentrated. The crude product was dissolved in ethyl acetate, washed with water (2×), brine (2×) dried over sodium sulfate and concentrated. Flash chromatography on silica gel afforded 23.4 g (88%) of the desired compound. $^1$H-NMR (CDCl$_3$, 500 MHz) δ 9.02 (s, H), 8.66 (s, 1H), 8.61 (s, 1H), 4.03 (s, 3H).

Intermediate 71

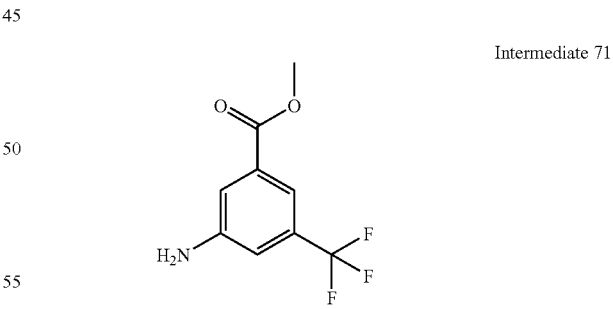

Methyl 3-amino-5-(trifluoromethyl)benzoate. Methyl 3-nitro-5-(trifluoromethyl)benzoate (9.0 g, 36.1 mmol) in methanol (30 mL) was flushed with nitrogen, and treated with palladium (10% on charcoal, 0.90 g). The flask was flushed with hydrogen and allowed to stir under an atmosphere of hydrogen overnight. The reaction was flushed with nitrogen, filtered through celite, and concentrated. Flash chromatography on silica gel (30% ethyl acetate/hexanes) afforded 6.8 g (86%). $^1$H-NMR (CDCl$_3$, 500 MHz) δ 7.64 (s, H), 7.49 (s, 1H), 7.05 (s, 1H), 3.91 (s, 3H). Mass spec.: 220.05 (MH)$^+$.

Intermediate 72

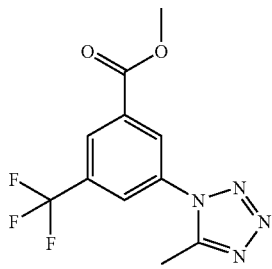

Methyl 3-(5-methyl-1H-tetrazol-1-yl)-5-(trifluoromethyl) benzoate. Trimethylorthoacetate (0.41 mL, 3.4 mmol) in acetic acid (3 mL) was added dropwise to a solution of methyl 3-amino-5-(trifluoromethyl)benzoate (0.5 g, 2.28 mmol) in acetic acid (5 mL) at 75° C. After stirring for 45 min at 75° C., the reaction was treated with sodium azide (0.21 g, 3.4 mmol) carefully in portions over 15 min and stirring continued for 3 h. After cooling to room temperature, the reaction was concentrated and the residue dissolved in ethyl acetate. This was washed with water (2×), 1 N hydrochloric acid (2×), brine (2×), dried over sodium sulfate, and concentrated. Flash chromatography on silica gel (20% ethyl acetate/hexanes) gave 0.38 g (58%). LC/MS (HPLC method 3): $t_R$=2.17 min, 287.12 (MH)+.

Intermediate 73

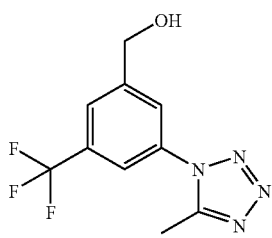

3-(5-Methyl-1H-tetrazol-1-yl)-5-(trifluoromethyl)phenyl)methanol. Methyl 3-(5-methyl-1H-tetrazol-1-yl)-5-(trifluoromethyl)benzoate (0.38 g, 1.33 mmol) was dissolved in a diethyl ether (5 mL) and tetrahydrofuran (2.5 mL) mixture and cooled to 0° C. The reaction was treated with water (24.0 µL, 1.33 mmol) and lithium borohydride (32.0 mg, 1.46 mmol), stirred at 0° C. for 30 min, and at room temperature for 1 h. The reaction mixture was diluted with ethyl acetate, carefully quenched with methanol (1.8 mL) and washed with water (2×), brine (2×), dried over sodium sulfate, and concentrated. Flash chromatography on silica gel gave 0.14 g (41%). $^1$H-NMR (CDCl$_3$, 500 MHz) δ 7.83 (s, H), 7.75 (s, 1H), 7.63 (s, 1H), 4.91 (s, 2H), 2.63 (s, 3H). Mass spec.: 259.10 (MH)+.

Intermediate 74

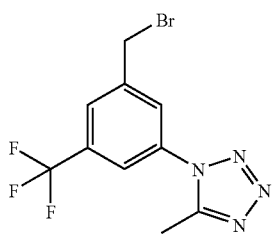

1-(3-(Bromomethyl)-5-(trifluoromethyl)phenyl)-5-methyl-1H-tetrazole. (3-(5-Methyl-1H-tetrazol-1-yl)-5-(trifluoromethyl)phenyl)methanol (110 mg, 0.46 mmol) and triphenylphosphine (240 mg, 0.93 mmol) were combined in methylene chloride (4 mL) and cooled to 0° C. N-Bromosuccinimide (171 mg, 0.96 mmol) was introduced in portions and the reaction allowed to warm to room temperature. After 16 h, the reaction mixture was diluted with ethyl acetate, washed with concentrated sodium bicarbonate (2×), brine (2×), dried over sodium sulfate, and concentrated. Column chromatography on silica gel (20% ethyl acetate/hexanes) gave 120 mg (82%). LC/MS (HPLC method 3): $t_R$=2.30 min, 323.01 (MH)+.

Intermediate 75

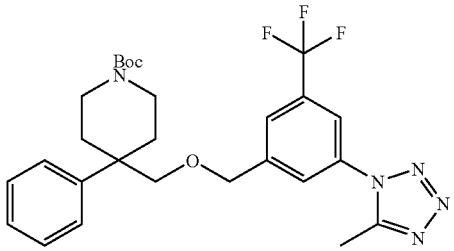

tert-Butyl 4-((3-(5-methyl-1H-tetrazol-1-yl)-5-(trifluoromethyl)benzyloxy)methyl)-4-phenylpiperidine-1-carboxylate. 1-(3-(Bromomethyl)-5-(trifluoromethyl)phenyl)-5-methyl-1H-tetrazole (30.0 mg, 0.09 mmol) and tert-butyl 4-(hydroxymethyl)-4-phenylpiperidine-1-carboxylate (29.0 mg, 0.1 mmol) were combined in dimethylformamide (2 mL) and cooled to 0° C. The reaction was treated with sodium hydride (2.4 mg, 0.1 mmol), stirred at 0° C. for 1 hr and at room temperature for 30 min. The reaction mixture was diluted with water and extracted with ethyl acetate (2×). The organic layers were pooled together, washed with brine (2×), dried over sodium sulfate, and concentrated. Column chromatography on silica gel (40% ethyl acetate/hexanes) gave 40 mg (81%). LC/MS (HPLC method 3): $t_R$=3.14 min, 532.24 (MH)+.

Intermediate 76 tert-Butyl 4-((2-methoxy-5-nitrobenzyloxy)methyl)-4-phenylpiperidine-1-carboxylate. 2-(Bromomethyl)-1-methoxy-4-nitrobenzene (100.0 mg, 0.34 mmol) and tert-butyl 4-(hydroxymethyl)-4-phenylpiperidine-1-carboxylate (93.0 mg, 0.38 mmol) were combined in dimethylformamide (4 mL) and cooled to 0° C. The reaction was treated with sodium hydride (9.0 mg, 0.38 mmol), stirred at 0° C. for 1 hr and at room temperature for 30 min. The reaction mixture was diluted with water and extracted with ethyl acetate (2×). The organic layers were pooled together, washed with brine (2×), dried over sodium sulfate, and concentrated. Column chromatography on silica gel (15% ethyl acetate/hexanes) gave 110 mg (71%). $^1$H-NMR (CDCl$_3$, 500 MHz) δ 8.11 (dd, J=6.1, 3.1 Hz, 1H), 8.08 (d, J=2.8 Hz, 1H), 7.34 (m, 4H), 7.21-7.24 (m, 1H), 6.80 (d, J=8.9 Hz, 1H), 4.37 (s, 2H), 3.85 (s, 3H), 3.74-3.75 (m, 2H), 3.48 (s, 2H), 3.02-3.07 (m, 2H), 2.21-2.24 (m, 2H), 1.87-1.93 (m, 2H), 1.43 (s, 9H). Mass spec.: 479.16 (MNa)+.

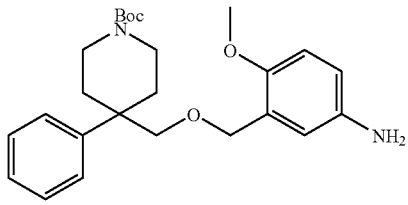

Intermediate 77 tert-Butyl 4-((5-amino-2-methoxybenzyloxy)methyl)-4-phenylpiperidine-1-carboxylate. tert-Butyl 4-((2-methoxy-5-nitrobenzyloxy)methyl)-4-phenylpiperidine-1-carboxylate (110 mg, 0.24 mmol) in methanol (3 mL) was flushed with nitrogen, and treated with palladium (10% on charcoal, 11.0 mg). The flask was flushed with hydrogen and allowed to stir under an atmosphere of hydrogen overnight. The reaction was flushed with nitrogen, filtered through celite, and concentrated to afford 96.0 mg (94%). $^1$H-NMR (CDCl$_3$, 500 MHz) δ 7.33-7.38 (m, 4H), 7.22-7.25 (m, 1H), 6.62 (d, J=8.5 Hz, 1H), 6.51 (dd, J=5.8, 2.7 Hz, 1H), 6.29 (d, J=2.8 Hz, 1H), 4.37 (s, 2H), 3.70-3.74 (m, 2H), 3.43 (s, 3H), 3.42 (s, 2H), 3.03-3.07 (m, 2H), 2.15-2.18 (m, 2H), 1.88-1.93 (m, 2H), 1.43 (s, 9H). Mass spec.: 427.25 (MH)$^+$.

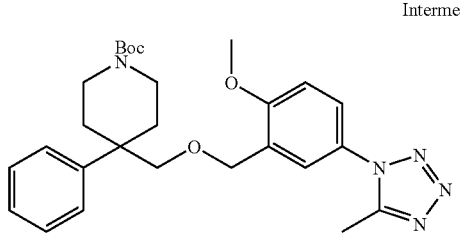

Intermediate 78 tert-Butyl 4-((2-methoxy-5-(5-methyl-1H-tetrazol-1-yl)benzyloxy)methyl)-4-phenylpiperidine-1-carboxylate. Trimethylorthoacetate (40.0 μL, 0.32 mmol) in acetic acid (0.5 mL) was added dropwise to a solution of methyl 3-amino-5-(trifluoromethyl)benzoate (0.5 g, 2.28 mmol) in acetic acid (1.5 mL) at 75° C. After stirring for 45 min at 75° C., the reaction was treated with sodium azide (21.0 mg, 0.32 mmol) carefully and stirring continued for 3 h. After cooling to room temperature, the reaction was concentrated and the residue dissolved in ethyl acetate, washed with water (2×), 1 N hydrochloric acid (2×), brine (2×), dried over sodium sulfate, and concentrated. Flash chromatography on silica gel (30% ethyl acetate/hexanes) gave 50.0 mg (56%). LC/MS (HPLC method 3): t$_R$=3.06 min, 494.23 (MH)$^+$.

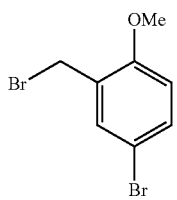

Intermediate 79

4-Bromo-2-(bromomethyl)-1-methoxybenzene. To a solution of (5-bromo-2-methoxyphenyl)methanol (1.0 g, 4.6 mmol) in dichloromethane (10 mL) at 0° C. was added tribromophosphine (1 M in dichloromethane, 9.2 mL, 9.2 mmol). The ice bath was removed and the reaction stirred for 15 min. The reaction was concentrated, poured onto cold saturated sodium bicarbonate, extracted with pentane, dried over magnesium sulfate, and concentrated to give 1.15 g (89%) as a white crystalline solid. $^1$H NMR (500 MHz, CDCl$_3$) δ ppm 7.44 (d, J=2.5 Hz, 1H), 7.38 (dd, J=8.9, 6.1 Hz, 1H), 4.47 (s, 2H), 3.87 (s, 3H); $^{13}$C NMR (126 MHz, CDCl$_3$) δ ppm 156.7, 133.6, 132.8, 128.4, 112.8, 112.7, 56.0, 27.5.

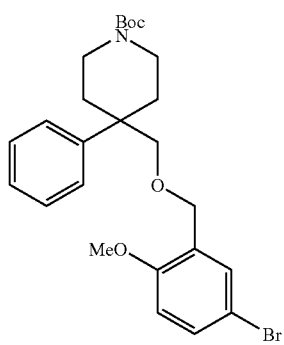

Intermediate 80 tert-Butyl 4-((5-bromo-2-methoxybenzyloxy)methyl)-4-phenylpiperidine-1-carboxylate. To a solution of tert-butyl 4-(hydroxymethyl)-4-phenylpiperidine-1-carboxylate (0.40 g, 1.37 mmol) and 4-bromo-2-(bromomethyl)-1-methoxybenzene (0.46 g, 1.65 mmol) in dimethylformamide (4 mL) at 0° C. was added sodium hydride (66 mg, 2.75 mmol). After 20 min at 0° C., the ice bath was removed and the reaction stirred for 15 min. The reaction was poured into a separatory funnel containing ether and water. The ethereal was washed with water (2×), then brine, dried over magnesium sulfate, and concentrated. Column chromatography (10% ethyl acetate/hexanes→25% ethyl acetate/hexanes) gave 640 mg (95%) as a colorless viscous oil. $^1$H NMR (500 MHz, CDCl$_3$) δ ppm 7.20-7.45 (m, 7H), 6.65 (d, J=8.9 Hz, 1H), 4.36 (s, 2H), 3.76 (m, 2H), 3.72 (s, 3H), 3.44 (s, 2H), 3.08 (m, 2H), 2.19 (m, 2H), 1.91 (m, 2H), 1.44 (s, 9H); $^{13}$C NMR (126 MHz, CDCl$_3$) δ ppm 155.8, 155.1, 143.0, 130.8, 129.5, 128.6, 127.3, 126.5, 113.0, 111.8, 104.3, 79.8, 79.4, 67.6, 55.6, 41.8, 40.3, 32.0, 28.6.

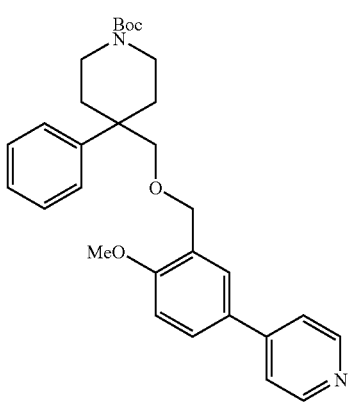

Intermediate 81 tert-Butyl 4-((2-methoxy-5-(pyridin-4-yl)benzyloxy)methyl)-4-phenylpiperidine-1-carboxylate. A microwave tube was charged with tert-butyl 4-((5-bromo-2-methoxybenzyloxy)methyl)-4-phenylpiperidine-1-carboxylate (50 mg, 0.102 mmol), pyridin-4-ylboronic acid (50.1 mg, 0.408 mmol), and tetrakis(triphenylphosphine)-palladium(0) (12 mg, 10 mmol). The tube was flushed with nitrogen, treated with tetrahydrofuran (2 mL) and potassium hydroxide (1 M in water, 0.401 mL, 0.41 mmol). The tube was sealed and heated at 120° C. for 1 h via microwave. The reaction was cooled, poured into ether, washed with water (2×), then brine, dried over magnesium sulfate, and concentrated. Column chromatography (ethyl acetate/hexanes) gave 26 mg (52%) as a colorless oil. $^1$H NMR (500 MHz, CDCl$_3$) δ ppm 8.61 (d, J=5.8 Hz, 2H), 7.50 (dd, J=8.6, 2.5, 1H), 7.30-7.45 (m, 7H), 7.21 (m, 1H), 6.89 (d, J=8.5, 1H), 4.47 (s, 2H), 3.82 (s, 3H), 3.73 (bs, 2H), 3.50 (s, 2H), 3.07 (m, 2H), 2.20 (m, 2H), 1.91 (m, 2H), 1.42 (s, 9H); $^{13}$C NMR (126 MHz, CDCl$_3$) δ ppm 157.7, 155.1, 150.1, 148.1, 143.3, 130.1, 128.5, 128.1, 127.3, 126.7, 126.6, 126.4, 121.2, 110.6, 79.8, 79.3, 67.9, 55.6, 41.8, 40.3, 32.2, 28.6. Mass spec.: 489.37 (MH)$^+$.

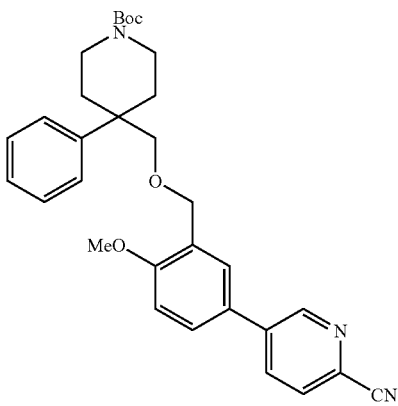

Intermediate 82 tert-Butyl 445-(6-cyanopyridin-3-yl)-2-methoxybenzyloxy)methyl)-4-phenylpiperidine-1-carboxylate. A microwave tube was charged with tert-butyl 4-((5-bromo-2-methoxybenzyloxy)methyl)-4-phenylpiperidine-1-carboxylate (50 mg, 0.102 mmol), 5-(4,4,5,5-tetramethyl-1,3,2-dioxaborolan-2-yl)picolinonitrile (94 mg, 0.408 mmol), and tetrakis(triphenylphosphine)-palladium(0) (11.78 mg, 10.20 mmol). The tube was flushed with nitrogen, treated with tetrahydrofuran (2 mL) and potassium hydroxide (1 M in water, 0.41 mL, 0.41 mmol). The tube was sealed and heated at 120° C. for 1 h via microwave. The reaction was cooled, poured into ether, washed with water (2×), then brine, dried over magnesium sulfate, and concentrated. Column chromatography (ethyl acetate/hexanes) gave 46 mg (88%) as a colorless oil. $^1$H NMR (500 MHz, CDCl$_3$) δ ppm 8.80 (d, J=2.1 Hz, 1H), 7.80 (dd, J=7.9, 2.1 Hz, 1H), 7.72 (d, J=8.2 Hz, 1H), 7.44 (dd, J=8.5, 2.4 Hz, 1H), 7.37 (m, 2H), 7.31 (m, 3H), 7.20 (m, 1H), 6.92 (d, J=8.5 Hz, 1H), 4.47 (s, 2H), 3.83 (s, 3H), 3.73 (m, 2H), 3.50 (s, 2H), 3.06 (m, 2H), 2.20 (m, 2H), 1.89 (m, 2H), 1.42 (s, 9H); $^{13}$C NMR (126 MHz, CDCl$_3$) δ ppm 157.8, 155.1, 149.3, 143.2, 139.6, 134.1, 131.5, 128.7, 128.5, 128.4, 127.9, 127.3, 127.1, 126.6, 126.4, 117.6, 110.9, 102.9, 79.9, 79.4, 67.7, 55.6, 41.8, 40.3, 32.2, 28.6. Mass spec.: 514.45 (MH)$^+$.

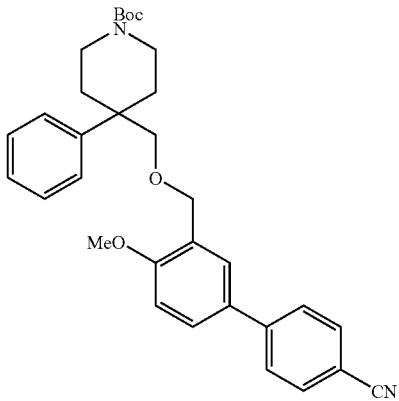

Intermediate 83 tert-Butyl 4-(((4'-cyano-4-methoxybiphenyl-3-yl)methoxy)methyl)-4-phenylpiperidine-1-carboxylate. A microwave tube was charged with tert-butyl 4-((5-bromo-2-methoxybenzyloxy)methyl)-4-phenylpiperidine-1-carboxylate (50 mg, 0.102 mmol), 4-cyanophenylboronic acid (60 mg, 0.41 mmol), and tetrakis(triphenylphosphine)-palladium(0) (12 mg, 10 mmol). The tube was flushed with nitrogen, treated with tetrahydrofuran (2 mL) and potassium hydroxide (1 M in water, 0.41 mL, 0.41 mmol). The tube was sealed and heated at 120° C. for 1 h via microwave. The reaction was cooled, poured into ether, washed with water (2×), then brine, dried over magnesium sulfate, and concentrated. Column chromatography (12%→18% ethyl acetate/hexanes) gave 47 mg (90%) as a white solid. $^1$H NMR (500 MHz, CDCl$_3$) δ ppm 7.69 (d, J=8.5 Hz, 2H), 7.53 (d, J=8.5 Hz, 2H), 7.44 (dd, J=8.6, 2.4 Hz, 1H), 7.37 (m, 3H), 7.32 (m, 2H), 7.20 (m, 1H), 6.89 (m, 1H), 4.48 (s, 2H), 3.82 (s, 3H), 3.74 (m, 2H), 3.50 (s, 2H), 3.07 (m, 2H), 2.20 (m, 2H), 1.91 (m, 2H), 1.43 (s, 9H); $^{13}$C NMR (126 MHz, CDCl$_3$) δ ppm 157.4, 155.2, 145.4, 143.2, 134.2, 132.6, 131.3, 128.5, 128.1, 127.3, 127.2, 126.9, 126.8, 126.3, 116.5, 110.6, 79.8, 79.5, 67.9, 55.6, 41.8, 40.3, 32.2, 28.6. Mass spec.: 513.45 (MH)$^+$.

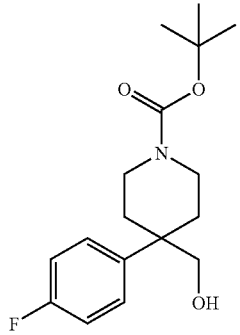

Intermediate 84 tert-Butyl 4-(4-fluorophenyl)-4-(hydroxymethyl)piperidine-1-carboxylate. 1-(tert-Butoxycarbonyl)-4-(4-fluorophenyl)piperidine-4-carboxylic acid (9.5 g, 29.3 mmol) was suspended in tetrahydrofuran (60 mL) and cooled to 0° C. To this solution was added borane tetrahydrofuran complex (1 M in tetrahydrofuran, 59 mL, 59 mmol) cautiously over 15 min. The reaction mixture was allowed to warm to room temperature overnight and then heated at reflux for 24 h. The mixture was cooled to 0° C., treated with excess methanol, diluted with ethyl acetate, washed with 1 N sodium hydroxide (2×), then brine (2×), dried over sodium sulfate, and concentrated. Column chromatography on silica gel (40% ethyl acetate/hexanes) gave 6.6 g (72%) as a white powder. $^1$H-NMR (CDCl$_3$, 300 MHz) 7.24-7.29 (m, 2H), 7.00-7.05 (m, 2H), 3.66-3.71 (m, 2H), 3.49 (s, 2H), 2.96-3.05 (m, 2H), 2.06-2.10 (m, 2H), 1.69-1.77 (m, 2H), 1.40 (s, 9H). Mass spec.: 310.21 (MH)$^+$.

Intermediate 85

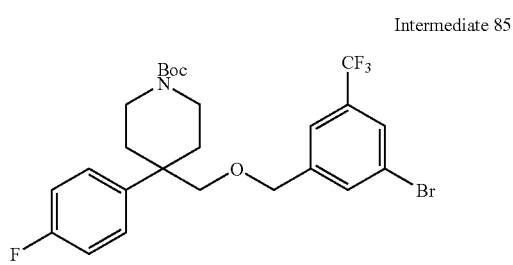 [SMILES: CC(C)(C)OC(=O)N1CCC(COCc2cc(Br)cc(C(F)(F)F)c2)(c2ccc(F)cc2)CC1]

tert-Butyl 4-((3-bromo-5-(trifluoromethyl)benzyloxy)methyl)-4-(4-fluorophenyl)piperidine-1-carboxylate. 1-Bromo-3-(bromomethyl)-5-(trifluoromethyl)benzene (1.2 g, 3.78 mmol) and tert-butyl 4-(4-fluorophenyl)-4-(hydroxymethyl)piperidine-1-carboxylate (0.96 g, 3.2 mmol) were combined in dimethylformamide (10 mL) and cooled to 0° C. The reaction was treated with sodium hydride (151 mg, 6.3 mmol), stirred at 0° C. for 1 h, and at room temperature for 30 min. The reaction mixture was diluted with water and extracted with ethyl acetate (2×). The organic layers were pooled together, washed with brine (2×), dried over sodium sulfate, and concentrated. Column chromatography on silica gel (15% ethyl acetate/hexanes) gave 1.1 g (61%) as a clear oil. $^1$H-NMR (CDCl$_3$, 500 MHz) δ 7.61 (s, 1H), 7.35 (s, 1H), 7.30-7.31 (m, 2H), 7.26 (s, 1H), 7.03-7.07 (m, 2H), 4.36 (s, 2H), 3.72-3.75 (m, 2H), 3.38 (s, 2H), 3.01-3.06 (m, 2H), 2.13-2.16 (m, 2H), 1.81-1.87 (m, 2H), 1.43 (s, 9H). 13C-NMR (CDCl$_3$, 126 MHz) δ 161.6 (d, J=245.7 Hz), 152.0, 141.9, 138.3, 133.3, 132.4 (q, J=32.6 Hz), 128.8, 127.5 123.2 (q, J=273.5 Hz), 122.8, 122.4, 115.5, 115.3, 79.7, 79.5, 71.7, 68.0, 41.4, 32.2, 28.5, 25.7. Mass spec.: 548.16 (MH)+.

Intermediate 86

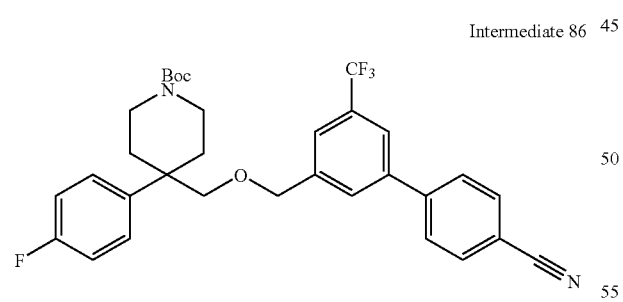

tert-Butyl 4-(((4'-cyano-5-(trifluoromethyl)biphenyl-3-yl)methoxy)methyl)-4-(4-fluorophenyl)piperidine-1-carboxylate. tert-Butyl 4-((3-bromo-5-(trifluoromethyl)benzyloxy)methyl)-4-(4-fluorophenyl)piperidine-1-carboxylate (130.0 mg, 0.24 mmol), 4-cyanophenylboronic acid (140.0 mg, 0.95 mmol), and tetrakis(triphenylphosphine) palladium(0) (37.1 mg, 0.024 mmol) were combined in dry tetrahydrofuran (3 mL) in a microwave tube and sealed. The mixture was flushed with nitrogen. To this was added potassium hydroxide (1 N in water, 0.75 mL, 0.75 mmol). The mixture was heated at 120° C. for 1 h via microwave. After cooling to room temperature, the reaction mixture was concentrated and purified by flash chromatography on silica gel (25% ethyl acetate/hexanes) to afford 61.0 mg (48%). $^1$H-NMR (CDCl$_3$, 500 MHz) δ 7.74-7.76 (m, 2H), 7.67 (s, 1H), 7.57-7.60 (m, 2H), 7.41 (s, 1H), 7.40 (s, 1H), 7.29-7.32 (m, 2H), 6.98-7.02 (m, 2H), 4.47 (s, 2H), 3.71-3.74 (m, 2H), 3.43 (s, 2H), 3.01-3.06 (m, 2H), 2.14-2.17 (m, 2H), 1.82-1.88 (m, 2H), 1.42 (s, 9H). Mass spec.: 569.25 (MH)$^+$.

Intermediate 87

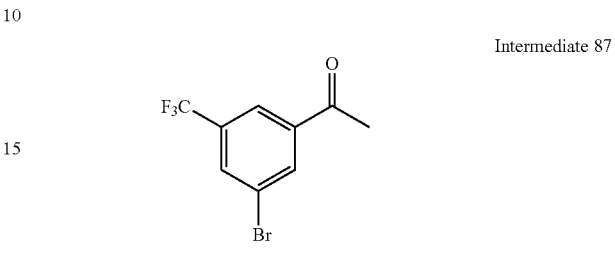

1-(3-Bromo-5-(trifluoromethyl)phenyl)ethanone. A flask was charged with water (42 ml), cooled to 0° C., and treated with concentrated hydrochloric acid (21.7 ml) and sulfuric acid (5.66 ml). To this was added 3-amino-5-bromobenzotrifluoride (8.77 ml, 62.5 mmol). The reaction was treated with a solution of sodium nitrite (5.39 g, 78 mmol) in water (10 mL). The resulting reaction mixture was stirred for 30 min at 0° C. The reaction was transferred to a solution of acetaldoxime (5.71 ml, 94 mmol) and copper(II) sulfate (0.499 g, 3.12 mmol) in water (30 mL) at room temperature. After stirring for 1 h at room temperature, the reaction was heated to reflux and held there for 3 h. The reaction was cooled and diluted with pentane. It gave an intractable suspension. The reaction mixture was filtered through a sintered glass funnel. The layers were separated. The organics were washed with water, then brine, dried over magnesium sulfate, and concentrated. The crude residue was distilled (high vacuum, 75° C.) to give 3 fractions of varying levels of purity. Total yield was 8.5 g (51%) with purity that ranged from 10:1 to 1:1. $^1$H NMR (500 MHz, CDCl$_3$) δ ppm 8.25 (s, 1H), 8.11 (s, 1H), 7.95 (s, 1H), 2.63 (s, 3H).

Intermediate 88

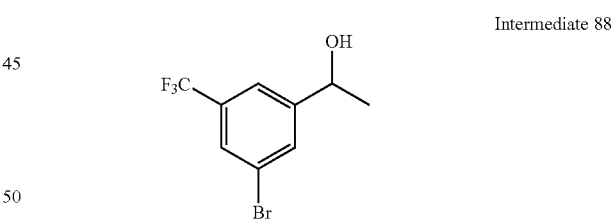

(±)-1-(3-Bromo-5-(trifluoromethyl)phenyl)ethanol. To a solution of 1-(3-bromo-5-(trifluoromethyl)phenyl)ethanone (ca. 60% pure, 500 mg, 1.1 mmol) in ethanol (10 mL) at 0° C. was added sodium borohydride (32 mg, 0.85 mmol). The ice bath was removed and the reaction stirred at room temperature for 20 min. The reaction was cooled to 0° C., quenched by the cautious addition of saturated ammonium chloride, and concentrated to remove most of the ethanol. The residue was dissolved in water and extracted with ether. The ethereal was washed with water, then brine, dried over magnesium sulfate, and concentrated. Column chromatography (8%→16% ethyl acetate/hexanes) gave 216 mg (72%) as a colorless oil which solidified upon standing. $^1$H NMR (500 MHz, CDCl$_3$) δ ppm 7.71 (s, 1H), 7.66 (s, 1H), 7.56 (s, 1H), 4.93 (q, J=6.4 Hz, 1H), 2.03 (bs, 1H), 1.50 (d, J=6.7 Hz, 3H); $^{13}$C NMR (126 MHz, CDCl₃) δ ppm 149.1, 132.6 (q, J=33.6 Hz), 132.1, 127.5 (q, J=3.8 Hz), 123.2 (q, J=273 Hz), 122.9, 121.1 (q, J=3.8 Hz), 69.4, 25.5.

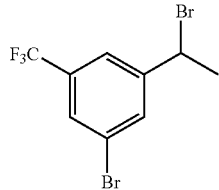

Intermediate 89

(±)-1-Bromo-3-(1-bromoethyl)-5-(trifluoromethyl)benzene. To a solution of (±)-1-(3-bromo-5-(trifluoromethyl)phenyl)ethanol (390 mg, 1.45 mmol) and carbon tetrabromide (577 mg, 1.74 mmol) in tetrahydrofuran (2 mL) at 0° C. was added triphenylphosphine (456 mg, 1.74 mmol). The resulting solution was stirred at room temperature for 2 h. The reaction was treated with an additional portion of carbon tetrabromide (289 mg, 0.87 mmol)) and triphenylphosphine (228 mg, 0.87 mmol). The reaction was stirred at room temperature for 1 h, diluted with several volumes of pentane, and filtered to remove undissolved solids. The organics were concentrated and purified by column chromatography (1→3% ethyl acetate/hexanes) to give 439 mg (91%) as a colorless oil. ¹H NMR (500 MHz, CDCl₃) δ ppm 7.76 (s, 1H), 7.68 (s, 1H), 7.60 (s, 1H), 5.12 (q, J=7.0 Hz, 1H), 2.03 (d, J=7.0 Hz, 3H); ¹³C NMR (126 MHz, CDCl₃) δ ppm 146.4, 133.5, 132.9 (q, J=32.6 Hz), 128.4 (q, J=3.8 Hz), 123.0, 123.0 (q, J=273 Hz), 122.6 (q, J=3.8 Hz), 46.1, 26.6.

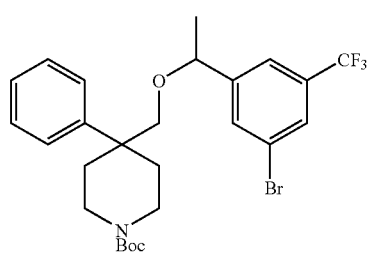

Intermediate 90

(±)-tert-Butyl 4-((1-(3-bromo-5-(trifluoromethyl)phenyl)ethoxy)methyl)-4-phenylpiperidine-1-carboxylate. To a solution of tert-butyl 4-(hydroxymethyl)-4-phenylpiperidine-1-carboxylate (435 mg, 1.49 mmol) and (±)-1-bromo-3-(1-bromoethyl)-5-(trifluoromethyl)benzene (496 mg, 1.49 mmol) in dimethylformamide (1.5 mL) at 0° C. was added sodium hydride (72 mg, 3.0 mmol). The ice bath was removed and the resulting mixture stirred at room temperature for 1 h. The reaction was cooled to 0° C., diluted with ether, and quenched by the cautious addition of saturated ammonium chloride. The mixture was poured into water and extracted into ether. The ethereal was washed with water, then brine, dried over magnesium sulfate, and concentrated. Column chromatography (8→12% ethyl acetate/hexanes) gave 188 mg (23%) as a colorless oil. ¹H NMR (500 MHz, CDCl₃) δ ppm 7.59 (s, 1H), 7.28-7.42 (m, 5H), 7.24 (m, 2H), 4.17 (q, J=6.4 Hz, 1H), 3.76 (m, 2H), 3.27 (d, J=8.9 Hz, 1H), 3.21 (d, J=8.9 Hz, 1H), 3.03 (m, 2H), 2.17 (m, 2H), 1.87 (m, 2H), 1.44 (s, 9H), 1.28 (d, J=6.4 Hz, 3H); ¹³C NMR (126 MHz, CDCl₃) δ ppm 155.1, 147.7, 142.6, 132.5 (q, J=32.6 Hz), 132.4, 128.5, 127.4 (q, J=3.8 Hz), 127.2, 126.6, 123.2 (q, J=273 Hz), 122.8, 121.6 (q, J=3.8 Hz), 79.4, 78.3, 41.7, 40.2, 32.1, 31.7, 28.6, 23.8. Mass spec.: 542.13 (MH)⁺.

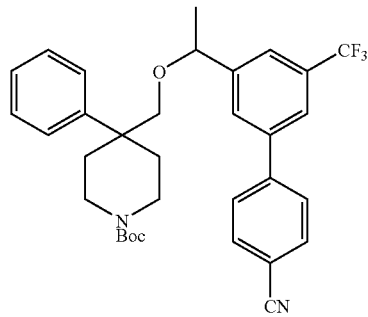

Intermediate 91

(±)-tert-Butyl 4-((1-(4'-cyano-5-(trifluoromethyl)biphenyl-3-yl)ethoxy)methyl)-4-phenylpiperidine-1-carboxylate. A microwave tube was charged with (±)-tert-butyl 4-((1-(3-bromo-5-(trifluoromethyl)phenyl)ethoxy)methyl)-4-phenylpiperidine-1-carboxylate (40 mg, 0.074 mmol), 4-cyanophenylboronic acid (43 mg, 0.30 mmol), and tetrakis(triphenylphosphine) palladium(0) (8.5 mg, 7.4 µmol). The tube was flushed with nitrogen, treated with tetrahydrofuran (2 mL) and potassium hydroxide (1 M in water, 0.30 mL, 0.30 mmol). The tube was sealed and heated at 120° C. for 1 h via microwave. The reaction was cooled, poured into ether, washed with water (2×), then brine, dried over magnesium sulfate, and concentrated. Column chromatography (12%→25% ethyl acetate/hexanes) gave 36 mg (86%) as a colorless film. ¹H NMR (500 MHz, CDCl₃) δ ppm 7.74 (m, 2H), 7.65 (s, 1H), 7.55 (m, 2H), 7.37 (s, 2H), 7.26-7.34 (m, 4H), 7.17 (m, 1H), 4.30 (q, J=6.4 Hz, 1H), 3.74 (m, 2H), 3.32 (m, 1H), 3.25 (m, 1H), 3.02 (m, 2H), 2.23 (m, 1H), 2.12 (m, 1H), 1.75-1.97 (m, 2H), 1.43 (m, 9H), 1.35 (m, 3H). Mass spec.: 587.22 (MNa)⁺.

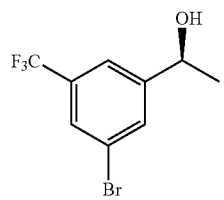

Intermediate 92

(S)-1-(3-Bromo-5-(trifluoromethyl)phenyl)ethanol. A flask was charged with isopropanol (10 mL), dichloro(p-cymene)ruthenium (II) dimer (8.60 mg, 0.014 mmol), and (1R,2S)-1-amino-2,3-dihydro-1H-inden-2-ol (4.19 mg, 0.028 mmol). After aging for 30 min, 1-(3-bromo-5-(trifluoromethyl)phenyl)ethanone (375 mg, 1.4 mmol) was added and the reaction degassed by cooling it to −78 C, putting it under high vacuum, venting to nitrogen, and repeating the process ca. 6 times. The reaction was warmed to room temperature, treated with sodium hydroxide (5 M in water, 0.013 mL, 0.063 mmol), and stirred at room temperature for 5 hours. The reaction was quenched by addition of 1 M hydrochloric acid and extracted into pentane. The organics were washed with water, then brine, dried over magnesium sulfate, and concentrated. Column chromatography (10→20% ethyl acetate/hexanes) gave 292 mg (77%) as a light brown oil. Chiral SFC (ChiralCel OD-H, 1:99 ethanol/carbon dioxide)

showed the optical purity to be 81% ee. $^1$H NMR (500 MHz, CDCl$_3$) δ ppm 7.71 (s, 1H), 7.66 (s, 1H), 7.56 (s, 1H), 4.93 (q, J=6.4 Hz, 1H), 2.03 (bs, 1H), 1.50 (d, J=6.7 Hz, 3H); $^{13}$C NMR (126 MHz, CDCl$_3$) δ ppm 149.1, 132.6 (q, J=33.6 Hz), 132.1, 127.5 (q, J=3.8 Hz), 123.2 (q, J=273 Hz), 122.9, 121.1 (q, J=3.8 Hz), 69.4, 25.5.

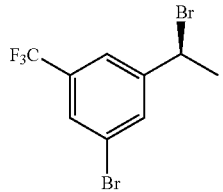

Intermediate 93

(S)-1-Bromo-3-(1-bromoethyl)-5-(trifluoromethyl)benzene. To a solution of (S)-1-(3-bromo-5-(trifluoromethyl)phenyl)ethanol (150 mg, 0.56 mmol) in dichloromethane (3 mL) at 0° C. was added thionyl bromide (0.086 mL, 1.12 mmol). The ice bath was removed and stirring continued for 1 h. The reaction was warmed to reflux and held there for 1 h. The reaction was treated with a second portion of thionyl bromide (0.086 mL, 1.12 mmol) and the reaction held at reflux for 2 h. The reaction was cooled to 0° C., quenched by addition of water, and diluted with pentane. The organics were washed with water (2×), then brine, dried over magnesium sulfate, and concentrated. Column chromatography (100% hexanes) gave 78 mg (42%). $^1$H NMR (500 MHz, CDCl$_3$) δ ppm 7.76 (s, 1H), 7.68 (s, 1H), 7.60 (s, 1H), 5.12 (q, J=7.0 Hz, 1H), 2.03 (d, J=7.0 Hz, 3H); $^{13}$C NMR (126 MHz, CDCl$_3$) δ ppm 146.4, 133.5, 132.9 (q, J=32.6 Hz), 128.4 (q, J=3.8 Hz), 123.0, 123.0 (q, J=273 Hz), 122.6 (q, J=3.8 Hz), 46.1, 26.6.

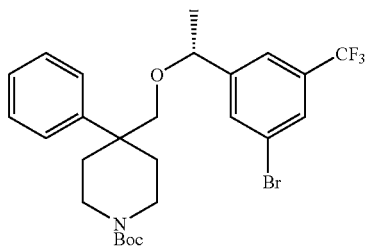

Intermediate 94

(R)-tert-butyl 4-((1-(3-bromo-5-(trifluoromethyl)phenyl)ethoxy)methyl)-4-phenylpiperidine-1-carboxylate. To a solution of tert-butyl 4-(hydroxymethyl)-4-phenylpiperidine-1-carboxylate (65.8 mg, 0.23 mmol) and (S)-1-bromo-3-(1-bromoethyl)-5-(trifluoromethyl)benzene (75 mg, 0.23 mmol) in dimethylformamide (0.4 mL) at 0° C. was added sodium hydride (10.8 mg, 0.45 mmol). The reaction was stirred at 0° C. for 1 h. The reaction was quenched by addition of saturated ammonium chloride. The mixture was extracted with ether which was washed with water (2×), then brine, dried over magnesium sulfate, and concentrated to give 37 mg (30%) as a colorless oil. Chiral SFC (ChiralCel OJ-H, 1:99 methanol/carbon dioxide) showed the optical purity to be 44% ee. $^1$H NMR (500 MHz, CDCl$_3$) δ ppm 7.59 (s, 1H), 7.28-7.42 (m, 5H), 7.24 (m, 2H), 4.17 (q, J=6.4 Hz, 1H), 3.76 (m, 2H), 3.27 (d, J=8.9 Hz, 1H), 3.21 (d, J=8.9 Hz, 1H), 3.03 (m, 2H), 2.17 (m, 2H), 1.87 (m, 2H), 1.44 (s, 9H), 1.28 (d, J=6.4 Hz, 3H); $^{13}$C NMR (126 MHz, CDCl$_3$) δ ppm 155.1, 147.7, 142.6, 132.5 (q, J=32.6 Hz), 132.4, 128.5, 127.4 (q, J=3.8 Hz), 127.2, 126.6, 123.2 (q, J=273 Hz), 122.8, 121.6 (q, J=3.8 Hz), 79.4, 78.3, 41.7, 40.2, 32.1, 31.7, 28.6, 23.8. Mass spec.: 542.13 (MH)$^+$.

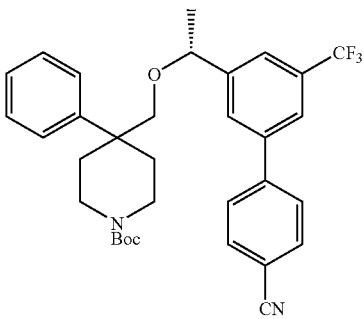

Intermediate 95

(R)-tert-Butyl 441-(4'-cyano-5-(trifluoromethyl)biphenyl-3-yl)ethoxy)methyl)-4-phenylpiperidine-1-carboxylate. A microwave tube was charged with (R)-tert-butyl 4-((1-(3-bromo-5-(trifluoromethyl)phenyl)ethoxy)methyl)-4-phenylpiperidine-1-carboxylate (20 mg, 0.037 mmol), 4-cyanophenylboronic acid (21.7 mg, 0.15 mmol), and tetrakis(triphenylphosphine) palladium(0) (4.3 mg, 3.7 µmol). The tube was flushed with nitrogen, treated with tetrahydrofuran (1 mL) and potassium hydroxide (1 M in water, 0.15 mL, 0.15 mmol). The tube was sealed and heated at 120° C. for 1 h via microwave. The reaction was cooled, poured into ether, washed with water (2×), then brine, dried over magnesium sulfate, and concentrated. Column chromatography (12%→25% ethyl acetate/hexanes) gave 15.4 mg (74%) as a colorless film. $^1$H NMR (500 MHz, CDCl$_3$) δ ppm 7.74 (m, 2H), 7.65 (s, 1H), 7.55 (m, 2H), 7.37 (s, 2H), 7.26-7.34 (m, 4H), 7.17 (m, 1H), 4.30 (q, J=6.4 Hz, 1H), 3.74 (m, 2H), 3.32 (m, 1H), 3.25 (m, 1H), 3.02 (m, 2H), 2.23 (m, 1H), 2.12 (m, 1H), 1.75-1.97 (m, 2H), 1.43 (m, 9H), 1.35 (m, 3H). Mass spec.: 587.22 (MNa)$^+$.

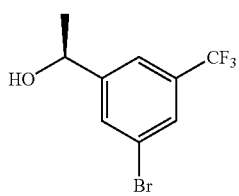

Intermediate 96

(S)-1-(3-Bromo-5-(trifluoromethyl)phenyl)ethanol. A flask was flushed with nitrogen, charged with isopropanol (15 mL), and degassed by bubbling nitrogen for 20 min. To this was added bis-[rutheniumdichloride(p-cymene)] (0.017 g, 0.028 mmol), and (1R,2S)-1-amino-2,3-dihydro-1H-inden-2-ol (8.4 mg, 0.056 mmol). The mixture was stirred while bubbling nitrogen for 30 min. The resulting mixture was cooled to 0° C. and treated with 1-(3-bromo-5-(trifluoromethyl)phenyl)ethanone (1.5 g, 5.62 mmol) and sodium hydroxide (5 M, 0.025 mL, 0.126 mmol). The reaction was stirred for 7 h at 0° C. The reaction was quenched by addition of 1 M hydrochloric acid and extracted into pentane (2×). The organics were washed with brine, dried over magnesium sulfate, and concentrated. Column chromatography (10→20% ethyl acetate/hexanes) gave 1.45 g (96%) as a light yellow oil. $^1$H NMR (500 MHz, CDCl$_3$) δ ppm 7.71 (s, 1H), 7.66 (s, 1H), 7.56 (s, 1H), 4.93 (q, J=6.4 Hz, 1H), 2.03 (bs, 1H), 1.50 (d, J=6.7 Hz, 3H); ¹³C NMR (126 MHz, CDCl₃) δ ppm 149.1, 132.6 (q, J=33.6 Hz), 132.1, 127.5 (q, J=3.8 Hz), 123.2 (q, J=273 Hz), 122.9, 121.1 (q, J=3.8 Hz), 69.4, 25.5.

Intermediate 97

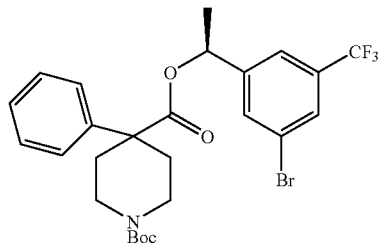

(S)-4-(1-(3-Bromo-5-(trifluoromethyl)phenyl)ethyl) 1-tert-butyl 4-phenylpiperidine-1,4-dicarboxylate. To a suspension of 1-(tert-butoxycarbonyl)-4-phenylpiperidine-4-carboxylic acid (1.98 g, 6.47 mmol) in toluene (18 mL) and dichloromethane (3 mL) at 0° C. was added dicyclohexylcarbodiimide (1.56 g, 7.54 mmol) in small portions. The ice bath was removed and the resulting slurry stirred at room temperature for 30 min. The reaction was recooled to 0° C., treated with (S)-1-(3-bromo-5-(trifluoromethyl)phenyl)ethanol (1.45 g, 5.39 mmol) and dimethylaminopyridine (0.658 g, 5.39 mmol). The reaction was allowed to warm to room temperature overnight and stirred for 3 d. The reaction was poured into pentane (~100 mL). The resulting solid was filtered and discarded. The eluent was washed with 1 M hydrochloric acid, then 1 M sodium hydroxide, then brine, dried over magnesium sulfate, and concentrated. Column chromatography (8%→12% ethyl acetate/hexanes) gave 2.48 g (83%) as a colorless gum. ¹H NMR (500 MHz, CDCl₃) δ ppm 7.58 (s, 1H), 7.23-7.33 (m, 6H), 7.19 (s, 1H), 5.80 (q, J=6.6 Hz, 1H), 3.82-3.97 (m, 2H), 2.97-3.09 (m, 2H), 2.44-2.53 (m, 2H), 1.76-2.01 (m, 2H), 1.42 (s, 9H), 1.40 (m, 3H). Mass spec.: 558.06 (MH)⁺.

Intermediate 98

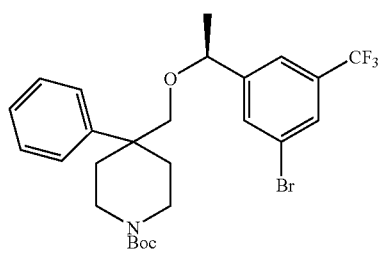

(S)-tert-Butyl 4-((1-(3-bromo-5-(trifluoromethyl)phenyl) ethoxy)methyl)-4-phenylpiperidine-1-carboxylate. To a solution of (S)-4-(1-(3-bromo-5-(trifluoromethyl)phenyl) ethyl) 1-tert-butyl 4-phenylpiperidine-1,4-dicarboxylate (1.5 g, 2.70 mmol) in dichloromethane (15 ml) at −78° C. was added diisobutylaluminum hydride (1 M in dichloromethane, 5.39 mL, 5.39 mmol) dropwise. The reaction was stirred at −78° C. for 1 h, and treated with pyridine (0.654 ml, 8.09 mmol), dimethylaminopyridine (0.659 g, 5.39 mmol), and acetic anhydride (1.53 ml, 16.2 mmol). The reaction was allowed to slowly warm to −10° C. in the dewar over 2 h. The reaction was diluted with diethyl ether, quenched by a few drops of methanol, and treated with saturated sodium potassium tartrate. The suspension was stirred vigorously at room temperature for a couple of hours. The mixture was poured into a separatory funnel and the layers separated. The aqueous was extracted with diethyl ether twice more. The pooled organics were washed with 1 M sodium bisulfate, then saturated sodium bicarbonate, then brine, dried over magnesium sulfate, and concentrated. Column chromatography (ethyl acetate/hexanes on silica gel that was pre-treated with 2% Et₃N in ethyl acetate/hexanes) gave the intermediate acetate (0.80 g, 49%) as an oil which was used immediately without purification. To a solution of the intermediate acetate (0.80 g, 1.3 mmol) and triethylsilane (1.06 ml, 6.66 mmol) in dichloromethane (15 mL) at −78° C. was added boron trifluoride-etherate (0.253 mL, 2.0 mmol). The reaction was allowed to slowly warm to 0° C. in the dewar. The reaction was stirred at 0° C. for 7 h, quenched by addition of saturated sodium bicarbonate, poured into diethyl ether, and the layers separated. The ethereal was washed with water, then brine, dried over magnesium sulfate, and concentrated. Column chromatography (8→12% ethyl acetate/hexanes) gave 36 mg (5%) as a colorless oil. ¹H NMR (500 MHz, CDCl₃) δ ppm 7.59 (s, 1H), 7.28-7.42 (m, 5H), 7.24 (m, 2H), 4.17 (q, J=6.4 Hz, 1H), 3.76 (m, 2H), 3.27 (d, J=8.9 Hz, 1H), 3.21 (d, J=8.9 Hz, 1H), 3.03 (m, 2H), 2.17 (m, 2H), 1.87 (m, 2H), 1.44 (s, 9H), 1.28 (d, J=6.4 Hz, 3H); ¹³C NMR (126 MHz, CDCl₃) δ ppm 155.1, 147.7, 142.6, 132.5 (q, J=32.6 Hz), 132.4, 128.5, 127.4 (q, J=3.8 Hz), 127.2, 126.6, 123.2 (q, J=273 Hz), 122.8, 121.6 (q, J=3.8 Hz), 79.4, 78.3, 41.7, 40.2, 32.1, 31.7, 28.6, 23.8. Mass spec.: 542.13 (MH)⁺.

Intermediate 99

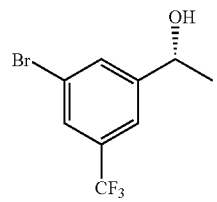

(R)-1-(3-Bromo-5-(trifluoromethyl)phenyl)ethanol. A flask was charged with isopropanol (10 mL), dichloro(p-cymene)ruthenium (II) dimer (32 mg, 0.05 mmol), and (1S, 2R)-1-amino-2,3-dihydro-1H-inden-2-ol (16 mg, 0.1 mmol). After aging for 30 min, 1-(3-bromo-5-(trifluoromethyl)phenyl)ethanone (2.8 g, 10.5 mmol) was added and the reaction degassed by cooling it to −78° C., putting it under high vacuum, venting to nitrogen, and repeating the process ca. 6 times. The reaction was warmed to 0° C., treated with sodium hydroxide (5 M in water, 48 µL, 0.23 mmol), stirred at 0° C. for 5 hours and at room temperature overnight. The reaction was quenched by addition of 1 M hydrochloric acid and extracted into pentane. The organics were washed with water (2×), then brine (2×), dried over sodium sulfate, and concentrated. Column chromatography (15% ethyl acetate/hexanes) gave 2.79 g (99%) as a yellowish oil. ¹H NMR (500 MHz, CDCl₃) δ ppm 7.69 (s, 1H), 7.63 (s, 1H), 7.53 (s, 1H), 4.91 (q, J=6.6 Hz, 1H), 1.49 (d, J=6.6 Hz, 3H).

Intermediate 100

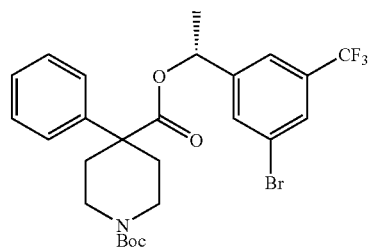

(R)-4-(1-(3-Bromo-5-(trifluoromethyl)phenyl)ethyl) 1-tert-butyl 4-phenylpiperidine-1,4-dicarboxylate. A suspension of 1-(tert-butoxycarbonyl)-4-phenylpiperidine-4-carboxylic acid (3.8 g, 10.3 mmol) in a dichloromethane (5 mL) and toluene (30 mL) mixture was treated with 1,3-dicyclohexylcarbodiimide (2.96 g, 14.4 mmol) and stirred for 30 min. The suspension was cooled to 0° C. and treated with (R)-1-(3-bromo-5-(trifluoromethyl)phenyl)ethanol (2.79 g, 10.3 mmol) and dimethylaminopyridine (1.26 g, 10.3 mmol). The ice bath was removed and the suspension stirred at room temperature for 60 h. The reaction mixture was poured into pentane, filtered, and the solids washed several times with pentane. The filtrate was washed with 1 N hydrochloric acid (1×), water (2×), then 1 N sodium hydroxide, then brine (2×), dried over sodium sulfate, and concentrated. Flash chromatography on silica gel (12% ethyl acetate/hexanes) gave 4.8 g (84%) as a light yellow oil. $^1$H NMR (500 MHz, CDCl$_3$) δ ppm 7.58 (s, 1H), 7.23-7.33 (m, 6H), 7.19 (s, 1H), 5.80 (q, J=6.6 Hz, 1H), 3.82-3.97 (m, 2H), 2.97-3.09 (m, 2H), 2.44-2.53 (m, 2H), 1.76-2.01 (m, 2H), 1.42 (s, 9H), 1.40 (m, 3H). Mass spec.: 558.06 (MH)$^+$.

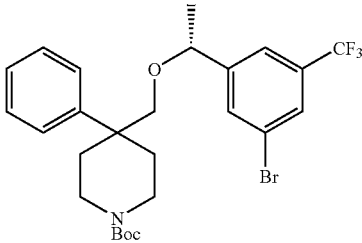

Intermediate 101

(R)-tert-Butyl 4-((1-(3-bromo-5-(trifluoromethyl)phenyl)ethoxy)methyl)-4-phenylpiperidine-1-carboxylate. (R)-4-(1-(3-Bromo-5-(trifluoromethyl)phenyl)ethyl) 1-tert-butyl 4-phenylpiperidine-1,4-dicarboxylate (3.8 g, 6.9 mmol) was dissolved in methylene chloride (40 mL), cooled to −78° C. and treated with diisobutylaluminum hydride (1 M in methylene chloride (13.8 mL, 13.8 mmol). After stirring at −78° C. for 1 h, the reaction was treated with pyridine (1.64 mL, 20.6 mmol), dimethylaminopyridine (1.68 g, 13.8 mmol), and acetic anhydride (2.9 mL, 41.2 mmol). The reaction was warmed to −10° C. over several hours in a dewar, quenched by addition of a few drops of methanol (until no bubbling was observed) followed by addition of excess saturated sodium potassium tartarate. The reaction was stirred at room temperature overnight. The layers were separated and the organic layer washed with brine (2×), dried over sodium sulfate, and concentrated to afford a precipitate which was immediately dissolved in methylene chloride (50 mL) and treated with triethylsilane (6.7 mL, 45.3 mmol). The solution was cooled to −78° C. and treated with boron trifluoride diethyl etherate (1.8 mL, 3.8 mmol). After 1 h, the reaction mixture was allowed to warm slowly to 0° C. and stirred for 7 h. The reaction was quenched by addition concentrated sodium bicarbonate and the layers were separated. The organic layer was washed with water (2×), then brine (2×), dried over sodium sulfate, and concentrated. Flash chromatography on silica gel (10% ethyl acetate/hexanes) gave 1.7 g in a 1:1 ratio of the desired material and the ester starting material which could not be separated. The mixture in 1:1 tetrahydrofuran/methanol (12 mL) at room temperature was treated with a solution of lithium hydroxide monohydrate (271 mg, 1.62 mmol) in water (6 mL). The solution was stirred at room temperature for 1 h, diluted with ethyl acetate, washed with water (2×), then brine (2×), dried over sodium sulfate, and concentrated to afford 900 mg (24%) as a clear oil. Chiral SFC (ChiralCel OJ-H, 1:99 methanol/carbon dioxide) showed the optical purity to be 92% ee. $^1$H NMR (500 MHz, CDCl$_3$) δ ppm 7.59 (s, 1H), 7.29-7.36 (m, 5H), 7.22-7.25 (m, 2H), 4.16 (q, J=6.4 Hz, 1H), 3.74 (m, 2H), 3.25 (d, J=9.2 Hz, 1H), 3.21 (d, J=8.9 Hz, 1H), 2.99-3.06 (m, 2H), 2.11-2.21 (m, 2H), 1.83-1.90 (m, 2H), 1.43 (s, 9H), 1.28 (m, 3H). Mass spec.: 544.01 (MH)$^+$.

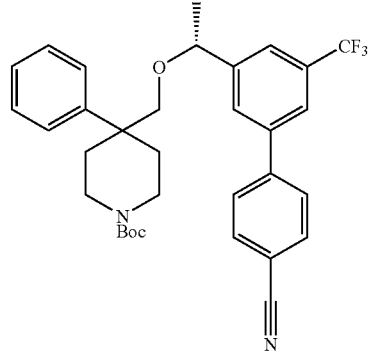

Intermediate 102

(R)-tert-Butyl 4-((1-(4'-cyano-5-(trifluoromethyl)biphenyl-3-yl)ethoxy)methyl)-4-phenylpiperidine-1-carboxylate. (R)-tert-Butyl 4-((1-(3-bromo-5-(trifluoromethyl)phenyl)ethoxy)methyl)-4-phenylpiperidine-1-carboxylate (0.35 g, 0.65 mmol), 4-cyanophenylboronic acid (284 mg, 1.93 mmol), and tetrakis(triphenylphosphine) palladium(0) (75 mg, 0.07 mmol) were combined in dry tetrahydrofuran (5 mL) in a microwave tube and sealed. After flushing with nitrogen, 2.3 mL of a 1 N potassium hydroxide aqueous solution was introduced. The mixture was heated at 120° C. for 1 h via microwave. After cooling to room temperature, the reaction mixture was concentrated and purified by flash chromatography on silica gel (15% ethyl acetate/hexanes) to afford 300 mg (82%) as an oil. LC/MS: $t_R$=3.51 min, 565.23 (MH)$^+$. (Phenomenex C18 4.6×50 mm, 10% MeOH/90% H$_2$O/0.1% TFA→90% MeOH/10% H$_2$O/0.1% TFA, Gradient time=4 min., Flow rate=4 mL/min.).

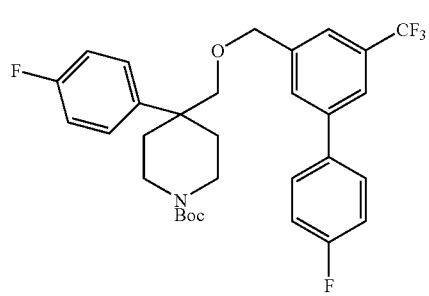

Intermediate 103 tert-Butyl 4-(((4'-fluoro-5-(trifluoromethyl)biphenyl-3-yl)methoxy)methyl)-4-(4-fluorophenyl)piperidine-1-carboxylate. $^1$H-NMR (CDCl$_3$, 500 MHz) δ 7.64 (s, 1H), 7.46 (m, 2H), 7.40 (s, 1H), 7.28-7.35 (m, 3H), 7.15 (m, 2H), 7.01 (m, 2H), 4.46 (s, 2H), 3.73 (m, 2H), 3.43 (s, 2H), 3.05 (m, 2H), 2.16 (m, 4H), 1.86 (m, 2H), 1.43 (s, 9H); $^{13}$C NMR (126 MHz, CDCl$_3$) δ ppm 164.0, 162.5, 162.1, 160.5, 155.0, 141.2, 140.3, 138.6 (m), 135.8 (m), 131.5 (q, J=32 Hz), 128.9, 129.83, 128.80, 124.1 (q, J=273 Hz), 122.9 (q, J=3.8 Hz), 122.6 (q, J=3.8 Hz), 116.1, 115.9, 115.4, 115.2, 79.5, 72.5, 41.3, 40.1, 32.3, 28.5.

Intermediate 103

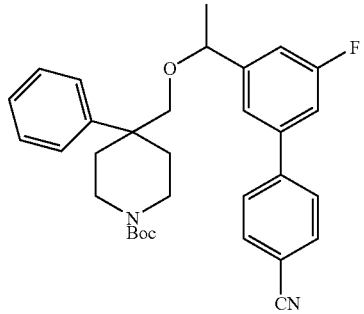

(±)-tert-Butyl 4-((1-(4'-cyano-5-fluorobiphenyl-3-yl)ethoxy)methyl)-4-phenylpiperidine-1-carboxylate.
$^1$H-NMR (CDCl$_3$, 500 MHz) δ 7.71 (d, J=8.2 Hz, 2H), 7.54 (d, J=8.2 Hz, 2H), 7.32 (m, 4H), 7.20 (m, 1H), 7.10 (m, 1H), 7.00 (s, 1H), 6.77 (d, J=9.2 Hz, 1H), 4.22 (q, J=6.4 Hz, 1H), 3.74 (m, 2H), 3.27 (q$_{AB}$, J$_{AB}$=9.2 Hz, 2H), 3.02 (m, 2H), 2.21 (m, 1H), 2.13 (m, 1H), 1.88 (m, 2H), 1.43 (s, 9H), 1.32 (d, J=6.4 Hz, 3H). Mass spec.: 515.32 (MH)$^+$.

Intermediate 105

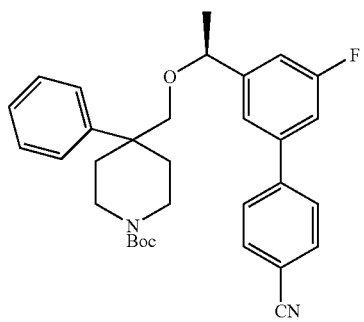

(S)-tert-Butyl 4-((1-(4'-cyano-5-(trifluoromethyl)biphenyl-3-yl)ethoxy)methyl)-4-phenylpiperidine-1-carboxylate.
A microwave tube was charged with (S)-tert-butyl 4-((1-(3-bromo-5-(trifluoromethyl)phenyl)ethoxy)methyl)-4-phenylpiperidine-1-carboxylate (36 mg, 0.066 mmol), 4-cyanophenylboronic acid (39 mg, 0.27 mmol), and tetrakis(triphenylphosphine) palladium(0) (7.7 mg, 6.6 µmol). The tube was flushed with nitrogen, treated with tetrahydrofuran (2 mL) and potassium hydroxide (1 M in water, 0.265 mL, 0.265 mmol). The tube was sealed and heated at 110° C. for 1 h via microwave. The reaction was cooled, poured into diethyl ether, washed with water (2×), then brine, dried over magnesium sulfate, and concentrated. Column chromatography (12%→15% ethyl acetate/hexanes) gave 21 mg (56%) as a white foam solid. $^1$H NMR (500 MHz, CDCl$_3$) δ ppm 7.74 (m, 2H), 7.65 (s, 1H), 7.55 (m, 2H), 7.37 (s, 2H), 7.26-7.34 (m, 4H), 7.17 (m, 1H), 4.30 (q, J=6.4 Hz, 1H), 3.74 (m, 2H), 3.32 (m, 1H), 3.25 (m, 1H), 3.02 (m, 2H), 2.23 (m, 1H), 2.12 (m, 1H), 1.75-1.97 (m, 2H), 1.43 (m, 9H), 1.35 (m, 3H). Mass spec.: 587.22 (MNa)$^+$.

Intermediate 106

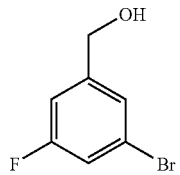

(3-Bromo-5-fluorophenyl)methanol. 3-Bromo-5-fluorobenzoic acid (1.0 g, 4.52 mmol) was suspended in tetrahydrofuran (8 mL) and cooled to 0° C. To this solution was added borane tetrahydrofuran complex (1 M in tetrahydrofuran, 9 mL, 9.0 mmol) cautiously over 15 min. The reaction mixture was allowed to warm to room temperature overnight. The mixture was cooled to 0° C., treated with excess methanol, diluted with ethyl acetate, washed with 1 N sodium hydroxide (2×), then brine (2×), dried over sodium sulfate, and concentrated to afford 0.88 g (95%) as a white powder. $^1$H-NMR (CDCl$_3$, 500 MHz) 7.29 (s, 1H), 7.16 (d, J=7.9 Hz, 1H), 7.03 (d, J=9.2 Hz, 1H), 4.66 (s, 2H).

Intermediate 107

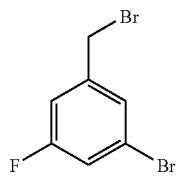

1-Bromo-3-(bromomethyl)-5-fluorobenzene. (3-Bromo-5-fluorophenyl)methanol (0.78 g, 3.8 mmol) and triphenylphosphine (2.0 g, 7.6 mmol) were combined in tetrahydrofuran (20 mL) and cooled to 0° C. N-Bromosuccinimide (1.4 g, 7.98 mmol) was introduced in portions and the reaction allowed to warm to room temperature. After 16 h, the reaction mixture was diluted with ethyl acetate, washed with concentrated sodium bicarbonate (2×), then brine (2×), dried over sodium sulfate, and concentrated. Column chromatography on silica gel (5% ethyl acetate/hexanes) gave 0.8 g (79%) as a white powder. $^1$H-NMR (CDCl$_3$, 300 MHz) 7.30 (s, 1H), 7.14-7.18 (m, 1H), 7.01-7.05 (m, 1H), 4.36 (s, 2H).

Intermediate 108

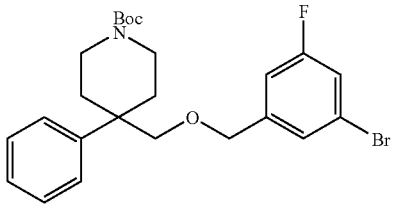

tert-Butyl 4-((3-bromo-5-fluorobenzyloxy)methyl)-4-phenylpiperidine-1-carboxylate. 1-Bromo-3-(bromomethyl)-5-fluorobenzene (0.8 g, 3.0 mmol) and tert-butyl 4-(hydroxymethyl)-4-phenylpiperidine-1-carboxylate (0.72 g, 2.5 mmol) were combined in dimethylformamide (8 mL) and cooled to 0° C. The reaction was treated with sodium hydride (120 mg, 4.98 mmol), stirred at 0° C. for 1 h, and at room temperature for 30 min. The reaction mixture was diluted with water and extracted with ethyl acetate (2×). The organic layers were pooled together, washed with brine (2×), dried over sodium sulfate, and concentrated. Column chromatography on silica gel (20% ethyl acetate/hexanes) gave 1.2 g (84%). ¹H-NMR (CDCl₃, 500 MHz) δ 7.34-7.38 (m, 4H), 7.24-7.25 (m, 1H), 7.08-7.10 (m, 1H), 7.01 (s, 1H), 6.70-6.72 (m, 1H), 4.29 (s, 2H), 3.74-3.77 (m, 2H), 3.38 (s, 2H), 3.00-3.06 (m, 2H), 2.17-2.20 (m, 2H), 1.84-1.90 (m, 2H), 1.44 (s, 9H). Mass spec.: 501.32 (MNa)⁺.

Intermediate 109

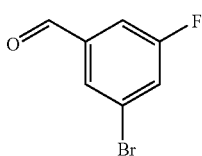

3-Bromo-5-fluorobenzaldehyde. To a solution of (3-bromo-5-fluorophenyl)methanol (2 g, 9.75 mmol) and triethylamine (2.72 mL, 19.5 mmol) in dimethylsulfoxide (25 mL) at 10° C. was added sulfur trioxide-pyridine (3.11 g, 19.5 mmol) in several portions. The mixture was stirred at room temperature for 30 min. The reaction was poured into ice water/pentane and the layers separated. The organics were washed with 1 M potassium bisulfate, then water, then brine, dried over magnesium sulfate, and concentrated. Column chromatography (3% ethyl acetate/hexanes) gave 1.45 g (73%) as a white solid. ¹H-NMR (CDCl₃, 500 MHz) δ 9.92 (d, J=1.8 Hz, 1H), 7.80 (m, 1H), 7.50 (m, 2H); ¹³C NMR (126 MHz, CDCl₃) δ ppm 189.2, 164.0, 162.0, 139.3, 129.0 (m), 125.0, 124.8, 123.8, 123.7, 114.8, 114.6.

Intermediate 110

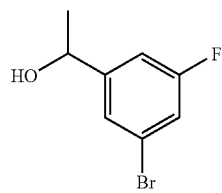

(±)-1-(3-Bromo-5-fluorophenyl)ethanol. To a solution of 3-bromo-5-fluorobenzaldehyde (1.45 g, 7.14 mmol) in tetrahydrofuran (15 mL) at −78° C. was added methylmagnesium bromide (3M in diethyl ether, 2.98 mL, 8.93 mmol). The reaction was stirred at −78° C. for 30 min and then at 0° C. for 30 min. The reaction was quenched by addition of saturated ammonium chloride and poured into pentane/water. The organics were washed with water (2×), then brine, dried over magnesium sulfate, and concentrated. Column chromatography (12%→25% ethyl acetate/hexanes) gave 1.38 g (88%) as a colorless oil. ¹H-NMR (CDCl₃, 500 MHz) δ 7.29 (s, 1H), 7.13 (m, 1H), 7.02 (m, 1H), 4.84 (q, J=6.4 Hz, 1H), 2.06 (bs, 1H), 1.46 (d, J=6.4 Hz, 3H); ¹³C NMR (126 MHz, CDCl₃) δ ppm 163.9, 161.9, 150.1 (m), 124.5 (m), 122.7, 122.6, 118.1, 117.9, 111.6, 111.4, 69.4, 25.3.

Intermediate 111

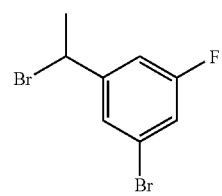

(±)-1-Bromo-3-(1-bromoethyl)-5-fluorobenzene. To a solution of (±)-1-(3-bromo-5-fluorophenyl)ethanol (1.0 g, 4.6 mmol) and carbon tetrabromide (1.82 g, 5.48 mmol) in tetrahydrofuran (5 mL) at 0° C. was added triphenylphosphine (1.44 g, 5.48 mmol). The resulting solution was stirred at room temperature for 45 min. The reaction was diluted with several volumes of pentane, and filtered to remove the undissolved solids which were discarded. The organics were concentrated and purified by column chromatography (1% ethyl acetate/hexanes) to give 1.26 g (98%) as a colorless oil. ¹H-NMR (CDCl₃, 500 MHz) δ 7.35 (s, 1H), 7.17 (m, 1H), 7.09 (m, 1H), 5.06 (q, J=7.0 Hz, 1H), 2.00 (d, J=7.0 Hz, 3H); ¹³C NMR (126 MHz, CDCl₃) δ ppm 163.6, 161.6, 147.2 (m), 126.0 (m), 122.8, 122.7, 119.2, 119.0, 113.3, 113.1, 46.5, 26.7.

Intermediate 112

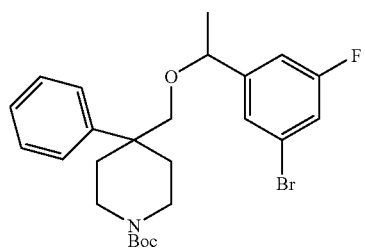

(±)-tert-Butyl 4-((1-(3-bromo-5-fluorophenyl)ethoxy)methyl)-4-phenylpiperidine-1-carboxylate. To a solution of tert-butyl 4-(hydroxymethyl)-4-phenylpiperidine-1-carboxylate (827 mg, 2.84 mmol) and (±)-1-bromo-3-(1-bromoethyl)-5-fluorobenzene (800 mg, 2.84 mmol) in dimethylformamide (3 mL) at 0° C. was added sodium hydride (75 mg, 3.1 mmol). The ice bath was removed and the resulting mixture stirred at room temperature for 1 h. The reaction was cooled to 0° C., diluted with diethyl ether, and quenched by the cautious addition of saturated ammonium chloride. The mixture was poured into water and extracted into diethyl ether. The ethereal was washed with water, then brine, dried over magnesium sulfate, and concentrated. Column chromatography (12→18% ethyl acetate/hexanes) gave 260 mg (19%) as a colorless oil. ¹H-NMR (CDCl₃, 500 MHz) δ 7.33 (m, 4H), 7.24 (m, 1H), 7.06 (m, 1H), 6.95 (s, 1H), 6.63 (d, J=9.2 Hz, 1H), 4.09 (t, J=6.4 Hz, 1H), 3.75 (m, 2H), 3.22 (q_{AB}, J_{AB}=8.9 Hz, 2H), 3.02 (m, 2H), 2.16 (m, 2H), 1.87 (m, 2H), 1.44 (s, 9H), 1.25 (d, J=6.4 Hz, 3H); ¹³C NMR (126 MHz, CDCl₃) δ ppm 163.8, 161.8, 155.1, 148.63, 148.57, 142.7, 128.5, 127.3, 126.5, 125.0 (m), 122.5, 122.4, 118.0, 117.8, 111.9, 111.8, 79.4, 78.1, 77.5, 41.7, 40.3 (br), 32.0, 31.7, 28.6, 23.8. Mass spec.: 492.15 (MH)⁺.

Intermediate 113

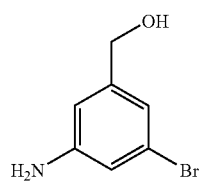

(3-Amino-5-bromophenyl)methanol. (3-Bromo-5-nitrophenyl)methanol (3.9 g, 16.8 mmol) in methanol (35 mL) was flushed with nitrogen, and treated with platinum (IV) oxide (390 mg). The flask was flushed with hydrogen and allowed to stir under an atmosphere of hydrogen for 1 h. The reaction was flushed with nitrogen, filtered through celite, and concentrated to afford 3.1 g (94%). ¹H-NMR (CDCl₃, 300 MHz) δ 6.95 (s, 1H), 6.80 (s, 1H), 6.79 (s, 1H), 4.61 (s, 2H). Mass spec.: 203.96 (MH)⁺.

Intermediate 114

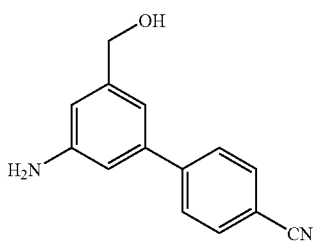

3'-Amino-5'-(hydroxymethyl)biphenyl-4-carbonitrile. A microwave tube was charged with (3-amino-5-bromophenyl) methanol (1.0 g, 4.98 mmol), 4-cyanophenylboronic acid (2.2 g, 15 mmol), and tetrakis(triphenylphosphine) palladium(0) (77.6 mg, 0.05 mmol). The tube was flushed with nitrogen, treated with tetrahydrofuran (6 mL) and potassium hydroxide (2 M in water, 3.0 mL, 6.0 mmol). The tube was sealed and heated at 120° C. for 1 h via microwave. The reaction was cooled, poured into ethyl acetate, washed with water (2×), brine, dried over sodium sulfate, and concentrated. Column chromatography (10% ethyl acetate/hexanes) gave 0.51 g (46%) as a colorless oil. LC/MS: $t_R$=1.25 min, 225.11 (MH)$^+$. (Phenomenex C18 4.6×50 mm, 10% MeOH/90% H$_2$O/0.1% TFA→90% MeOH/10% H$_2$O/0.1% TFA, Gradient time=4 min., Flow rate=4 mL/min.).

Intermediate 115

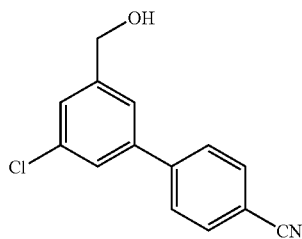

3'-Chloro-5'-(hydroxymethyl)biphenyl-4-carbonitrile. A solution of 3'-amino-5'-(hydroxymethyl)biphenyl-4-carbonitrile (120 mg, 0.54 mmol) in dry acetonitrile (1 mL) was added dropwise to a solution of copper (II) chloride (86 mg, 0.64 mmol) and tert-butyl nitrite (91 μL, 0.78 mmol) in acetonitrile (2 mL) at 65° C. After stirring for 30 min at 65° C., the reaction mixture was cooled to room temperature, poured into a 1 N hydrochloric acid solution, and extracted with ethyl acetate (2×). The organic layers were pooled together, washed with brine (2×), dried over sodium sulfate, and concentrated. Column chromatography on silica gel (20% ethyl acetate/hexanes) afforded 46 mg (35%). LC/MS: $t_R$=2.54 min, 244.03 (MH)$^+$. (Phenomenex C18 4.6×50 mm, 10% MeOH/ 90% H$_2$O/0.1% TFA→90% MeOH/10% H$_2$O/0.1% TFA, Gradient time=4 min., Flow rate=4 mL/min.).

Intermediate 116

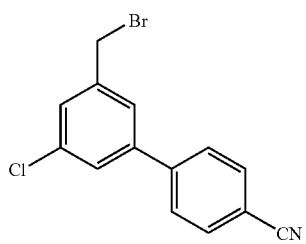

3'-(Bromomethyl)-5'-chlorobiphenyl-4-carbonitrile. (3-Bromo-5-(trifluoromethyl)phenyl)methanol (34 mg, 0.14 mmol) and triphenylphosphine (73.4 mg, 0.28 mmol) were combined in tetrahydrofuran (2 mL) and cooled to 0° C. N-Bromosuccinimide (51.1 mg, 0.29 mmol) was introduced in portions and the reaction allowed to warm to room temperature. After 16 h, the reaction mixture was diluted with ethyl acetate, washed with concentrated sodium bicarbonate (2×), then brine (2×), dried over sodium sulfate, and concentrated. Column chromatography on silica gel (5% ethyl acetate/hexanes) gave 40 mg (93%). $^1$H-NMR (CDCl$_3$, 300 MHz) δ 7.71-7.74 (m, 2H), 7.62-7.64 (m, 2H), 7.45-7.47 (m, 2H), 7.40-7.42 (m, 1H), 4.46 (s, 2H).

Intermediate 117

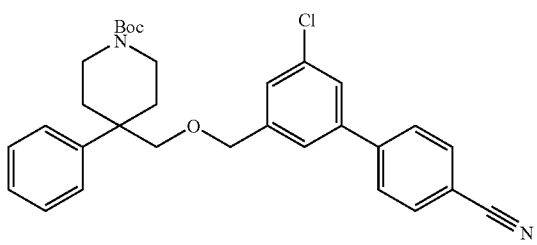

tert-Butyl 4-(((5-chloro-4'-cyanobiphenyl-3-yl)methoxy) methyl)-4-phenylpiperidine-1-carboxylate. 3'-(Bromomethyl)-5'-chlorobiphenyl-4-carbonitrile (38.3 mg, 0.12 mmol) and tert-butyl 4-(hydroxymethyl)-4-phenylpiperidine-1-carboxylate (30.3 mg, 0.1 mmol) were combined in dimethylformamide (2 mL) and cooled to 0° C. The reaction was treated with sodium hydride (5 mg, 0.2 mmol), stirred at 0° C. for 1 h, and at room temperature for 30 min. The reaction mixture was diluted with water and extracted with ethyl acetate (2×). The organic layers were pooled together, washed with brine (2×), dried over sodium sulfate, and concentrated. Column chromatography on silica gel (25% ethyl acetate/ hexanes) gave 35 mg (56%). $^1$H-NMR (CDCl$_3$, 300 MHz) δ 7.71 (s, 1H), 7.68 (s, 1H), 7.55 (s, 1H), 7.52 (s, 1H), 7.39 (s, 1H), 7.28-7.35 (m, 4H), 7.19-7.21 (m, 1H), 7.10-7.13 (m, 2H), 4.36 (s, 2H), 3.69-3.76 (m, 2H), 3.41 (s, 2H), 2.97-3.06 (m, 2H), 2.15-2.19 (m, 2H), 1.80-1.90 (m, 2H), 1.40 (s, 9H). Mass spec.: 517.21 (MH)$^+$.

Intermediate 118

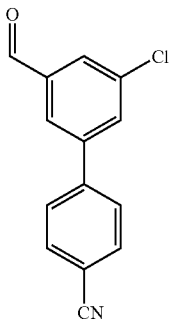

3'-Chloro-5'-formylbiphenyl-4-carbonitrile. To a solution of 3'-chloro-5'-(hydroxymethyl)biphenyl-4-carbonitrile (330 mg, 1.35 mmol) and triethylamine (0.377 mL, 2.71 mmol) in dimethylsulfoxide (5 mL) at 10° C. was added sulfur trioxide-pyridine (259 mg, 1.63 mmol) in one portion. The bath was removed and stirring continued for 30 min. The reaction was poured into ice water and extracted with ethyl acetate (3×)

and the layers separated. The organics were washed with 1 M potassium bisulfate, then water, then brine, dried over magnesium sulfate, and concentrated. Column chromatography (12%→50% ethyl acetate/hexanes) gave 280 mg (86%) as a white solid. $^1$H-NMR (CDCl$_3$, 500 MHz) δ 10.04 (s, 1H), 8.01 (s, 1H), 7.89 (s, 1H), 7.85 (s, 1H), 7.80 (m, 2H), 7.75 (m, 2H).

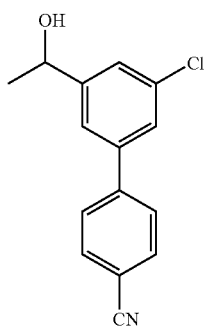

Intermediate 119

(±)-3'-Chloro-5'-(1-hydroxyethyl)biphenyl-4-carbonitrile. To a solution of 3'-chloro-5'-formylbiphenyl-4-carbonitrile (280 mg, 1.16 mmol) in tetrahydrofuran (5 mL) at −78° C. was added methylmagnesium bromide (3M in diethyl ether, 0.772 mL, 2.32 mmol). The reaction was stirred at −78° C. for 15 min and then allowed to gradually warm to −20° C. over 1 h. The reaction was recooled to −78° C. and quenched by the dropwise addition of saturated ammonium chloride. The mixture was poured into water and extracted into diethyl ether. The ethereal was washed with brine, dried over magnesium sulfate, and concentrated. Column chromatography (25%→50% ethyl acetate/hexanes) gave 171 mg (57%) as a colorless oil. $^1$H-NMR (CDCl$_3$, 500 MHz) δ 7.69 (d, J=8.2 Hz, 2H), 7.64 (d, J=8.2 Hz, 2H), 7.46 (s, 1H), 7.43 (s, 1H), 7.40 (s, 1H), 4.93 (q, J=6.4 Hz, 1H), 2.37 (bs, 1H), 1.51 (d, J=6.7 Hz, 3H); $^{13}$C NMR (126 MHz, CDCl$_3$) δ ppm 149.0, 144.3, 141.1, 135.2, 132.8, 127.9, 126.3, 125.9, 122.6, 118.7, 111.7, 69.7, 25.6.

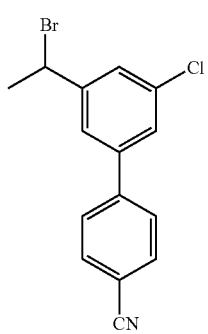

Intermediate 120

(±)-3'-(1-Bromoethyl)-5'-chlorobiphenyl-4-carbonitrile. To a solution of (±)-3'-chloro-5'-(1-hydroxyethyl)biphenyl-4-carbonitrile (171 mg, 0.664 mmol) and carbon tetrabromide (264 mg, 0.796 mmol) in tetrahydrofuran (2 mL) at 0° C. was added triphenylphosphine (209 mg, 0.796 mmol). The resulting solution was stirred at room temperature for 45 min. The reaction was diluted with ca. 2 volumes of pentane and filtered to remove the undissolved solids which were discarded. The organics were concentrated and purified by column chromatography (3%→8% ethyl acetate/hexanes) to give 201 mg (94%) as a colorless oil. $^1$H-NMR (CDCl$_3$, 500 MHz) δ 7.74 (d, J=8.2 Hz, 2H), 7.66 (d, J=8.2 Hz, 2H), 7.50 (s, 1H), 7.47 (s, 2H), 5.18 (q, J=6.7 Hz, 1H), 2.06 (d, J=7.0 Hz, 3H); $^{13}$C NMR (126 MHz, CDCl$_3$) δ ppm 146.1, 143.8, 141.5, 135.4, 132.8, 127.9, 127.3, 127.1, 124.2, 118.6, 112.1, 47.4, 26.8.

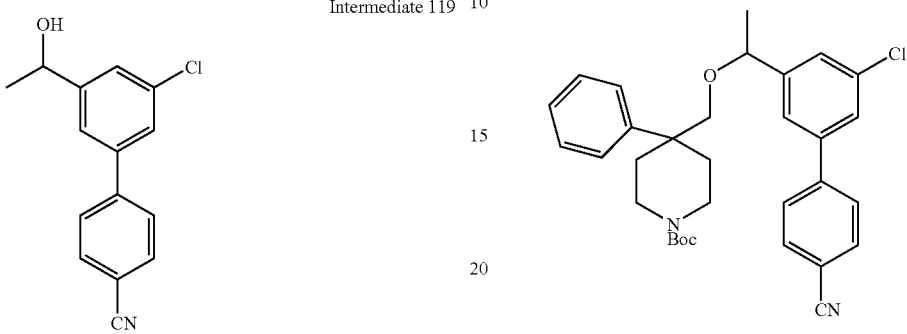

Intermediate 121

(±)-tert-Butyl 4-((1-(5-chloro-4'-cyanobiphenyl-3-yl)ethoxy)methyl)-4-phenylpiperidine-1-carboxylate. To a solution of tert-butyl 4-(hydroxymethyl)-4-phenylpiperidine-1-carboxylate (182 mg, 0.624 mmol) and (±)-3'-(1-bromoethyl)-5'-chlorobiphenyl-4-carbonitrile (200 mg, 0.624 mmol) in dimethylformamide (1.5 mL) at 0° C. was added sodium hydride (16.5 mg, 0.686 mmol). The reaction was stirred at room temperature for 1 h. The reaction was cooled to 0° C., diluted with diethyl ether, and quenched by the cautious addition of saturated ammonium chloride. The mixture was poured into water and extracted into diethyl ether. The ethereal was washed with water, then brine, dried over magnesium sulfate, and concentrated. Column chromatography (12→18% ethyl acetate/hexanes) gave 82 mg (25%) as a colorless foam. $^1$H-NMR (CDCl$_3$, 500 MHz) δ 7.71 (d, J=8.5 Hz, 2H), 7.52 (d, J=8.5 Hz, 2H), 7.38 (s, 1H), 7.31 (m, 4H), 7.18 (m, 1H), 7.07 (s, 1H), 7.05 (s, 1H), 4.20 (q, J=6.4 Hz, 1H), 3.74 (m, 2H), 3.26 (q$_{AB}$, J$_{AB}$=8.9 Hz, 2H), 3.01 (m, 2H), 2.22 (m, 1H), 2.11 (m, 1H), 1.87 (m, 2H), 1.43 (s, 9H), 1.32 (d, J=6.7 Hz, 3H); $^{13}$C NMR (126 MHz, CDCl$_3$) δ ppm 155.1, 147.3, 144.2, 142.8, 141.0, 135.1, 132.7, 128.5, 127.9, 127.4, 126.4, 126.3, 126.2, 122.9, 118.8, 111.7, 79.4, 78.1, 77.8, 41.6, 40.2 (br), 32.1, 31.7, 28.6, 24.1. Mass spec.: 531.31 (MH)$^+$.

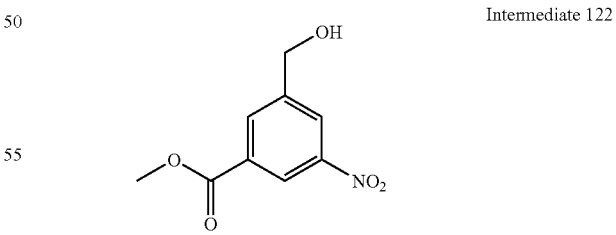

Intermediate 122

Methyl 3-(hydroxymethyl)-5-nitrobenzoate. 3-(Methoxycarbonyl)-5-nitrobenzoic acid (20.0 g, 88.9 mmol) was combined with tetrahydrofuran (150 mL) and cooled to 0° C. To this solution was added a 1 M borane tetrahydrofuran complex (178 mL, 178 mmol) cautiously over 15 min and the reaction mixture allowed to warm to room temperature overnight. The mixture was cooled to 0° C., treated with excess methanol and concentrated in vacuo to afford to afford a precipitate which was dissolved in ethyl acetate, washed with concentrated sodium bicarbonate (2×), then brine (2×), dried over sodium sulfate, and concentrated to afford 18.2 g (97%) which was used without further purification. $^1$H-NMR (CDCl$_3$, 300 MHz) δ 8.70 (s, 1H), 8.39 (s, 1H), 8.30 (s, 1H), 4.84 (s, 2H), 3.95 (s, 3H). Mass spec.: 212.06 (MH)$^+$.

Intermediate 123

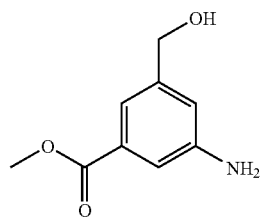

Methyl 3-amino-5-(hydroxymethyl)benzoate. Methyl 3-(hydroxymethyl)-5-nitrobenzoate (11.2 g, 53 mmol) in methanol (50 mL) was flushed with nitrogen, and treated with palladium (10% on charcoal, 1.1 g). The flask was flushed with hydrogen and allowed to stir under an atmosphere of hydrogen overnight. The reaction was flushed with nitrogen, filtered through celite, and concentrated. Column chromatography on silica gel (50% ethyl acetate/hexanes) afforded 2.8 g (29%). $^1$H-NMR (CD$_3$OD, 300 MHz) δ 7.34 (s, 1H), 7.27 (s, 1H), 6.94 (s, 1H), 4.55 (s, 2H), 3.88 (s, 3H). Mass spec.: 182.09 (MH)$^+$.

Intermediate 124

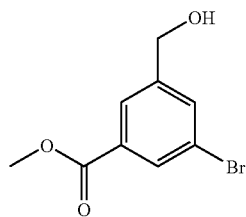

Methyl 3-bromo-5-(hydroxymethyl)benzoate. Methyl 3-amino-5-(hydroxymethyl)benzoate (2.4 g, 13.2 mmol) in dry acetonitrile (10 mL) was added dropwise to a solution of copper (II) bromide (3.54 g, 15.8 mmol) and tert-butyl nitrite (2.24 mL, 18.9 mmol) in acetonitrile (20 mL) at 65° C. After stirring for 30 min at 65° C., the reaction mixture was cooled to room temperature, poured into a 1 N hydrochloric acid solution, and extracted with ethyl acetate (2×). The organic layers were pooled together, washed with brine (2×), dried over sodium sulfate, and concentrated. Column chromatography on silica gel (30% ethyl acetate/hexanes) afforded 2.0 g (62%). $^1$H-NMR (CDCl$_3$, 300 MHz) δ 8.04 (s, 1H), 7.90 (s, 1H), 7.69 (s, 1H), 4.70 (s, 2H), 3.89 (s, 3H). Mass spec.: 246.98 (MH)$^+$.

Intermediate 125

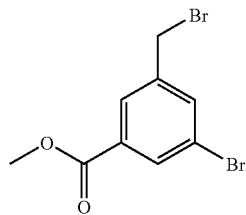

Methyl 3-bromo-5-(bromomethyl)benzoate. Methyl 3-bromo-5-(hydroxymethyl)benzoate (2.0 g, 8.2 mmol) and triphenylphosphine (4.28 g, 16.3 mmol) were combined in tetrahydrofuran (20 mL) and cooled to 0° C. N-Bromosuccinimide (3.05 g, 17.1 mmol) was introduced in portions and the reaction allowed to warm to room temperature. After 16 h, the reaction mixture was diluted with ethyl acetate, washed with concentrated sodium bicarbonate (2×), then brine (2×), dried over sodium sulfate, and concentrated. Column chromatography on silica gel (10% ethylacete/hexanes) gave 2.1 g (83%) as a light brown oil. $^1$H-NMR (CDCl$_3$, 300 MHz) δ 8.07 (s, 1H), 7.96 (s, 1H), 7.70 (s, 1H), 4.42 (s, 2H), 3.90 (s, 3H). Mass spec.: 308.93 (MH)$^+$.

Intermediate 126

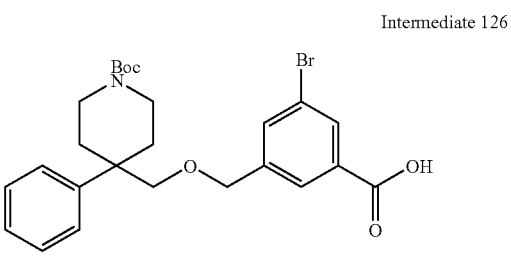 [SMILES: CC(C)(C)OC(=O)N1CCC(COCc2cc(Br)cc(C(=O)O)c2)(c2ccccc2)CC1]

3-Bromo-5-(((1-(tert-butoxycarbonyl)-4-phenylpiperidin-4-yl)methoxy)methyl)benzoic acid. Methyl 3-bromo-5-(bromomethyl)benzoate (2.1 g, 6.81 mmol) and tert-butyl 4-(hydroxymethyl)-4-phenylpiperidine-1-carboxylate (1.8 g, 6.2 mmol) were combined in dimethylformamide (21 mL) and cooled to 0° C. The reaction was treated with sodium hydride (298 mg, 12.4 mmol), stirred at 0° C. for 1 h, and at room temperature for 30 min. The reaction was cooled to 0° C. and treated lithium hydroxide monohydrate (0.54 g, 13.6 mmol). The solution was stirred at room temperature for 16 h and the solvents evaporated. The resultant residue was diluted with water (10 mL) and the pH adjusted to ca. 1 with 1 N hydrochloric acid. The resultant white suspension was stored at 4° C. overnight and the product was collected by filtration, washed with a small amount of water, and dried in vacuo for several hours to afford 2.4 g (70%) as a white powder. LC/MS: $t_R$=3.33 min, 506.20 (MH)$^+$. (Phenomenex C18 4.6× 50 mm, 10% MeOH/90% H$_2$O/0.1% TFA→90% MeOH/ 10% H$_2$O/0.1% TFA, Gradient time=4 min., Flow rate=4 mL/min.).

Intermediate 127

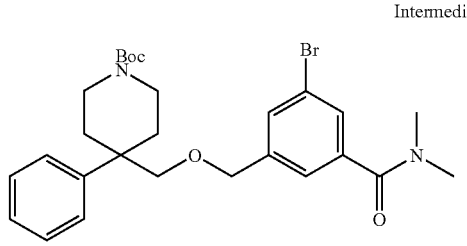

tert-Butyl 4-((3-bromo-5-(dimethylcarbamoyl)benzyloxy)methyl)-4-phenylpiperidine-1-carboxylate. A stirred solution of 3-bromo-5-(((1-(tert-butoxycarbonyl)-4-phenylpiperidin-4-yl)methoxy)methyl)benzoic acid (160 mg, 0.32 mmol) in dimethylformamide (5 mL) was cooled to 0° C. and sequentially treated with methylene chloride (2 mL), dimethylamine (1 N in tetrahydrofuran, 0.32 mL, 0.32 mmol), N,N-diisopropylethylamine (90 µL, 0.64 mmol), and PyBop® (0.21 g, 0.38 mmol). The solution was stirred for 1.5 h and concentrated. The product was purified by column chromatography (30% ethyl acetate/hexanes) to give 120 mg (70%). $^1$H-NMR (CDCl$_3$, 500 MHz) δ 7.38-7.40 (m, 1H), 7.33-7.35 (m, 4H), 7.22-7.24 (m, 2H), 7.03 (s, 1H), 4.32 (s, 2H), 3.74-3.77 (m, 2H), 3.38 (s, 2H), 3.08 (s, 3H), 2.99-3.05 (m, 2H), 2.90 (s, 3H), 2.16-2.19 (m, 2H), 1.83-1.89 (m, 2H), 1.43 (s, 9H). Mass spec.: 533.24 (MH)+.

Intermediate 128

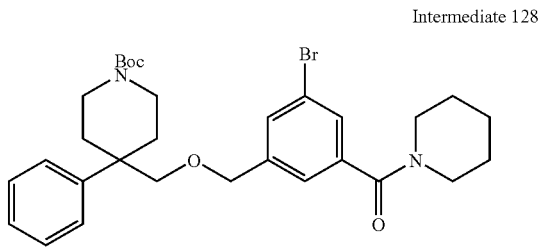 [SMILES: CC(C)(C)OC(=O)N1CCC(COCc2cc(Br)cc(C(=O)N3CCCCC3)c2)(c2ccccc2)CC1]

tert-Butyl 4-((3-bromo-5-(piperidine-1-carbonyl)benzyloxy)methyl)-4-phenylpiperidine-1-carboxylate. LC/MS: $t_R$=3.31 min, 573.38 (MH)+. (Phenomenex C18 4.6×50 mm, 10% MeOH/90% H$_2$O/0.1% TFA→90% MeOH/10% H$_2$O/ 0.1% TFA, Gradient time=4 min., Flow rate=4 mL/min.).

Intermediate 129

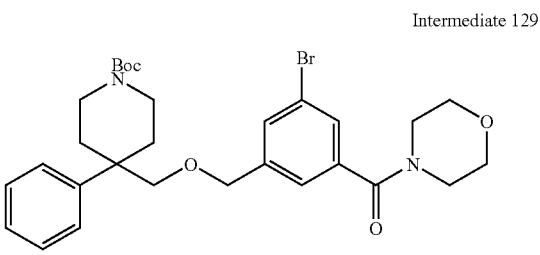 [SMILES: CC(C)(C)OC(=O)N1CCC(COCc2cc(Br)cc(C(=O)N3CCOCC3)c2)(c2ccccc2)CC1]

tert-Butyl 4-((3-bromo-5-(morpholine-4-carbonyl)benzyloxy)methyl)-4-phenylpiperidine-1-carboxylate. LC/MS: $t_R$=3.15 min, 575.36 (MH)+. (Phenomenex C18 4.6×50 mm, 10% MeOH/90% H$_2$O/0.1% TFA→90% MeOH/10% H$_2$O/ 0.1% TFA, Gradient time=4 min., Flow rate=4 mL/min.).

Intermediate 130

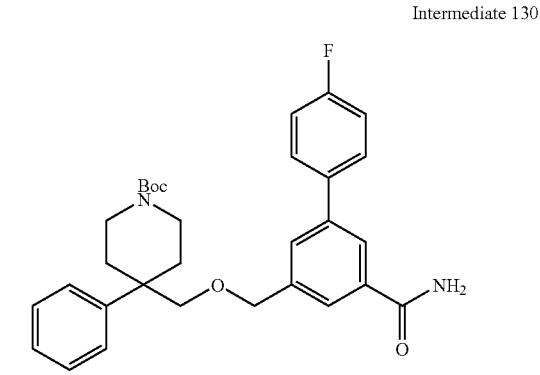 [SMILES: CC(C)(C)OC(=O)N1CCC(COCc2cc(C(N)=O)cc(-c3ccc(F)cc3)c2)(c2ccccc2)CC1]

tert-Butyl 4-(((5-carbamoyl-4'-fluorobiphenyl-3-yl)methoxy)methyl)-4-phenylpiperidine-1-carboxylate. 3-Bromo-5-(((1-(tert-butoxycarbonyl)-4-phenylpiperidin-4-yl)methoxy)methyl)benzoic acid (0.66 g, 1.31 mmol), 4-fluorophenylboronic acid (0.55 g, 3.93 mmol), and tetrakis (triphenylphosphine) palladium(0) (82 mg, 0.05 mmol) were combined in dry tetrahydrofuran (10 mL) in a microwave tube and sealed. After flushing with nitrogen, 5.5 mL of a 1 N potassium hydroxide aqueous solution was introduced. The mixture was heated at 120° C. for 1 h via microwave. After cooling to room temperature, the reaction mixture was concentrated, dissolved in dimethylformamide (6 mL) and cooled to 0° C. The reaction mixture was sequentially treated with methylene chloride (2 mL), 7 N ammonia in methanol (0.33 mL, 2.3 mmol), N,N-diisopropylethylamine (0.51 mL, 2.9 mmol), and PyBop® (0.72 g, 1.4 mmol). The ice bath was removed and the solution stirred for 1.5 h and concentrated. The product was purified by column chromatography (50% ethyl acetate/hexanes) to give 0.4 g (66%). $^1$H-NMR (CDCl$_3$, 500 MHz) δ 7.85 (s, 1H), 7.43-7.46 (m, 2H), 7.41 (s, 1H), 7.37 (s, 1H), 7.28-7.31 (m, 4H), 7.15-7.18 9 (m, 1H), 7.07-7.10 (m, 2H), 4.40 (s, 2H), 3.67-3.69 (m, 2H), 3.40 (s, 2H), 2.96-3.00 (m, 2H), 2.14-2.16 (m, 2H), 1.80-1.86 (m, 2H), 1.37 (s, 9H). Mass spec.: 519.39 (MH)+.

Intermediate 131

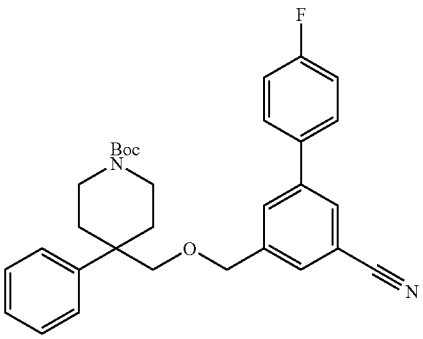

tert-Butyl 4-(((5-cyano-4'-fluorobiphenyl-3-yl)methoxy) methyl)-4-phenylpiperidine-1-carboxylate. A stirred solution of tert-butyl 4-(((5-carbamoyl-4'-fluorobiphenyl-3-yl) methoxy)methyl)-4-phenylpiperidine-1-carboxylate (0.38 g, 0.72 mmol) in pyridine (6 mL) at 0° C. was treated with trifluoroacetic anhydride (1.0 mL, 7.2 mmol). The ice bath was removed and the reaction stirred at room temperature for 4 h. The reaction was cooled to 0° C. and quenched by the addition of excess methanol. The solvents were evaporated and the crude mixture dissolved in ethyl acetate and washed with 5% citric acid (2x), then water (2x), then brine (2x), dried over sodium sulfate, and concentrated. The residue was purified by column chromatography (30% ethyl acetate/hexanes) to afford 0.3 g (83%) as a white powder. $^1$H-NMR (CDCl$_3$, 500 MHz) δ 7.65 (s, 1H), 7.41-7.44 (m, 3H), 7.34-7.36 (m, 4H), 7.22-7.24 (m, 2H), 7.13-7.17 (m, 2H), 4.41 (s, 2H), 3.75 (m, 2H), 3.44 (s, 2H), 2.01-3.06 (m, 2H), 2.19-2.22 (m, 2H), 1.83-1.88 (m, 2H), 1.43 (s, 9H). Mass spec.: 501.37 (MH)+.

Intermediate 132

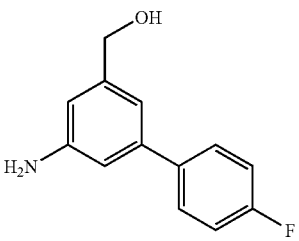

(5-Amino-4'-fluorobiphenyl-3-yl)methanol. A dry round bottomed flask was charged with (3-amino-5-bromophenyl) methanol (2.5 g, 12.4 mmol), 4-fluorophenylboronic acid (5.2 g, 37.2 mmol), and tetrakis(triphenylphosphine) palladium (0) (0.39 g, 0.25 mmol). The flask was flushed with nitrogen and treated with tetrahydrofuran (30 mL) and potassium hydroxide (2 M in water, 19 mL, 38 mmol). The mixture was heated at reflux for 4 h. The reaction was cooled, poured into ethyl acetate, washed with water (2×), then brine, dried over magnesium sulfate, and concentrated. Column chromatography (40% ethyl acetate/hexanes) gave 1.52 g (56%) as a colorless oil. LC/MS: $t_R$=1.48 min, 218.18 (MH)$^+$. (Phenomenex C18 4.6×50 mm, 10% MeOH/90% H$_2$O/0.1% TFA→90% MeOH/10% H$_2$O/0.1% TFA, Gradient time=4 min., Flow rate=4 mL/min.).

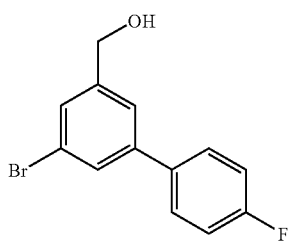

Intermediate 133

(5-Bromo-4'-fluorobiphenyl-3-yl)methanol. A solution of (5-bromo-4'-fluorobiphenyl-3-yl)methanol (1.52 g, 7.0 mmol) in dry acetonitrile (6 mL) was added dropwise to a solution of copper (II) bromide (1.88 g, 8.4 mmol) and tert-butyl nitrite (1.2 mL, 10.0 mmol) in acetonitrile (3 mL) at 65° C. After stirring for 30 min at 65° C., the reaction mixture was cooled to room temperature, poured into a 1 N hydrochloric acid solution, and extracted with ethyl acetate (2×). The organic layers were pooled together, washed with brine (2×), dried over sodium sulfate, and concentrated. Column chromatography on silica gel (30% ethyl acetate/hexanes) afforded 420 mg (17%). $^1$H-NMR (CDCl$_3$, 300 MHz) δ 7.55-7.57 (m, 1H), 7.46-7.50 (m, 3H), 7.42 (m, 1H), 7.02-7.12 (m, 2H), 4.70 (s, 2H).

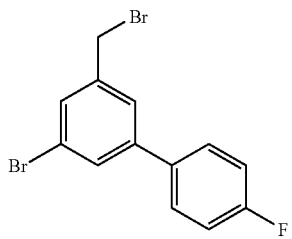

Intermediate 134

3-Bromo-5-(bromomethyl)-4'-fluorobiphenyl. (5-Bromo-4'-fluorobiphenyl-3-yl)methanol (0.42 g, 1.5 mmol) and triphenylphosphine (0.78 g, 2.98 mmol) were combined in tetrahydrofuran (8 mL) and cooled to 0° C. N-Bromosuccinimide (0.59 g, 3.1 mmol) was introduced in portions and the reaction allowed to warm to room temperature. After 16 h, the reaction mixture was diluted with ethyl acetate, washed with concentrated sodium bicarbonate (2×), then brine (2×), dried over sodium sulfate, and concentrated. Column chromatography on silica gel (5% ethyl acetate/hexanes) gave 0.4 g (78%) as a white powder. $^1$H-NMR (CDCl$_3$, 500 MHz) 7.60 (m, 1H), 7.50-7.54 (m, 3H), 7.47 (m, 1H), 7.12-7.15 (m, 2H), 4.47 (s, 2H).

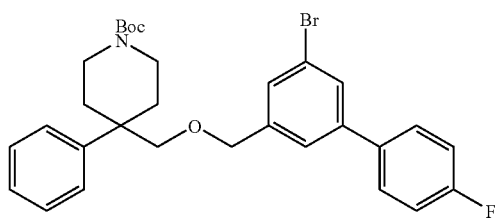

Intermediate 135 tert-Butyl 4-(((5-bromo-4'-fluorobiphenyl-3-yl)methoxy)methyl)-4-phenylpiperidine-1-carboxylate. 3-Bromo-5-(bromomethyl)-4'-fluorobiphenyl (398 mg, 1.16 mmol) and tert-butyl 4-(hydroxymethyl)-4-phenylpiperidine-1-carboxylate (280 mg, 0.96 mmol) were combined in dimethylformamide (5 mL) and cooled to 0° C. The reaction was treated with sodium hydride (46 mg, 1.92 mmol), stirred at 0° C. for 1 h, and at room temperature for 30 min. The reaction mixture was diluted with water and extracted with ethyl acetate (2×). The organic layers were pooled together, washed with brine (2×), dried over sodium sulfate, and concentrated. Column chromatography on silica gel (20% ethyl acetate/hexanes) gave 470 mg (73%). $^1$H-NMR (CDCl$_3$, 500 MHz) δ 7.51 (s, 1H), 7.28-7.42 (m, 6H), 7.19-7.23 (m, 2H), 7.06-7.14 (m, 3H), 4.34 (s, 2H), 3.69-3.74 (m, 2H), 3.40 (s, 2H), 2.98-3.06 (m, 2H), 2.14-2.19 (m, 2H), 1.81-1.90 (m, 2H), 1.41 (s, 9H). Mass spec.: 556.37 (MH)$^+$.

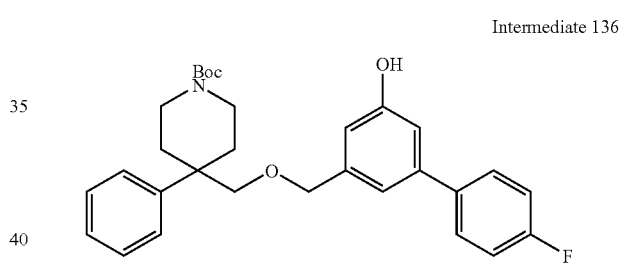

Intermediate 136 tert-Butyl 4-(((4'-fluoro-5-hydroxybiphenyl-3-yl)methoxy)methyl)-4-phenylpiperidine-1-carboxylate. tert-Butyl 4-(((5-bromo-4'-fluorobiphenyl-3-yl)methoxy)methyl)-4-phenylpiperidine-1-carboxylate (0.47 g, 0.85 mmol) was dissolved in dry tetrahydrofuran (5 mL) and stirred at room temperature for 15 min. The stirred mixture was cooled to −78° C. and treated with a solution of n-butyllithium (1.6 M in hexanes, 0.61 mL, 0.98 mmol) over several minutes. After 30 min, the mixture was treated with trimethylborate (0.28 mL, 2.55 mmol). The reaction mixture was stirred at 78° C. for 1 h, then allowed to warm to room temperature over several hours. The mixture was cooled to 0° C. and treated with a 10 N sodium hydroxide solution (60 μL) and hydrogen peroxide (30% in water, 0.44 mL, 3.9 mmol). The reaction was warmed to room temperature over several hours and then treated with saturated ammonium chloride. The reaction was diluted with ethyl acetate. The layers were separated and the organic layer washed with brine (2×), dried over sodium sulfate, filtered, and concentrated. Flash chromatography on silica gel (30% ethyl acetate/hexanes) afforded 280 mg (67%). $^1$H-NMR (CDCl$_3$, 500 MHz) δ 7.38-7.43 (m, 2H), 7.19-7.35 (m, 5H), 7.02-7.09 (m, 2H), 6.86-6.88 (m, 1H), 6.79 (s, 1H), 6.46 (s, 1H), 4.33 (s, 2H), 3.70-3.74 (m, 2H), 3.38 (s, 2H), 2.98-3.07 (m, 2H), 2.13-2.17 (m, 2H), 1.83-1.92 (m, 2H), 1.41 (s, 9H). Mass spec.: 492.41 (MH)$^+$.

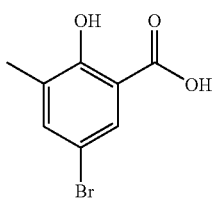

Intermediate 137

5-Bromo-2-hydroxy-3-methylbenzoic acid. To a mixture of 2-hydroxy-3-methylbenzoic acid (2.1 g, 13.5 mmol) in acetic acid (30 mL) was added bromine (0.7 mL, 13.7 mmol) slowly over 5 minutes. After 24 h, water was added slowly to the reaction mixture and the reaction stirred for 30 min. The resulting precipitate was collected by filtration and washed several times with water. The product was dried overnight under high vacuum to afford 2.8 g (90%). LC/MS: $t_R$=2.86 min, 229.14 (MH)$^+$. (Phenomenex C18 4.6×50 mm, 10% MeOH/90% H$_2$O/0.1% TFA→90% MeOH/10% H$_2$O/0.1% TFA, Gradient time=4 min., Flow rate=4 mL/min.).

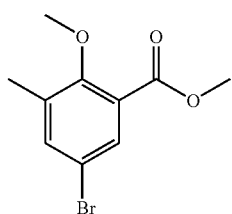

Intermediate 138

Methyl 5-bromo-2-methoxy-3-methylbenzoate. 5-Bromo-2-hydroxy-3-methylbenzoic acid (2.8 g, 12.1 mmol), iodomethane (1.97 mL, 31.6 mmol) and potassium carbonate (16.9 g, 123 mmol) were combined in dimethylformamide (30 mL). After stirring at room temperature for 16 h, the solvent was removed in vacuo and the crude product dissolved in ethyl acetate, which was washed with water (2×), then brine (2×), dried over sodium sulfate, and concentrated. Flash chromatography on silica gel (10% ethyl acetate/hexanes) gave 2.26 g (72%). $^1$H-NMR (CDCl$_3$, 500 MHz) δ 7.74-7.75 (m, 1H), 7.45-7.46 (m, 1H), 3.90 (s, 3H), 3.80 (s, 3H), 2.28 (s, 3H). Mass spec.: 261.08 (MH)$^+$.

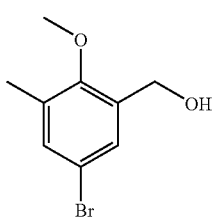

Intermediate 139

(5-Bromo-2-methoxy-3-methylphenyl)methanol. Methyl 5-bromo-2-methoxy-3-methylbenzoate (2.26 g, 8.7 mmol) was dissolved in methylene chloride (30 mL), cooled to −78° C., and treated with diisobutylaluminum hydride (1 M in methylene chloride, 26.1 mL, 26.1 mmol). After stirring at −78° C. for 1 h the reaction was quenched by a few drops of methanol (until no bubbling was observed) followed by addition of excess saturated sodium potassium tartarate (2 mL). The reaction was stirred at room temperature overnight. The layers were separated and the organic layer washed with brine (2×), dried over sodium sulfate, and concentrated to afford 2.0 g (quant). $^1$H-NMR (CDCl$_3$, 500 MHz) δ 7.30-7.31 (m, 1H), 7.21-7.22 (m, 1H), 4.62 (s, 2H), 3.71 (s, 3H), 2.23 (s, 3H).

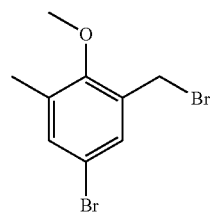

Intermediate 140

5-Bromo-1-(bromomethyl)-2-methoxy-3-methylbenzene. (5-Bromo-2-methoxy-3-methylphenyl)methanol (2.0 g, 8.7 mmol) and triphenylphosphine (4.5 g, 17.4 mmol) were combined in tetrahydrofuran (30 mL) and cooled to 0° C. N-Bromosuccinimide (3.2 g, 17.4 mmol) was introduced in portions and the reaction allowed to warm to room temperature. After 16 h, the reaction mixture was diluted with ethyl acetate, washed with concentrated sodium bicarbonate (2×), then brine (2×), dried over sodium sulfate, and concentrated. Column chromatography on silica gel (hexanes) gave 1.87 g (73%) as a white powder. $^1$H-NMR (CDCl$_3$, 300 MHz) δ 7.32-7.33 (m, 1H), 7.23-7.24 (m, 1H), 4.46 (s, 2H), 3.82 (s, 3H), 2.25 (s, 3H).

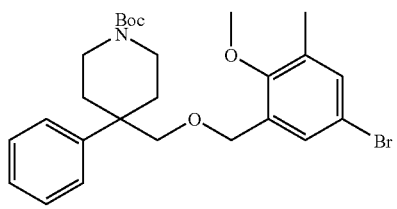

Intermediate 141 tert-Butyl 4-((5-bromo-2-methoxy-3-methylbenzyloxy)methyl)-4-phenylpiperidine-1-carboxylate. 5-Bromo-1-(bromomethyl)-2-methoxy-3-methylbenzene (0.88 g, 3.0 mmol) and tert-butyl 4-(hydroxymethyl)-4-phenylpiperidine-1-carboxylate (0.79 g, 2.7 mmol) were combined in dimethylformamide (9 mL) and cooled to 0° C. The reaction was treated with sodium hydride (144 mg, 5.99 mmol), stirred at 0° C. for 1 h, and at room temperature for 30 min. The reaction mixture was diluted with water and extracted with ethyl acetate (2×). The organic layers were pooled together, washed with brine (2×), dried over sodium sulfate, and concentrated. Column chromatography on silica gel (10% ethyl acetate/hexanes) gave 1.24 g (82%). $^1$H-NMR (CDCl$_3$, 500 MHz) δ 7.34-7.35 (m, 4H), 7.21-7.24 (m, 1H), 7.19-7.20 (m, 1H), 7.10 (m, 1H), 4.34 (s, 2H), 3.72-3.76 (m, 2H), 3.53 (s, 3H), 3.43 (s, 2H), 3.01-3.07 (m, 2H), 2.21 (s, 3H), 2.17-2.19 (m, 2H), 1.85-1.91 (m, 2H), 1.43 (s, 9H). Mass spec.: 506.45 (MH)$^+$.

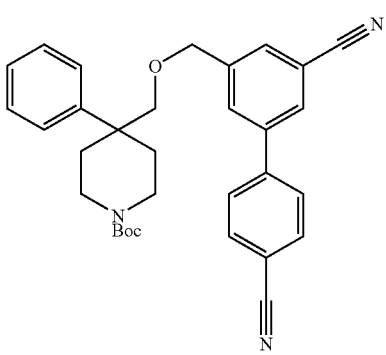

Intermediate 142 tert-Butyl 4-(((4',5-dicyanobiphenyl-3-yl)methoxy)methyl)-4-phenylpiperidine-1-carboxylate. tert-Butyl 4-(((5-bromo-4'-cyanobiphenyl-3-yl)methoxy)methyl)-4-phenylpiperidine-1-carboxylate (52 mg, 0.09 mmol), tetrakis(triphenylphosphine) palladium(0) (14 mg, 0.01 mmol), and zinc cyanide (12 mg, 0.1 mmol) were combined in dimethylformamide (1.5 mL). The reaction mixture was degassed repeatedly using the freeze-pump-thaw method. After warming to room temperature, the reaction was heated at 90° C. for 1 h, cooled to room temperature, and concentrated. Flash chromatography on silica gel (30% ethyl acetate/hexanes) gave 15 mg (33%). $^1$H-NMR (CDCl$_3$, 300 MHz) δ 7.78-7.75 (m, 3H), 7.52-7.55 (m, 2H), 7.31-7.33 (m, 4H), 7.20-7.23 (m, 2H), 4.41 (s, 2H), 3.70-3.77 (m, 2H), 3.43 (s, 2H), 2.97-3.06 (m, 2H), 2.17-2.21 (m, 2H), 1.78-1.88 (m, 2H), 1.40 (s, 9H). Mass spec.: 508.28 (MH)$^+$.

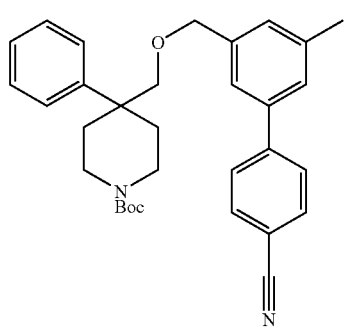

Intermediate 143 tert-Butyl 4-(((4'-cyano-5-methylbiphenyl-3-yl)methoxy)methyl)-4-phenylpiperidine-1-carboxylate. A microwave tube was charged with tert-butyl 4-(((5-bromo-4'-cyanobiphenyl-3-yl)methoxy)methyl)-4-phenylpiperidine-1-carboxylate (48 mg, 0.09 mmol), trimethyl boroxine (13 μL, 0.09 mmol), and tetrakis(triphenylphosphine) palladium(0) (10 mg, 9 μmol). The tube was flushed with nitrogen, treated with a mixture of 1,4-dioxane/water (9:1, 2 mL) and potassium carbonate (35.1 mg, 0.25 mmol). The tube was sealed and heated at 120° C. for 1 h via microwave. After cooling to room temperature, the reaction was concentrated and purified by preparative HPLC to give 11 mg (27%). LC/MS: t$_R$=3.50 min, 497.33 (MH)$^+$. (Phenomenex C18 4.6×50 mm, 10% MeOH/90% H$_2$O/0.1% TFA→90% MeOH/10% H$_2$O/0.1% TFA, Gradient time=4 min., Flow rate=4 mL/min.).

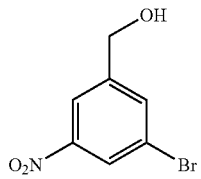

Intermediate 144

(3-Bromo-5-nitrophenyl)methanol. 3-Bromo-5-nitrobenzoic acid (3.2 g, 13.0 mmol) was suspended in tetrahydrofuran (25 mL) and cooled to 0° C. To this solution was added borane tetrahydrofuran complex (1 M in tetrahydrofuran, 26 mL, 26 mmol) cautiously over 15 min. The reaction mixture was allowed to warm to room temperature overnight. The mixture was cooled to 0° C., treated with excess methanol, diluted with ethyl acetate, washed with 1 N sodium hydroxide (2×), then brine (2×), dried over sodium sulfate, and concentrated to afford 3.0 g (99%) as a white powder. $^1$H-NMR (CDCl$_3$, 300 MHz) 8.24 (s, 1H), 8.13 (s, 1H), 7.82 (s, 1H), 4.78 (s, 2H). Mass spec.: 233.88 (MH)$^+$.

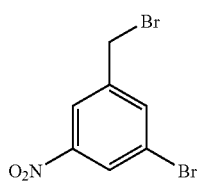

Intermediate 145

1-Bromo-3-(bromomethyl)-5-nitrobenzene. (3-Bromo-5-nitrophenyl)methanol (2.0 g, 8.65 mmol) and triphenylphosphine (4.5 g, 17.3 mmol) were combined in tetrahydrofuran (40 mL) and cooled to 0° C. N-Bromosuccinimide (3.2 g, 18.2 mmol) was introduced in portions and the reaction allowed to warm to room temperature. After 16 h, the reaction mixture was diluted with ethyl acetate, washed with concentrated sodium bicarbonate (2×), brine (2×), dried over sodium sulfate, and concentrated. Column chromatography on silica gel (5% ethyl acetate/hexanes) gave 2.2 g (84%) as a white powder. $^1$H-NMR (CDCl$_3$, 300 MHz) 8.27 (s, 1H), 8.16 (s, 1H), 7.84 (s, 1H), 4.45 (s, 2H).

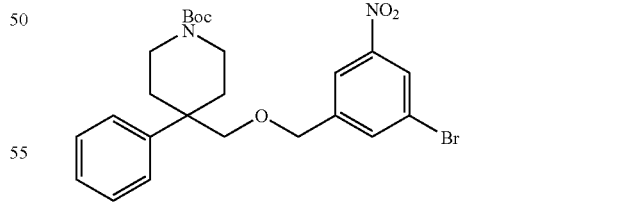

Intermediate 146 tert-Butyl 4-((3-bromo-5-nitrobenzyloxy)methyl)-4-phenylpiperidine-1-carboxylate. 1-Bromo-3-(bromomethyl)-5-nitrobenzene (2.12 g, 7.21 mmol) and tert-butyl 4-(hydroxymethyl)-4-phenylpiperidine-1-carboxylate (1.75 g, 6.0 mmol) were combined in dimethylformamide (18 mL) and cooled to 0° C. The reaction was treated with sodium hydride (288 mg, 12.0 mmol), stirred at 0° C. for 1 h, and at room temperature for 30 min. The reaction mixture was diluted with water and extracted with ethyl acetate (2×). The organic Intermediate 147

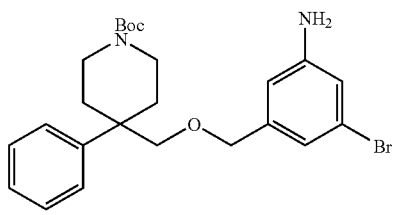

tert-Butyl 4-((3-amino-5-bromobenzyloxy)methyl)-4-phenylpiperidine-1-carboxylate. tert-Butyl 4-((3-bromo-5-nitrobenzyloxy)methyl)-4-phenylpiperidine-1-carboxylate (1.36 g, 2.69 mmol) and tin (II) chloride dihydrate (6.48 g, 28.7 mmol) were combined in ethyl acetate (20 mL) and heated at reflux for 4 h. After cooling to room temperature, the reaction mixture was diluted with ethyl acetate and washed with saturated sodium bicarbonate (2×), brine (2×), dried over sodium sulfate and concentrated. The crude product was dissolved in tetrahydrofuran (10 mL), cooled to 0° C. and treated with di-tert-butyl carbonate (0.59 g, 2.69 mmol) and 10 N sodium hydroxide (0.65 mL). The reaction was allowed to warm to room temperature overnight. The reaction mixture was diluted with ethyl acetate, washed with water (2×), brine (2×), dried over sodium sulfate and concentrated. Column chromatography on silica gel (30% ethyl acetate/hexanes) gave 0.25 g (19%). LC/MS (HPLC method 3): $t_R$=2.99 min, 477.05 (MH)$^+$.

Intermediate 148

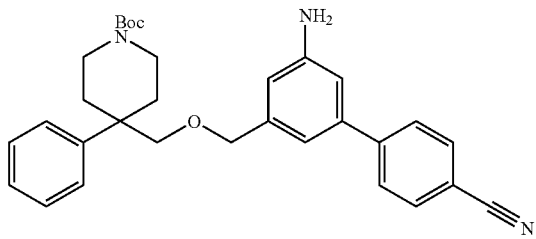

tert-Butyl 4-(((5-amino-4'-cyanobiphenyl-3-yl)methoxy)methyl)-4-phenylpiperidine-1-carboxylate. tert-Butyl 4-((3-amino-5-bromobenzyloxy)methyl)-4-phenylpiperidine-1-carboxylate (220.0 mg, 0.46 mmol), 4-cyanophenylboronic acid (273.0 mg, 1.86 mmol), and tetrakis(triphenylphosphine) palladium(0) (71.7 mg, 0.046 mmol) were combined in dry tetrahydrofuran (5 mL) in a microwave tube and sealed. The mixture was flushed with nitrogen. To this was added potassium hydroxide (1 N in water, 1.4 mL, 1.4 mmol). The mixture was heated at 120° C. for 1 h via microwave. After cooling to room temperature, the reaction mixture was concentrated and purified by flash chromatography on silica gel (25% ethyl acetate/hexanes) to afford 140.0 mg (61%). LC/MS (HPLC method 3): $t_R$=2.85 min, 498.24 (MH)$^+$.

Intermediate 149

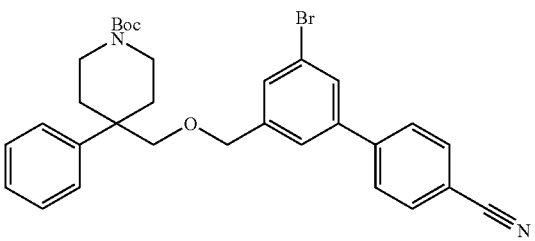

tert-Butyl 4-(((5-bromo-4'-cyanobiphenyl-3-yl)methoxy)methyl)-4-phenylpiperidine-1-carboxylate. A solution of tert-Butyl 4-(((5-amino-4'-cyanobiphenyl-3-yl)methoxy)methyl)-4-phenylpiperidine-1-carboxylate (136.0 mg, 0.27 mmol) in dry acetonitrile (2.0 mL) was added dropwise to a solution of copper (II) bromide (71.6 g, 0.32 mmol) and tert-butyl nitrite (46.0 μL, 0.39 mmol) in acetonitrile (1.0 mL) at 65° C. After stirring for 30 min at 65° C., the reaction mixture was cooled to room temperature, poured into a 1 N hydrochloric acid solution, and extracted with ethyl acetate (2×). The organic layers were pooled together, washed with brine (2×), dried over sodium sulfate, and concentrated. Column chromatography on silica gel (20% ethyl acetate/hexanes) afforded 30.0 g (20%). $^1$H-NMR (CDCl$_3$, 300 MHz) δ 7.68-7.71 (m, 2H), 7.51-7.55 (m, 3H), 7.25-7.38 (m, 5H), 7.17-7.20 (m, 2H), 4.36 (s, 2H), 3.68-3.76 (m, 2H), 3.41 (s, 2H), 2.97-3.06 (m, 2H), 2.14-2.19 (m, 2H), 1.80-1.89 (m, 2H), 1.40 (s, 9H). Mass spec.: 563.12 (MH)$^+$.

Intermediate 150

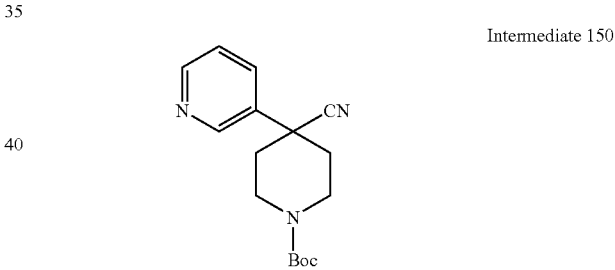

tert-Butyl 4-cyano-4-(pyridin-3-yl)piperidine-1-carboxylate. A flask was charged with sodium hydride (5.08 g, 127 mmol) and dimethylformamide (100 ml) at 0° C. under nitrogen. 2-(Pyridin-3-yl)acetonitrile (5 g, 42.3 mmol) was added in 25 mL of dimethylformamide via addition funnel over 20 min. After 20 min, tert-butyl bis(2-chloroethyl)carbamate (12.81 g, 52.9 mmol) was added in 20 mL of dimethylformamide via addition funnel over 20 min. The reaction was allowed to stir at 0° C. for 2 h and then at 60° C. for 12 h. The reaction was quenched with 10% sodium bicarbonate (100 mL) and extracted with ethyl acetate (5×100 mL). The organics were collected, washed with brine, dried over sodium sulfate, and concentrated in vacuo. The residue was purified via column chromatography (10% 2M ammonia in methanol, 90% dichloromethane) to yield 7.5 g (49%) of desired product. Mass Spec.: 288.20 (MH)$^+$. LC $t_r$=1.380 min (Phenomenex-Luna 4.6×50 mm S10, 10% MeOH/90% H$_2$O/0.1% TFA→90% MeOH/10% H$_2$O/0.1% TFA Gradient Time=2 min, Flow rate=4 mL/min)

layers were pooled together, washed with brine (2×), dried over sodium sulfate, and concentrated. Column chromatography on silica gel (20% ethyl acetate/hexanes) gave 1.4 g (38%). $^1$H-NMR (CDCl$_3$, 500 MHz) δ 8.20 (s, 1H), 7.88 (s, 1H), 7.50 (s, 1H), 7.33-7.38 (m, 4H), 4.37 (s, 2H), 3.75-3.78 (m, 2H), 3.43 (s, 2H), 3.00-3.04 (m, 2H), 2.20-2.22 (m, 2H), 1.82-1.87 (m, 2H), 1.42 (s, 9H). Mass spec.: 507.10 (MH)$^+$.

Intermediate 151

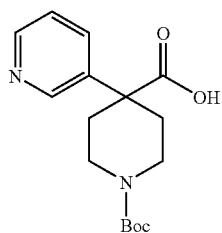

1-(tert-Butoxycarbonyl)-4-(pyridin-3-yl)piperidine-4-carboxylic acid. A flask was charged with tert-butyl 4-cyano-4-(pyridin-3-yl)piperidine-1-carboxylate (7.5 g, 26.1 mmol) and NaOH (50% in water, 100 mL) in ethanol (100 ml) and heated at reflux for 6 h. The ethanol was removed, and the resulting solution was acidified to pH=5 using concentrated hydrochloric acid. The desired product was collected by filtration, and dried overnight to yield 4.1 g (51%). Mass Spec.: 307.18 (MH)$^+$. LC $t_r$=1.31 min (Phenomenex-Luna 4.6×50 mm S10, 10% MeOH/90% H$_2$O/0.1% TFA→90% MeOH/10% H$_2$O/0.1% TFA Gradient Time=2 min, Flow rate=4 mL/min)

Intermediate 152

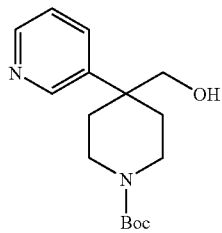

tert-Butyl 4-(hydroxymethyl)-4-(pyridin-3-yl)piperidine-1-carboxylate. A flask was charged with 1-(tert-butoxycarbonyl)-4-(pyridin-3-yl)piperidine-4-carboxylic acid (4.0 g, 13.1 mmol) and tetrahydrofuran (25 mL). The reaction was placed under nitrogen. To the flask was added borane-tetrahydrofuran complex (1 M in tetrahydrofuran, 26.1 mL, 26.1 mmol) and heated at reflux for 2 h. The reaction was cooled to 0° C. and quenched with methanol (100 mL). The solution was then concentrated in vacuo. The residue was purified via column chromatography (5% methanol/95% dichloromethane) to yield 3.2 g (84%). Mass Spec.: 293.26 (MH)$^+$. LC: $t_r$=1.65 min (Phenomenex-Luna 4.6×50 mm S10, 10% MeOH/90% H$_2$O/0.1% TFA→90% MeOH/10% H$_2$O/0.1% TFA Gradient Time=2 min, Flow rate=4 mL/min).

Intermediate 153

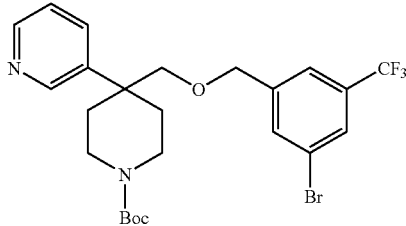

tert-Butyl 4-((3-bromo-5-(trifluoromethyl)benzyloxy)methyl)-4-(pyridin-3-yl)piperidine-1-carboxylate. A flask was charged with 1-bromo-3-(bromomethyl)-5-(trifluoromethyl) benzene (2.53 g, 7.96 mmol) and tert-butyl 4-(hydroxymethyl)-4-(pyridin-3-yl)piperidine-1-carboxylate (1.1 g, 3.8 mmol) in tetrahydrofuran (10 mL) at 0° C. The reaction was treated with sodium tert-butoxide (364 mg, 3.79 mmol), stirred at 0° C. for 20 min, and treated with another aliquot of sodium tert-butoxide (364 mg, 3.79 mmol). The reaction was allowed to warm to room temperature for 30 min then diluted with 10% sodium bicarbonate and extracted with ethyl acetate (2×). The organic layers were pooled together, washed with brine (1×), dried over sodium sulfate, and concentrated. Column chromatography on silica gel (0%-60% ethyl acetate/hexanes) gave 1.23 g (62%). Mass spec.: 529.12 (MH)$^+$ LC $t_r$=2.248 min. (Phenomenex-Luna 4.6×50 mm S10, 10% MeOH/90% H$_2$O/0.1% TFA→90% MeOH/10% H$_2$O/0.1% TFA Gradient Time=2 min, Flow rate=4 mL/min).

Intermediate 154

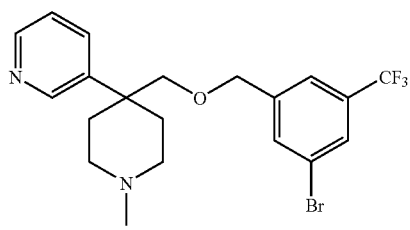

3-(4-O-Bromo-5-(trifluoromethyl)benzyloxy)methyl)-1-methylpiperidin-4-yl)pyridine. A flask was charged with tert-butyl 4-((3-bromo-5-(trifluoromethyl)benzyloxy)methyl)-4-(pyridin-3-yl)piperidine-1-carboxylate (900 mg, 1.70 mmol) in methanol (5 mL). Hydrochloric acid (gas) was bubbled through for 20 seconds and the mixture was allowed to stir for 20 min. The solvent was concentrated in vacuo. The solid white intermediate was redissolved in dichloromethane (5 mL) and treated with formaldehyde (37 wt. % solution in water, 1.5 mL) at 0° C. After 20 min the reaction was treated with sodium triacetoxyborohydride (1.4 g, 6.8 mmol). The reaction was stirred at 0° C. for 30 min and at room temperature for 1 h. The solvent was removed in vacuo and the resulting residue purified via preparative HPLC to yield 330 mg (44%) of desired product. Mass spec.: 443.03 (MH)$^+$ LC $t_r$=1.398 min (Phenomenex-Luna 4.6×50 mm S10, 10% MeOH/90% H$_2$O/0.1% TFA→90% MeOH/10% H$_2$O/0.1% TFA Gradient Time=2 min, Flow rate=4 mL/min)

Intermediate 155

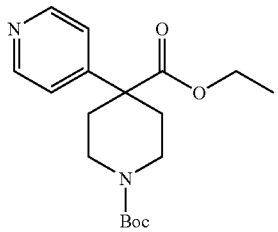

1-tert-Butyl 4-ethyl 4-(pyridin-4-yl)piperidine-1,4-dicarboxylate. Prepared in the same fashion as tert-butyl 4-cyano-4-(pyridin-3-yl)piperidine-1-carboxylate. Mass Spec.: 335.01 (MH)$^+$. LC: $t_r$=1.460 min (Phenomenex-Luna 4.6×50 mm S10, 10% MeOH/90% H$_2$O/0.1% TFA→90% MeOH/10% H$_2$O/0.1% TFA Gradient Time=2 min, Flow rate=4 mL/min)

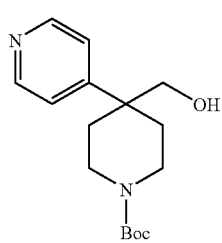

Intermediate 156

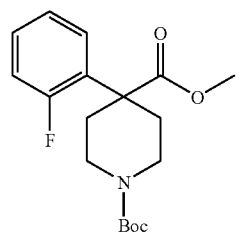

Intermediate 158 tert-Butyl 4-(hydroxymethyl)-4-(pyridin-4-yl)piperidine-1-carboxylate. A flask was charged with 1-tert-butyl 4-ethyl 4-(pyridin-4-yl)piperidine-1,4-dicarboxylate (250 mg, 0.748 mmol) in tetrahydrofuran (3 mL) and cooled to −50° C. (acetonitrile/dry ice). Lithium aluminum hydride (0.785 ml, 1.570 mmol) was added dropwise, and the reaction was allowed to stir for 30 min. The flask was then warmed to room temperature and slowly diluted with ethyl acetate (5 mL). Water (61 μL) was added and the reaction allowed to stir for 5 min. Sodium Hydroxide (1 N in water, 120 μL) was then added and the reaction allowed to stir for 5 min. An additional portion of water (61 μL) and a small amount of sodium sulfate was added and the resulting mixture allowed to stir for 5 min. The suspension was filtered through celite, and the resulting pad washed with hot ethyl acetate. The filtrate was concentrated in vacuo to yield 90 mg (41%) of desired product. Mass Spec.: 294.05 (MH)$^+$. LC $t_r$=1.79 min (HPLC Method 1).

1-tert-butyl 4-methyl 4-(2-fluorophenyl)piperidine-1,4-dicarboxylate. A flask was charged with sodium hydride (2.14 g, 89.2 mmol) and dimethylformamide (70 ml) at 0° C. under nitrogen. Methyl 2-(2-fluorophenyl)acetate (5 g, 29.7 mmol) was added to the flask, and after stirring for 25 min, tert-butyl bis(2-chloroethyl)carbamate (8.6 g, 35.6 mmol) was added. The reaction was allowed to warm to rt and stirred overnight. The reaction was quenched with a saturated solution of ammonium chloride and extracted with ethyl acetate (5×100 mL). The organics were collected, washed with brine, dried over sodium sulfate, and concentrated in vacuo. The residue was purified via silica gel chromatography (10/90→50/50 ethyl acetate/hexanes) to yield 1.7 g (17%) of the desired product. $^1$H-NMR (CDCl$_3$, 400 MHz) δ ppm 7.29 (m, 1H), 7.24 (m, 1H), 7.12 (m, 1H), 7.00 (m, 1H), 3.86 (m, 2H), 3.67 (m, 3H), 3.22 (m, 2H), 2.37 (m, 2H), 1.96 (m, 2H), 1.44 (s, 9H). Mass spec.: 360.22 (MNa)$^+$. LC $t_r$=3.503 min (Phenomenex-Luna 4.6×50 mm S10, 10% MeOH/90% H$_2$O/0.1% TFA→90% MeOH/10% H$_2$O/0.1% TFA Gradient Time=4 min, Flow rate=4 mL/min)

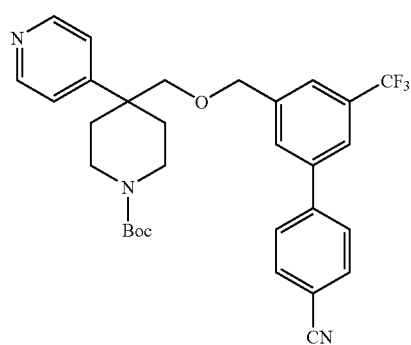

Intermediate 157

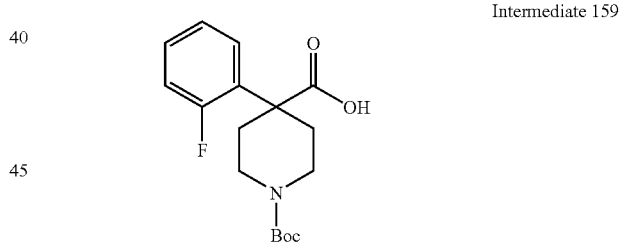

Intermediate 159 tert-Butyl 4-(((4'-cyano-5-(trifluoromethyl)biphenyl-3-yl)methoxy)methyl)-4-(pyridin-4-yl)piperidine-1-carboxylate. A flask was charged with 3'-(bromomethyl)-5'-(trifluoromethyl)biphenyl-4-carbonitrile (157 mg, 0.462 mmol) and tert-butyl 4-(hydroxymethyl)-4-(pyridin-4-yl)piperidine-1-carboxylate (90 mg, 0.308 mmol) in tetrahydrofuran (10 mL) at 0° C. The reaction was treated with potassium tert-butoxide (34.6 mg, 0.308 mmol), stirred at 0° C. for 20 min, and treated with another aliquot of potassium tert-butoxide (34.6 mg, 0.308 mmol). The reaction was allowed to warm to room temperature for 30 min, then diluted with 10% sodium bicarbonate, and extracted with ethyl acetate (2×). The organic layers were pooled together, washed with brine (1×), dried over sodium sulfate, and concentrated. Column chromatography on silica gel (0%→65% ethyl acetate/hexanes) gave 50 mg (29%). Mass spec.: 552.18 (MH)$^+$ LC $t_r$=2.54 min (HPLC Method 1).

1-(tert-butoxycarbonyl)-4-(2-fluorophenyl)piperidine-4-carboxylic acid. A flask was charged with 1-tert-butyl 4-methyl 4-(2-fluorophenyl)piperidine-1,4-dicarboxylate (1.7 g, 5.04 mmol) and LiOH (2.11 g, 50.4 mmol) in 25 mL of a 4:1 THF:H$_2$O solution. The flask was equipped with a reflux condenser and heated to reflux for 48 hr. The reaction was cooled to rt, and the solution was acidified to pH=1 with 6N hydrochloric acid. The aqueous solution was extracted with ethyl acetate, and the organic layer was separated, washed with brine, and dried over Na$_2$SO$_4$. The organic solvent was evaporated in vacuo affording 1.51 g (92%) of the desired acid. Mass Spec.: 347.23 (MNa)$^+$. LC $t_r$=3.253 min (Phenomenex-Luna 4.6×50 mm S10, 10% MeOH/90% H$_2$O/0.1% TFA→90% MeOH/10% H$_2$O/0.1% TFA Gradient Time=4 min, Flow rate=4 mL/min).

Intermediate 160

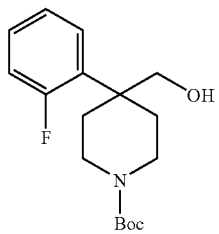

tert-butyl 4-(2-fluorophenyl)-4-(hydroxymethyl)piperidine-1-carboxylate. A flask was charged with 1-(tert-butoxycarbonyl)-4-(2-fluorophenyl)piperidine-4-carboxylic acid (1.51 g, 4.6 mmol) and tetrahydrofuran (10 mL). The reaction was placed under nitrogen. To the flask was added borane-tetrahydrofuran complex (1 M in tetrahydrofuran, 9.2 mL, 9.2 mmol). The reaction was allowed to stir at rt for 48 hr. The reaction was cooled to 0° C. and quenched with methanol (50 mL). The solution was then concentrated in vacuo. The residue was purified via column chromatography (25% ethyl acetate/75% hexanes→60% ethyl acetate/hexanes) to yield 1.0 g (70%) of the desired alcohol. $^1$H-NMR (CDCl$_3$, 400 MHz) δ ppm 7.26 (m, 2H), 7.11 (m, 1H), 7.01 (m, 1H), 3.72 (m, 4H), 3.09 (m, 2H), 2.27 (m, 2H), 1.79 (m, 2H), 1.42 (s, 9H). Mass Spec.: 332.18 (MNa)$^+$. LC: t$_r$=3.301 min (Phenomenex-Luna 4.6×50 mm S10, 10% MeOH/90% H$_2$O/0.1% TFA→90% MeOH/10% H$_2$O/0.1% TFA Gradient Time=4 min, Flow rate=4 mL/min).

Intermediate 161

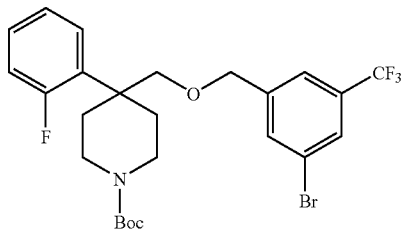

tert-butyl 4-((3-bromo-5-(trifluoromethyl)benzyloxy)methyl)-4-(2-fluorophenyl)piperidine-1-carboxylate. A flask was charged with 1-bromo-3-(bromomethyl)-5-(trifluoromethyl)benzene (0.149 g, 0.47 mmol) and tert-butyl 4-(2-fluorophenyl)-4-(hydroxymethyl)piperidine-1-carboxylate (0.112 g, 0.36 mmol) in tetrahydrofuran (2 mL) at 0° C. The reaction was treated with potassium tert-butoxide (0.41 mg, 0.36 mmol), stirred at 0° C. for 20 min, and treated with another aliquot of potassium tert-butoxide (0.41 mg, 0.36 mmol). The reaction was allowed to warm to room temperature and was stirred for 16 h. The reaction mixture was evaporated in vacuo and the crude oil was purified by silica gel chromatography (5% ethyl acetate/95% hexanes→30% ethyl acetate/70% hexanes) to afford 0.138 g (70%) of the desired ether. Mass spec.: 546.03 (MH)$^+$ LC t$_r$=4.501 min. (Phenomenex-Luna 4.6×50 mm S10, 10% MeOH/90% H$_2$O/0.1% TFA→90% MeOH/10% H$_2$O/0.1% TFA Gradient Time=4 min, Flow rate=4 mL/min).

Intermediate 162

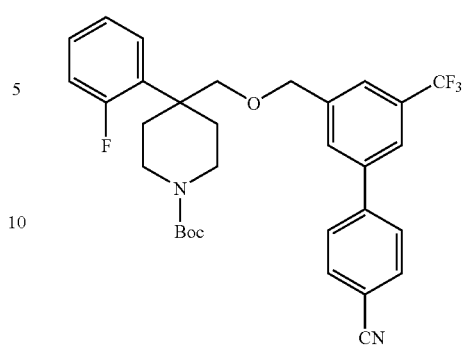

tert-butyl 4-(((4'-cyano-5-(trifluoromethyl)biphenyl-3-yl)methoxy)methyl)-4-(2-fluorophenyl)piperidine-1-carboxylate. A sealable vial was charged with tert-butyl 4-((3-bromo-5-(trifluoromethyl)benzyloxy)methyl)-4-(2-fluorophenyl)piperidine-1-carboxylate (0.138 g, 0.25 mmol) and 4-cyanophenylboronic acid (0.111 g, 0.75 mmol) in tetrahydrofuran (2 mL) at 0° C. To the reaction solution was added 1N potassium hydroxide (0.88 mL, 0.88 mmol) and Tetrakis (triphenylphosphine)palladium(0) (0.058 g, 0.05 mmol). The vial was purged with nitrogen and sealed. The sealed vial was heated in a microwave reactor at 120° C. for 2 hr. The reaction was cooled to room temperature and diluted with 4 mL ethyl acetate. The organic layer was separated, dried over Na$_2$SO$_4$ and evaporated in vacuo. The crude oil was purified by silica gel chromatography (5% ethyl acetate/95% hexanes→35% ethyl acetate/65% hexanes) to afford 0.123 g (87%) of the desired ether. Mass spec.: 591.22 (MNa)$^+$; LC t$_r$=4.318 min. (Phenomenex-Luna 4.6×50 mm S10, 10% MeOH/90% H$_2$O/0.1% TFA→90% MeOH/10% H$_2$O/0.1% TFA Gradient Time=4 min, Flow rate=4 mL/min).

Example 1

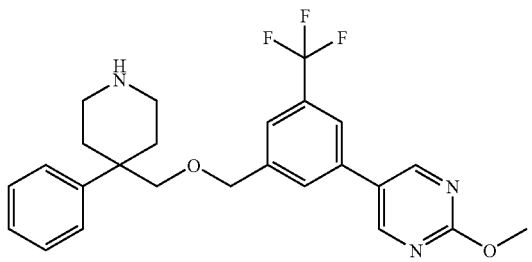 [SMILES: COc1ncc(-c2cc(COCC3(c4ccccc4)CCNCC3)cc(C(F)(F)F)c2)cn1]

2-Methoxy-5-(3-(((4-phenylpiperidin-4-yl)methoxy)methyl)-5-(trifluoromethyl)phenyl)pyrimidine. tert-Butyl 4-((3-bromo-5-(trifluoromethyl)benzyloxy)methyl)-4-phenylpiperidine-1-carboxylate (60.0 mg, 0.11 mmol), 2-methoxy-5-pyridine boronic acid (72.0 mg, 0.47 mmol), and tetrakis (triphenylphosphine) palladium(0) (17.1 mg, 0.011 mmol) were combined in dry tetrahydrofuran (2 mL) in a microwave tube and sealed. The mixture was flushed with nitrogen then 0.35 mL of a 1 N potassium hydroxide aqueous solution was introduced. The mixture was heated at 120° C. for 1 h via microwave. After cooling to room temperature, the reaction mixture was concentrated and treated with a trifluoroacetic acid/methylene chloride mixture (1:1, 2 mL) for 1 h. The solvent was removed in vacuo and the resulting crude mixture passed through a strong cation exchange column. After washing the column with several volumes of methanol, the product was eluted by washing the column with 2 M ammonia in methanol. Concentration and preparative HPLC afforded 21.0 mg (42%) of the desired compound as its TFA salt. $^1$H-NMR (CDCl$_3$, 500 MHz) δ 8.57 (s, 2H), 7.54 (s, 1H), 7.25-7.31 (m, 8H), 4.40 (s, 2H), 4.03 (s, 3H), 3.40 (s, 2H), 2.83-2.88 (m, 2H), 2.64-2.69 (m, 2H), 2.10-2.18 (m, 2H), 1.77-1.86 (m, 2H). Mass spec.: 458.18 (MH)$^+$.

Example 2

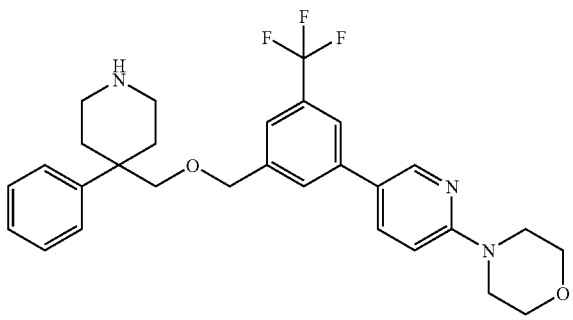 [SMILES: FC(F)(F)c1cc(COCC2(c3ccccc3)CCNCC2)cc(-c2ccc(N3CCOCC3)nc2)c1]

4-(5-(3-(((4-Phenylpiperidin-4-yl)methoxy)methyl)-5-(trifluoromethyl)phenyl)pyridin-2-yl)morpholine. $^1$H-NMR (CDCl$_3$, 500 MHz) δ 8.49 (d, J=2.1 Hz, 1H), 8.08 (dd, J=7.0, 2.5 Hz, 1H), 7.72 (s, 1H), 7.61 (s, 1H), 7.35-7.38 (m, 3H), 7.26-7.30 (m, 3H), 7.10 (d, J=9.5 Hz, 1H), 4.48 (s, 2H), 3.86-3.88 (m, 4H), 3.71-3.73 (m, 4H), 3.42 (s, 2H), 3.28-3.31 (m, 2H), 2.86-2.90 (m, 2H), 2.39-2.42 (m, 2H), 2.27-2.33 (m, 2H). Mass spec.: 512.37 (MH)$^+$. Accurate mass spec.: m/z 512.2530 [MH]$^+$, Δ=1.0 ppm.

Example 3

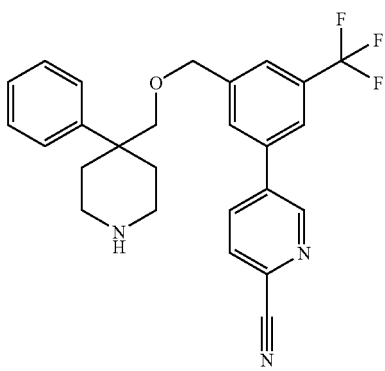

5-(3-(((4-Phenylpiperidin-4-yl)methoxy)methyl)-5-(trifluoromethyl)phenyl)picolinonitrile. $^1$H-NMR (CDCl$_3$, 500 MHz) δ 8.85 (s, 1H), 7.91 (dd, J=5.8, 2.4 Hz, 1H), 7.80 (d, J=8.2 Hz, 1H), 7.67 (s, 1H), 7.47 (s, 1H), 7.43 (s, 1H), 7.38 (d, J=1.2 Hz, 1H), 7.36 (s, 1H), 7.30-7.33 (m, 2H), 7.17-7.20 (m, 1H), 4.48 (s, 2H), 3.49 (s, 2H), 2.91-2.94 (m, 2H), 2.74-2.79 (m, 2H), 2.19-2.22 (m, 2H), 1.88-1.93 (m, 2H). Mass spec.: 452.22 (MH)$^+$. Accurate mass spec.: m/z 452.1945 [MH]$^+$, Δ=1.0 ppm.

Example 4

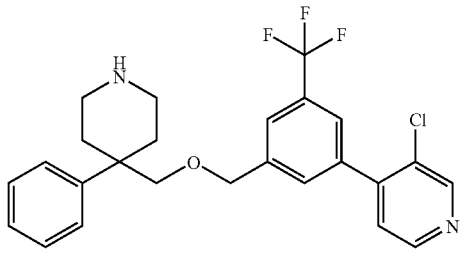 [SMILES: FC(F)(F)c1cc(COCC2(c3ccccc3)CCNCC2)cc(-c2ccncc2Cl)c1]

3-Chloro-4-(3-(((4-phenylpiperidin-4-yl)methoxy)methyl)-5-(trifluoromethyl)phenyl)pyridine. $^1$H-NMR (CDCl$_3$, 500 MHz) δ 8.83 (s, 1H), 8.69 (d, J=5.5 Hz, 1H), 7.63 (s, 1H), 7.55 (d, J=5.5 Hz, 1H), 7.50 (s, 1H), 7.47 (s, 1H), 7.29-7.41 (m, 6H), 4.52 (s, 2H), 3.46 (s, 2H), 3.34-3.37 (m, 2H), 2.93-2.96 (m, 2H), 2.45-2.48 (m, 2H), 2.20-2.26 (m, 2H). Mass spec.: 461.32 (MH)$^+$. Accurate mass spec.: m/z 461.1596 [MH]$^+$, Δ=2.5 ppm.

Example 5

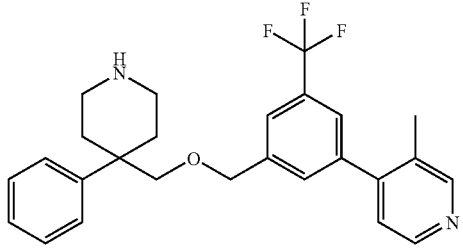

3-Methyl-4-(3-(((4-phenylpiperidin-4-yl)methoxy)methyl)-5-(trifluoromethyl)phenyl)pyridine. $^1$H-NMR (CDCl$_3$, 500 MHz) δ 8.74 (s, 1H), 8.72 (d, J=5.8 Hz, 1H), 7.72 (d, J=5.8 Hz, 1H), 7.53 (s, 1H), 7.47 (s, 1H), 7.42 (s, 1H), 7.35-7.38 (m, 2H), 7.24-7.31 (m, 3H), 4.54 (s, 2H), 3.47 (s, 2H), 3.34-3.37 (m, 2H), 2.90-2.97 (m, 2H), 2.43 (s, 3H), 2.38-2.45 (m, 2H), 2.25-2.31 (m, 2H). Mass spec.: 441.37 (MH)$^+$. Accurate mass spec.: m/z 441.2167 [MH]$^+$, Δ=3.0 ppm.

Example 6

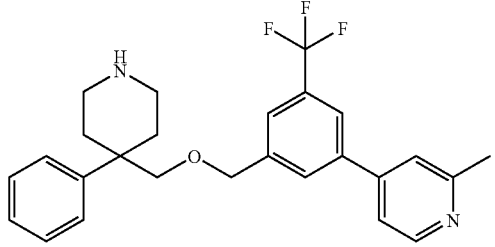 [SMILES: Cc1cc(-c2cc(COCC3(c4ccccc4)CCNCC3)cc(C(F)(F)F)c2)ccn1]

2-Methyl-4-(3-(((4-phenylpiperidin-4-yl)methoxy)methyl)-5-(trifluoromethyl)phenyl)pyridine. $^1$H-NMR (CDCl$_3$, 500 MHz) δ 8.81 (d, J=6.1 Hz, 1H), 7.86 (d, J=6.1 Hz, 1H), 7.78-7.80 (m, 3H), 7.56 (s, 1H), 7.38-7.41 (m, 2H), 7.28-7.32 (m, 3H), 4.54 (s, 2H), 3.47 (s, 2H), 3.33-3.35 (m, 2H), 2.90-

2.96 (m, 2H), 2.83 (s, 3H), 2.41-2.44 (m, 2H), 2.29-2.35 (m, 2H). Mass spec.: 441.37 (MH)⁺. Accurate mass spec.: m/z 441.2165 [MH]⁺, Δ=2.6 ppm.

Example 7

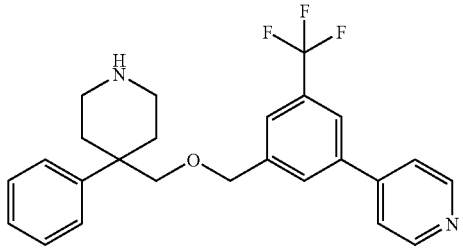

4-(3-(((4-Phenylpiperidin-4-yl)methoxy)methyl)-5-(trifluoromethyl)phenyl)pyridine. ¹H-NMR (CD$_3$OD, 500 MHz) δ 8.97 (s, 1H), 8.96 (s, 1H), 8.42 (s, 1H), 8.41 (s, 1H), 8.17 (s, 1H), 7.98 (s, 1H), 7.75 (s, 1H), 7.41-7.51 (m, 2H), 7.41-7.44 (m, 2H), 7.28-7.31 (m, 1H), 4.65 (s, 2H), 3.61 (s, 2H), 3.36-3.38 (m, 2H), 2.95-3.00 (m, 2H), 2.56-2.59 (m, 2H), 2.24-2.29 (m, 2H). ¹³C-NMR (CD$_3$OD, 126 MHz) δ 156.7, 142.4, 142.3, 141.9, 136.3, 132.2 (q, J=33.6 Hz), 130.4, 129.1, 127.2, 126.9, 125.3, 124.0, 124.1 (q, J=271.6 Hz), 123.9, 79.6, 71.8, 41.1, 28.9. Mass spec.: 427.17 (MH)⁺.

Example 8

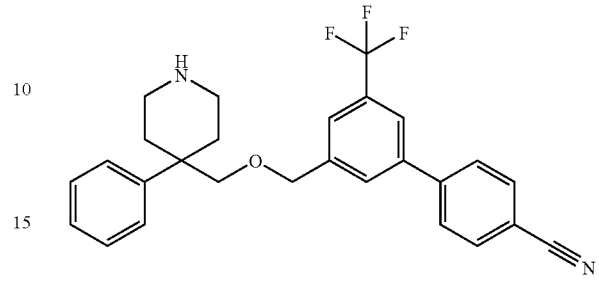

3'-(((4-Phenylpiperidin-4-yl)methoxy)methyl)-5'-(trifluoromethyl)biphenyl-4-carbonitrile. ¹H-NMR (CD$_3$OD, 500 MHz) δ 7.84-7.87 (m, 2H), 7.78-7.87 (m, 2H), 8.42 (s, 1H), 7.67 (s, 1H), 7.55 (s, 1H), 7.48-7.50 (m, 2H), 7.40-7.43 (m, 2H), 7.27-7.30 (m, 1H), 4.59 (s, 2H), 3.57 (s, 2H), 3.36-3.38 (m, 2H), 2.94-2.99 (m, 2H), 2.55-2.58 (m, 2H), 2.20-2.26 (m, 2H). ¹³C-NMR (CD$_3$OD, 126 MHz) δ 142.2, 141.4, 141.1, 140.7, 133.0, 131.6 (q, J=32.6 Hz), 130.0, 129.0, 128.2, 127.2, 124.4 (q, J=272.6 Hz), 124.0, 123.0, 118.5. Mass spec.: 451.18 (MH)⁺.

TABLES 3

| | The following compounds were prepared by method A. | | | |
|---|---|---|---|---|
| Example | Structure | HPLC Method | retention time | Mass Spec. (MH+) |
| 8 | | 2 | 1.42 | 451.28 |
| 9 | | 2 | 1.23 | 525.37 |

TABLES 3-continued

The following compounds were prepared by method A.

| Example | Structure | HPLC Method | retention time | Mass Spec. (MH+) |
|---|---|---|---|---|
| 10 | 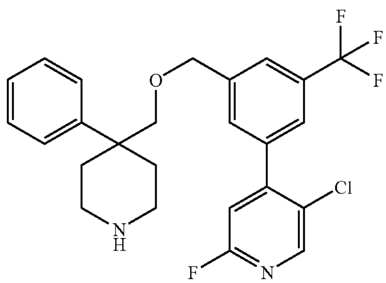 [SMILES: Fc1cc(-c2cc(COCC3(c4ccccc4)CCNCC3)cc(C(F)(F)F)c2)c(Cl)cn1] | 2 | 1.48 | 479.25 |
| 11 | 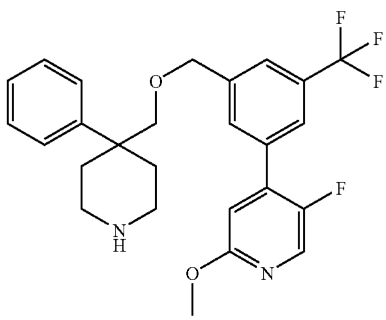 [SMILES: COc1cc(-c2cc(COCC3(c4ccccc4)CCNCC3)cc(C(F)(F)F)c2)c(F)cn1] | 2 | 1.40 | 475.26 |
| 12 | 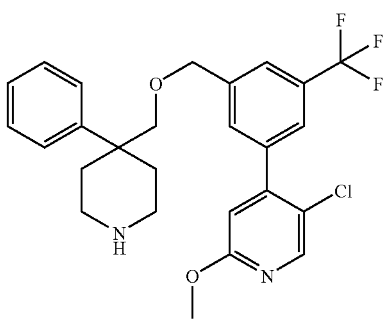 [SMILES: COc1cc(-c2cc(COCC3(c4ccccc4)CCNCC3)cc(C(F)(F)F)c2)c(Cl)cn1] | 2 | 1.53 | 491.24 |
| 13 | 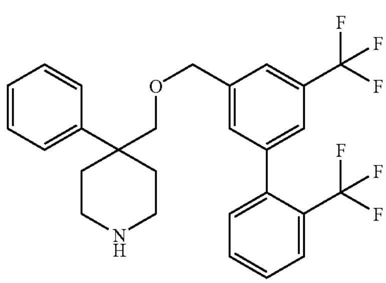 [SMILES: FC(F)(F)c1cc(COCC2(c3ccccc3)CCNCC2)cc(-c2ccccc2C(F)(F)F)c1] | 2 | 1.51 | 494.25 |
| 14 | 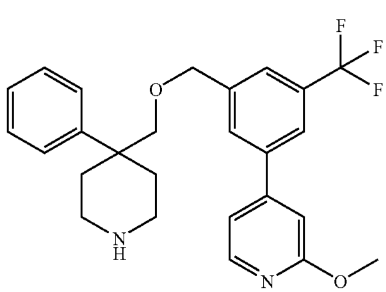 [SMILES: COc1cc(-c2cc(COCC3(c4ccccc4)CCNCC3)cc(C(F)(F)F)c2)ccn1] | 2 | 1.16 | 457.30 |

TABLES 3-continued
The following compounds were prepared by method A.
| Example | Structure | HPLC Method | retention time | Mass Spec. (MH+) |
|---|---|---|---|---|
| 15 | 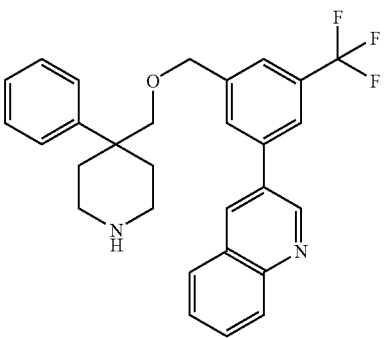 [SMILES: FC(F)(F)c1cc(COCC2(c3ccccc3)CCNCC2)cc(-c2cnc3ccccc3c2)c1] | 2 | 1.35 | 477.29 |
| 16 | 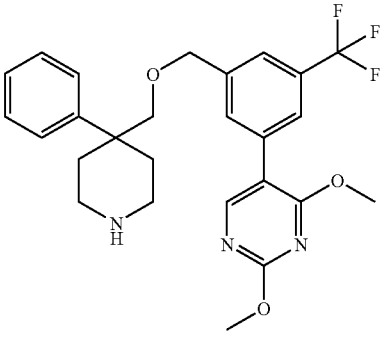 [SMILES: COc1ncc(-c2cc(COCC3(c4ccccc4)CCNCC3)cc(C(F)(F)F)c2)c(OC)n1] | 2 | 1.11 | 488.30 |
| 17 | 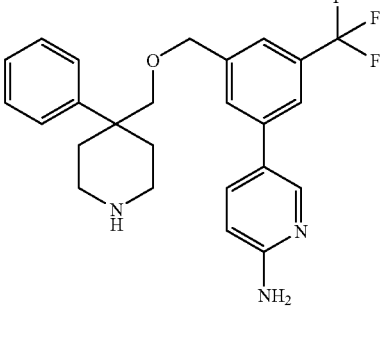 | 4 | 2.06 | 442.20 |
| 18 | 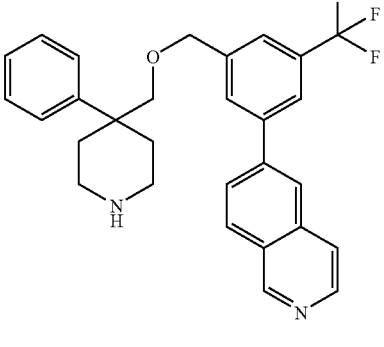 | 4 | 2.30 | 477.20 |

TABLES 3-continued
The following compounds were prepared by method A.
| Example | Structure | HPLC Method | retention time | Mass Spec. (MH+) |
|---|---|---|---|---|
| 19 | 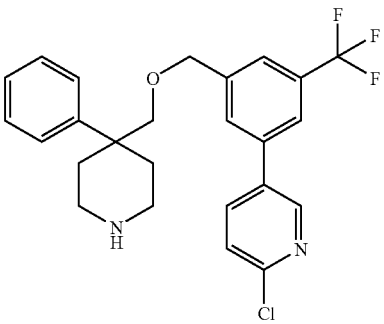 [SMILES: FC(F)(F)c1cc(COCC2(c3ccccc3)CCNCC2)cc(-c2ccc(Cl)nc2)c1] | 4 | 2.49 | 461.10 |
| 20 | 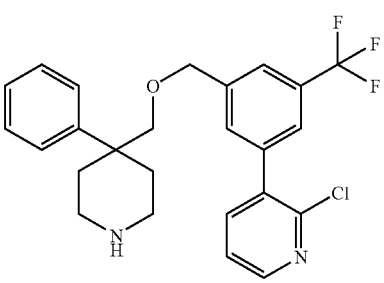 [SMILES: FC(F)(F)c1cc(COCC2(c3ccccc3)CCNCC2)cc(-c2cccnc2Cl)c1] | 4 | 2.31 | 461.20 |
| 21 | 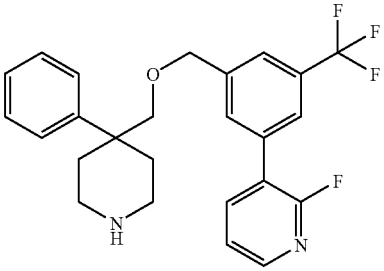 [SMILES: Fc1ncccc1-c1cc(COCC2(c3ccccc3)CCNCC2)cc(C(F)(F)F)c1] | 4 | 2.39 | 445.20 |
| 22 | 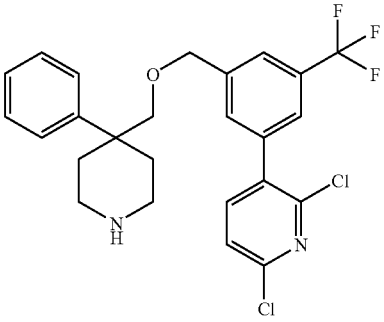 [SMILES: FC(F)(F)c1cc(COCC2(c3ccccc3)CCNCC2)cc(-c2ccc(Cl)nc2Cl)c1] | 4 | 2.70 | 495.10 |
| 23 | 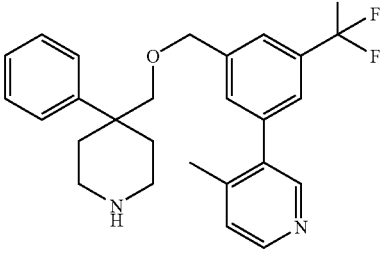 | 4 | 2.16 | 441.20 |

TABLES 3-continued
The following compounds were prepared by method A.
| Example | Structure | HPLC Method | retention time | Mass Spec. (MH+) |
|---|---|---|---|---|
| 24 | 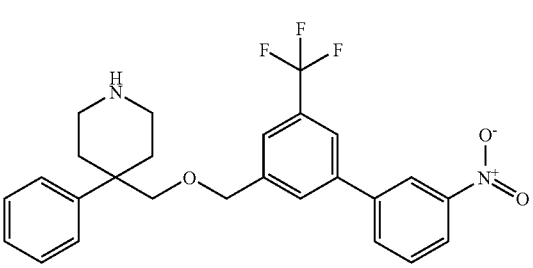 [SMILES: O=[N+]([O-])c1cccc(-c2cc(COCC3(c4ccccc4)CCNCC3)cc(C(F)(F)F)c2)c1] | 2 | 1.39 | 470.96 |
| 25 | 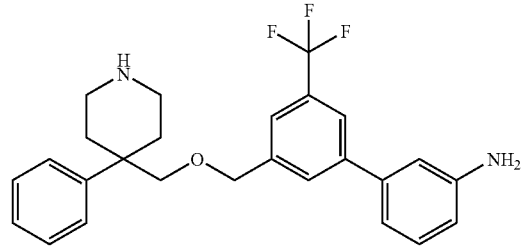 [SMILES: Nc1cccc(-c2cc(COCC3(c4ccccc4)CCNCC3)cc(C(F)(F)F)c2)c1] | 2 | 1.22 | 440.99 |
| 26 | 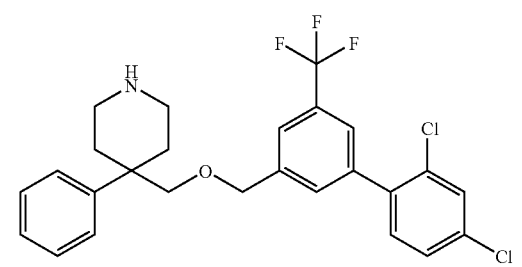 [SMILES: FC(F)(F)c1cc(COCC2(c3ccccc3)CCNCC2)cc(-c2ccc(Cl)cc2Cl)c1] | 2 | 1.59 | 493.89 |
| 27 | 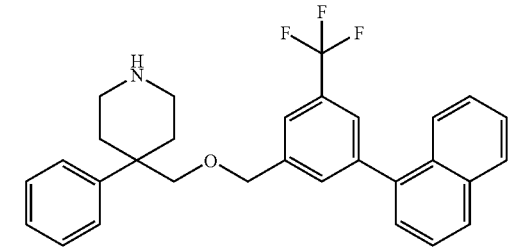 [SMILES: FC(F)(F)c1cc(COCC2(c3ccccc3)CCNCC2)cc(-c2cccc3ccccc23)c1] | 2 | 1.55 | 475.98 |
| 28 | 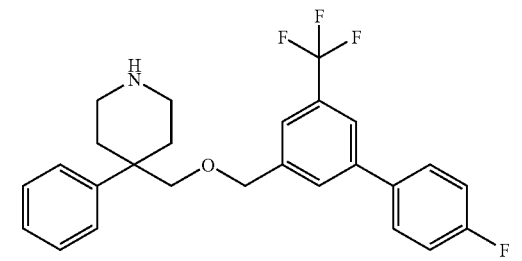 [SMILES: Fc1ccc(-c2cc(COCC3(c4ccccc4)CCNCC3)cc(C(F)(F)F)c2)cc1] | 2 | 1.43 | 443.97 |

TABLES 3-continued

The following compounds were prepared by method A.

| Example | Structure | HPLC Method | retention time | Mass Spec. (MH+) |
|---|---|---|---|---|
| 29 | 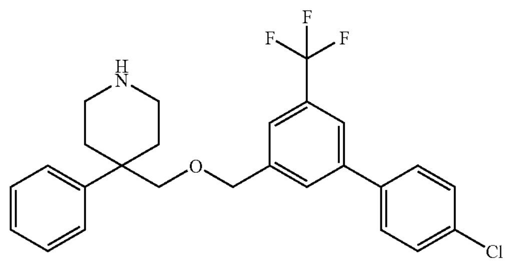 [SMILES: FC(F)(F)c1cc(COCC2(c3ccccc3)CCNCC2)cc(-c2ccc(Cl)cc2)c1] | 2 | 1.71 | 459.96 |
| 30 | 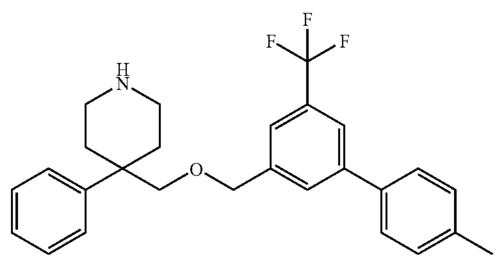 [SMILES: Cc1ccc(-c2cc(COCC3(c4ccccc4)CCNCC3)cc(C(F)(F)F)c2)cc1] | 2 | 1.39 | 439.98 |
| 31 | 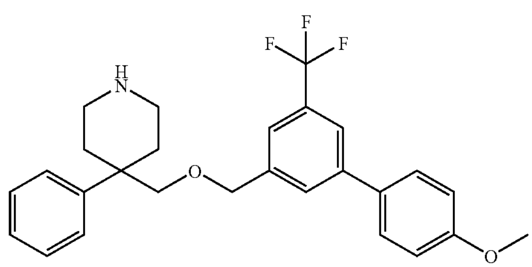 [SMILES: COc1ccc(-c2cc(COCC3(c4ccccc4)CCNCC3)cc(C(F)(F)F)c2)cc1] | 2 | 1.35 | 456.02 |
| 32 | 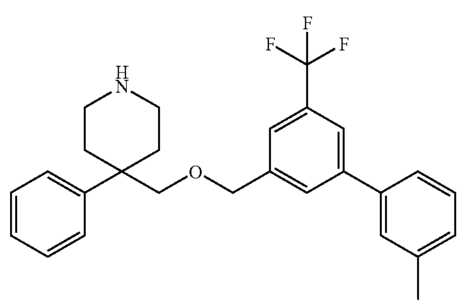 [SMILES: Cc1cccc(-c2cc(COCC3(c4ccccc4)CCNCC3)cc(C(F)(F)F)c2)c1] | 2 | 1.48 | 439.99 |
| 33 | 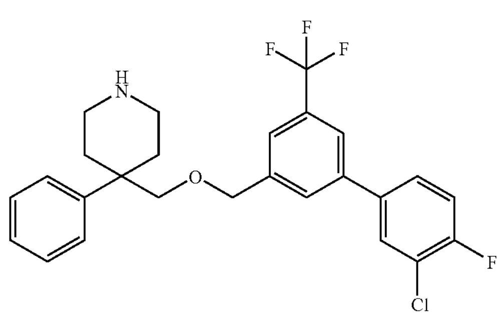 [SMILES: Fc1ccc(-c2cc(COCC3(c4ccccc4)CCNCC3)cc(C(F)(F)F)c2)cc1Cl] | 2 | 1.72 | 477.94 |

TABLES 3-continued
The following compounds were prepared by method A.
| Example | Structure | HPLC Method | retention time | Mass Spec. (MH+) |
|---|---|---|---|---|
| 34 | 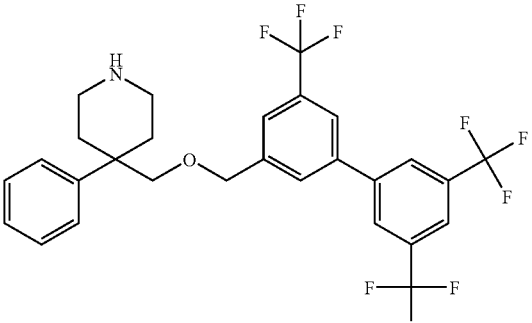 | 2 | 1.53 | 561.90 |
| 35 | 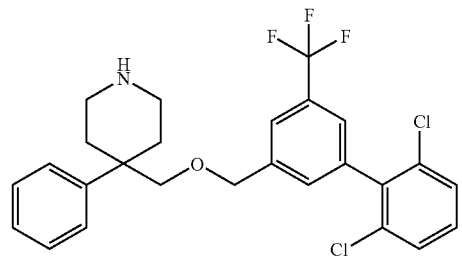 [SMILES: FC(F)(F)c1cc(COCC2(c3ccccc3)CCNCC2)cc(-c2c(Cl)cccc2Cl)c1] | 2 | 1.47 | 493.88 |
| 36 | 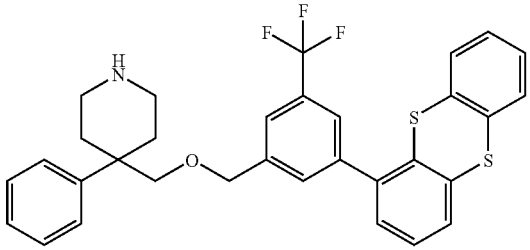 [SMILES: FC(F)(F)c1cc(COCC2(c3ccccc3)CCNCC2)cc(-c2cccc3c2Sc2ccccc2S3)c1] | 2 | 1.64 | 563.88 |
| 37 | 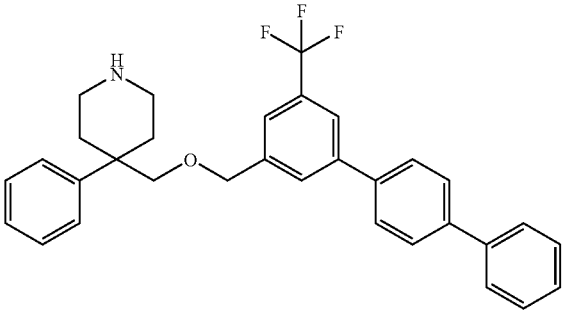 [SMILES: FC(F)(F)c1cc(COCC2(c3ccccc3)CCNCC2)cc(-c2ccc(-c3ccccc3)cc2)c1] | 2 | 1.75 | 502.02 |
| 38 | 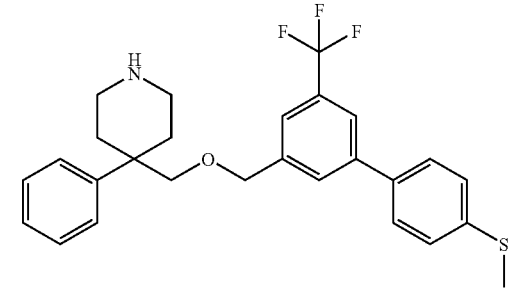 [SMILES: CSc1ccc(-c2cc(COCC3(c4ccccc4)CCNCC3)cc(C(F)(F)F)c2)cc1] | 2 | 1.70 | 471.97 |

TABLES 3-continued
The following compounds were prepared by method A.
| Example | Structure | HPLC Method | retention time | Mass Spec. (MH+) |
|---|---|---|---|---|
| 39 | 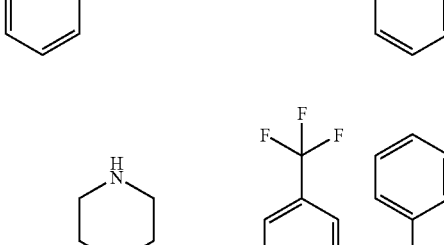 | 2 | 1.39 | 440.14 |
| 40 | 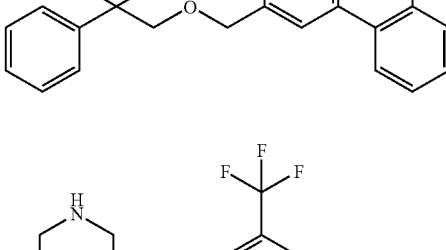 | 2 | 1.48 | 501.96 |
| 41 | 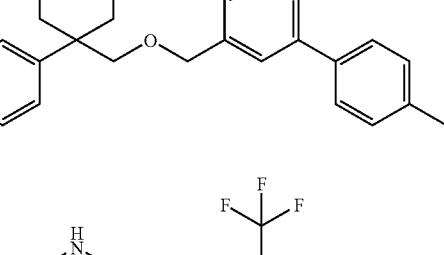 | 2 | 1.28 | 453.98 |
| 42 | 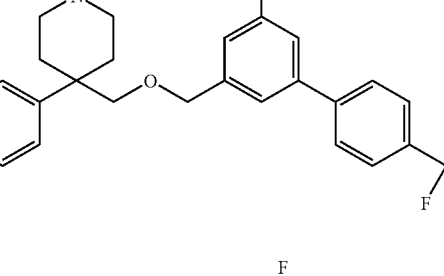 | 2 | 1.52 | 493.95 |
| 43 | 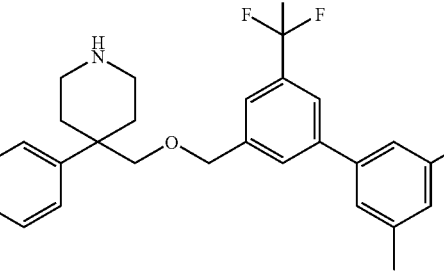 | 2 | 1.57 | 454.00 |

TABLES 3-continued
The following compounds were prepared by method A.
| Example | Structure | HPLC Method | retention time | Mass Spec. (MH+) |
|---|---|---|---|---|
| 44 | 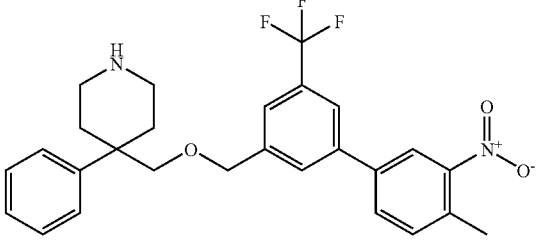 | 2 | 1.54 | 484.96 |
| 45 | 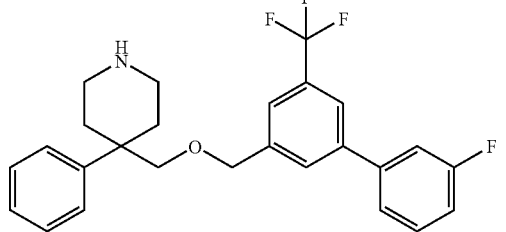 | 2 | 1.38 | 443.94 |
| 46 | 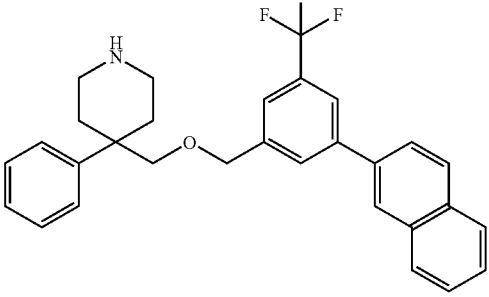 | 2 | 1.60 | 475.97 |
| 47 | 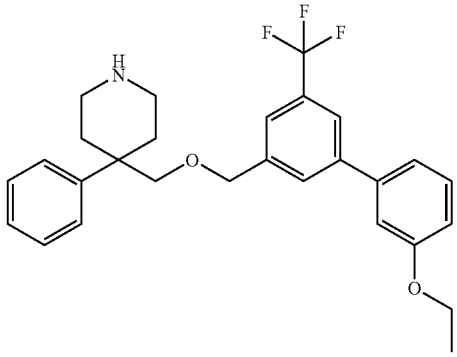 [SMILES: CCOc1cccc(-c2cc(COCC3(c4ccccc4)CCNCC3)cc(C(F)(F)F)c2)c1] | 2 | 1.55 | 469.95 |
| 48 | 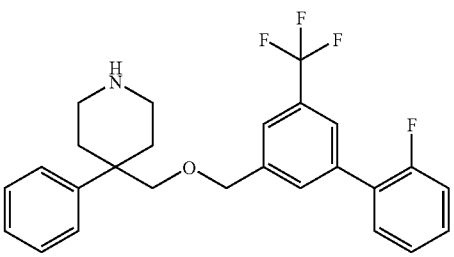 | 2 | 1.31 | 443.92 |

TABLES 3-continued

The following compounds were prepared by method A.

| Example | Structure | HPLC Method | retention time | Mass Spec. (MH+) |
|---|---|---|---|---|
| 49 | 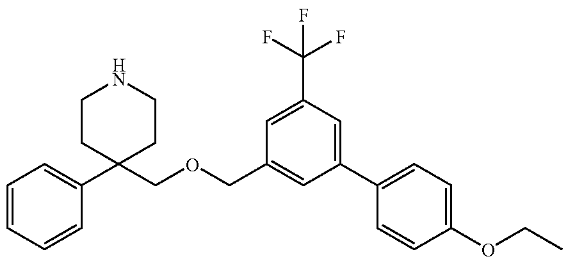 [SMILES: CCOc1ccc(-c2cc(COCC3(c4ccccc4)CCNCC3)cc(C(F)(F)F)c2)cc1] | 2 | 1.60 | 469.95 |
| 50 | 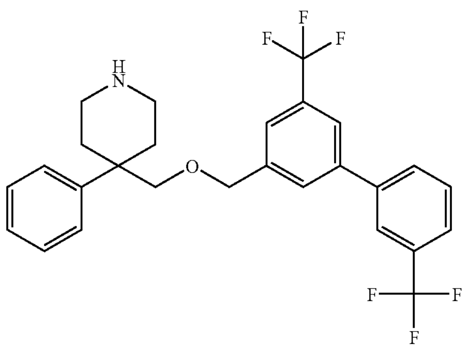 [SMILES: FC(F)(F)c1cccc(-c2cc(COCC3(c4ccccc4)CCNCC3)cc(C(F)(F)F)c2)c1] | 2 | 1.42 | 493.90 |
| 51 | 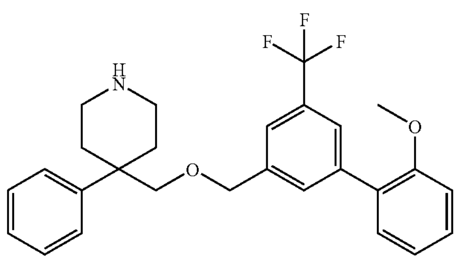 [SMILES: COc1ccccc1-c1cc(COCC2(c3ccccc3)CCNCC2)cc(C(F)(F)F)c1] | 2 | 1.39 | 455.94 |
| 52 | 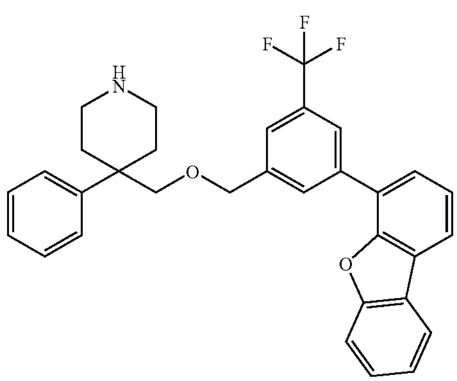 [SMILES: FC(F)(F)c1cc(COCC2(c3ccccc3)CCNCC2)cc(-c2cccc3c2oc2ccccc23)c1] | 2 | 1.79 | 515.95 |
| 53 | 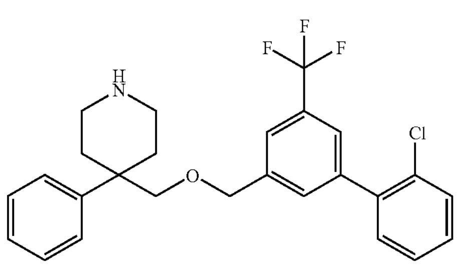 | 2 | 1.35 | 459.89 |

TABLES 3-continued

The following compounds were prepared by method A.

| Example | Structure | HPLC Method | retention time | Mass Spec. (MH+) |
|---|---|---|---|---|
| 54 | 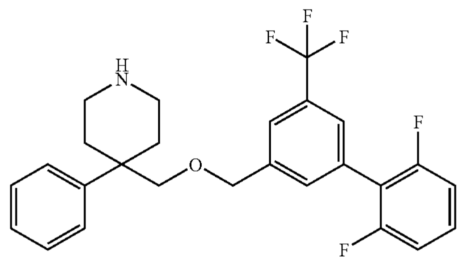 | 2 | 1.37 | 461.83 |
| 55 | 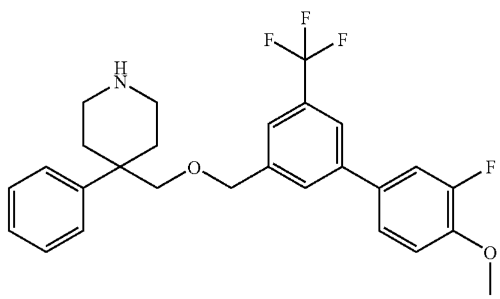 [SMILES: COc1ccc(-c2cc(COCC3(c4ccccc4)CCNCC3)cc(C(F)(F)F)c2)cc1F] | 2 | 1.43 | 473.86 |
| 56 | 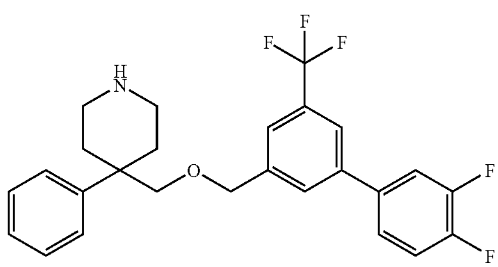 [SMILES: Fc1ccc(-c2cc(COCC3(c4ccccc4)CCNCC3)cc(C(F)(F)F)c2)cc1F] | 2 | 1.55 | 461.83 |
| 57 | 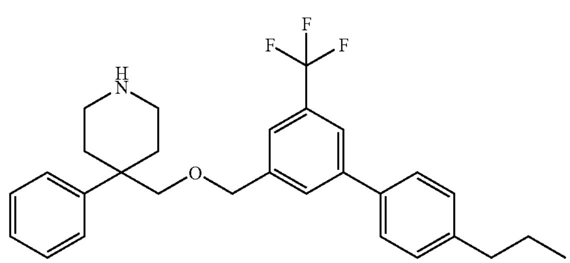 [SMILES: CCCc1ccc(-c2cc(COCC3(c4ccccc4)CCNCC3)cc(C(F)(F)F)c2)cc1] | 2 | 1.82 | 467.93 |
| 58 | 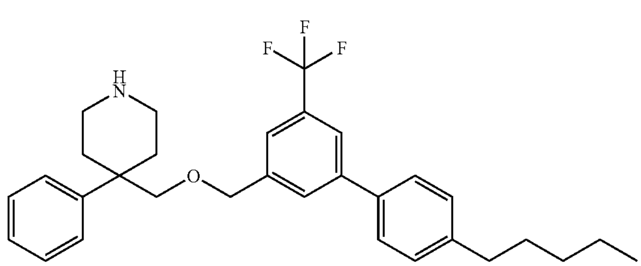 [SMILES: CCCCCc1ccc(-c2cc(COCC3(c4ccccc4)CCNCC3)cc(C(F)(F)F)c2)cc1] | 2 | 2.08 | 495.92 |

TABLES 3-continued

The following compounds were prepared by method A.

| Example | Structure | HPLC Method | retention time | Mass Spec. (MH+) |
|---|---|---|---|---|
| 59 | 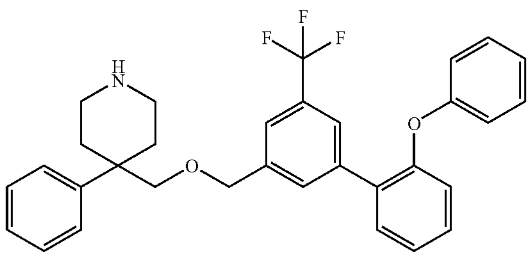 [SMILES: FC(F)(F)c1cc(COCC2(c3ccccc3)CCNCC2)cc(-c2ccccc2Oc2ccccc2)c1] | 2 | 1.72 | 517.83 |
| 60 | 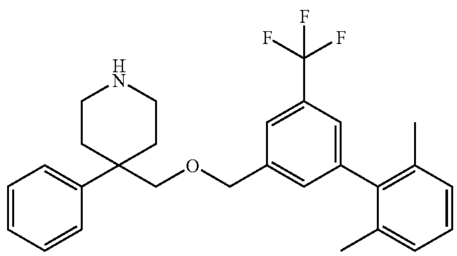 | 2 | 1.52 | 453.89 |
| 61 | 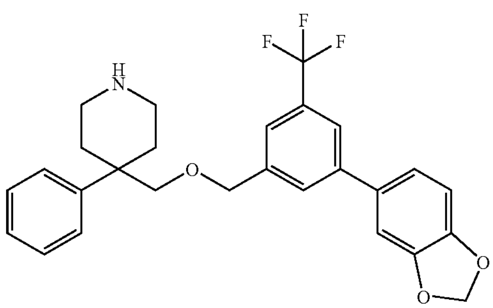 [SMILES: FC(F)(F)c1cc(COCC2(c3ccccc3)CCNCC2)cc(-c2ccc3c(c2)OCO3)c1] | 2 | 1.41 | 469.87 |
| 62 | 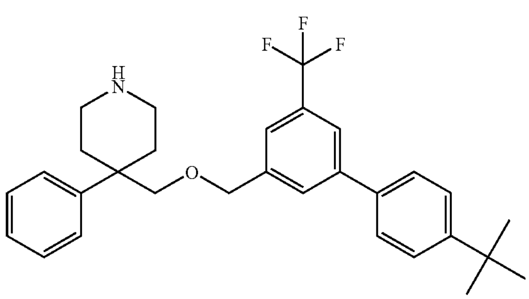 [SMILES: CC(C)(C)c1ccc(-c2cc(COCC3(c4ccccc4)CCNCC3)cc(C(F)(F)F)c2)cc1] | 2 | 1.84 | 481.92 |
| 63 | 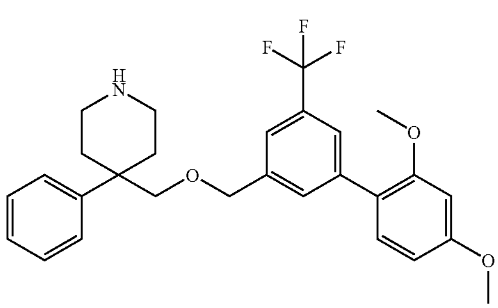 [SMILES: COc1ccc(-c2cc(COCC3(c4ccccc4)CCNCC3)cc(C(F)(F)F)c2)c(OC)c1] | 2 | 1.41 | 485.87 |

TABLES 3-continued

The following compounds were prepared by method A.

| Example | Structure | HPLC Method | retention time | Mass Spec. (MH+) |
|---------|-----------|-------------|----------------|------------------|
| 64 | 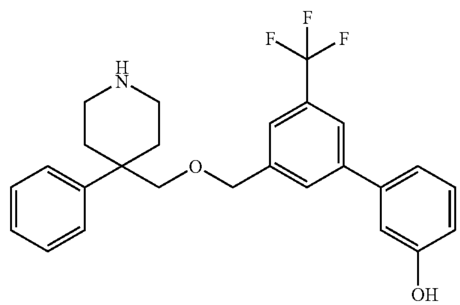 [SMILES: Oc1cccc(-c2cc(COCC3(c4ccccc4)CCNCC3)cc(C(F)(F)F)c2)c1] | 2 | 1.20 | 441.87 |
| 65 | 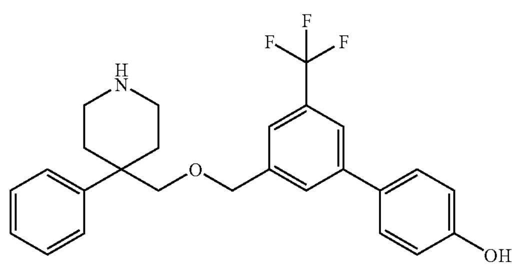 [SMILES: Oc1ccc(-c2cc(COCC3(c4ccccc4)CCNCC3)cc(C(F)(F)F)c2)cc1] | 2 | 1.22 | 441.88 |
| 66 | 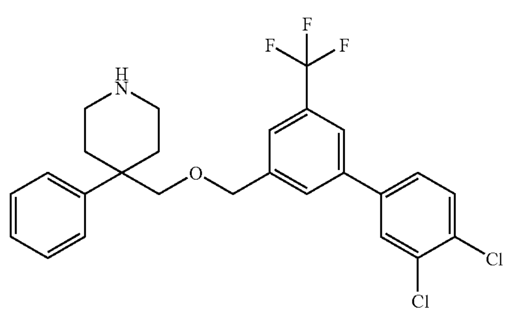 [SMILES: FC(F)(F)c1cc(COCC2(c3ccccc3)CCNCC2)cc(-c2ccc(Cl)c(Cl)c2)c1] | 2 | 1.81 | 493.78 |
| 67 | 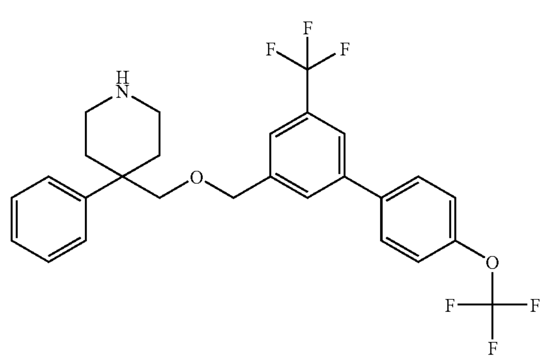 [SMILES: FC(F)(F)Oc1ccc(-c2cc(COCC3(c4ccccc4)CCNCC3)cc(C(F)(F)F)c2)cc1] | 2 | 1.55 | 509.80 |

TABLES 3-continued

The following compounds were prepared by method A.

| Example | Structure | HPLC Method | retention time | Mass Spec. (MH+) |
|---|---|---|---|---|
| 68 | 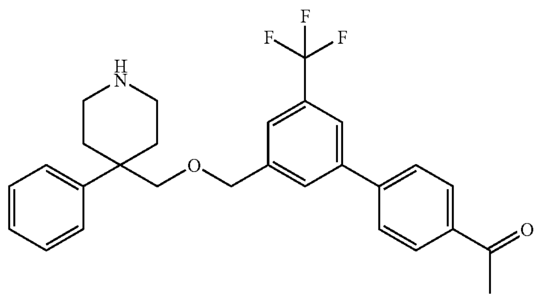 [SMILES: CC(=O)c1ccc(-c2cc(COCC3(c4ccccc4)CCNCC3)cc(C(F)(F)F)c2)cc1] | 2 | 1.28 | 467.86 |
| 69 | 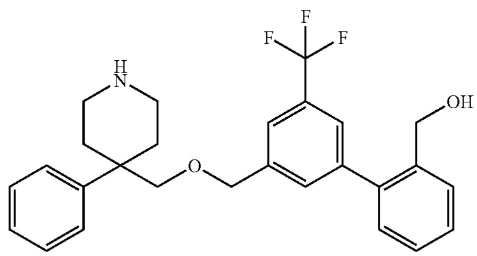 [SMILES: OCc1ccccc1-c1cc(COCC2(c3ccccc3)CCNCC2)cc(C(F)(F)F)c1] | 2 | 1.25 | 455.88 |
| 70 | 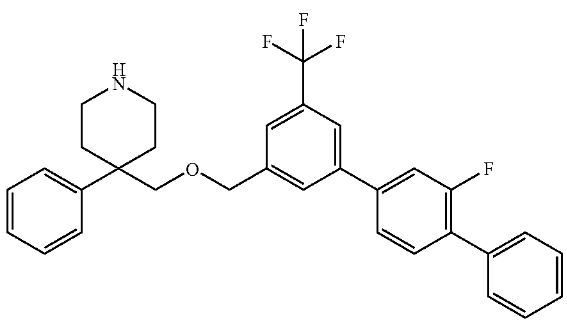 [SMILES: Fc1cc(-c2cc(COCC3(c4ccccc4)CCNCC3)cc(C(F)(F)F)c2)ccc1-c1ccccc1] | 2 | 1.71 | 519.85 |
| 71 | 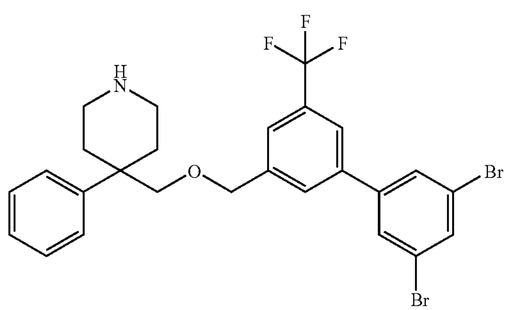 [SMILES: FC(F)(F)c1cc(COCC2(c3ccccc3)CCNCC2)cc(-c2cc(Br)cc(Br)c2)c1] | 2 | 1.86 | 583.63 |
| 72 | 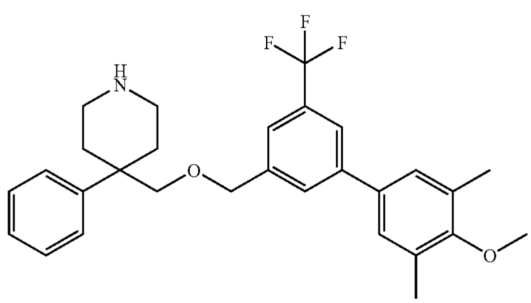 [SMILES: COc1c(C)cc(-c2cc(COCC3(c4ccccc4)CCNCC3)cc(C(F)(F)F)c2)cc1C] | 2 | 1.71 | 483.89 |

TABLES 3-continued

The following compounds were prepared by method A.

| Example | Structure | HPLC Method | retention time | Mass Spec. (MH+) |
|---------|-----------|-------------|----------------|------------------|
| 73 | 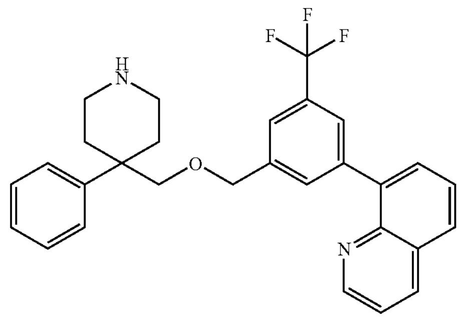 [SMILES: FC(F)(F)c1cc(COCC2(c3ccccc3)CCNCC2)cc(-c2cccc3cccnc23)c1] | 2 | 1.37 | 476.86 |
| 74 | 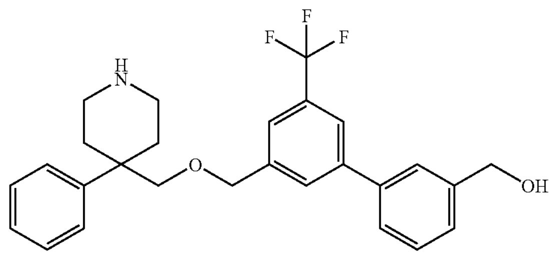 [SMILES: OCc1cccc(-c2cc(COCC3(c4ccccc4)CCNCC3)cc(C(F)(F)F)c2)c1] | 2 | 1.18 | 455.87 |
| 75 | 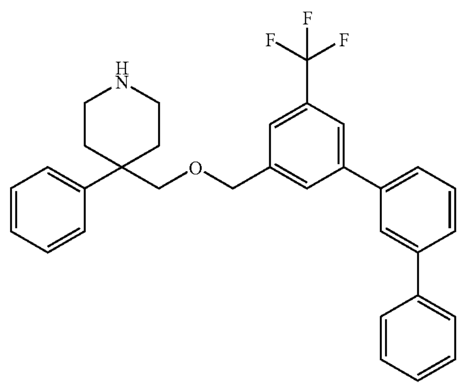 [SMILES: FC(F)(F)c1cc(COCC2(c3ccccc3)CCNCC2)cc(-c2cccc(-c3ccccc3)c2)c1] | 2 | 1.73 | 501.87 |
| 76 | 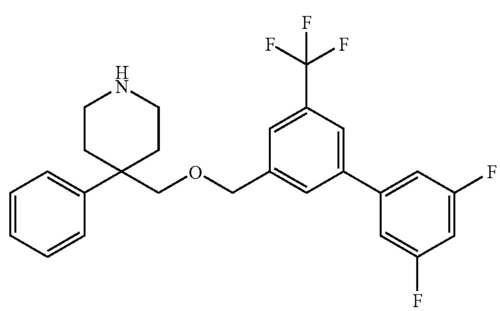 [SMILES: Fc1cc(F)cc(-c2cc(COCC3(c4ccccc4)CCNCC3)cc(C(F)(F)F)c2)c1] | 2 | 1.65 | 461.85 |
| 77 | 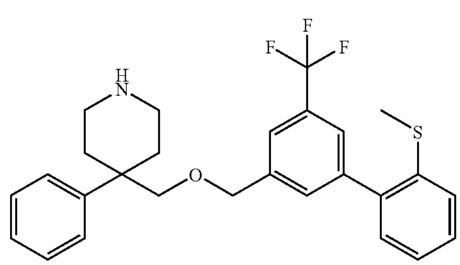 | 2 | 1.45 | 471.83 |

TABLES 3-continued

The following compounds were prepared by method A.

| Example | Structure | HPLC Method | retention time | Mass Spec. (MH+) |
|---------|-----------|-------------|----------------|------------------|
| 78 | 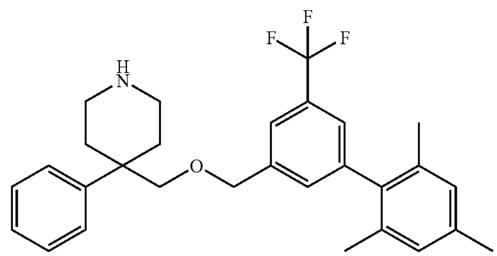 [SMILES: Cc1cc(C)c(-c2cc(COCC3(c4ccccc4)CCNCC3)cc(C(F)(F)F)c2)c(C)c1] | 2 | 1.70 | 467.93 |
| 79 | 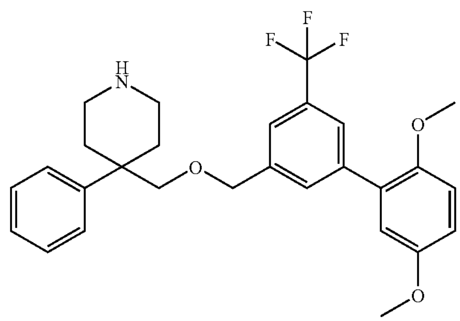 [SMILES: COc1ccc(OC)c(-c2cc(COCC3(c4ccccc4)CCNCC3)cc(C(F)(F)F)c2)c1] | 2 | 1.51 | 485.85 |
| 80 | 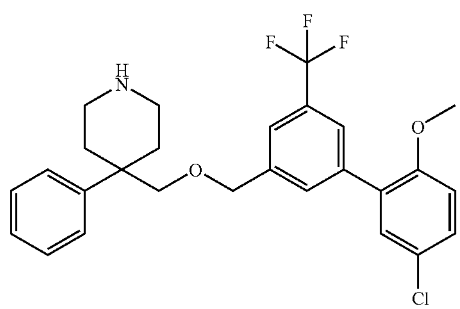 [SMILES: COc1ccc(Cl)cc1-c1cc(COCC2(c3ccccc3)CCNCC2)cc(C(F)(F)F)c1] | 2 | 1.49 | 489.81 |
| 81 | 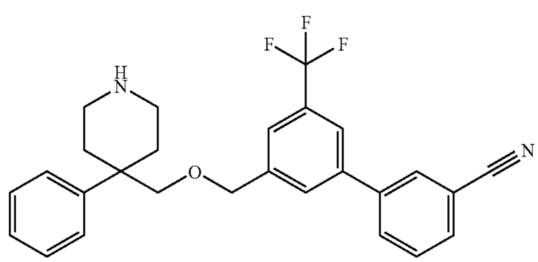 [SMILES: N#Cc1cccc(-c2cc(COCC3(c4ccccc4)CCNCC3)cc(C(F)(F)F)c2)c1] | 2 | 1.35 | 450.86 |
| 82 | 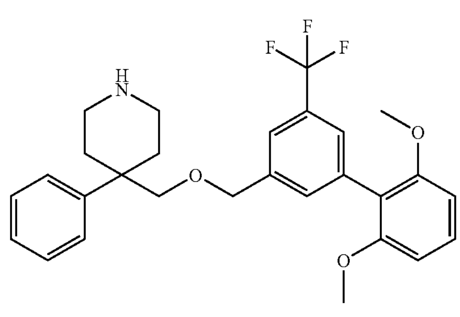 [SMILES: COc1cccc(OC)c1-c1cc(COCC2(c3ccccc3)CCNCC2)cc(C(F)(F)F)c1] | 2 | 1.52 | 485.86 |

TABLES 3-continued

The following compounds were prepared by method A.

| Example | Structure | HPLC Method | retention time | Mass Spec. (MH+) |
|---------|-----------|-------------|----------------|------------------|
| 83 | 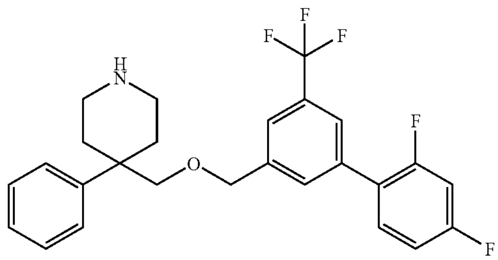 [SMILES: Fc1ccc(-c2cc(COCC3(c4ccccc4)CCNCC3)cc(C(F)(F)F)c2)c(F)c1] | 2 | 1.45 | 461.84 |
| 84 | 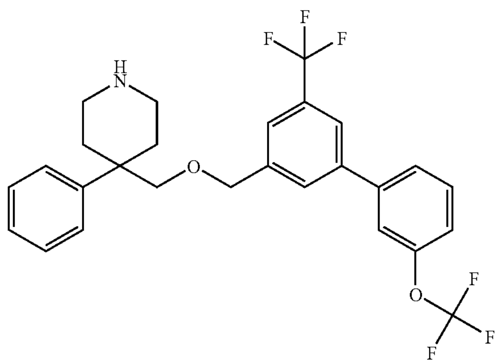 [SMILES: FC(F)(F)Oc1cccc(-c2cc(COCC3(c4ccccc4)CCNCC3)cc(C(F)(F)F)c2)c1] | 4 | 2.96 | 510.27 |
| 85 | 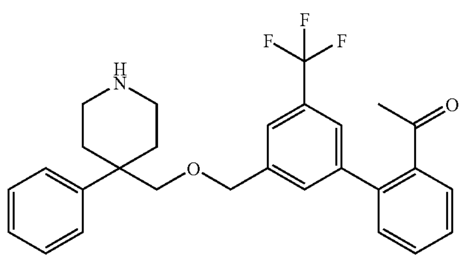 [SMILES: CC(=O)c1ccccc1-c1cc(COCC2(c3ccccc3)CCNCC2)cc(C(F)(F)F)c1] | 4 | 2.41 | 468.24 |
| 86 | 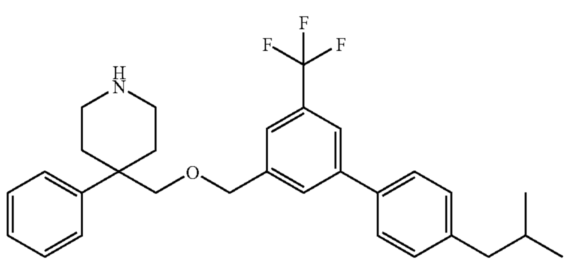 [SMILES: CC(C)Cc1ccc(-c2cc(COCC3(c4ccccc4)CCNCC3)cc(C(F)(F)F)c2)cc1] | 4 | 3.23 | 482.32 |
| 87 | 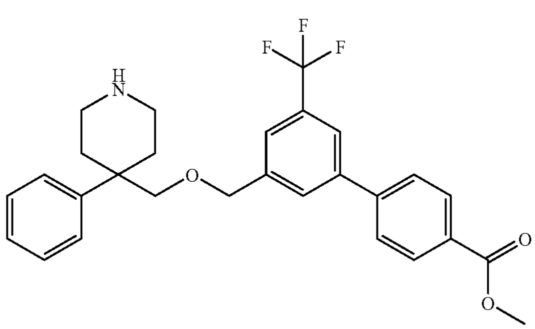 [SMILES: COC(=O)c1ccc(-c2cc(COCC3(c4ccccc4)CCNCC3)cc(C(F)(F)F)c2)cc1] | 4 | 2.66 | 484.23 |

TABLES 3-continued

The following compounds were prepared by method A.

| Example | Structure | HPLC Method | retention time | Mass Spec. (MH+) |
|---------|-----------|-------------|----------------|------------------|
| 88 | 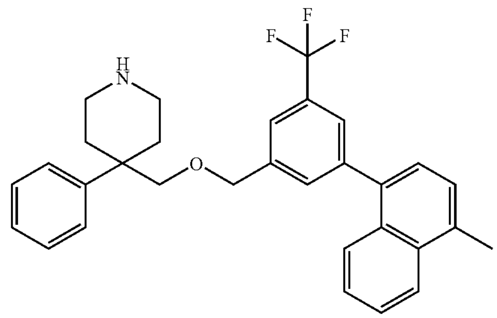 [SMILES: Cc1ccc(-c2cc(COCC3(c4ccccc4)CCNCC3)cc(C(F)(F)F)c2)c2ccccc12] | 4 | 3.15 | 490.34 |
| 89 | 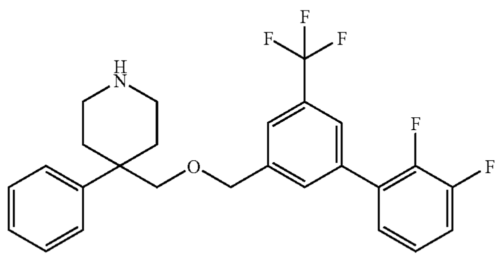 | 4 | 2.75 | 462.2 |
| 90 | 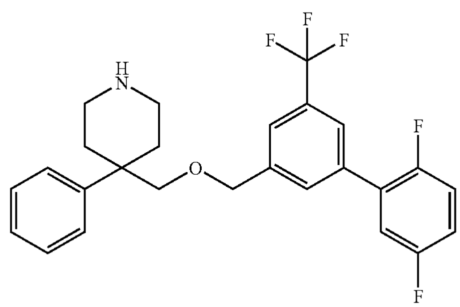 | 4 | 2.74 | 462.2 |
| 91 | 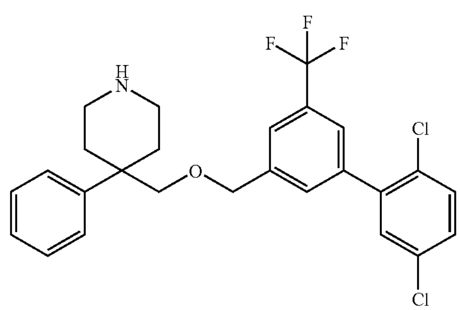 | 4 | 2.94 | 494.2 |
| 92 | 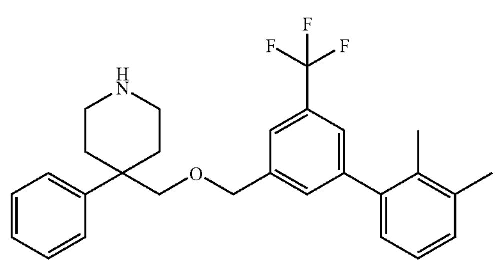 [SMILES: Cc1cccc(-c2cc(COCC3(c4ccccc4)CCNCC3)cc(C(F)(F)F)c2)c1C] | 4 | 2.98 | 454.33 |

TABLES 3-continued

The following compounds were prepared by method A.

| Example | Structure | HPLC Method | retention time | Mass Spec. (MH+) |
|---------|-----------|-------------|----------------|------------------|
| 93 | 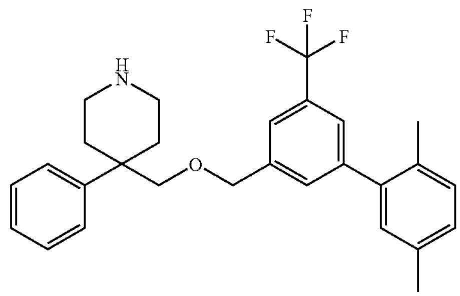 | 4 | 2.94 | 454.28 |
| 94 | 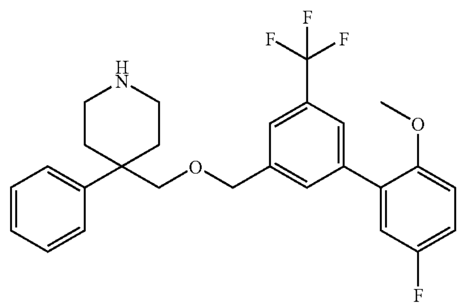 [SMILES: COc1ccc(F)cc1-c1cc(COCC2(c3ccccc3)CCNCC2)cc(C(F)(F)F)c1] | 4 | 2.77 | 474.27 |
| 95 | 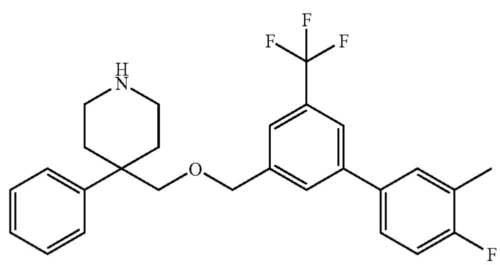 [SMILES: Cc1cc(-c2cc(COCC3(c4ccccc4)CCNCC3)cc(C(F)(F)F)c2)ccc1F] | 4 | 2.9 | 458.31 |
| 96 | 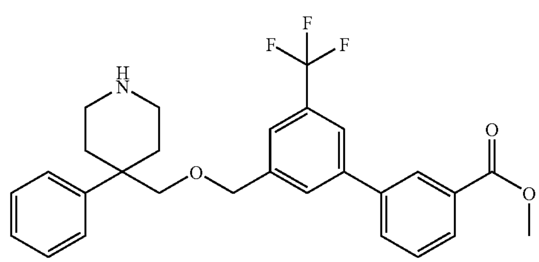 [SMILES: COC(=O)c1cccc(-c2cc(COCC3(c4ccccc4)CCNCC3)cc(C(F)(F)F)c2)c1] | 4 | 2.7 | 484.25 |
| 97 | 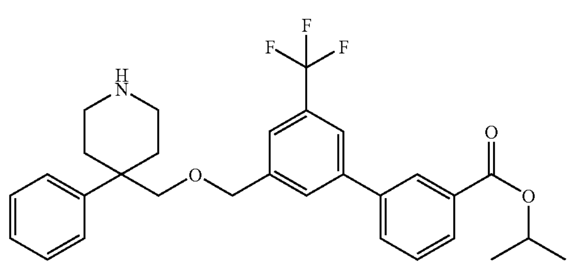 [SMILES: CC(C)OC(=O)c1cccc(-c2cc(COCC3(c4ccccc4)CCNCC3)cc(C(F)(F)F)c2)c1] | 4 | 3.02 | 512.3 |

TABLES 3-continued

The following compounds were prepared by method A.

| Example | Structure | HPLC Method | retention time | Mass Spec. (MH+) |
|---------|-----------|-------------|----------------|------------------|
| 98 | 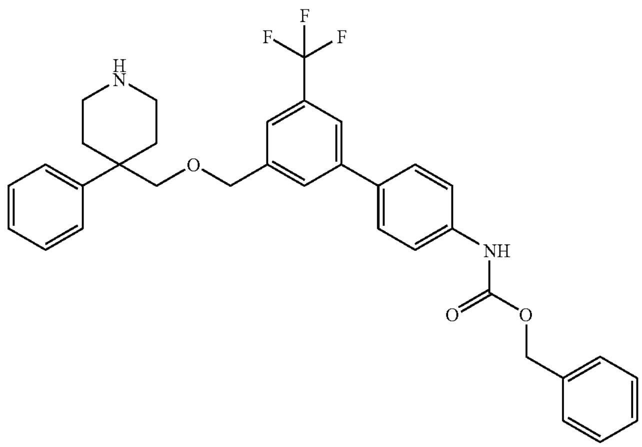 [SMILES: O=C(Nc1ccc(-c2cc(COCC3(c4ccccc4)CCNCC3)cc(C(F)(F)F)c2)cc1)OCc1ccccc1] | 4 | 2.89 | 575.38 |
| 99 | 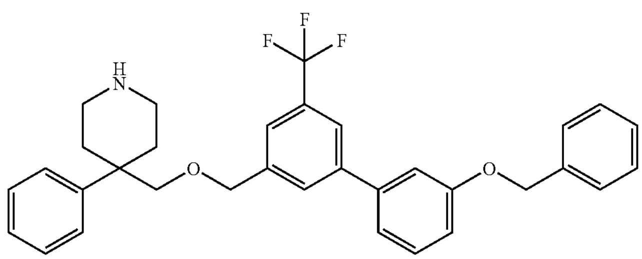 [SMILES: FC(F)(F)c1cc(COCC2(c3ccccc3)CCNCC2)cc(-c2cccc(OCc3ccccc3)c2)c1] | 4 | 2.93 | 532.31 |
| 100 | 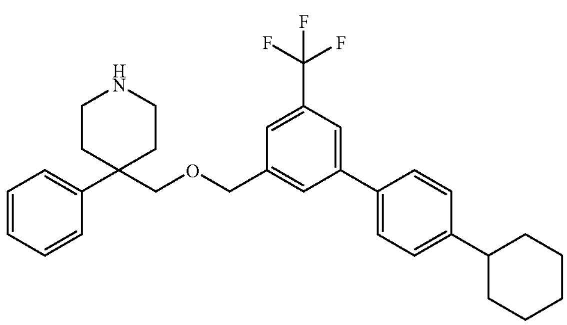 [SMILES: FC(F)(F)c1cc(COCC2(c3ccccc3)CCNCC2)cc(-c2ccc(C3CCCCC3)cc2)c1] | 4 | 3.67 | 508.42 |
| 101 | 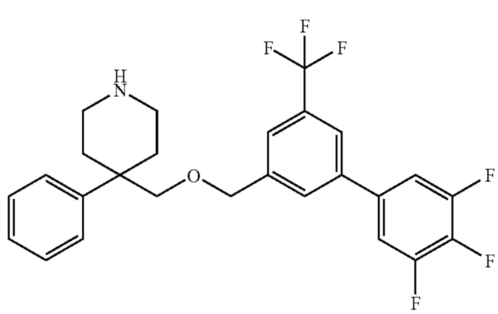 [SMILES: Fc1cc(-c2cc(COCC3(c4ccccc4)CCNCC3)cc(C(F)(F)F)c2)cc(F)c1F] | 4 | 2.88 | 480.22 |

TABLES 3-continued

The following compounds were prepared by method A.

| Example | Structure | HPLC Method | retention time | Mass Spec. (MH+) |
|---|---|---|---|---|
| 102 | 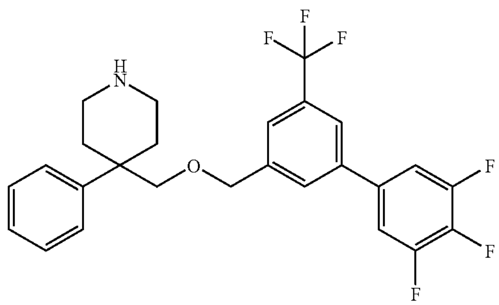 | 4 | 3 | 454.33 |
| 103 | 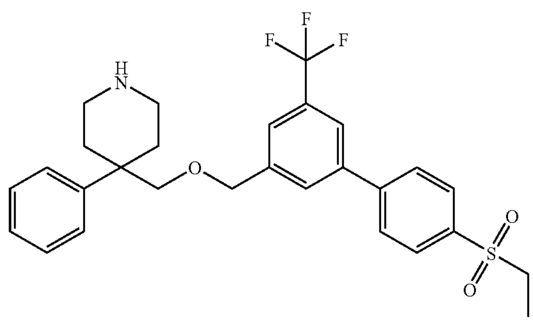 [SMILES: CCS(=O)(=O)c1ccc(-c2cc(COCC3(c4ccccc4)CCNCC3)cc(C(F)(F)F)c2)cc1] | 4 | 2.38 | 518.29 |
| 104 | 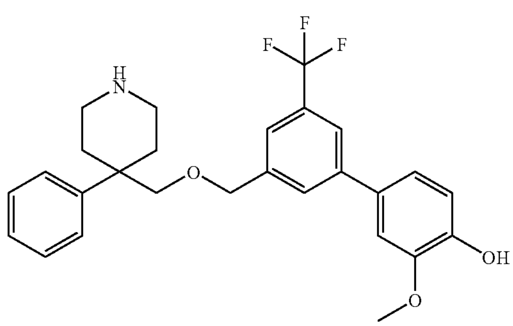 [SMILES: COc1cc(-c2cc(COCC3(c4ccccc4)CCNCC3)cc(C(F)(F)F)c2)ccc1O] | 4 | 2.29 | 472.26 |
| 105 | 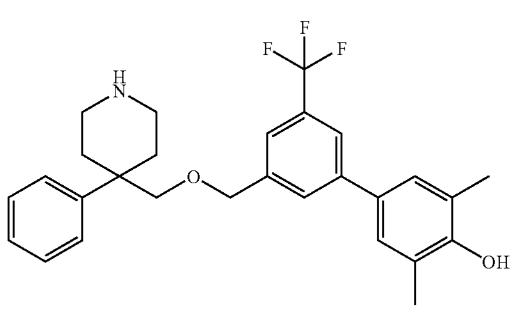 [SMILES: Cc1cc(-c2cc(COCC3(c4ccccc4)CCNCC3)cc(C(F)(F)F)c2)cc(C)c1O] | 4 | 2.62 | 470.33 |

TABLES 3-continued
The following compounds were prepared by method A.
| Example | Structure | HPLC Method | retention time | Mass Spec. (MH+) |
|---|---|---|---|---|
| 106 | 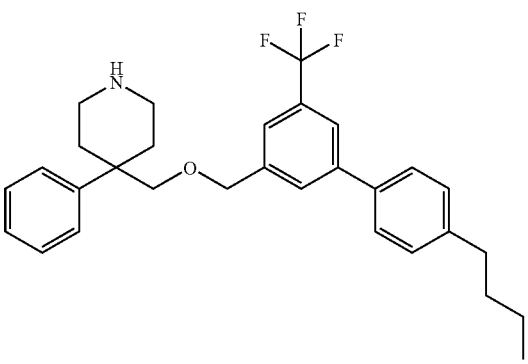 [SMILES: CCCCc1ccc(-c2cc(COCC3(c4ccccc4)CCNCC3)cc(C(F)(F)F)c2)cc1] | 4 | 3.34 | 482.34 |
| 107 | 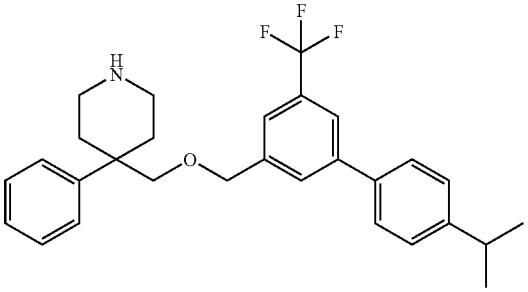 [SMILES: CC(C)c1ccc(-c2cc(COCC3(c4ccccc4)CCNCC3)cc(C(F)(F)F)c2)cc1] | 4 | 3.08 | 468.3 |
| 108 | 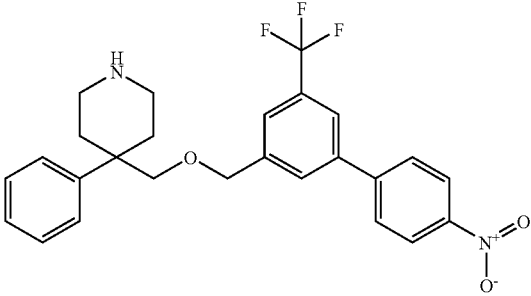 [SMILES: O=[N+]([O-])c1ccc(-c2cc(COCC3(c4ccccc4)CCNCC3)cc(C(F)(F)F)c2)cc1] | 4 | 2.71 | 471.25 |
| 109 | 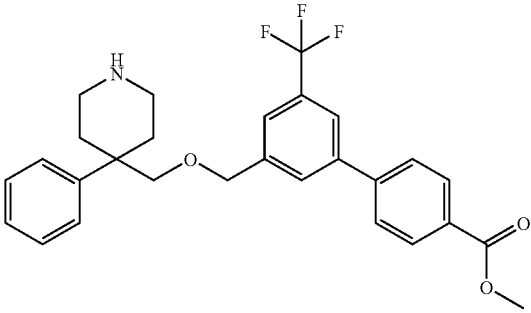 [SMILES: COC(=O)c1ccc(-c2cc(COCC3(c4ccccc4)CCNCC3)cc(C(F)(F)F)c2)cc1] | 4 | 2.73 | 484.32 |

TABLES 3-continued

The following compounds were prepared by method A.

| Example | Structure | HPLC Method | retention time | Mass Spec. (MH+) |
|---------|-----------|-------------|----------------|------------------|
| 110 | 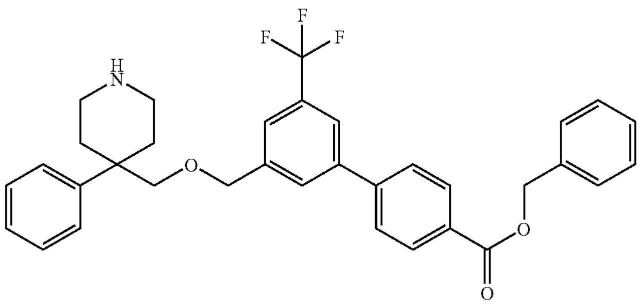 [SMILES: O=C(OCc1ccccc1)c1ccc(-c2cc(COCC3(c4ccccc4)CCNCC3)cc(C(F)(F)F)c2)cc1] | 4 | 3.16 | 560.37 |
| 111 | 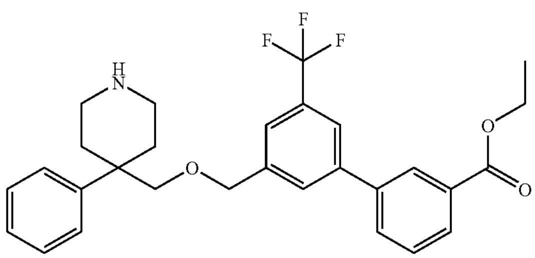 [SMILES: CCOC(=O)c1cccc(-c2cc(COCC3(c4ccccc4)CCNCC3)cc(C(F)(F)F)c2)c1] | 4 | 2.92 | 498.31 |
| 112 | 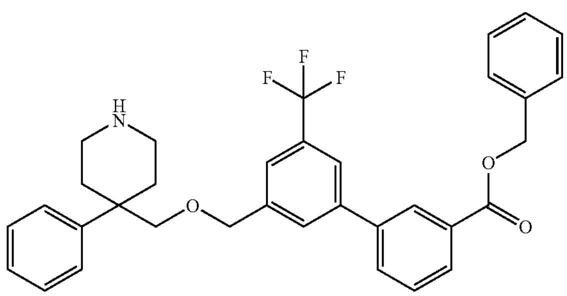 [SMILES: O=C(OCc1ccccc1)c1cccc(-c2cc(COCC3(c4ccccc4)CCNCC3)cc(C(F)(F)F)c2)c1] | 4 | 3.14 | 560.37 |
| 113 | 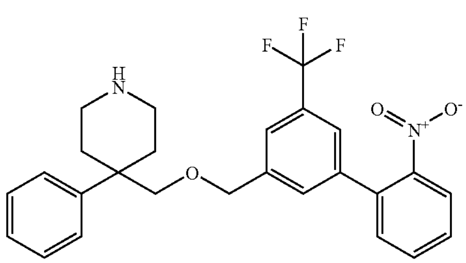 [SMILES: O=[N+]([O-])c1ccccc1-c1cc(COCC2(c3ccccc3)CCNCC2)cc(C(F)(F)F)c1] | 4 | 2.58 | 471.25 |
| 114 | 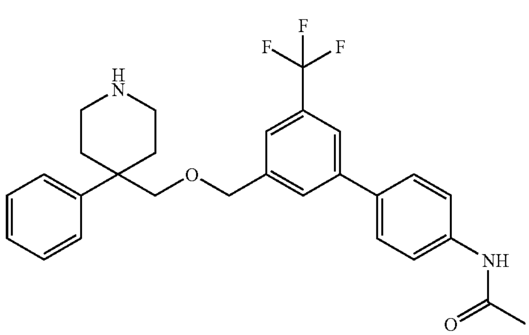 [SMILES: CC(=O)Nc1ccc(-c2cc(COCC3(c4ccccc4)CCNCC3)cc(C(F)(F)F)c2)cc1] | 4 | 2.24 | 483.29 |

TABLES 3-continued
The following compounds were prepared by method A.
| Example | Structure | HPLC Method | retention time | Mass Spec. (MH+) |
|---|---|---|---|---|
| 115 | 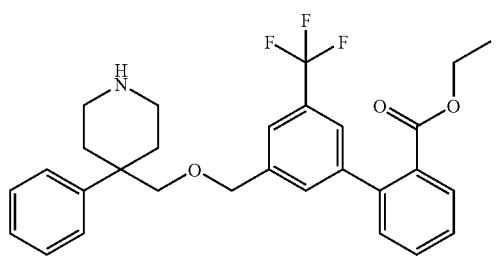 [SMILES: CCOC(=O)c1ccccc1-c1cc(COCC2(c3ccccc3)CCNCC2)cc(C(F)(F)F)c1] | 4 | 2.77 | 498.31 |
| 116 | 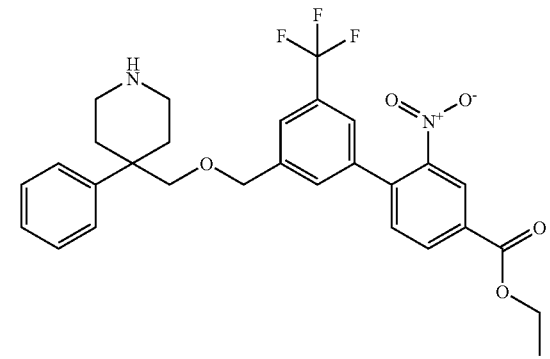 [SMILES: CCOC(=O)c1ccc(-c2cc(COCC3(c4ccccc4)CCNCC3)cc(C(F)(F)F)c2)c([N+](=O)[O-])c1] | 4 | 2.83 | 543.35 |
| 117 | 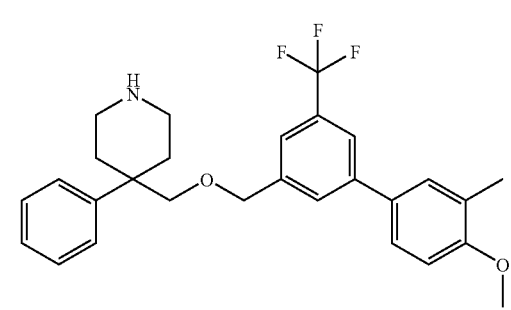 [SMILES: COc1ccc(-c2cc(COCC3(c4ccccc4)CCNCC3)cc(C(F)(F)F)c2)cc1C] | 4 | 2.99 | 470.33 |
| 118 | 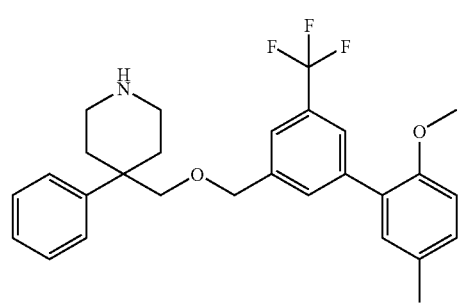 | 4 | 2.94 | 470.28 |

TABLES 3-continued
The following compounds were prepared by method A.
| Example | Structure | HPLC Method | retention time | Mass Spec. (MH+) |
|---------|-----------|-------------|----------------|------------------|
| 119 | 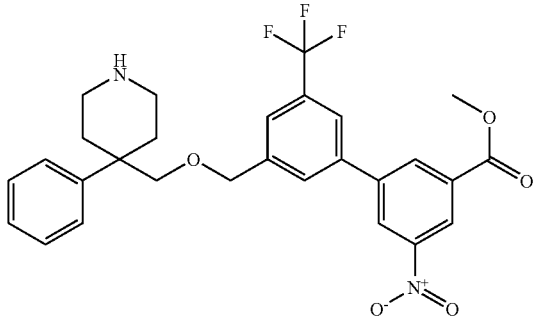 [SMILES: COC(=O)c1cc(-c2cc(COCC3(c4ccccc4)CCNCC3)cc(C(F)(F)F)c2)cc([N+](=O)[O-])c1] | 4 | 2.77 | 529.29 |
| 120 | 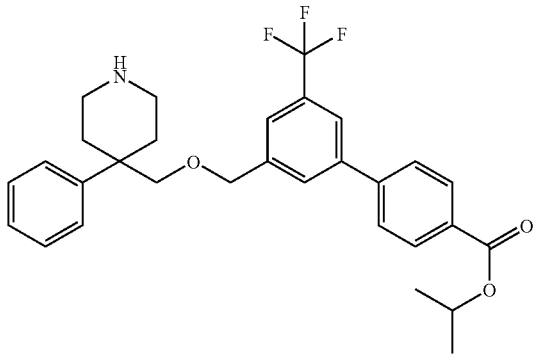 [SMILES: CC(C)OC(=O)c1ccc(-c2cc(COCC3(c4ccccc4)CCNCC3)cc(C(F)(F)F)c2)cc1] | 4 | 2.98 | 512.32 |
| 121 | 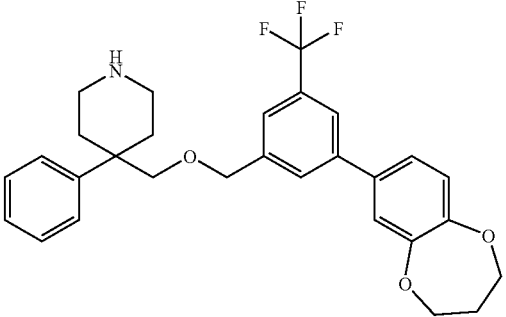 [SMILES: FC(F)(F)c1cc(COCC2(c3ccccc3)CCNCC2)cc(-c2ccc3c(c2)OCCCO3)c1] | 4 | 2.83 | 498.34 |
| 122 | 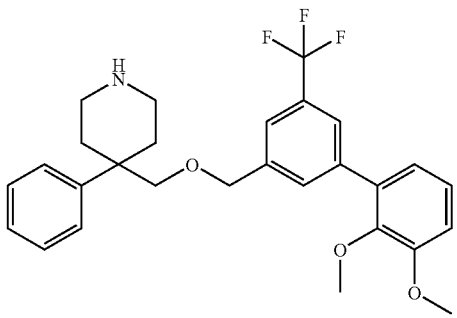 [SMILES: COc1cccc(-c2cc(COCC3(c4ccccc4)CCNCC3)cc(C(F)(F)F)c2)c1OC] | 4 | 2.76 | 486.27 |

TABLES 3-continued
The following compounds were prepared by method A.
| Example | Structure | HPLC Method | retention time | Mass Spec. (MH+) |
|---------|-----------|-------------|----------------|------------------|
| 123 | 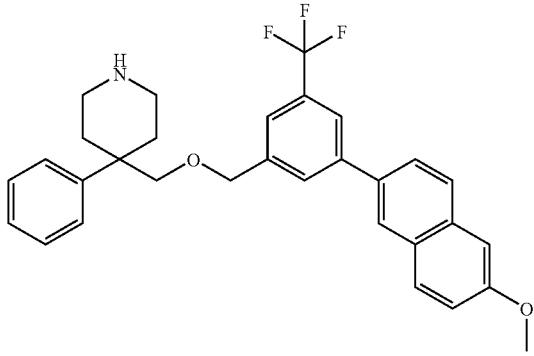 [SMILES: COc1ccc2cc(-c3cc(COCC4(c5ccccc5)CCNCC4)cc(C(F)(F)F)c3)ccc2c1] | 4 | 3.01 | 506.31 |
| 124 | 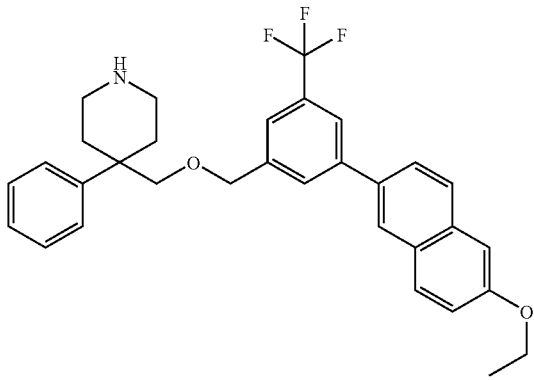 [SMILES: CCOc1ccc2cc(-c3cc(COCC4(c5ccccc5)CCNCC4)cc(C(F)(F)F)c3)ccc2c1] | 4 | 3.17 | 520.35 |
| 125 | 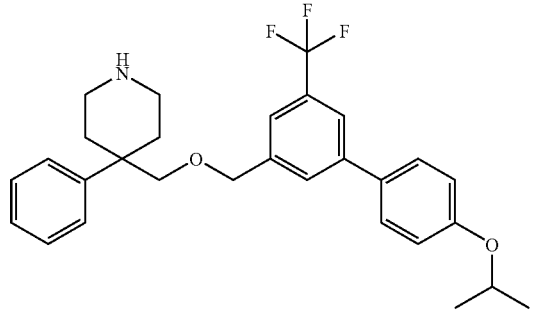 [SMILES: CC(C)Oc1ccc(-c2cc(COCC3(c4ccccc4)CCNCC3)cc(C(F)(F)F)c2)cc1] | 4 | 3.01 | 484.33 |
| 126 | 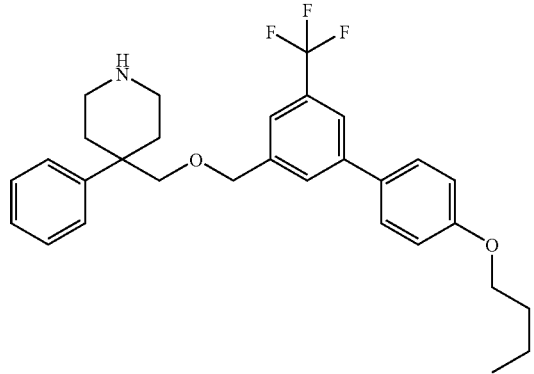 [SMILES: CCCCOc1ccc(-c2cc(COCC3(c4ccccc4)CCNCC3)cc(C(F)(F)F)c2)cc1] | 6 | 1.82 | 498.01 |

TABLES 3-continued
The following compounds were prepared by method A.
| Example | Structure | HPLC Method | retention time | Mass Spec. (MH+) |
|---|---|---|---|---|
| 127 | 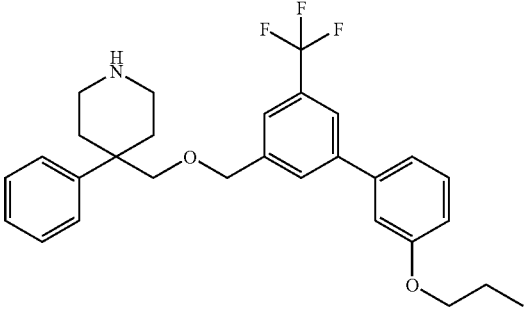 [SMILES: CCCOc1cccc(-c2cc(COCC3(c4ccccc4)CCNCC3)cc(C(F)(F)F)c2)c1] | 6 | 1.65 | 484.63 |
| 128 | 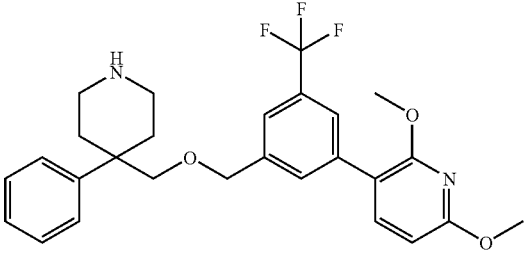 [SMILES: COc1ccc(-c2cc(COCC3(c4ccccc4)CCNCC3)cc(C(F)(F)F)c2)c(OC)n1] | 6 | 1.43 | 486.96 |
| 129 | 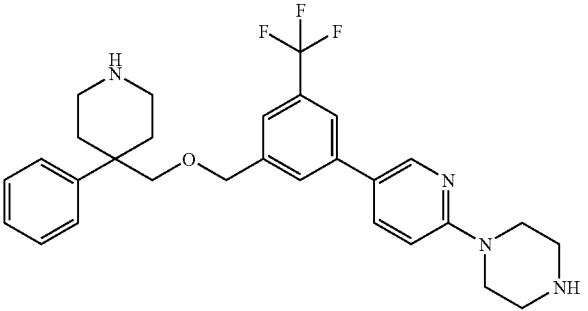 [SMILES: FC(F)(F)c1cc(COCC2(c3ccccc3)CCNCC2)cc(-c2ccc(N3CCNCC3)nc2)c1] | 6 | 1 | 511.02 |
| 130 | 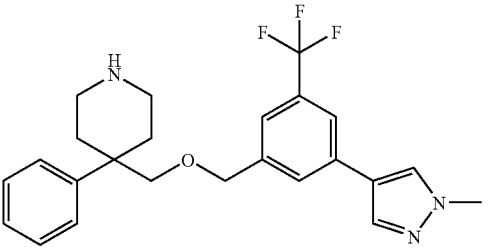 [SMILES: Cn1cc(-c2cc(COCC3(c4ccccc4)CCNCC3)cc(C(F)(F)F)c2)cn1] | 6 | 1.12 | 429.99 |
| 131 | 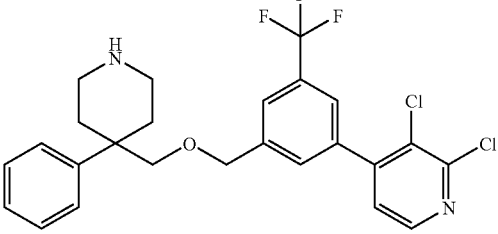 | 6 | 1.37 | 495.54 |

TABLES 3-continued

The following compounds were prepared by method A.

| Example | Structure | HPLC Method | retention time | Mass Spec. (MH+) |
|---|---|---|---|---|
| 132 | 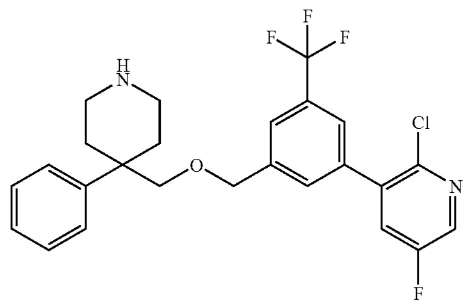 [SMILES: Fc1cnc(Cl)c(-c2cc(COCC3(c4ccccc4)CCNCC3)cc(C(F)(F)F)c2)c1] | 6 | 1.32 | 478.9 |
| 133 | 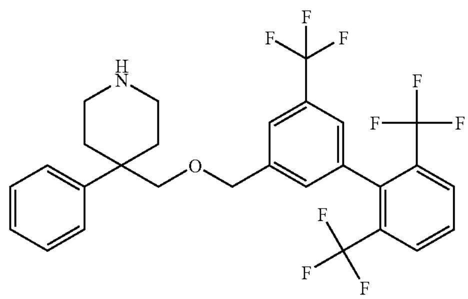 [SMILES: FC(F)(F)c1cc(COCC2(c3ccccc3)CCNCC2)cc(-c2c(C(F)(F)F)cccc2C(F)(F)F)c1] | 6 | 1.75 | 561.9 |

TABLE 4

| Example | Structure | Synthetic Method | HPLC Method | retention time | Mass Spec. (MH+) |
|---|---|---|---|---|---|
| 134 | 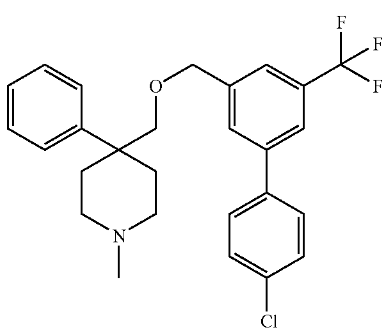 | A, D | 1 | 2.54 | 474.12 |
| 135 | 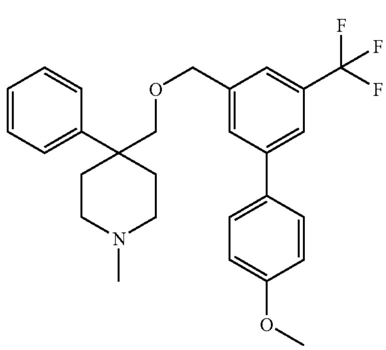 [SMILES: COc1ccc(-c2cc(COCC3(c4ccccc4)CCN(C)CC3)cc(C(F)(F)F)c2)cc1] | A, D | 1 | 2.40 | 470.30 |

TABLE 4-continued

| Example | Structure | Synthetic Method | HPLC Method | retention time | Mass Spec. (MH+) |
| --- | --- | --- | --- | --- | --- |
| 136 | 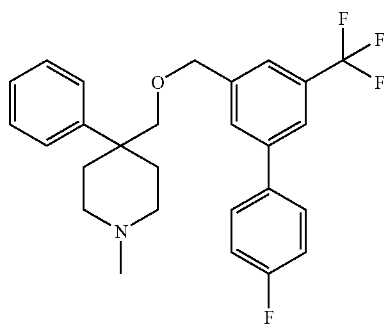 [SMILES: CN1CCC(COCc2cc(-c3ccc(F)cc3)cc(C(F)(F)F)c2)(c2ccccc2)CC1] | A, D | 1 | 2.40 | 458.15 |
| 137 | 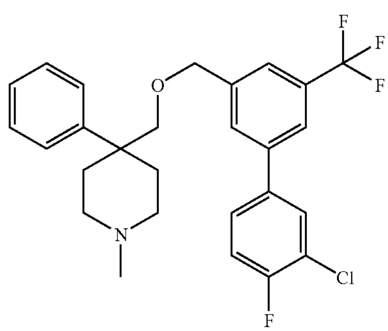 [SMILES: CN1CCC(COCc2cc(-c3ccc(F)c(Cl)c3)cc(C(F)(F)F)c2)(c2ccccc2)CC1] | A, D | 1 | 2.49 | 492.05 |
| 138 | 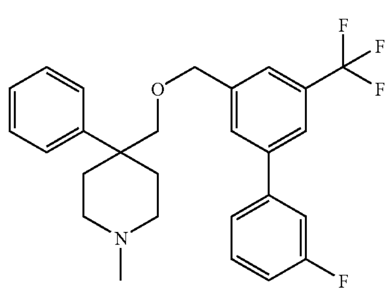 [SMILES: CN1CCC(COCc2cc(-c3cccc(F)c3)cc(C(F)(F)F)c2)(c2ccccc2)CC1] | A, D | 1 | 2.47 | 458.53 |
| 139 | 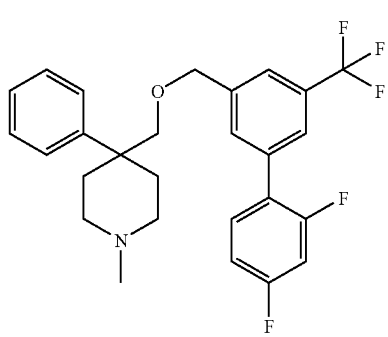 [SMILES: CN1CCC(COCc2cc(-c3ccc(F)cc3F)cc(C(F)(F)F)c2)(c2ccccc2)CC1] | A, D | 1 | 2.46 | 476.18 |

TABLE 4-continued

| Example | Structure | Synthetic Method | HPLC Method | retention time | Mass Spec. (MH+) |
|---|---|---|---|---|---|
| 140 | 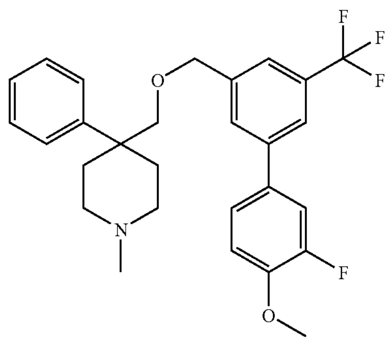 | A, D | 1 | 2.39 | 488.90 |

Example 141

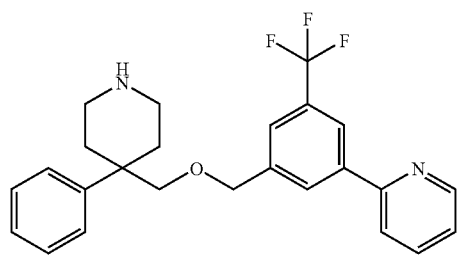 [SMILES: FC(F)(F)c1cc(COCC2(c3ccccc3)CCNCC2)cc(-c2ccccn2)c1]

2-(3-(((4-Phenylpiperidin-4-yl)methoxy)methyl)-5-(trifluoromethyl)phenyl)pyridine. tert-Butyl 4-((3-bromo-5-(trifluoromethyl)benzyloxy)methyl)-4-phenylpiperidine-1-carboxylate (50.0 mg, 0.094 mmol), 2-tri-n-butyl stanyl-pyridine (44.2 mg, 0.12 mmol) and bis(triphenylphosphine) palladium(II) dichloride (3.0 mg, 0.004 mmol) were combined in dry acetonitrile (2 mL) and heated at 150° C. for 1 h via microwave. After cooling to room temperature, the reaction mixture was concentrated and treated with a trifluoroacetic acid/methylene chloride mixture (1:1, 2 mL) for 1 h. The solvent was removed in vacuo and the resulting crude mixture passed through a strong cation exchange column. After washing the column with several volumes of methanol, the product was eluted by washing the column with 2 M ammonia in methanol. Concentration and preparative HPLC afforded 21.0 mg (41%) as its TFA salt. $^1$H-NMR (CDCl$_3$, 500 MHz) δ 8.71 (m, 1H), 8.14 (s, 1H), 7.91 (s, 1H), 7.80 (m, 1H), 7.67 (d, J=7.9 Hz, 1H), 7.43 (s, 1H), 7.31-7.38 (m, 4H), 7.27-7.29 (m, 1H), 7.19-7.22 (m, 1H), 4.47 (s, 2H), 3.47 (s, 2H), 2.90-2.95 (m, 2H), 2.73-2.79 (m, 2H), 2.18-2.21 (m, 2H), 1.89-1.96 (m, 2H). Mass spec.: 427.24 (MH)$^+$. Accurate mass spec.: m/z 427.2015 [MH]$^+$, Δ=4.2 ppm.

TABLE 5

The following compounds were prepared by method B.

| Example | Structure | Mass spec. (MH)$^+$ | HPLC retention time ($t_R$, min) (method 2) |
|---|---|---|---|
| 142 | 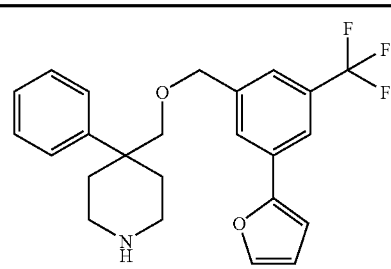 | 415.93 | 1.67 |
| 143 | 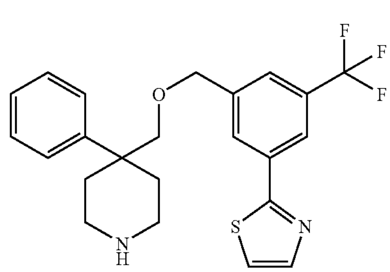 [SMILES: FC(F)(F)c1cc(COCC2(c3ccccc3)CCNCC2)cc(-c2nccs2)c1] | 432.86 | 1.46 |

TABLE 5-continued
The following compounds were prepared by method B.
| Example | Structure | Mass spec. (MH)+ | HPLC retention time ($t_R$, min) (method 2) |
|---|---|---|---|
| 144 | 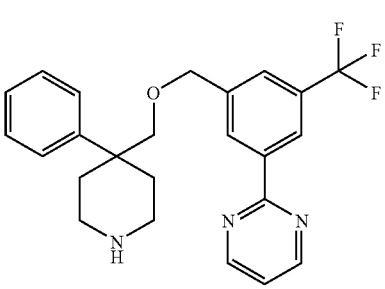 [SMILES: FC(F)(F)c1cc(COCC2(c3ccccc3)CCNCC2)cc(-c2ncccn2)c1] | 427.93 | 1.44 |
| 145 | 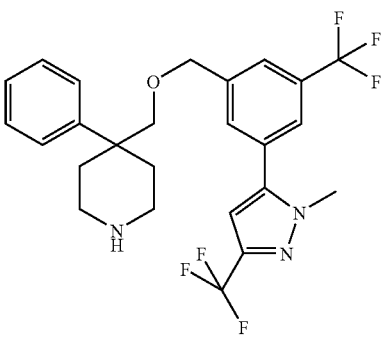 [SMILES: Cn1nc(C(F)(F)F)cc1-c1cc(COCC2(c3ccccc3)CCNCC2)cc(C(F)(F)F)c1] | 497.87 | 1.45 |
| 146 | 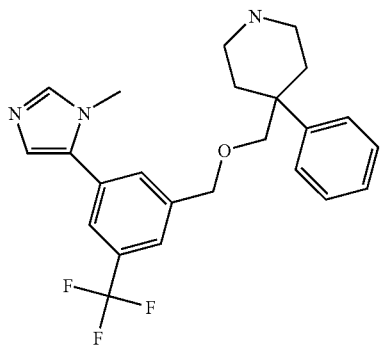 [SMILES: Cn1cncc1-c1cc(COCC2(c3ccccc3)CCNCC2)cc(C(F)(F)F)c1] | 429.93 | 1.2 |
| 147 | 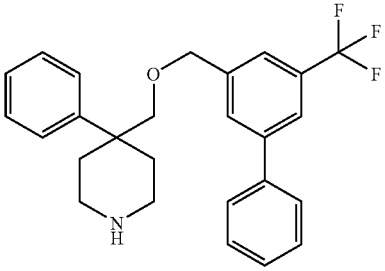 [SMILES: FC(F)(F)c1cc(COCC2(c3ccccc3)CCNCC2)cc(-c2ccccc2)c1] | 425.92 | 1.67 |

TABLE 5-continued

The following compounds were prepared by method B.

| Example | Structure | Mass spec. (MH)+ | HPLC retention time ($t_R$, min) (method 2) |
|---|---|---|---|
| 148 | 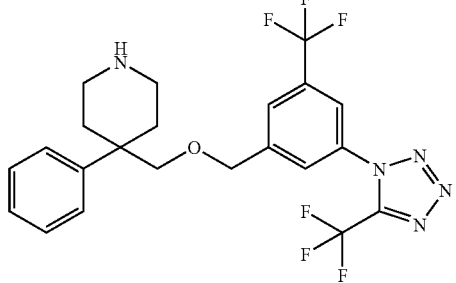 | 445.9 | 1.71 |

Example 149

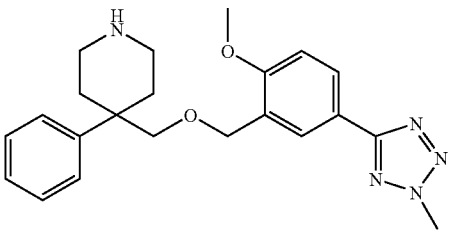 [SMILES: COc1ccc(-c2nnn(C)n2)cc1COCC1(c2ccccc2)CCNCC1]

4-Phenyl-4-O-(trifluoromethyl)-5-(5-(trifluoromethyl)-1H-tetrazol-1-yl)benzyloxy)methyl)piperidine. tert-Butyl 4-phenyl-4-((3-(trifluoromethyl)-5-(5-(trifluoromethyl)-1H-tetrazol-1-yl)benzyloxy)methyl)piperidine-1-carboxylate (46.0 mg, 0.078 mmol) was dissolved in a trifluoroacetic acid/methylene chloride mixture (1:1, 2 mL) and stirred under nitrogen for 1 h. The solvent was removed in vacuo and the resulting crude mixture passed through a strong cation exchange column. After washing the column with several volumes of methanol, the product was eluted by washing the column with 2 M ammonia in methanol. Concentration afforded 29.0 mg (77%). $^1$H-NMR (CDCl$_3$, 500 MHz) δ 7.61 (s, 1H), 7.58 (s, 1H), 7.3-7.33 (m, 2H), 7.21-7.26 (m, 2H), 7.12 (s, 1H), 7.02-7.06 (m, 1H), 4.50 (s, 2H), 3.48 (s, 2H), 2.89-2.93 (m, 2H), 2.72-2.77 (m, 2H), 2.19-2.22 (m, 2H), 1.84-1.89 (m, 2H). $^{13}$C-NMR (CDCl$_3$, 125 MHz) δ 146.2 (q, J=42.2 Hz), 146.1, 143.8, 143.5, 133.2, 132.7 (q, J=35.6 Hz), 128.3, 127.2, 126.6, 126.5, 126.2, 122.8 (q, J=272.6 Hz), 121.1, 119.0, 116.8, 80.7, 71.1, 42.6, 41.9, 33.4. Mass spec.: 486.18 (MH)+. Accurate mass spec.: m/z 486.1739 [MH]+, Δ=2.1 ppm.

Example 150

4-((2-Methoxy-5-(2-methyl-2H-tetrazol-5-yl)benzyloxy) methyl)-4-phenylpiperidine. tert-Butyl 4-((2-methoxy-5-(2-methyl-2H-tetrazol-5-yl)benzyloxy)methyl)-4-phenylpiperidine-1-carboxylate (28.0 mg, 0.057 mmol) was dissolved in a minimum amount of ethyl acetate, followed by addition of 4 N hydrochloric acid (1 mL). The mixture was stirred under nitrogen for 1 h. After removing the solvents, the crude mixture was precipitated in diethyl ether and filtered to afford 16.0 g (73%) as its HCl salt. $^1$H-NMR (CD$_3$OD, 500 MHz) δ 7.99-8.04 (m, 2H), 7.50 (s, 1H), 7.49 (s, 1H), 7.41-7.45 (m, 3H), 7.10 (d, J=8.5 Hz, 1H), 4.51 (s, 2H), 4.43 (s, 3H), 3.88 (s, 3H), 3.55 (s, 2H), 3.35-3.37 (m, 2H), 2.94-3.09 (m, 2H), 2.45-2.54 (m, 2H), 2.31-2.37 (m, 2H). $^{13}$C-NMR (CD$_3$OD, 76 MHz) δ 165.3, 159.2, 141.2, 129.0, 129.1, 127.7, 127.6, 127.1, 127.0, 119.8, 110.9, 79.5, 68.0, 55.2, 41.3, 38.9, 28.8, 28.3. Mass spec.: 394.25 (MH)+. Accurate mass spec.: m/z 394.2247 [MH]+, Δ=4.1 ppm.

Example 151

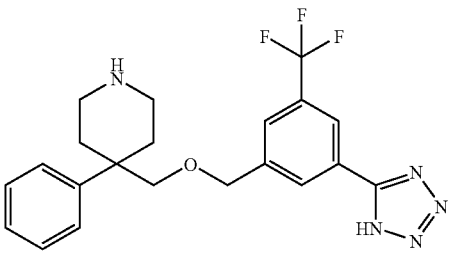 [SMILES: FC(F)(F)c1cc(COCC2(c3ccccc3)CCNCC2)cc(-c2nnn[nH]2)c1]

4-((3-(1H-Tetrazol-5-yl)-5-(trifluoromethyl)benzyloxy) methyl)-4-phenylpiperidine. tert-Butyl 4-((3-(1H-tetrazol-5- yl)-5-(trifluoromethyl)benzyloxy)methyl)-4-phenylpiperidine-1-carboxylate (30.0 mg, 0.058 mmol) was dissolved in a trifluoroacetic acid/methylene chloride mixture (1:1, 1 mL) and stirred under nitrogen for 1 h. The solvent was removed in vacuo and the resulting crude mixture passed through a strong cation exchange column. After washing the column with several volumes of methanol, the product was eluted by washing the column with 2 M ammonia in methanol. Concentration afforded 11.0 mg (45%). LC/MS (HPLC method 3): $t_R$=1.89 min, 418.88 (MH)$^+$.

Example 152

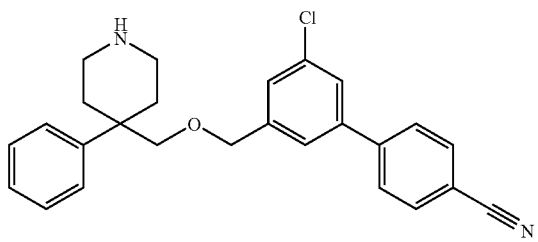 [SMILES: N#Cc1ccc(-c2cc(Cl)cc(COCC3(c4ccccc4)CCNCC3)c2)cc1]

3'-Chloro-5'-(((4-phenylpiperidin-4-yl)methoxy)methyl)biphenyl-4-carbonitrile. $^1$H-NMR (CDCl$_3$, 500 MHz) δ 8.71 (m, 1H), 8.14 (s, 1H), 7.91 (s, 1H), 7.80 (m, 1H), 7.67 (d, J=7.9 Hz, 1H), 7.43 (s, 1H), 7.31-7.38 (m, 4H), 7.27-7.29 (m, 1H), 7.19-7.22 (m, 1H), 4.47 (s, 2H), 3.47 (s, 2H), 2.90-2.95 (m, 2H), 2.73-2.79 (m, 2H), 2.18-2.21 (m, 2H), 1.89-1.96 (m, 2H). Mass spec.: 417.27 (MH)$^+$. Accurate mass spec.: m/z 417.1716 [MH]$^+$, Δ=4.2 ppm.

Example 153

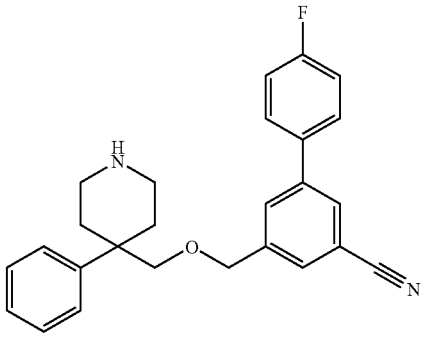 [SMILES: N#Cc1cc(COCC2(c3ccccc3)CCNCC2)cc(-c2ccc(F)cc2)c1]

4'-Fluoro-5-(((4-phenylpiperidin-4-yl)methoxy)methyl)biphenyl-3-carbonitrile. $^1$H-NMR (CDCl$_3$, 500 MHz) δ 7.65 (s, 1H), 7.41-7.44 (m, 3H), 7.32-7.37 (m, 4H), 7.21-7.26 (m, 2H), 7.13-7.16 (m, 2H), 4.40 (s, 2H), 3.45 (s, 2H), 2.91-2.95 (m, 2H), 2.74-2.79 (m, 2H), 2.19-2.22 (m, 2H), 1.88-1.93 (m, 2H). $^{13}$C-NMR (CDCl$_3$, 126 MHz) δ 163.2 (d, J=248.6 Hz), 141.5, 141.0, 135.1, 129.8, 129.5, 129.1, 128.9, 128.5, 127.3, 126.4, 118.7, 116.2, 116.0, 113.1, 80.3, 72.0, 42.6, 41.9, 33.4. Mass spec.: 401.36 (MH)$^+$. Accurate mass spec.: m/z 401.2046 [MH]$^+$, Δ=4.2 ppm.

Example 154

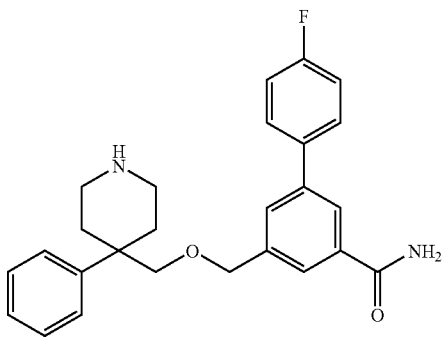 [SMILES: NC(=O)c1cc(COCC2(c3ccccc3)CCNCC2)cc(-c2ccc(F)cc2)c1]

4'-Fluoro-5-(((4-phenylpiperidin-4-yl)methoxy)methyl)biphenyl-3-carboxamide. $^1$H-NMR (CDCl$_3$, 500 MHz) δ 7.95 (s, 1H), 7.68 (s, 1H), 7.47-7.50 (m, 2H), 7.38 (s, 1H), 7.32-7.33 (m, 4H), 7.20-7.23 (m, 1H), 7.08-7.11 (m, 2H), 4.47 (s, 2H), 3.41 (s, 2H), 3.02-3.04 (m, 2H), 2.70-2.75 (m, 2H), 2.16-2.19 (m, 4H). $^{13}$C-NMR (CDCl$_3$, 126 MHz) δ 169.3, 163.8 (d, J=247.6 Hz), 140.7, 139.8, 136.2, 134.3, 128.9, 128.3, 128.7, 127.2, 126.6, 125.7, 124.5, 115.9, 115.7, 79.7, 72.6, 50.7, 41.9, 31.6. Mass spec.: 419.37 (MH)$^+$. Accurate mass spec.: m/z 419.2133 [MH]$^+$, Δ=0.4 ppm.

Example 155

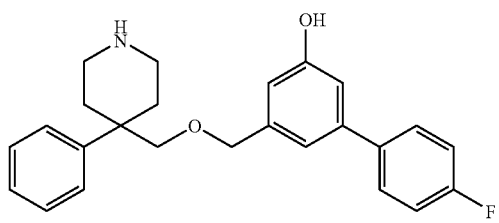 [SMILES: Oc1cc(COCC2(c3ccccc3)CCNCC2)cc(-c2ccc(F)cc2)c1]

4'-Fluoro-5-(((4-phenylpiperidin-4-yl)methoxy)methyl)biphenyl-3-ol. $^1$H-NMR (CDCl$_3$, 500 MHz) δ 7.51-7.54 (m, 2H), 7.46-7.48 (m, 2H), 7.40-7.43 (m, 2H), 7.29-7.31 (m, 1H), 7.14-7.18 (m, 2H), 6.91-6.92 (m, 1H), 6.86 (s, 1H), 6.69 (m, 1H), 4.41 (s, 2H), 3.49 (s, 2H), 3.31 (m, 2H), 2.93-2.98 (m, 2H), 2.49-2.52 (m, 2H), 2.21-2.27 (m, 2H). Mass spec.: 392.36 (MH)$^+$. Accurate mass spec.: m/z 392.2009 [MH]$^+$, Δ=4.3 ppm.

Example 156

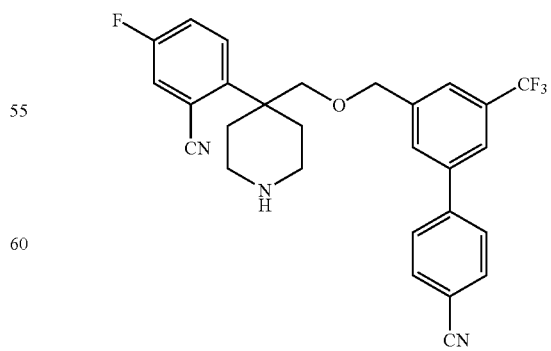

3'-(((4-(2-cyano-4-fluorophenyl)piperidin-4-yl)methoxy)methyl)-5'-(trifluoromethyl)biphenyl-4-carbonitrile.

$^1$H-NMR (CDCl$_3$, 400 MHz) δ 7.73 (d, J=8.8 Hz, 2H), 7.69 (s, 1H), 7.60 (d, J=8.4 Hz, 2H), 7.25-7.43 (m, 5H), 4.51 (s, 2H), 3.81 (s, 2H), 3.27 m, 2H), 2.95 (m, 2H), 2.65 (m, 2H), 2.29 (m, 2H). Mass spec.: 494.16 (M+H), HPLC (method 5) 3.06 min Example 157

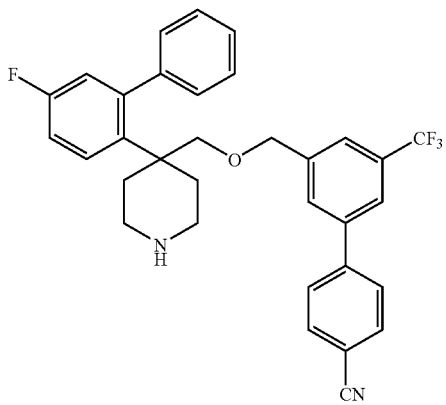 [SMILES: N#Cc1ccc(-c2cc(COCC3(c4ccc(F)cc4-c4ccccc4)CCNCC3)cc(C(F)(F)F)c2)cc1]

3'-(((4-(5-fluorobiphenyl-2-yl)piperidin-4-yl)methoxy)methyl)-5'-(trifluoromethyl)biphenyl-4-carbonitrile. $^1$H-NMR (CDCl$_3$, 400 MHz) δ 7.73 (m, 3H), 7.58 (d, J=8.6 Hz, 2H), 7.43 (d, J=8.3 Hz, 2H), 7.31 (M, 1H), 7.18-7.28 (M, 3H), 7.04 (m, 1H), 6.90 (d, 6.9 Hz, 2H), 6.73 (m, 1H), 4.53 (s, 2H), 3.47 (s, 2H), 3.04 (m, 2H), 2.75 (m, 2H), 2.09 (m, 2H), 1.78 (m, 2H). Mass spec.: 545.2 (M+H), HPLC (method 5) 3.57 min.

Example 158

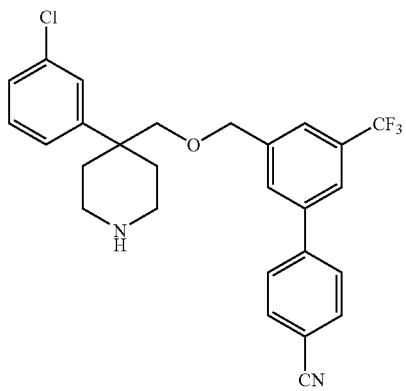

3'-(((4-(3-Chlorophenyl)piperidin-4-yl)methoxy)methyl)-5'-(trifluoromethyl)biphenyl-4-carbonitrile. $^1$H-NMR (CDCl$_3$, 500 MHz) δ ppm 7.75 (m, 2H), 7.68 (s, 1H), 7.61 (s, 1H), 7.44 (s, 1H), 7.37 (s, 1H), 7.21-7.30 (m, 4H), 7.16 (m, 1H), 4.48 (s, 2H), 3.43 (s, 2H), 3.32 (m, 2H), 2.88 (m, 2H), 2.42 (m, 2H), 2.21 (m, 2H). Mass spec.: 485.17 (MH)$^+$.

Example 159

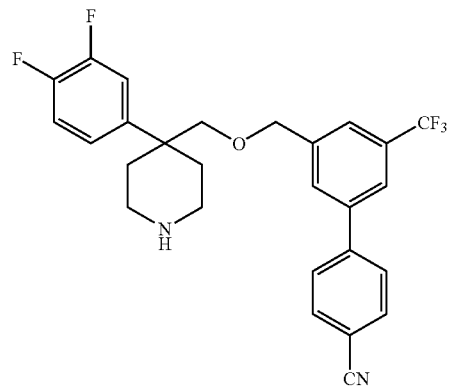 [SMILES: N#Cc1ccc(-c2cc(COCC3(c4ccc(F)c(F)c4)CCNCC3)cc(C(F)(F)F)c2)cc1]

3'-(((4-(3,4-Difluorophenyl)piperidin-4-yl)methoxy)methyl)-5'-(trifluoromethyl)biphenyl-4-carbonitrile. $^1$H-NMR (CDCl$_3$, 500 MHz) δ ppm 7.75 (m, 2H), 7.68 (s, 1H), 7.61 (m, 2H), 7.44 (s, 1H), 7.37 (s, 1H), 6.99-7.17 (br m, 3H), 4.48 (s, 2H), 3.42 (m, 2H), 3.09 (m, 2H), 2.80 (m, 2H), 2.20 (m, 2H), 2.05 (m, 2H). Mass spec.: 487.17 (MH)$^+$.

Example 160

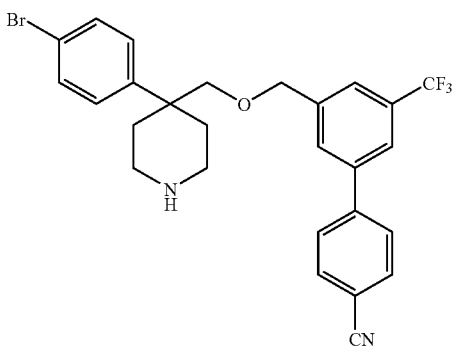 [SMILES: N#Cc1ccc(-c2cc(COCC3(c4ccc(Br)cc4)CCNCC3)cc(C(F)(F)F)c2)cc1]

3'-(((4-(4-Bromophenyl)piperidin-4-yl)methoxy)methyl)-5'-(trifluoromethyl)biphenyl-4-carbonitrile. $^1$H-NMR (CDCl$_3$, 500 MHz) δ ppm 7.77 (m, 2H), 7.67 (s, 1H), 7.59 (m, 2H), 7.43 (m, 4H), 7.22 (m, 2H), 4.46 (s, 2H), 3.44 (s, 2H), 2.98 (m, 2H), 2.75 (m, 2H), 2.17 (m, 2H), 1.94 (m, 2H). Mass spec.: 531.11 (MH)$^+$.

Example 161

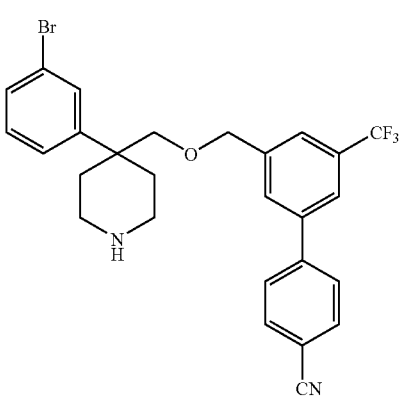 [SMILES: N#Cc1ccc(-c2cc(COCC3(c4cccc(Br)c4)CCNCC3)cc(C(F)(F)F)c2)cc1]

3'-(((4-(3-Bromophenyl)piperidin-4-yl)methoxy)methyl)-5'-(trifluoromethyl)biphenyl-4-carbonitrile. $^1$H-NMR (CDCl$_3$, 500 MHz) δ ppm 7.75 (m, 2H), 7.67 (s, 1H), 7.60 (m, 2H), 7.48 (s, 1H), 7.41 (m, 2H), 7.15-7.34 (m, 3H), 4.46 (s, 2H), 3.45 (s, 2H), 2.97 (m, 2H), 2.76 (m, 2H), 2.17 (m, 2H), 1.96 (m, 2H). Mass spec.: 531.11 (MH)+.

Example 162

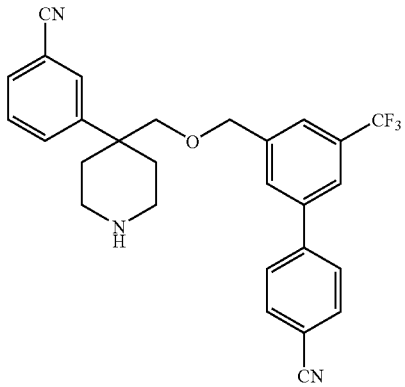 [SMILES: N#Cc1ccc(-c2cc(COCC3(c4cccc(C#N)c4)CCNCC3)cc(C(F)(F)F)c2)cc1]

3'-(((4-(3-Cyanophenyl)piperidin-4-yl)methoxy)methyl)-5'-(trifluoromethyl)biphenyl-4-carbonitrile. ¹H-NMR (CDCl₃, 500 MHz) δ ppm 7.76 (m, 2H), 7.68 (s, 1H), 7.61 (m, 2H), 7.57-7.61 (m, 2H), 7.49 (m, 1H), 7.39-7.44 (m, 2H), 7.34 (s, 1H), 4.47 (s, 2H), 3.46 (s, 2H), 3.03 (m, 2H), 2.76 (m, 2H), 2.22 (m, 2H), 2.03 (m, 2H). Mass spec.: 476.18 (MH)+.

Example 163

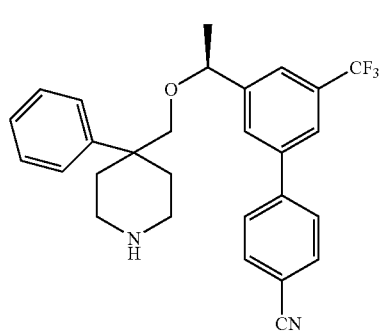 [SMILES: C[C@H](OCC1(c2ccccc2)CCNCC1)c1cc(-c2ccc(C#N)cc2)cc(C(F)(F)F)c1]

(S)-3'-(1-(((4-Phenylpiperidin-4-yl)methoxy)ethyl)-5'-(trifluoromethyl)biphenyl-4-carbonitrile. ¹H NMR (500 MHz, CDCl₃) δ ppm 7.73 (d, J=8.6 Hz, 2H), 7.64 (s, 1H), 7.55 (d, J=8.6 Hz, 2H), 7.38 (s, 2H), 7.20-7.35 (m, 4H), 7.16 (m, 1H), 4.29 (q, J=6.4 Hz, 1H), 3.46 (s, 1H), 3.33 (d, J=9.2 Hz, 1H), 3.25 (d, J=8.9 Hz, 1H), 2.90 (m, 2H), 2.73 (m, 2H), 2.00-2.25 (m, 2H), 1.80-1.99 (m, 2H), 1.35 (d, J=6.4 Hz, 3H). Mass spec.: 465.20 (MH)+. Accurate mass spec.: m/z 465.2136 [MH]+, Δ=3.8 ppm.

Example 164

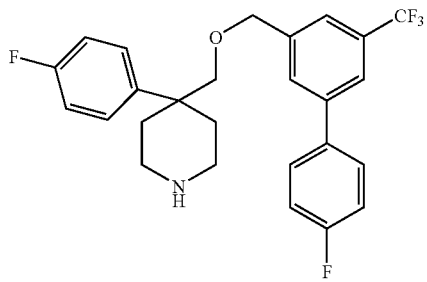 [SMILES: Fc1ccc(-c2cc(COCC3(c4ccc(F)cc4)CCNCC3)cc(C(F)(F)F)c2)cc1]

4-(((4'-Fluoro-5-(trifluoromethyl)biphenyl-3-yl)methoxy)methyl)-4-(4-fluorophenyl)piperidine. ¹H-NMR (CDCl₃, 500 MHz) δ 7.63 (s, 1H), 7.46 (m, 2H), 7.40 (s, 1H), 7.28-7.37 (m, 3H), 7.15 (m, 2H), 7.00 (m, 2H), 4.45 (s, 2H), 3.44 (s, 2H), 2.91 (m, 2H), 2.74 (m, 2H), 2.14 (m, 2H), 1.91 (bs, 1H), 1.89 (m, 2H); ¹³C NMR (126 MHz, CDCl₃) δ ppm 164.0, 162.3, 162.0, 160.4, 141.2, 140.5, 139.9, 135.8, 131.4 (q, J=33 Hz), 128.9 (m), 128.8 (m), 124.1 (q, J=273 Hz), 122.8 (q, J=3.8 Hz), 122.6 (q, J=3.8 Hz), 116.1, 115.9, 115.1, 115.0, 79.8, 72.4, 42.6, 41.5, 33.8. Mass spec.: 462.20 (MH)+. Accurate mass spec.: m/z 462.1875 [MH]+, Δ=4.0 ppm.

Example 165

(±)-3'-Fluoro-5'-(1-((4-phenylpiperidin-4-yl)methoxy)ethyl)biphenyl-4-carbonitrile. ¹H-NMR (CDCl₃, 500 MHz) δ 7.71 (d, J=8.2 Hz, 2H), 7.54 (d, J=8.2 Hz, 2H), 7.31 (m, 4H), 7.19 (m, 1H), 7.10 (m, 1H), 7.02 (s, 1H), 6.78 (m, 1H), 4.21 (q, J=6.4 Hz, 1H), 3.28 (q_{AB}, J_{AB}=8.9 Hz, 2H), 2.90 (m, 2H), 2.74 (m, 2H), 2.19 (m, 1H), 2.12 (m, 1H), 1.91 (m, 2H), 1.83 (bs, 1H), 1.32 (d, J=6.4 Hz, 3H); ¹³C NMR (126 MHz, CDCl₃) δ ppm 164.4, 162.4, 148.3, 148.2, 144.4, 144.3, 141.3, 141.2, 132.7, 128.3, 127.8, 127.4, 126.1, 120.3, 118.7, 113.2, 113.1, 113.0, 112.8, 111.7, 78.4, 77.8, 50.8, 42.8, 42.7, 41.9, 33.6, 33.3, 24.0. Mass spec.: 415.32 (MH)+. Accurate mass spec.: m/z 415.2167 [MH]+, Δ=4.5 ppm.

Example 166

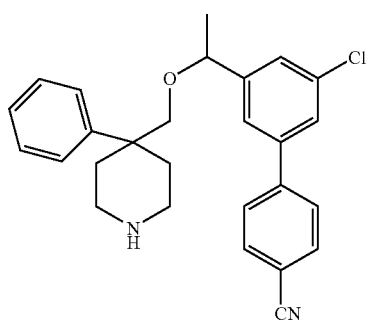 [SMILES: CC(OCC1(c2ccccc2)CCNCC1)c1cc(Cl)cc(-c2ccc(C#N)cc2)c1]

(±)-3'-Chloro-5'-(1-((4-phenylpiperidin-4-yl)methoxy)ethyl)biphenyl-4-carbonitrile. $^1$H-NMR (CDCl$_3$, 500 MHz) δ 7.70 (d, J=8.6 Hz, 2H), 7.52 (d, J=8.6 Hz, 2H), 7.38 (m, 1H), 7.25-7.42 (m, 4H), 7.17 (m, 1H), 7.09 (s, 1H), 7.06 (s, 1H), 4.19 (q, J=6.4 Hz, 1H), 3.27 (q$_{AB}$, J$_{AB}$=8.9, 2H), 2.89 (m, 2H), 2.72 (m, 2H), 2.19 (m, 1H), 2.10 (m, 1H), 1.90 (m, 2H), 1.78 (bs, 1H), 1.31 (d, J=6.4 Hz, 3H); $^{13}$C NMR (126 MHz, CDCl$_3$) δ ppm 147.5, 144.2, 141.0, 135.0, 132.7, 128.3, 127.9, 127.4, 126.4, 126.13, 126.10, 123.0, 118.8, 111.6, 78.4, 77.2, 42.79, 42.75, 41.8, 33.7, 33.3, 24.2. Mass spec.: 431.30 (MH)$^+$. Accurate mass spec.: m/z 431.1899 [MH]$^+$, Δ=2.0 ppm.

Example 167

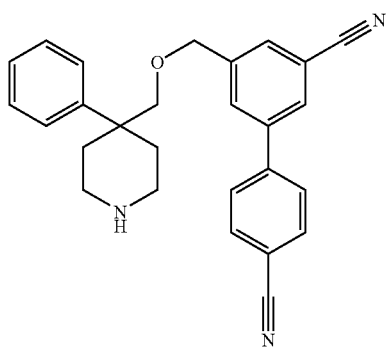 [SMILES: N#Cc1ccc(-c2cc(C#N)cc(COCC3(c4ccccc4)CCNCC3)c2)cc1]

5-(((4-Phenylpiperidin-4-yl)methoxy)methyl)biphenyl-3,4'-dicarbonitrile. $^1$H-NMR (CDCl$_3$, 500 MHz) δ 7.74-7.76 (m, 2H), 7.69 (m, 1H), 7.55-7.57 (m, 2H), 7.47 (m, 1H), 7.32-7.37 (m, 5H), 7.20-7.23 (m, 1H), 4.43 (s, 2H), 3.47 (s, 2H), 2.92-2.94 (m, 2H), 2.74-2.79 (m, 2H), 2.19-2.22 (m, 2H), 1.88-1.93 (m, 2H). Mass spec.: 408.23 (MH)$^+$. Accurate mass spec.: m/z 408.2072 [MH]$^+$, Δ=0.9 ppm.

Example 168

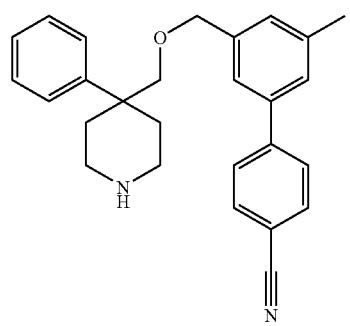 [SMILES: Cc1cc(COCC2(c3ccccc3)CCNCC2)cc(-c2ccc(C#N)cc2)c1]

3'-Methyl-5'-(((4-phenylpiperidin-4-yl)methoxy)methyl)biphenyl-4-carbonitrile. $^1$H-NMR (CDCl$_3$, 500 MHz) δ 7.69-7.70 (m, 2H), 7.58-7.59 (m, 2H), 7.29-7.37 (m, 4H), 7.19-7.25 (m, 2H), 7.10 (m, 1H), 6.95 (m, 1H), 4.39 (s, 2H), 3.43 (s, 2H), 2.92-2.96 (m, 2H), 2.73-2.78 (m, 2H), 2.36 (s, 3H), 2.18-2.21 (m, 2H), 1.91-1.97 (m, 2H). Mass spec.: 397.40 (MH)$^+$. Accurate mass spec.: m/z 397.2296 [MH]$^+$, Δ=4.1 ppm.

Example 169

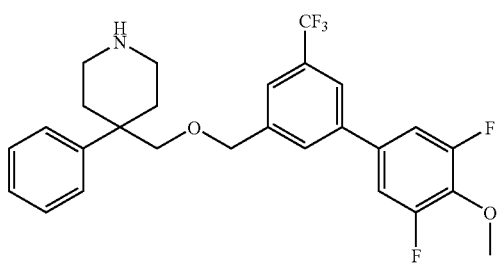 [SMILES: COc1c(F)cc(-c2cc(COCC3(c4ccccc4)CCNCC3)cc(C(F)(F)F)c2)cc1F]

4-(((3',5'-Difluoro-4'-methoxy-5-(trifluoromethyl)biphenyl-3-yl)methoxy)methyl)-4-phenylpiperidine. $^1$H-NMR (CD$_3$OD, 500 MHz) δ 7.76 (s, 1H), 7.56 (s, 1H), 7.48-7.49 (m, 3H), 7.41-7.44 (m, 2H), 7.25-7.31 (m, 3H), 4.56 (s, 2H), 4.04 (s, 3H), 3.35 (s, 2H), 3.35-3.36 (m, 2H), 2.94-2.99 (m, 2H), 2.55-2.58 (m, 2H), 2.18-2.24 (m, 2H). Mass spec.: 492.04 (MH)$^+$. Accurate mass spec.: m/z 492.1976 [MH]$^+$, Δ=2.9 ppm.

Example 170

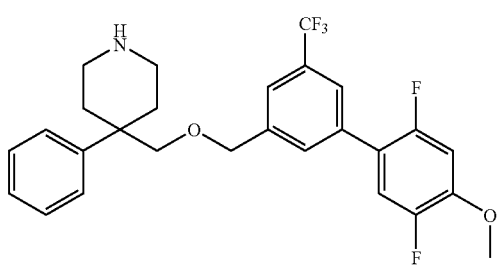 [SMILES: COc1cc(F)c(-c2cc(COCC3(c4ccccc4)CCNCC3)cc(C(F)(F)F)c2)cc1F]

4-(((2',5'-Difluoro-4'-methoxy-5-(trifluoromethyl)biphenyl-3-yl)methoxy)methyl)-4-phenylpiperidine. $^1$H-NMR (CDCl$_3$, 500 MHz) δ 7.57 (s, 1H), 7.23-7.33 (m, 6H), 7.15-7.18 (m, 1H), 7.02-7.09 (m, 1H), 6.73-6.80 (m, 1H), 4.39 (s, 2H), 3.89 (s, 3H), 3.42 (s, 2H), 2.88-2.94 (m, 2H), 2.68-2.77 (m, 2H), 2.17-2.21 (m, 2H), 1.89-1.95 (m, 2H). Mass spec.: 492.20 (MH)$^+$. Accurate mass spec.: m/z 492.1978 [MH]$^+$, Δ=3.3 ppm.

Example 171

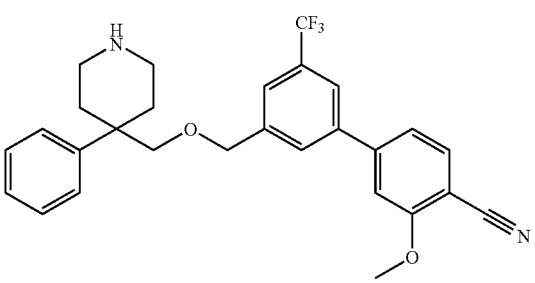 [SMILES: COc1cc(-c2cc(COCC3(c4ccccc4)CCNCC3)cc(C(F)(F)F)c2)ccc1C#N]

3-Methoxy-3'-(((4-phenylpiperidin-4-yl)methoxy)methyl)-5'-(trifluoromethyl)biphenyl-4-carbonitrile. LC/MS:

$t_R$=2.59 min, 481.18 (MH)⁺. Accurate mass spec.: m/z 481.2103 [MH]⁺, Δ=0.4 ppm. (Phenomenex C18 4.6×50 mm, 10% MeOH/90% H₂O/0.1% TFA→90% MeOH/10% H₂O/0.1% TFA, Gradient time=4 min., Flow rate=4 mL/min.).

Example 172

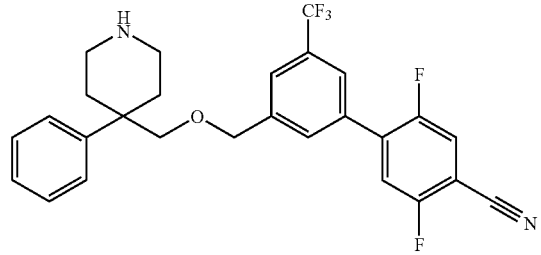 [SMILES: N#Cc1cc(F)c(-c2cc(COCC3(c4ccccc4)CCNCC3)cc(C(F)(F)F)c2)cc1F]

2,5-Difluoro-3'-(((4-phenylpiperidin-4-yl)methoxy)methyl)-5'-(trifluoromethyl)biphenyl-4-carbonitrile. LC/MS: $t_R$=2.61 min, 487.15 (MH)⁺. Accurate mass spec.: m/z 487.1801 [MH]⁺, Δ=1.6 ppm. (Phenomenex C18 4.6×50 mm, 10% MeOH/90% H₂O/0.1% TFA→90% MeOH/10% H₂O/0.1% TFA, Gradient time=4 min., Flow rate=4 mL/min.).

Example 173

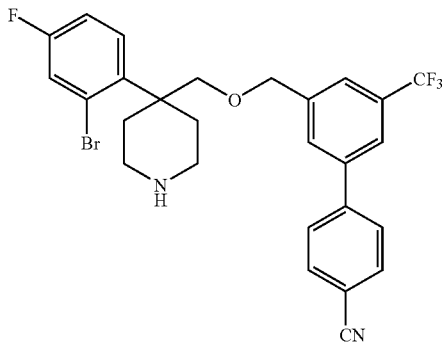 [SMILES: N#Cc1ccc(-c2cc(COCC3(c4ccc(F)cc4Br)CCNCC3)cc(C(F)(F)F)c2)cc1]

3'-(((4-(2-bromo-4-fluorophenyl)piperidin-4-yl)methoxy)methyl)-5'-(trifluoromethyl)biphenyl-4-carbonitrile. A solution of tert-butyl 4-(2-bromo-4-fluorophenyl)-4-(((4'-cyano-5-(trifluoromethyl)biphenyl-3-yl)methoxy)methyl) piperidine-1-carboxylate (50 mg, 0.077 mmol) in dichloromethane (0.5 mL) and trifluoroacetic acid (2 mL) was stirred at ambient temperature for 3 hours. The reaction was evaporated to dryness and the resulting residue was purified by chromatography on silica with gradient of methanol/dichloromethane of 2% to 10%. The product 3'-(((4-(2-bromo-4-fluorophenyl)piperidin-4-yl)methoxy)methyl)-5'-(trifluoromethyl)biphenyl-4-carbonitrile (29 mg, 69% yield) was obtained as a clear oil. ¹H-NMR (CDCl₃, 400 MHz) δ 7.74 (d, J=6.8 Hz, 2H), 7.68 (s, 1H), 7.58 (d, J=6.7 Hz, 2H), 7.36 (s, 1H), 7.33 (s, 1H), 7.22-7.33 (m, 2H), 7.03 (m, 1H), 4.49 (s, 2H), 3.88 (s, 2H), 3.25 (m, 2H), 2.94 (m, 2H), 2.85 (m, 2H), 2.23 (m, 2H). Mass spec.: 547.12 (M+H), HPLC (method 5) 3.37 min.

Example 174

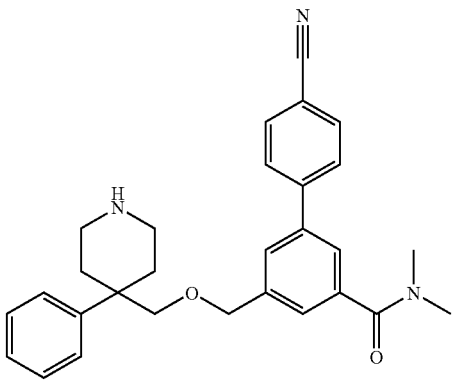 [SMILES: CN(C)C(=O)c1cc(COCC2(c3ccccc3)CCNCC2)cc(-c2ccc(C#N)cc2)c1]

4'-Cyano-N,N-dimethyl-5-(((4-phenylpiperidin-4-yl)methoxy)methyl)biphenyl-3-carboxamide. tert-Butyl 4-((3-bromo-5-(dimethylcarbamoyl)benzyloxy)methyl)-4-phenylpiperidine-1-carboxylate (41.2 mg, 0.08 mmol), 4-cyanophenylboronic acid (34.3 mg, 0.23 mmol), and tetrakis(triphenylphosphine) palladium(0) (12.1 mg, 0.01 mmol) were combined in dry tetrahydrofuran (3 mL) in a microwave tube and sealed. After flushing with nitrogen, 0.28 mL of a 1 N potassium hydroxide aqueous solution was introduced. The mixture was heated at 120° C. for 1 h via microwave. After cooling to room temperature, the reaction mixture was concentrated and treated with a trifluoroacetic acid/methylene chloride mixture (1:1, 2 mL) for 1 h. The solvent was removed in vacuo and the resulting crude mixture passed through a strong cation exchange column. After washing the column with several volumes of methanol, the product was eluted by washing the column with 2 M ammonia in methanol and concentrated to afford 29 mg (66%). ¹H-NMR (CD₃OD, 500 MHz) δ 7.81-7.84 (m, 2H), 7.76 (s, 1H), 7.74 (s, 1H), 7.59 (s, 1H), 7.49 (s, 1H), 7.42-7.44 (m, 2H), 7.32-7.35 (m, 2H), 7.17-7.22 (m, 2H), 4.51 (s, 2H), 3.52 (s, 2H), 3.15 (s, 3H), 2.99 (s, 3H), 2.88-2.95 (m, 2H), 2.67-2.72 (m, 2H), 2.24-2.27 (m, 2H), 1.91-1.97 (m, 2H). ¹³C-NMR (CD₃OD, 126 MHz) δ 172.2, 144.9, 144.2, 140.9, 139.9, 137.3, 132.9, 128.4, 128.1, 127.4, 127.2, 126.2, 125.7, 124.7, 118.7, 111.5, 79.9, 72.2, 42.1, 41.8, 39.1, 34.7, 32.7. Mass spec.: 454.31 (MH)⁺. Accurate mass spec.: m/z 454.2496 [MH]⁺, Δ=0.3 ppm.

Example 175

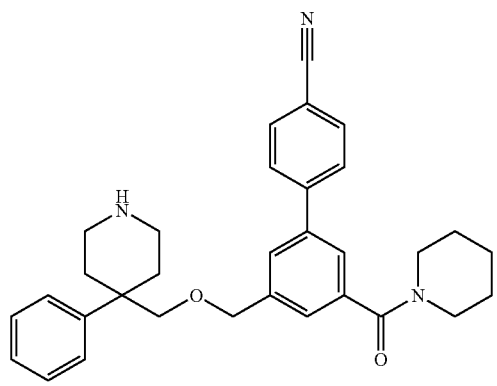 [SMILES: N#Cc1ccc(-c2cc(COCC3(c4ccccc4)CCNCC3)cc(C(=O)N3CCCCC3)c2)cc1]

3'-(((4-Phenylpiperidin-4-yl)methoxy)methyl)-5'-(piperidine-1-carbonyl)biphenyl-4-carbonitrile. ¹H-NMR (CDCl₃, 500 MHz) δ 7.73 (s, 1H), 7.71 (s, 1H), 7.59 (s, 1H), 7.51 (s, 1H), 7.45 (s, 1H), 7.35-7.36 (m, 2H), 7.31-7.32 (m, 3H), 7.17-7.20 (m, 2H), 4.43 (s, 2H), 3.71-3.73 (m, 2H), 3.45 (s, 2H), 3.31-3.33 (m, 2H), 2.90-2.95 (m, 2H), 2.73-2.78 (m, 2H), 2.16-2.20 (m, 2H), 1.89-1.95 (m, 2H), 1.68 (m, 4H), 1.49 (m, 2H). $^{13}$C-NMR (CDCl$_3$, 126 MHz) δ 169.7, 144.8, 144.0, 140.3, 139.6, 132.7, 128.4, 127.9, 127.3, 126.7, 126.2, 125.5, 124.7, 118.7, 111.5, 80.0, 77.7, 72.6, 50.9, 42.6, 41.9, 33.3, 27.7. Mass spec.: 494.47 (MH)$^+$. Accurate mass spec.: m/z 494.2809 [MH]$^+$, Δ=0.3 ppm.

Example 176

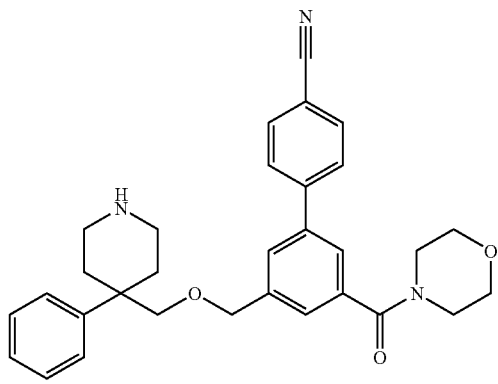 [SMILES: N#Cc1ccc(-c2cc(COCC3(c4ccccc4)CCNCC3)cc(C(=O)N3CCOCC3)c2)cc1]

3'-(Morpholine-4-carbonyl)-5'-(((4-phenylpiperidin-4-yl)methoxy)methyl)biphenyl-4-carbonitrile. $^1$H-NMR (CDCl$_3$, 500 MHz) δ 7.73 (s, 1H), 7.71 (s, 1H), 7.59 (s, 1H), 7.57 (s, 1H), 7.47 (s, 1H), 7.29-7.37 (m, 5H), 7.17-7.20 (m, 1H), 7.16 (s, 1H), 4.44 (s, 2H), 3.41-3.78 (m, 8H), 3.46 (s, 2H), 2.89-2.93 (m, 2H), 2.72-2.77 (m, 2H), 2.16-2.19 (m, 2H), 1.88-1.93 (m, 2H). $^{13}$C-NMR (CDCl$_3$, 126 MHz) δ 169.8, 144.6, 144.2, 140.6, 139.9, 136.5, 132.7, 128.4, 127.9, 127.3, 127.1, 126.2, 125.6, 125.0, 118.7, 111.7, 80.2, 77.7, 72.5, 67.0, 42.7, 42.0, 33.5. Mass spec.: 496.46 (MH)$^+$.

Example 177

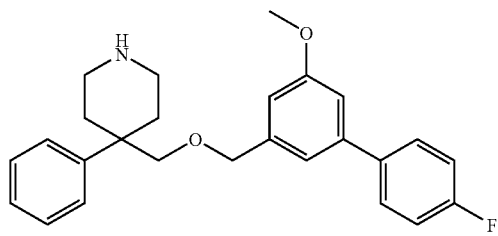 [SMILES: COc1cc(COCC2(c3ccccc3)CCNCC2)cc(-c2ccc(F)cc2)c1]

4-(((4'-Fluoro-5-methoxybiphenyl-3-yl)methoxy)methyl)-4-phenylpiperidine. tert-Butyl 4-(((4'-fluoro-5-hydroxybiphenyl-3-yl)methoxy)methyl)-4-phenylpiperidine-1-carboxylate (42.4 mg, 0.09 mmol), iodomethane (11 μL, 0.17 mmol) and potassium carbonate (23.5 mg, 0.17 mmol) were combined in dimethylformamide (2 mL). After stirring at room temperature for 16 h, the solvent was removed in vacuo and the crude product dissolved in ethyl acetate, washed with water (2×), then brine (2×), dried over sodium sulfate, and concentrated to afford a precipitate which was treated with a trifluoroacetic acid/methylene chloride mixture (1:1, 2 mL) for 1 h. The solvent was removed in vacuo and the resulting crude mixture passed through a strong cation exchange column. After washing the column with several volumes of methanol, the product was eluted by washing the column with 2 M ammonia in methanol. Concentration and preparative HPLC afforded 22 mg (61%) as its trifluoroacetic acid salt. $^1$H-NMR (CDCl$_3$, 300 MHz) δ 7.53-7.58 (m, 2H), 7.39-7.48 (m, 4H), 7.30-7.32 (m, 1H), 7.14-7.20 (m, 2H), 7.00-7.01 (m, 1H), 6.96 (s, 1H), 6.75 (s, 1H), 4.45 (s, 2H), 3.82 (s, 3H), 3.50 (s, 2H), 3.29-3.31 (m, 2H), 2.89-3.00 (m, 2H), 2.49-2.54 (m, 2H), 2.18-2.28 (m, 2H). Mass spec.: 406.37 (MH)$^+$. Accurate mass spec.: m/z 406.2173 [MH]$^+$, Δ=2.3 ppm.

Example 178

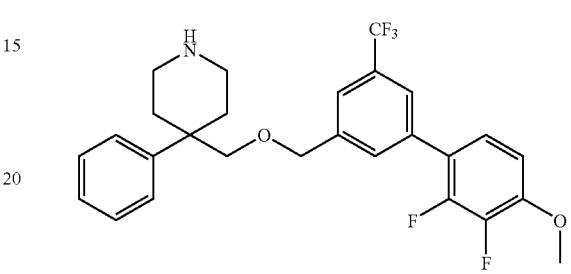

4-(((2',3'-Difluoro-4'-methoxy-5-(trifluoromethyl)biphenyl-3-yl)methoxy)methyl)-4-phenylpiperidine. tert-Butyl 4-((3-bromo-5-(trifluoromethyl)benzyloxy)methyl)-4-phenylpiperidine-1-carboxylate (150 mg, 0.28 mmol), 2,3-difluoro-4-methoxyphenylboronic acid (139 mg, 0.84 mmol), and tetrakis(triphenylphosphine) palladium(0) (33 mg, 0.03 mmol) were combined in dry tetrahydrofuran (3 mL) in a microwave tube and sealed. After flushing with nitrogen, 1.0 mL of a 1 N potassium hydroxide aqueous solution was introduced. The mixture was heated at 120° C. for 1 h via microwave. After cooling to room temperature, the reaction mixture was concentrated and treated with a trifluoroacetic acid/methylene chloride mixture (1:1, 2 mL) for 1 h. The solvent was removed in vacuo and the resulting crude mixture passed through a strong cation exchange column. After washing the column with several volumes of methanol, the product was eluted by washing the column with 2 M ammonia in methanol and concentrated to afford 45 mg (33%). $^1$H-NMR (CDCl$_3$, 500 MHz) δ 7.57 (s, 1H), 7.26-7.38 (m, 6H), 7.13-7.17 (m, 1H), 7.00-7.06 (m, 1H), 6.77-6.83 (m, 1H), 4.41 (s, 2H), 3.93 (s, 3H), 3.44 (s, 2H), 2.84-2.92 (m, 2H), 2.68-2.77 (m, 2H), 2.13-2.18 (m, 2H), 1.83-1.92 (m, 2H). Mass spec.: 492.01 (MH)$^+$. Accurate mass spec.: m/z 492.1978 [MH]$^+$, Δ=3.3 ppm.

Example 179

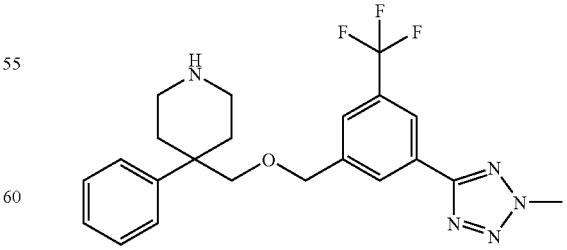

4-((3-(2-Methyl-2H-tetrazol-5-yl)-5-(trifluoromethyl)benzyloxy)methyl)-4-phenylpiperidine. tert-Butyl 4-((3-(2-methyl-2H-tetrazol-5-yl)-5-(trifluoromethyl)benzyloxy)methyl)-4-phenylpiperidine-1-carboxylate (48.0 mg, 0.09 mmol) was dissolved in a minimum amount of ethyl acetate, followed by addition of 4 N hydrochloric acid (1 mL). The mixture was stirred under nitrogen for 1 h. After removing the solvents, the crude mixture was precipitated in diethyl ether and filtered to afford 26.0 mg (67%) as a white powder. $^1$H-NMR (CDCl$_3$, 300 MHz) δ 8.23 (s, 1H), 8.10 (s, 1H), 7.40 (s, 1H), 7.28-7.36 (m, 4H), 7.20 (m, 1H), 4.41 (s, 2H), 4.38 (s, 3H), 3.44 (s, 2H), 2.86-2.93 (m, 2H), 2.69-2.77 (m, 2H), 2.16-2.20 (m, 2H), 1.83-1.96 (m, 2H). $^{13}$C-NMR (CDCl$_3$, 76 MHz) δ 164.0, 143.4, 141.0, 131.4 (q, J=32.8 Hz), 128.3, 128.0, 127.0, 126.1, 135.5, 124.0 (q, J=213.8 Hz), 122.6, 121.9, 79.9, 72.0, 42.3, 41.7, 39.5, 32.9. Mass spec.: 432.20 (MH)$^+$. Accurate mass spec.: m/z 432.1994 [MH]$^+$, Δ=4.0 ppm.

Example 180

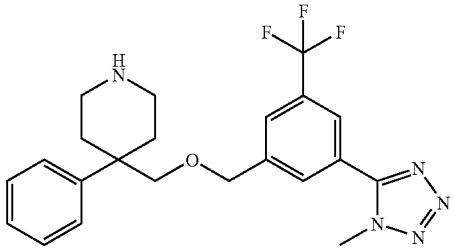 [SMILES: Cn1nnnc1-c1cc(COCC2(c3ccccc3)CCNCC2)cc(C(F)(F)F)c1]

4-((3-(1-Methyl-1H-tetrazol-5-yl)-5-(trifluoromethyl)benzyloxy)methyl)-4-phenylpiperidine. tert-Butyl 4-((3-(1-methyl-1H-tetrazol-5-yl)-5-(trifluoromethyl)benzyloxy)methyl)-4-phenylpiperidine-1-carboxylate (7.0 mg, 0.01 mmol) was dissolved in a minimum amount of ethyl acetate, followed by addition of 4 N hydrochloric acid (0.5 mL). The mixture was stirred under nitrogen for 1 h. After removing the solvents, the crude mixture was precipitated in diethyl ether and filtered to afford 4.0 mg (88%). $^1$H-NMR (CDCl$_3$, 500 MHz) δ 7.86 (s, 1H), 7.57 (s, 1H), 7.48 (s, 1H), 7.34 (s, 1H), 7.33 (s, 1H), 7.27-7.29 (m, 2H), 7.20 (m, 1H), 4.49 (s, 2H), 4.06 (s, 3H), 3.48 (s, 2H), 2.93-2.96 (m, 2H), 2.74-2.77 (m, 2H), 2.20-2.22 (m, 2H), 1.89-1.94 (m, 2H). Mass spec.: 432.20 (MH)$^+$. Accurate mass spec.: m/z 432.1994 [MH]$^+$, Δ=4.4 ppm.

Example 181

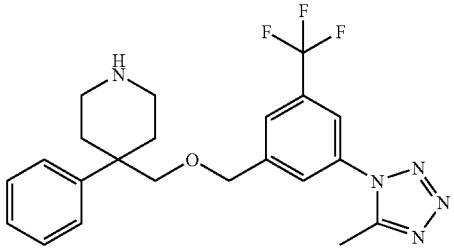 [SMILES: Cc1nnnn1-c1cc(COCC2(c3ccccc3)CCNCC2)cc(C(F)(F)F)c1]

4-((3-(5-Methyl-1H-tetrazol-1-yl)-5-(trifluoromethyl)benzyloxy)methyl)-4-phenylpiperidine. tert-Butyl 4-((3-(5-methyl-1H-tetrazol-1-yl)-5-(trifluoromethyl)benzyloxy)methyl)-4-phenylpiperidine-1-carboxylate (40.0 mg, 0.08 mmol) was dissolved in a minimum amount of ethyl acetate, followed by addition of 4 N hydrochloric acid (1.5 mL). The mixture was stirred under nitrogen for 1 h. After removing the solvents, the crude mixture was precipitated in diethyl ether and filtered to afford 30.0 mg (93%) as a white powder. $^1$H-NMR (CDCl$_3$, 500 MHz) δ 7.58 (s, 1H), 7.53 (s, 1H), 7.31-7.35 (m, 3H), 7.22-7.26 (m, 1H), 7.08-7.11 (m, 2H), 4.49 (s, 2H), 3.43 (s, 2H), 2.86-2.90 (m, 2H), 2.71-2.75 (m, 2H), 2.52 (s, 3H), 2.17-2.20 (m, 2H), 1.84-1.87 (m, 2H). $^{13}$C-NMR (CDCl$_3$, 126 MHz) δ 151.5, 143.9, 143.1, 134.5, 136.6 (q, J=33.6 Hz), 128.7, 128.3, 127.2, 126.3, 127.7, 125.1 (q, J=272.6 Hz), 120.4, 80.6, 71.3, 42.6, 41.9, 33.6, 33.3. Mass spec.: 432.22 (MH)$^+$.

Example 182

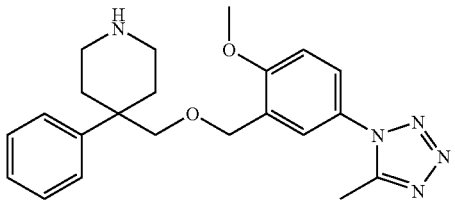 [SMILES: COc1ccc(-n2nnnc2C)cc1COCC1(c2ccccc2)CCNCC1]

4-((2-Methoxy-5-(5-methyl-JH-tetrazol-1-yl)benzyloxy)methyl)-4-phenylpiperidine. tert-Butyl 4-((2-methoxy-5-(5-methyl-1H-tetrazol-1-yl)benzyloxy)methyl)-4-phenylpiperidine-1-carboxylate (30.0 mg, 0.06 mmol) was dissolved in a minimum amount of ethyl acetate, followed by addition of 4 N hydrochloric acid (1 mL). The mixture was stirred under nitrogen for 1 h. After removing the solvents, the crude mixture was precipitated in diethyl ether and filtered to afford 18.0 mg (76%) as a white powder. $^1$H-NMR (CDCl$_3$, 500 MHZ) δ 7.32 (s, 1H), 7.30 (s, 1H), 7.18-7.25 (m, 3H), 7.04-7.07 (m, 1H), 6.91 (d, J=8.9 Hz, 1H), 6.81 (m, 1H), 4.46 (s, 2H), 3.85 (s, 3H), 3.48 (s, 2H), 2.88-2.93 (m, 2H), 2.72-2.76 (m, 2H), 2.41 (s, 3H), 2.18 (m, 2H), 1.85-1.90 (m, 2H). $^{13}$C-NMR (CDCl$_3$, 126 MHz) δ 157.5, 151.7, 144.2, 129.6, 128.2, 127.2, 126.6, 126.1, 124.6, 123.6, 110.5, 80.5, 67.0, 55.8, 42.7, 41.8, 33.6, 9.6. Mass spec.: 394.22 (MH)$^+$. Accurate mass spec.: m/z 394.2222 [MH]$^+$, Δ=4.1 ppm.

Example 183

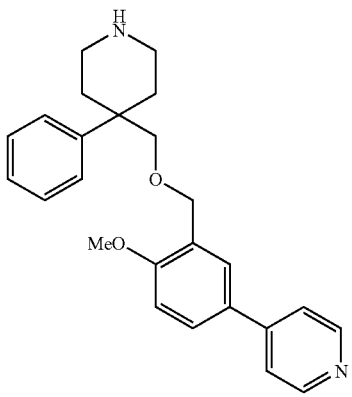 [SMILES: COc1ccc(-c2ccncc2)cc1COCC1(c2ccccc2)CCNCC1]

4-(4-Methoxy-3-(((4-phenylpiperidin-4-yl)methoxy)methyl)phenyl)pyridine. tert-Butyl 4-((2-methoxy-5-(pyridin-4-yl)benzyloxy)methyl)-4-phenylpiperidine-1-carboxylate (26 mg, 0.053 mmol) was dissolved in trifluoroacetic acid (33% in dichloromethane, 4 mL) and stirred for 1 h. The reaction was concentrated and purified by column chromatography (5% methanol/dichloromethane/2% trimethylamine in ethanol→10% methanol/dichloromethane/2% trimethylamine in ethanol) to give 30.7 mg (quant.) as a colorless oil. The product was tainted with trimethylamine 2,2,2-trifluoroacetate. $^1$H NMR (500 MHz, CDCl$_3$) δ ppm 13.28 (bs, 2H), 9.55 (m, 2H), 8.71 (d, J=5.2 Hz, 2H), 7.79 (d, J=5.2 Hz, 2H), 7.60 (m, 2H), 7.34 (m, 4H), 7.26 (m, 1H), 6.94 (d, J=8.6, 1H), 4.48 (s, 2H), 3.84 (s, 3H), 3.49 (s, 2H), 3.31 (m, 2H); $^{13}$C NMR (126 MHz, CDCl$_3$) δ ppm 159.1, 154.0, 144.0, 140.5, 129.2, 128.6, 127.7, 127.4, 127.2, 126.9, 122.5, 110.8, 80.0, 67.5, 55.7, 41.2, 40.6. Mass spec.: 389.33 (MH)$^+$. Accurate mass spec.: m/z 389.2228 [MH]$^+$, Δ=0.3 ppm.

Example 184

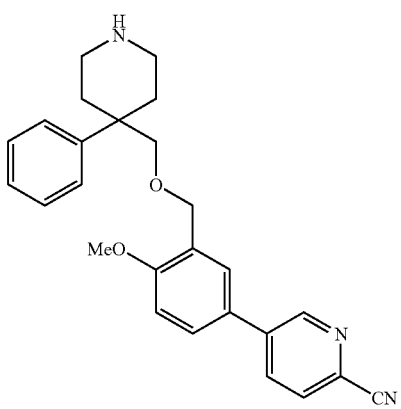

5-(4-Methoxy-3-(((4-phenylpiperidin-4-yl)methoxy)methyl)phenyl)picolinonitrile. tert-Butyl 4-((5-(6-cyanopyridin-3-yl)-2-methoxybenzyloxy)methyl)-4-phenylpiperidine-1-carboxylate (46 mg, 0.090 mmol) was dissolved in trifluoroacetic acid (33% in dichloromethane, 4 mL) and stirred for 1 h. The reaction was concentrated and purified by column chromatography (5% methanol/dichloromethane/2% trimethylamine in ethanol→10% methanol/dichloromethane/2% trimethylamine in ethanol) to give 43.6 mg (quant.) as a colorless oil. The product was tainted with trimethylamine 2,2,2-trifluoroacetate. $^1$H NMR (500 MHz, CDCl$_3$) δ ppm 9.47 (bs, 1H), 9.25 (bs, 1H), 8.79 (m, 1H), 7.84 (m, 1H), 7.70 (d, J=8.2 Hz, 1H), 7.44 (dd, J=8.5, 2.1, 1H), 7.33 (m, 5H), 7.25 (m, 1H), 6.91 (d, J=8.5 Hz, 1H), 4.47 (s, 2H), 3.82 (s, 3H), 3.48 (s, 2H), 3.27 (bd, 2H), 2.90 (m, 2H), 2.44 (m, 2H), 2.26 (m, 2H); $^{13}$C NMR (126 MHz, CDCl$_3$) δ ppm 157.8, 149.3, 140.5, 139.5, 134.3, 131.4, 129.1, 128.5, 128.2, 127.9, 127.2, 126.8, 126.6, 117.7, 110.8, 79.9, 67.7, 55.6, 41.1, 40.6, 29.1. Mass spec.: 414.19 (MH)$^+$. Accurate mass spec.: m/z 414.2188 [MH]$^+$, Δ=1.6 ppm.

Example 185

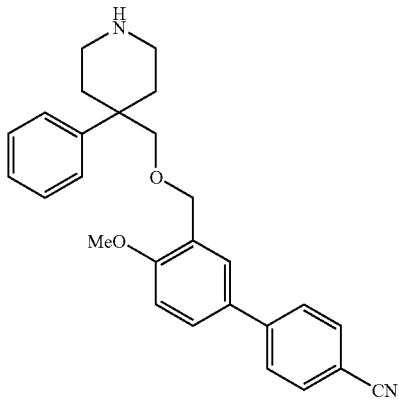 [SMILES: COc1ccc(-c2ccc(C#N)cc2)cc1COCC1(c2ccccc2)CCNCC1]

4'-Methoxy-3'-(((4-phenylpiperidin-4-yl)methoxy)methyl)biphenyl-4-carbonitrile. tert-Butyl 4-(((4'-cyano-4-methoxybiphenyl-3-yl)methoxy)methyl)-4-phenylpiperidine-1-carboxylate (47 mg, 0.092 mmol) was dissolved in dichloromethane (2 mL) and trifluoroacetic acid (1 mL). The reaction was stirred for 45 min and concentrated. The residue was dissolved in methanol and loaded onto an strong cation exchange cartridge. The cartridge was flushed with plenty of methanol which was discarded. The product was then eluted using 2 M ammonia in methanol. The solvent was evaporated to give 34 mg (90%) as a colorless oil. Retention time: 2.20 min. (Phenomenex C18 3.0×50 mm, 10% MeOH/90% H$_2$O/0.1% TFA→90% MeOH/10% H$_2$O/0.1% TFA, Gradient time=3 min., Flow rate=4 mL/min.) Mass spec.: 413.39 (MH)$^+$. Accurate mass spec.: m/z 413.2245 [MH]$^+$, Δ=3.9 ppm.

Example 186

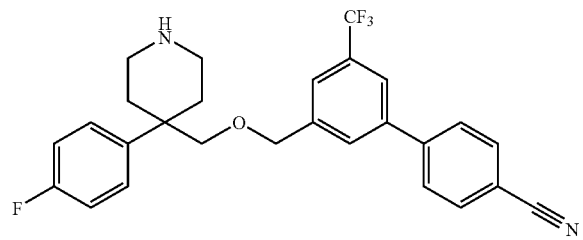 [SMILES: N#Cc1ccc(-c2cc(COCC3(c4ccc(F)cc4)CCNCC3)cc(C(F)(F)F)c2)cc1]

3'-(((4-(4-Fluorophenyl)piperidin-4-yl)methoxy)methyl)-5'-(trifluoromethyl)biphenyl-4-carbonitrile. tert-Butyl 4-(((4'-cyano-5-(trifluoromethyl)biphenyl-3-yl)methoxy)methyl)-4-(4-fluorophenyl)piperidine-1-carboxylate (47.0 mg, 0.09 mmol) was treated with a trifluoroacetic acid/methylene chloride mixture (1:1, 2 mL) for 1 h. The solvent was removed in vacuo and the resulting crude mixture passed through a strong cation exchange column. After washing the column with several volumes of methanol, the product was eluted by washing the column with 2 M ammonia in methanol. The solvents were removed in vacuo to afford 37.0 mg (92%). $^1$H-NMR (CDCl$_3$, 500 MHz) δ 7.75 (s, 1H), 7.73 (s, 1H), 7.66 (s, 1H), 7.58 (s, 1H), 7.57 (s, 1H), 7.41 (s, 1H), 7.40 s, 1H), 7.30-7.33 (m, 2H), 6.96-7.00 (m, 2H), 4.46 (s, 2H), 3.44 (s, 2H), 2.87-2.91 (m, 2H), 2.70-2.75 (m, 2H), 2.11-2.14 (m, 2H), 1.87-1.90 (m, 2H). Mass spec.: 469.33 (MH)+.

Example 187

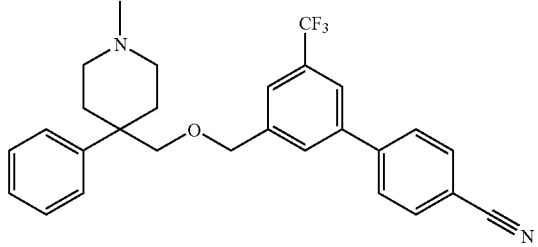

3'-(((1-Methyl-4-phenylpiperidin-4-yl)methoxy)methyl)-5'-(trifluoromethyl)biphenyl-4-carbonitrile. 3'-(((4-Phenylpiperidin-4-yl)methoxy)methyl)-5'-(trifluoromethyl)biphenyl-4-carbonitrile (18.3 mg, 0.04 mmol) and formaldehyde (37 wt. % solution in water, 86.4 µL, 3.22 mmol) were combined in acetonitrile (1.0 mL) and cooled to 0° C. The reaction was treated with sodium cyanoborohydride (12.6 mg, 0.2 mmol) and a few drops of acetic acid. The reaction was stirred at 0° C. for 30 min and at room temperature for 1 h. The solvent was removed in vacuo and the resulting crude mixture passed through a strong cation exchange column. After washing the column with several volumes of methanol, the product was eluted by washing the column with 2 M ammonia in methanol. The solvents were evaporated to afford 12.1 mg (65%). ¹H-NMR (CDCl₃, 500 MHz) δ 7.74-7.76 (m, 2H), 7.66 (s, 1H), 7.58-7.60 (m, 2H), 7.44 (s, 1H), 7.41 (s, 1H), 7.36-7.38 (m, 2H), 7.30-7.33 (m, 2H), 7.18-7.21 (m, 1H), 4.45 (s, 2H), 3.48 (s, 2H), 2.58-2.60 (m, 2H), 2.17-2.28 (m, 4H), 2.21 (s, 3H), 1.98-2.08 (m, 2H). Mass spec.: 465.11 (MH)+.

Example 188

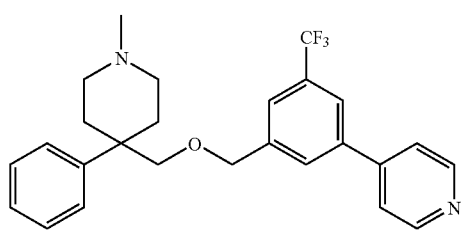 [SMILES: CN1CCC(COCc2cc(-c3ccncc3)cc(C(F)(F)F)c2)(c2ccccc2)CC1]

4-(3-(((1-Methyl-4-phenylpiperidin-4-yl)methoxy)methyl)-5-(trifluoromethyl)phenyl)pyridine. ¹H-NMR (CDCl₃, 500 MHz) δ 8.96 (s, 1H), 8.95 (s, 1H), 8.01 (s, 1H), 8.00 (s, 1H), 7.83 (s, 1H), 7.69 (s, 1H), 7.55 (s, 1H), 7.42-7.45 (m, 2H), 7.33-7.36 (m, 3H), 4.55 (s, 2H), 3.55-3.57 (m, 2H), 3.46 (s, 2H), 2.68-2.75 (m, 2H), 2.70 (s, 3H), 2.53-2.56 (m, 2H), 2.40-2.46 (m, 2H). Mass spec.: 441.13 (MH)+.

Example 189

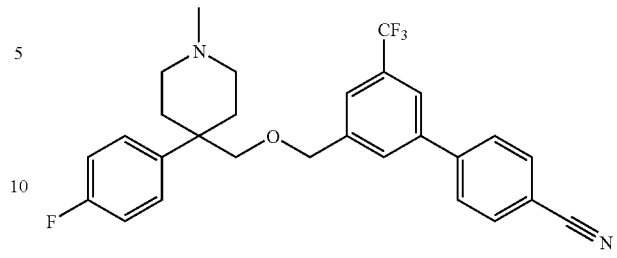

3'-(((4-(4-Fluorophenyl)-1-methylpiperidin-4-yl)methoxy)methyl)-5'-(trifluoromethyl)biphenyl-4-carbonitrile. ¹H-NMR (CDCl₃, 500 MHz) δ 7.76-7.74 (m, 2H), 7.67 (s, 1H), 7.59-7.57 (m, 2H), 7.39-7.41 (m, 2H), 7.30-7.33 (m, 2H), 6.97-7.00 (m, 2H), 4.46 (s, 2H), 3.44 (s, 2H), 2.54-2.56 (m, 2H), 2.16-2.25 (m, 4H), 2.20 (s, 3H), 1.97-1.99 (m, 2H). Mass spec.: 483.33 (MH)+.

Example 190

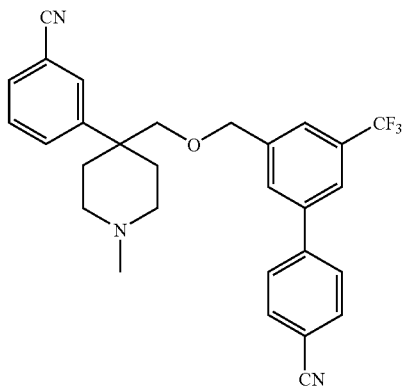

3'-(((4-(3-Cyanophenyl)-1-methylpiperidin-4-yl)methoxy)methyl)-5'-(trifluoromethyl)biphenyl-4-carbonitrile. ¹H-NMR (CDCl₃, 500 MHz) δ ppm 7.76 (m, 2H), 7.67 (s, 1H), 7.63 (m, 2H), 7.60 (m, 1H), 7.58 (m, 1H), 7.47 (m, 1H), 7.37-7.43 (m, 2H), 7.33 (s, 1H), 4.46 (s, 2H), 3.45 (s, 2H), 2.65 (m, 2H), 2.27 (s, 3H), 2.25-2.30 (m, 4H), 2.08 (m, 2H). Mass spec: 490.24 (MH)+.

Example 191

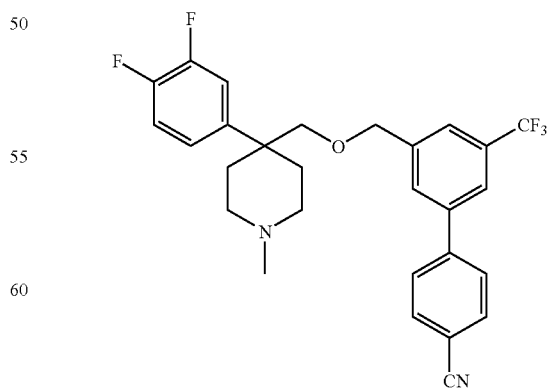

3'-(((4-(3,4-Difluorophenyl)-1-methylpiperidin-4-yl)methoxy)methyl)-5'-(trifluoromethyl)biphenyl-4-carbonitrile. ¹H-NMR (CDCl₃, 500 MHz) δ ppm 7.76 (m, 2H), 7.67

(s, 1H), 7.61 (m, 2H), 7.42 (s, 1H), 7.37 (s, 1H), 7.01-7.19 (br m, 3H), 4.47 (s, 2H), 3.43 (s, 2H), 2.53-2.57 (br m, 2H), 1.98-2.35 (m, 9H). Mass spec.: 501.25 (MH)+.

Example 192

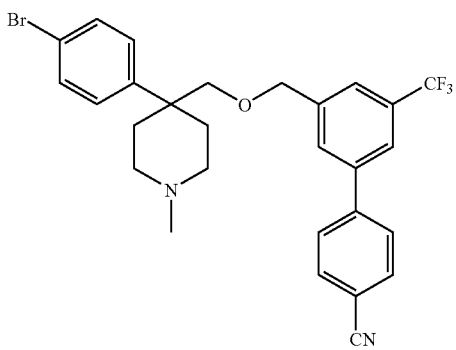

3'-(((4-(4-Bromophenyl)-1-methylpiperidin-4-yl)methoxy)methyl)-5'-(trifluoromethyl)biphenyl-4-carbonitrile.
1H-NMR (CDCl3, 500 MHz) δ ppm 7.76 (m, 2H), 7.67 (s, 1H), 7.62 (m, 2H), 7.45 (s, 1H), 7.42 (s, 1H), 7.35 (m, 2H), 7.18-7.27 (m, 2H), 4.47 (s, 2H), 3.45 (s, 2H), 2.35-2.55 (br m, 2H), 1.55 (m, 9H). Mass spec.: 543.16 (MH)+.

Example 193

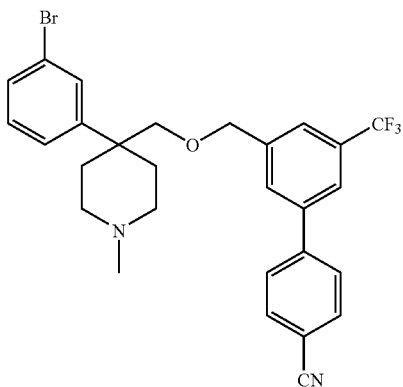

3'-(((4-(3-Bromophenyl)-1-methylpiperidin-4-yl)methoxy)methyl)-5'-(trifluoromethyl)biphenyl-4-carbonitrile.
1H-NMR (CDCl3, 500 MHz) δ ppm 7.78 (m, 2H), 7.67 (s, 1H), 7.60 (m, 2H), 7.45 (m, 3H), 7.37 (s, 1H), 7.22 (s, 1H), 7.20 (s, 1H), 4.46 (s, 2H), 3.44 (s, 2H), 2.14-2.45 (br m, 7H), 1.48-1.53 (br m, 4H). Mass spec.: 543.16 (MH)+.

Example 194

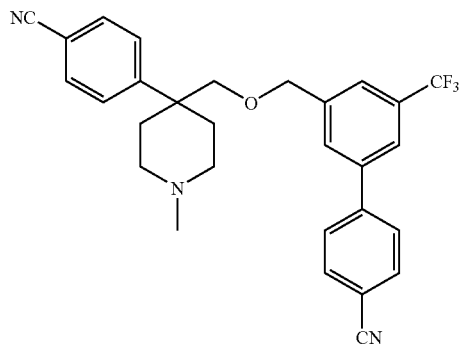

3'-(((4-(4-Cyanophenyl)-1-methylpiperidin-4-yl)methoxy)methyl)-5'-(trifluoromethyl)biphenyl-4-carbonitrile.
1H-NMR (CDCl3, 500 MHz) δ ppm 7.78 (m, 2H), 7.60-7.69 (m, 5H), 7.45 (m, 2H), 7.28 (br m, 2H), 4.46 (s, 2H), 3.48 (s, 1H), 1.62-2.55 (br m, 12H). Mass spec.: 490.14 (MH)+.

Example 195

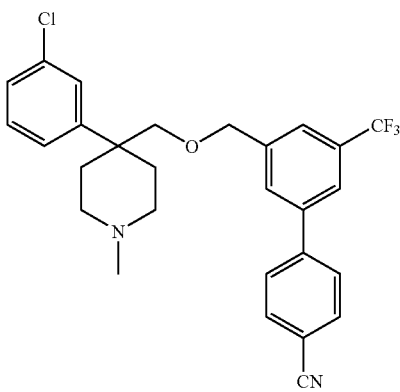 [SMILES: CN1CCC(COCc2cc(-c3ccc(C#N)cc3)cc(C(F)(F)F)c2)(c2cccc(Cl)c2)CC1]

3'-(((4-(3-Chlorophenyl)-1-methylpiperidin-4-yl)methoxy)methyl)-5'-(trifluoromethyl)biphenyl-4-carbonitrile.
1H-NMR (CDCl3, 500 MHz) δ ppm 7.75 (m, 2H), 7.66 (s, 1H), 7.60 (m, 2H), 7.42 (s, 1H), 7.38 (s, 1H), 7.32 (s, 1H), 7.23 (m, 2H), 7.16 (m, 1H), 4.46 (s, 2H), 3.46 (s, 2H), 2.74 (br m, 1H), 1.98-2.35 (br m, 10H). Mass spec.: 499.06 (MH)+.

Example 196

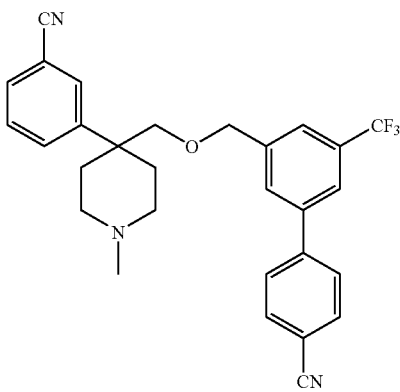 [SMILES: CN1CCC(COCc2cc(-c3ccc(C#N)cc3)cc(C(F)(F)F)c2)(c2cccc(C#N)c2)CC1]

3'-(((1-Methyl-4-(3-(trifluoromethyl)phenyl)piperidin-4-yl)methoxy)methyl)-5'-(trifluoromethyl)biphenyl-4-carbonitrile. ¹H-NMR (CDCl₃, 500 MHz) δ ppm 7.74 (m, 2H), 7.66 (s, 1H), 7.58 (m, 2H), 7.54 (m, 1H), 7.42 (m, 2H), 7.35 (s, 1H), 4.45 (s, 2H), 3.48 (s, 2H), 2.66 (br m, 1H), 1.98-2.30 (br m, 10H). Mass spec.: 533.19 (MH)⁺.

Example 197

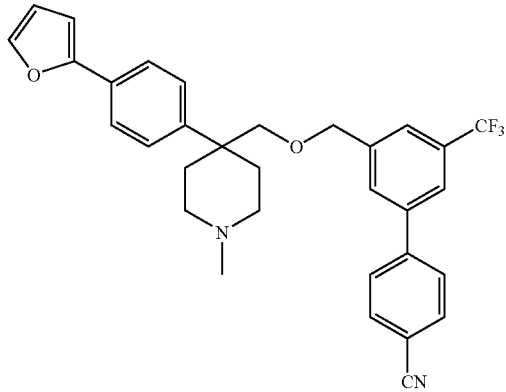 [SMILES: CN1CCC(COCc2cc(-c3ccc(C#N)cc3)cc(C(F)(F)F)c2)(c2ccc(-c3ccco3)cc2)CC1]

3'-(((4-(4-(Furan-2-yl)phenyl)-1-methylpiperidin-4-yl)methoxy)methyl)-5'-(trifluoromethyl)biphenyl-4-carbonitrile. ¹H-NMR (CDCl₃, 500 MHz) δ ppm 7.55-7.64 (m, 5H), 7.47-7.52 (m, 3H), 7.38 (s, 1H), 7.34 (m, 3H), 6.62 (m, 1H), 6.52 (m, 1H), 4.47 (s, 2H), 3.47 (s, 2H), 2.74-3.01 (br m, 2H), 1.98-2.30 (br m, 9H). Mass spec.: 531.11 (MH)⁺.

Example 198

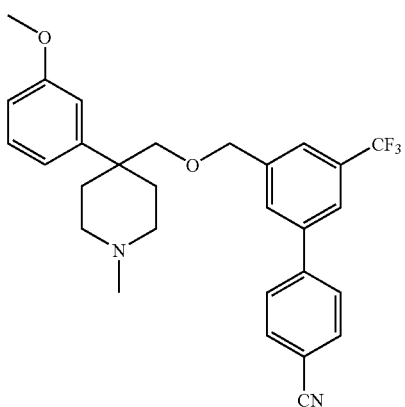 [SMILES: COc1cccc(C2(COCc3cc(-c4ccc(C#N)cc4)cc(C(F)(F)F)c3)CCN(C)CC2)c1]

3'-(((4-(3-Methoxyphenyl)-1-methylpiperidin-4-yl)methoxy)methyl)-5'-(trifluoromethyl)biphenyl-4-carbonitrile. ¹H-NMR (CDCl₃, 500 MHz) δ ppm 7.75 (m, 2H), 7.66 (s, 1H), 7.62 (m, 2H), 7.48 (s, 1H), 7.37 (s, 1H), 7.26 (m, 1H), 6.92 (m, 1H), 6.88 (m, 1H), 6.76 (m, 1H), 4.45 (s, 2H), 3.75 (s, 3H), 3.46 (s, 2H), 2.80 (br m, 2H), 2.15-2.81 (m, 9H). Mass spec.: 495.12 (MH)⁺.

Example 199

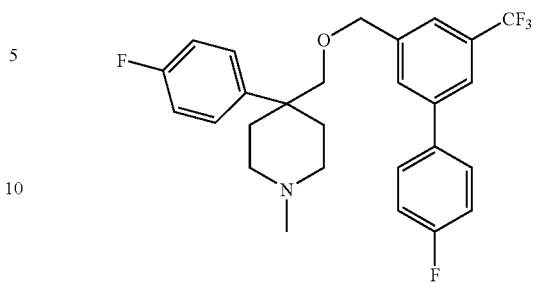

4-(((4'-Fluoro-5-(trifluoromethyl)biphenyl-3-yl)methoxy)methyl)-4-(4-fluorophenyl)-1-methylpiperidine. ¹H-NMR (CDCl₃, 500 MHz) δ 7.63 (s, 1H), 7.46 (m, 2H), 7.39 (s, 1H), 7.32 (m, 3H), 7.15 (m, 2H), 7.00 (m, 2H), 4.45 (s, 2H), 3.44 (s, 2H), 2.58 (m, 2H), 2.22 (s, 3H), 2.20 (m, 4H), 2.00 (m, 2H); ¹³C NMR (126 MHz, CDCl₃) δ ppm 164.0, 162.3, 162.0, 160.4, 141.2, 140.4, 139.6, 135.8, 131.5, 131.2, 128.9 (m), 128.8 (m), 124.1 (q, J=273 Hz), 122.8 (q, J=3.8 Hz), 122.6 (q, J=3.8 Hz), 116.1, 115.9, 115.1, 115.0, 79.6 (br), 72.4, 51.9, 46.2, 40.4, 32.6. Mass spec.: 476.34 (MH)⁺. Accurate mass spec.: m/z 476.2013 [MH]⁺, Δ=0.0 ppm.

Example 200

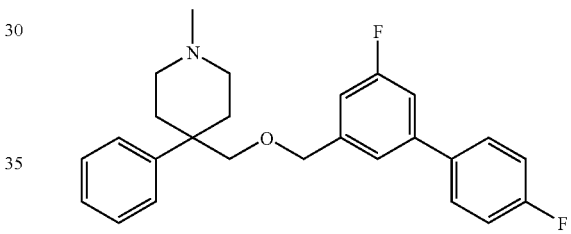

4-(((4',5-Difluorobiphenyl-3-yl)methoxy)methyl)-1-methyl-4-phenylpiperidine. ¹H-NMR (CDCl₃, 500 MHz) δ 7.74-7.76 (m, 2H), 7.66 (s, 1H), 7.58-7.60 (m, 2H), 7.44 (s, 1H), 7.41 (s, 1H), 7.36-7.38 (m, 2H), 7.30-7.33 (m, 2H), 7.18-7.21 (m, 1H), 4.45 (s, 2H), 3.48 (s, 2H), 2.58-2.60 (m, 2H), 2.17-2.28 (m, 4H), 2.21 (s, 3H), 1.98-2.08 (m, 2H). ¹³C-NMR (CDCl₃, 126 MHz) δ 164.0 (d, J=51.8 Hz), 162.1 (d, J=52.8 Hz), 142.3, 142.0, 136.1, 128.8, 128.3, 127.4, 126.1, 121.1, 115.9, 115.7, 112.8, 112.6, 72.5, 52.1, 46.3, 40.9, 32.5. Mass spec.: 408.16 (MH)⁺. Accurate mass spec.: m/z 408.2157 [MH]⁺, Δ=4.4 ppm.

Example 201

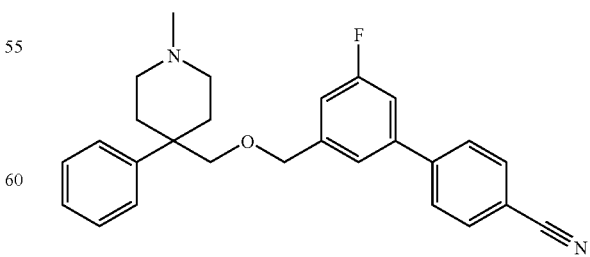

3'-Fluoro-5'-(((1-methyl-4-phenylpiperidin-4-yl)methoxy)methyl)biphenyl-4-carbonitrile. ¹H-NMR (CDCl₃, 500 MHz) δ 7.72 (s, 1H), 7.71 (s, 1H), 7.57 (s, 1H), 7.56 (s, 1H), 7.31-7.38 (m, 4H), 7.19-7.22 (m, 1H), 7.11-7.13 (m, 1H), 7.06 (s, 1H), 6.82-6.84 (s, 1H), 4.39 (s, 2H), 3.45 (s, 2H), 2.59-2.62 (m, 2H), 2.17-2.27 (m, 4H), 2.21 (s, 3H), 2.00-2.05 (m, 2H). Mass spec.: 415.18 (MH)⁺.

Example 202

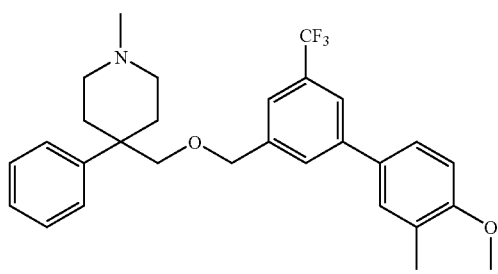 [SMILES: COc1ccc(-c2cc(COCC3(c4ccccc4)CCN(C)CC3)cc(C(F)(F)F)c2)cc1C]

4-(((4'-Methoxy-3'-methyl-5-(trifluoromethyl)biphenyl-3-yl)methoxy)methyl)-1-methyl-4-phenylpiperidine.
¹H-NMR (CD₃OD, 500 MHz) δ 7.69 (m, 1H), 7.58 (m, 1H), 7.28-7.53 (m, 8H), 6.99-7.02 (m, 1H), 4.52 (s, 2H), 3.89 (s, 3H), 3.48 (s, 2H), 3.44 (m, 2H), 2.66-2.93 (m, 4H), 2.75 (s, 3H), 2.28 (s, 3H), 2.12-2.22 (m, 2H). Mass spec.: 484.11 (MH)⁺. Accurate mass spec.: m/z 484.2471 [MH]⁺, Δ=1.6 ppm.

Example 203

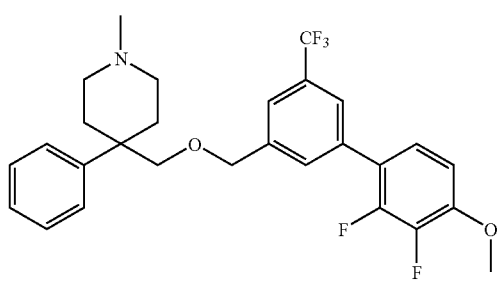 [SMILES: COc1ccc(-c2cc(COCC3(c4ccccc4)CCN(C)CC3)cc(C(F)(F)F)c2)c(F)c1F]

4-(((2',3'-Difluoro-4'-methoxy-5-(trifluoromethyl)biphenyl-3-yl)methoxy)methyl)-1-methyl-4-phenylpiperidine.
¹H-NMR (CD₃OD, 500 MHz) δ 7.63 (s, 1H), 7.40-7.44 (m, 4H), 7.28-7.32 (m, 2H), 7.14-7.18 (m, 2H), 7.02-7.07 (m, 1H), 4.48 (s, 2H), 3.97 (s, 3H), 3.51 (s, 2H), 2.61 (m, 2H), 2.22-2.30 (m, 4H), 2.19 (s, 3H), 2.02-2.07 (m, 2H). Mass spec.: 506.15 (MH)⁺. Accurate mass spec.: m/z 506.2096 [MH]⁺, Δ=4.4 ppm.

Example 204

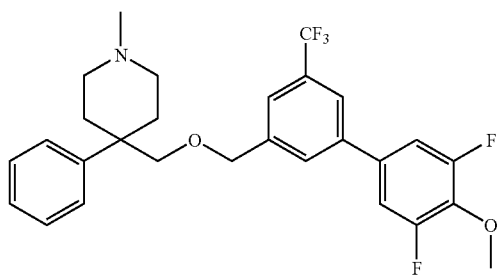 [SMILES: COc1c(F)cc(-c2cc(COCC3(c4ccccc4)CCN(C)CC3)cc(C(F)(F)F)c2)cc1F]

4-(((3',5'-difluoro-4'-methoxy-5-(trifluoromethyl)biphenyl-3-yl)methoxy)methyl)-1-methyl-4-phenylpiperidine.
¹H-NMR (CD₃OD, 500 MHz) δ 7.73-7.75 (m, 1H), 7.57 (s, 1H), 7.43-7.50 (m, 5H), 7.21-7.33 (m, 3H), 4.55 (s, 2H), 4.04 (s, 3H), 3.49 (s, 2H), 3.46 (m, 2H), 2.84-2.90 (m, 2H), 2.76 (s, 3H), 2.70-2.73 (m, 2H), 2.10-2.23 (m, 2H). Mass spec.: 505.93 (MH)⁺. Accurate mass spec.: m/z 506.2116 [MH]⁺, Δ=0.5 ppm.

Example 205

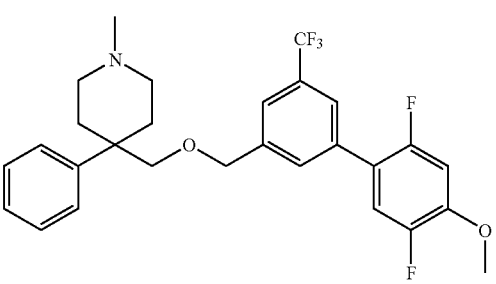 [SMILES: COc1cc(F)c(-c2cc(COCC3(c4ccccc4)CCN(C)CC3)cc(C(F)(F)F)c2)cc1F]

4-(((2',5'-Difluoro-4'-methoxy-5-(trifluoromethyl)biphenyl-3-yl)methoxy)methyl)-1-methyl-4-phenylpiperidine.
¹H-NMR (CD₃OD, 500 MHz) δ 7.65 (s, 1H), 7.40-7.42 (m, 4H), 7.28-7.33 (m, 2H), 7.03-7.20 (m, 3H), 4.48 (s, 2H), 3.95 (s, 3H), 3.50 (s, 2H), 2.65 (m, 2H), 2.30 (m, 4H), 2.18 (s, 3H), 2.04-2.08 (m, 2H). Mass spec.: 506.19 (MH)⁺. Accurate mass spec.: m/z 506.2110 [MH]⁺, Δ=1.7 ppm.

Example 206

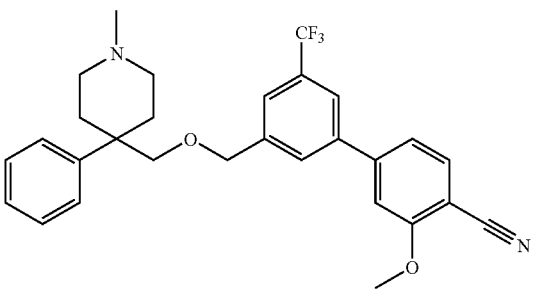 [SMILES: COc1cc(-c2cc(COCC3(c4ccccc4)CCN(C)CC3)cc(C(F)(F)F)c2)ccc1C#N]

3-Methoxy-3'-(((1-methyl-4-phenylpiperidin-4-yl)methoxy)methyl)-5'-(trifluoromethyl)biphenyl-4-carbonitrile.
¹H-NMR (CD₃OD, 500 MHz) δ 7.81 (s, 1H), 7.69-7.73 (m, 1H), 7.64 (s, 1H), 7.51 (s, 1H), 7.40-7.43 (m, 2H), 7.25-7.33 (m, 4H), 7.15-7.20 (m, 1H), 4.53 (s, 2H), 4.05 (s, 3H), 3.53 (s, 2H), 2.60-2.65 (m, 2H), 2.24-2.30 (m, 4H), 2.19 (s, 3H), 2.01-2.10 (m, 2H). Mass spec.: 495.20 (MH)⁺.

Example 207

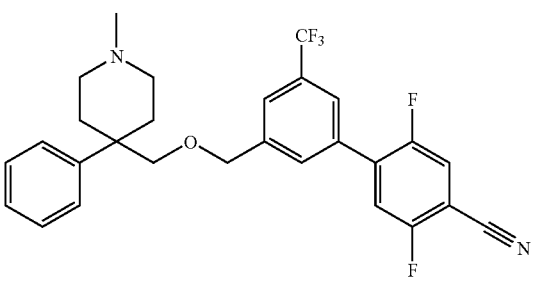 [SMILES: CN1CCC(COCc2cc(-c3cc(F)c(C#N)cc3F)cc(C(F)(F)F)c2)(c2ccccc2)CC1]

2,5-Difluoro-3'-(((1-methyl-4-phenylpiperidin-4-yl)methoxy)methyl)-5'-(trifluoromethyl)biphenyl-4-carbonitrile. ¹H-NMR (CD₃OD, 500 MHz) δ 7.79-7.81 (m, 2H), 7.55-7.62 (m, 3H), 7.41-7.50 (m, 4H), 7.28-7.29 (m, 1H), 4.58 (s, 2H), 3.49 (s, 2H), 3.45-3.49 (m, 2H), 2.85-2.90 (m, 2H), 2.76 (s, 3H), 2.71-2.74 (m, 2H), 2.17-2.22 (m, 2H). Mass spec.: 501.11 (MH)+. Accurate mass spec.: m/z 501.1964 [MH]+, Δ=0.3 ppm.

Example 208

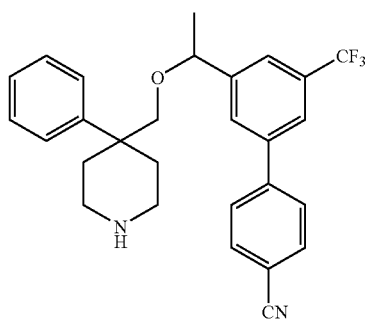 [SMILES: CC(OCC1(c2ccccc2)CCNCC1)c1cc(-c2ccc(C#N)cc2)cc(C(F)(F)F)c1]

(±)-3'-(1-((4-Phenylpiperidin-4-yl)methoxy)ethyl)-5'-(trifluoromethyl)biphenyl-4-carbonitrile. (±)-tert-Butyl 441-(4'-cyano-5-(trifluoromethyl)biphenyl-3-yl)ethoxy)methyl)-4-phenylpiperidine-1-carboxylate (36 mg, 0.064 mmol) was dissolved in trifluoroacetic acid (33% in dichloromethane, 1.5 mL). The resulting solution was stirred at room temperature for 1 h and concentrated. The crude salt was loaded onto an SCX cartridge in methanol. The cartridge was flushed with several volumes of methanol which was discarded. The product was eluted with 2 M ammonia in methanol and concentrated to give 29 mg (98%) as a colorless film. $^1$H NMR (500 MHz, CDCl$_3$) δ ppm 7.73 (d, J=8.6 Hz, 2H), 7.64 (s, 1H), 7.55 (d, J=8.6 Hz, 2H), 7.38 (s, 2H), 7.20-7.35 (m, 4H), 7.16 (m, 1H), 4.29 (q, J=6.4 Hz, 1H), 3.46 (s, 1H), 3.33 (d, J=9.2 Hz, 1H), 3.25 (d, J=8.9 Hz, 1H), 2.90 (m, 2H), 2.73 (m, 2H), 2.00-2.25 (m, 2H), 1.80-1.99 (m, 2H), 1.35 (d, J=6.4 Hz, 3H). Mass spec.: 465.20 (MH)+. Accurate mass spec.: m/z 465.2136 [MH]+, Δ=3.8 ppm.

Example 209

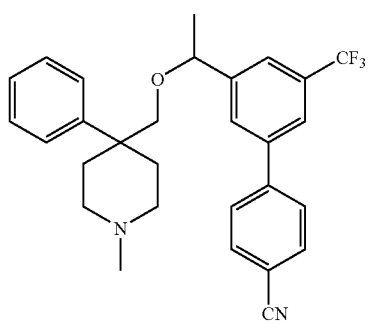 [SMILES: CC(OCC1(c2ccccc2)CCN(C)CC1)c1cc(-c2ccc(C#N)cc2)cc(C(F)(F)F)c1]

(±)-3'-(1-((1-Methyl-4-phenylpiperidin-4-yl)methoxy)ethyl)-5'-(trifluoromethyl)biphenyl-4-carbonitrile. To a suspension of (±)-3'-(1-((4-phenylpiperidin-4-yl)methoxy)ethyl)-5'-(trifluoromethyl)biphenyl-4-carbonitrile (15 mg, 0.032 mmol) and sodium cyanoborohydride (10.2 mg, 0.16 mmol) in acetonitrile (1 mL) at 0° C. was added formalin (0.1 mL, 3.6 mmol). The ice bath was removed and stirring continued for 1 h. The reaction was concentrated and loaded onto an SCX cartridge in methanol. The cartridge was flushed with several volumes of methanol which was discarded. The product was eluted with 2 M ammonia in methanol and concentrated to give 13 mg (84%) as a colorless film. $^1$H NMR (500 MHz, CDCl$_3$) δ ppm 7.74 (m, 2H), 7.64 (s, 1H), 7.56 (m, 2H), 7.37 (s, 2H), 7.22-7.35 (m, 5H), 7.16 (m, 1H), 4.29 (q, J=6.4 Hz, 1H), 3.32 (d, J=8.9 Hz, 1H), 3.25 (d, J=8.9 Hz, 1H), 2.61 (m, 2H), 2.11-2.35 (m, 7H), 1.95-2.10 (m, 2H), 1.34 (m, 3H). Mass spec.: 479.30 (MH)+. Accurate mass spec.: m/z 479.2300 [MH]+, Δ=2.1 ppm.

Example 210

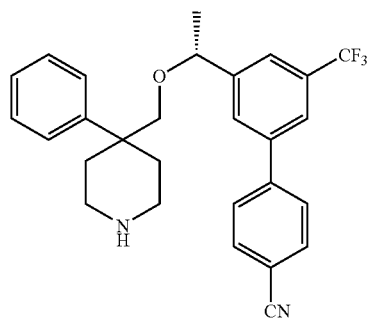

(R)-3'-(1-((4-phenylpiperidin-4-yl)methoxy)ethyl)-5'-(trifluoromethyl)biphenyl-4-carbonitrile. (R)-tert-Butyl 4-((1-(4'-cyano-5-(trifluoromethyl)biphenyl-3-yl)ethoxy)methyl)-4-phenylpiperidine-1-carboxylate (10 mg, 0.018 mmol) was dissolved in trifluoroacetic acid (33% in dichloromethane, 1.5 mL). The resulting solution was stirred at room temperature for 1 h and concentrated. The crude salt was loaded onto an SCX cartridge in methanol. The cartridge was flushed with several volumes of methanol which was discarded. The product was eluted with 2 M ammonia in methanol and concentrated to give 7.2 mg (88%) as a colorless film. $^1$H NMR (500 MHz, CDCl$_3$) δ ppm 7.73 (d, J=8.6 Hz, 2H), 7.64 (s, 1H), 7.55 (d, J=8.6 Hz, 2H), 7.38 (s, 2H), 7.20-7.35 (m, 4H), 7.16 (m, 1H), 4.29 (q, J=6.4 Hz, 1H), 3.46 (s, 1H), 3.33 (d, J=9.2 Hz, 1H), 3.25 (d, J=8.9 Hz, 1H), 2.90 (m, 2H), 2.73 (m, 2H), 2.00-2.25 (m, 2H), 1.80-1.99 (m, 2H), 1.35 (d, J=6.4 Hz, 3H). Mass spec.: 465.20 (MH)+. Accurate mass spec.: m/z 465.2136 [MH]+, Δ=3.8 ppm.

Example 211

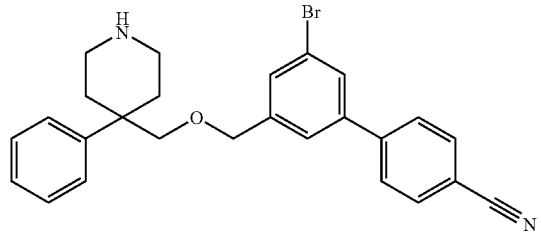

3'-Bromo-5'-(((4-phenylpiperidin-4-yl)methoxy)methyl)biphenyl-4-carbonitrile. tert-Butyl 4-(((5-bromo-4'-cyanobiphenyl-3-yl)methoxy)methyl)-4-phenylpiperidine-1-carboxylate (24.3 mg, 0.04 mmol) was treated with a trifluoroacetic acid/methylene chloride mixture (1:1, 2 mL) for 1 h. The solvent was removed in vacuo and the resulting crude mixture passed through a strong cation exchange column. After washing the column with several volumes of methanol, the product was eluted by washing the column with 2 M ammonia in methanol. The solvent was evaporated and the compound purified by column chromatography (10% ammonia in methanol/methylene chloride) to afford 13.2 mg (72%). $^1$H-NMR (CDCl$_3$, 500 MHz) δ 7.71-7.73 (m, 2H), 7.31-7.37 (m, 5H), 7.28 (s, 1H), 7.20-7.22 (m, 2H), 4.38 (s, 2H), 3.44 (s, 2H), 2.91-2.94 (m, 2H), 2.74-2.78 (m, 2H), 2.16-2.20 (m, 2H), 1.89-1.93 (m, 2H). Mass spec.: 463.09 (MH)$^+$. Accurate mass spec.: m/z 463.1205 [MH]$^+$, Δ=1.0 ppm.

Example 212

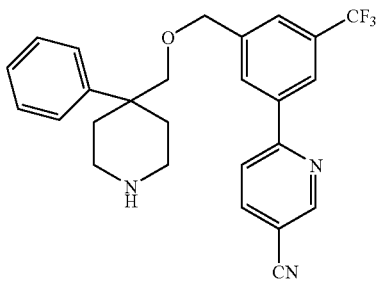 [SMILES: N#Cc1ccc(-c2cc(COCC3(c4ccccc4)CCNCC3)cc(C(F)(F)F)c2)nc1]

6-(3-(((4-Phenylpiperidin-4-yl)methoxy)methyl)-5-(trifluoromethyl)phenyl)nicotinonitrile. To a solution of tert-butyl 4-phenyl-4-((3-(tributylstannyl)-5-(trifluoromethyl)benzyloxy)methyl)piperidine-1-carboxylate (60 mg, 0.081 mmol) and 6-bromonicotinonitrile (16.4 mg, 0.089 mmol) in acetonitrile (1 mL) was added bis(triphenylphosphine)palladium(II) chloride (2.28 mg, 3.25 μmol). The reaction was heated at 150° C. via microwave for 1 h. The reaction was concentrated and purified by column chromatography (12%→25% ethyl acetate/hexanes) gave the Boc-protected amine: Mass spec.: 552.31 (MH)$^+$. The carbamate was dissolved in trifluoroacetic acid (33% in dichloromethane, 1.5 mL), stirred for 1 h, and concentrated. The crude trifluoroacetic acid salt was loaded onto a strong cation exchange cartridge which was flushed with several volumes of methanol which were discarded. The product was eluted using 2 M ammonia in methanol and concentrated. The reaction was repurified by preparative HPLC (TFA/MeOH/Water). The fraction was concentrated, loaded onto a strong cation exchange cartridge, and flushed with several volumes of methanol which were discarded. The product was eluted with 2 M ammonia in methanol and concentrated to give 9 mg (25%) as a colorless oil. $^1$H-NMR (CDCl$_3$, 500 MHz) δ 8.95 (s, 1H), 8.20 (s, 1H), 8.04 (m, 1H), 7.93 (s, 1H), 7.76 (d, J=8.2 Hz, 1H), 7.49 (s, 1H), 7.30-7.45 (m, 4H), 7.22 (m, 1H), 4.48 (s, 2H), 3.48 (s, 2H), 2.94 (m, 2H), 2.77 (m, 2H), 2.21 (m, 2H), 1.94 (m, 2H). Mass spec.: 452.27 (MH)$^+$. Accurate mass spec.: m/z 452.1934 [MH]$^+$, Δ=3.5 ppm.

Example 213

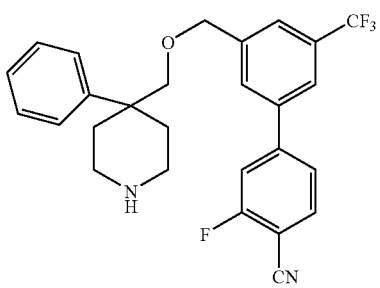 [SMILES: N#Cc1ccc(-c2cc(COCC3(c4ccccc4)CCNCC3)cc(C(F)(F)F)c2)cc1F]

3-Fluoro-3'-(((4-phenylpiperidin-4-yl)methoxy)methyl)-5'-(trifluoromethyl)biphenyl-4-carbonitrile. $^1$H-NMR (CDCl$_3$, 500 MHz) δ 7.71 (m, 1H), 7.65 (s, 1H), 7.28-7.47 (m, 8H), 7.20 (m, 1H), 4.46 (s, 2H), 3.49 (s, 2H), 2.91 (m, 2H), 2.76 (m, 2H), 2.20 (m, 2H), 1.88 (m, 2H), 1.59 (bs, 1H). Mass spec.: 469.37 (MH)$^+$. Accurate mass spec.: m/z 469.1924 [MH]$^+$, Δ=4.5 ppm.

Example 214

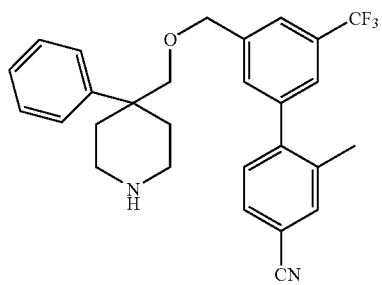 [SMILES: Cc1cc(C#N)ccc1-c1cc(COCC2(c3ccccc3)CCNCC2)cc(C(F)(F)F)c1]

2-Methyl-3'-(((4-phenylpiperidin-4-yl)methoxy)methyl)-5'-(trifluoromethyl)biphenyl-4-carbonitrile. $^1$H-NMR (CDCl$_3$, 500 MHz) δ 7.58 (s, 1H), 7.55 (d, J=7.9 Hz, 1H), 7.33-7.44 (m, 4H), 7.20-7.31 (m, 3H), 7.10-7.18 (m, 2H), 4.44 (s, 2H), 3.46 (s, 2H), 2.90 (m, 2H), 2.75 (m, 2H), 2.22 (s, 3H), 2.19 (m, 2H), 1.88 (m, 2H), 1.59 (bs, 1H). Mass spec.: 465.31 (MH)$^+$. Accurate mass spec.: m/z 465.2166 [MH]$^+$, Δ=2.6 ppm.

Example 215

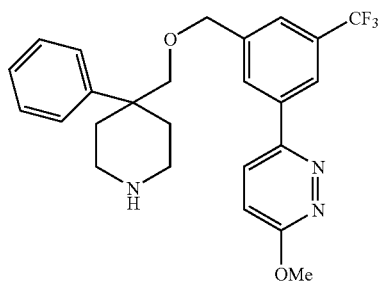 [SMILES: COc1ccc(-c2cc(COCC3(c4ccccc4)CCNCC3)cc(C(F)(F)F)c2)nn1]

3-Methoxy-6-(3-(((4-phenylpiperidin-4-yl)methoxy)methyl)-5-(trifluoromethyl)phenyl)pyridazine. To a solution of tert-butyl 4-phenyl-4-((3-(tributylstannyl)-5-(trifluoromethyl)benzyloxy)methyl)piperidine-1-carboxylate (100 mg, 0.135 mmol) and 3-chloro-6-methoxypyridazine (22 mg, 0.15 mmol) in acetonitrile (1.2 mL) was added bis(triphenylphosphine)palladium(II) chloride (3.80 mg, 5.42 μmol). The reaction was heated at 150° C. via microwave for 1 h. The reaction was diluted with pentane, filtered, and concentrated. Purification by column chromatography (12%→25% ethyl acetate/hexanes) gave the Boc-protected amine The carbamate was dissolved in trifluoroacetic acid (33% in dichloromethane, 1.5 mL), stirred for 1 h, and concentrated. The reaction was purified by preparative HPLC (TFA/MeOH/Water) to give the product as its trifluoroacetic acid salt. The salt was loaded onto a strong cation exchange cartridge in methanol and flushed with several volumes of methanol which were discarded. The product was eluted with 2 M ammonia in methanol and concentrated to give 10 mg (16%). $^1$H-NMR (CDCl$_3$, 500 MHz) δ 8.20 (s, 1H), 8.06 (m, 2H), 7.61 (s, 1H), 7.49 (m, 2H), 7.42 (m, 2H), 7.34 (d, J=9.2 Hz, 1H), 7.29 (m, 1H), 4.60 (s, 2H), 4.19 (s, 3H), 3.57 (s, 2H), 3.36

(m, 2H), 2.97 (m, 2H), 2.57 (m, 2H), 2.25 (m, 2H). Mass spec.: 458.19 (MH)⁺. Accurate mass spec.: m/z 458.2061 [MH]⁺, Δ=1.2 ppm.

Example 216

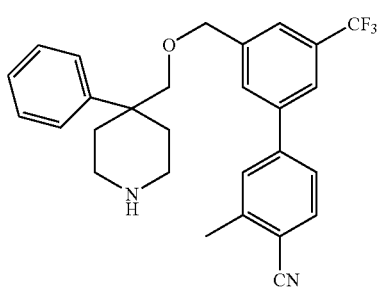 [SMILES: Cc1cc(-c2cc(COCC3(c4ccccc4)CCNCC3)cc(C(F)(F)F)c2)ccc1C#N]

3-Methyl-3'-(((4-phenylpiperidin-4-yl)methoxy)methyl)-5'-(trifluoromethyl)biphenyl-4-carbonitrile. $^1$H-NMR (CDCl$_3$, 500 MHz) δ 7.82 (s, 1H), 7.77 (d, J=7.9 Hz, 1H), 7.65 (s, 2H), 7.56 (m, 1H), 7.53 (s, 1H), 7.48 (m, 2H), 7.41 (m, 2H), 7.28 (m, 1H), 4.57 (s, 2H), 3.56 (s, 2H), 3.36 (m, 2H), 2.97 (m, 2H), 2.63 (s, 3H), 2.56 (m, 2H), 2.22 (m, 2H). Mass spec.: 465.19 (MH)⁺. Accurate mass spec.: m/z 465.2152 [MH]⁺, Δ=0.4 ppm.

Example 217

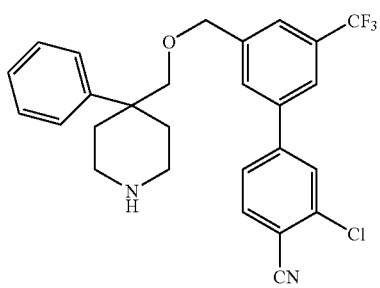 [SMILES: N#Cc1ccc(-c2cc(COCC3(c4ccccc4)CCNCC3)cc(C(F)(F)F)c2)cc1Cl]

3-Chloro-3'-(((4-phenylpiperidin-4-yl)methoxy)methyl)-5'-(trifluoromethyl)biphenyl-4-carbonitrile. $^1$H-NMR (CDCl$_3$, 500 MHz) δ 7.75-7.95 (m, 3H), 7.71 (m, 1H), 7.51-7.65 (m, 2H), 7.32-7.51 (m, 4H), 7.28 (m, 1H), 4.58 (s, 2H), 3.57 (s, 2H), 3.36 (m, 2H), 2.97 (m, 2H), 2.56 (m, 2H), 2.21 (m, 2H). Mass spec.: 485.11 (MH)⁺. Accurate mass spec.: m/z 485.1627 [MH]⁺, Δ=4.0 ppm.

Example 218

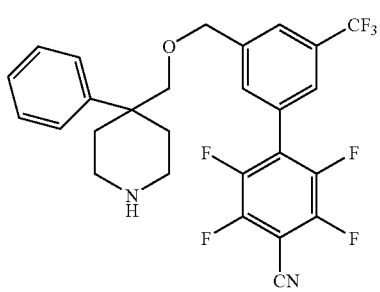 [SMILES: N#Cc1c(F)c(F)c(-c2cc(COCC3(c4ccccc4)CCNCC3)cc(C(F)(F)F)c2)c(F)c1F]

2,3,5,6-Tetrafluoro-3'-(((4-phenylpiperidin-4-yl)methoxy)methyl)-5'-(trifluoromethyl)biphenyl-4-carbonitrile. $^1$H-NMR (CDCl$_3$, 500 MHz) δ 7.78 (s, 1H), 7.67 (s, 1H), 7.48 (m, 3H), 7.40 (m, 2H), 7.25 (m, 1H), 4.59 (s, 2H), 3.56 (s, 2H), 3.35 (m, 2H), 2.96 (m, 2H), 2.57 (m, 2H), 2.20 (m, 2H). Mass spec.: 523.12 (MH)⁺. Accurate mass spec.: m/z 523.1608 [MH]⁺, Δ=2.4 ppm.

Example 219

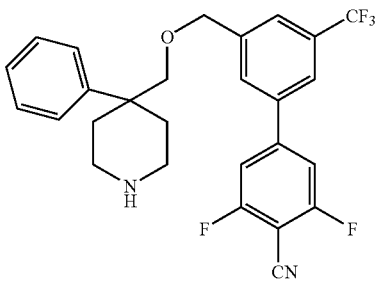 [SMILES: N#Cc1c(F)cc(-c2cc(COCC3(c4ccccc4)CCNCC3)cc(C(F)(F)F)c2)cc1F]

3,5-Difluoro-3'-(((4-phenylpiperidin-4-yl)methoxy)methyl)-5'-(trifluoromethyl)biphenyl-4-carbonitrile. $^1$H-NMR (CDCl$_3$, 500 MHz) δ 7.91 (s, 1H), 7.67 (s, 1H), 7.60 (s, 1H), 7.55 (m, 2H), 7.48 (m, 2H), 7.42 (m, 2H), 7.29 (m, 1H), 4.59 (s, 2H), 3.57 (s, 2H), 3.36 (m, 2H), 2.97 (m, 2H), 2.57 (m, 2H), 2.21 (m, 2H). Mass spec.: 487.16 (MH)⁺. Accurate mass spec.: m/z 487.1792 [MH]⁺, Δ=3.4 ppm.

Example 220

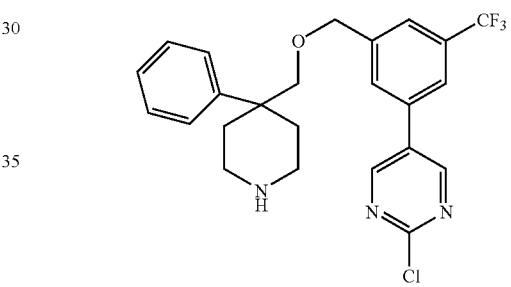

2-Chloro-5-(3-(((4-phenylpiperidin-4-yl)methoxy)methyl)-5-(trifluoromethyl)phenyl)pyrimidine. $^1$H-NMR (CDCl$_3$, 500 MHz) δ 8.95 (s, 2H), 7.94 (s, 1H), 7.64 (s, 1H), 7.61 (s, 1H), 7.49 (m, 2H), 7.41 (m, 2H), 7.28 (m, 1H), 4.60 (s, 2H), 3.56 (s, 2H), 3.36 (m, 2H), 2.96 (m, 2H), 2.57 (m, 2H), 2.20 (m, 2H). Mass spec.: 462.12 (MH)⁺. Accurate mass spec.: m/z 462.1579 [MH]⁺, Δ=4.1 ppm.

Example 221

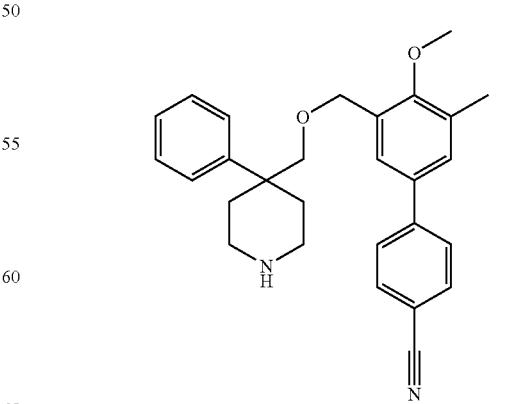

4'-Methoxy-3'-methyl-5'-(((4-phenylpiperidin-4-yl)methoxy)methyl)biphenyl-4-carbonitrile. tert-Butyl 4-((5-bromo- 2-methoxy-3-methylbenzyloxy)methyl)-4-phenylpiperidine-1-carboxylate (65 mg, 0.13 mmol), 4-cyanophenylboronic acid (76.4 mg, 0.52 mmol), and tetrakis(triphenylphosphine) palladium(0) (20 mg, 0.01 mmol) were combined in dry tetrahydrofuran (2 mL) in a microwave tube and sealed. After flushing with nitrogen, 0.46 mL of a 1 N potassium hydroxide aqueous solution was introduced. The mixture was heated at 120° C. for 1 h via microwave. After cooling to room temperature, the reaction mixture was concentrated and treated with a trifluoroacetic acid/methylene chloride mixture (1:1, 2 mL) for 1 h. The solvent was removed in vacuo and the resulting crude mixture passed through a strong cation exchange column. After washing the column with several volumes of methanol, the product was eluted by washing the column with 2 M ammonia in methanol and concentrated to afford 28 mg (51%). $^1$H-NMR (CDCl$_3$, 500 MHz) δ 7.69 (s, 1H), 7.68 (s, 1H), 7.55 (s, 1H), 7.53 (s, 1H), 7.37 (s, 1H), 7.36 (s, 1H), 7.27-7.30 (m, 3H), 7.17-7.20 (m, 2H), 4.46 (s, 2H), 3.61 (s, 3H), 3.50 (s, 2H), 2.89-2.92 (m, 2H), 2.72-2.76 (m, 2H), 2.31 (s, 3H), 2.16-2.19 (m, 2H), 1.88-1.93 (m, 2H). $^{13}$C-NMR (CDCl$_3$, 126 MHz) δ 157.1, 145.4, 144.4, 134.7, 132.5, 132.4, 131.7, 129.2, 128.3, 127.6, 127.4, 126.1, 125.8, 119.1, 110.6, 80.2, 68.2, 60.9, 42.7, 41.9, 33.6, 16.2. Mass spec.: 427.42 (MH)$^+$. Accurate mass spec.: m/z 427.2378 [MH]$^+$, Δ=1.8 ppm.

Example 222

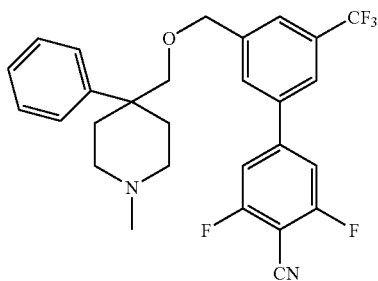 [SMILES: CN1CCC(COCc2cc(-c3cc(F)c(C#N)c(F)c3)cc(C(F)(F)F)c2)(c2ccccc2)CC1]

3,5-Difluoro-3'-(((1-methyl-4-phenylpiperidin-4-yl)methoxy)methyl)-5'-(trifluoromethyl)biphenyl-4-carbonitrile. To a solution of tert-butyl 4-phenyl-4-((3-(tributylstannyl)-5-(trifluoromethyl)benzyloxy)methyl)piperidine-1-carboxylate (100 mg, 0.135 mmol) and 4-bromo-2,6-difluorobenzonitrile (33 mg, 0.15 mmol) in acetonitrile (1.2 mL) was added bis(triphenylphosphine)palladium(II) chloride (3.80 mg, 5.42 μmol). The reaction was heated at 150° C. via microwave for 1 h. The reaction was diluted with pentane, filtered, and concentrated. Purification by column chromatography (12%→25% ethyl acetate/hexanes) gave the Boc-protected amine. The carbamate was dissolved in trifluoroacetic acid (33% in dichloromethane, 1.5 mL), stirred for 1 h, and concentrated. The crude trifluoroacetic acid salt was dissolved in acetonitrile (2.5 mL), cooled to 0° C., and treated with sodium cyanoborohydride (25.5 mg, 0.406 mmol), and then with formalin (0.25 mL). The crude product was purified by HPLC and concentrated. The trifluoroacetic acid salt was loaded onto a strong cation exchange cartridge and flushed with methanol which was discarded. The product was eluted with 2 M ammonia in methanol and concentrated to give 21 mg (31%). $^1$H-NMR (CDCl$_3$, 500 MHz) δ 7.62 (s, 1H), 7.45 (s, 1H), 7.30-7.40 (m, 5H), 7.21 (m, 1H), 7.17 (s, 1H), 7.16 (s, 1H), 4.46 (s, 2H), 3.48 (s, 2H), 2.58 (m, 2H), 2.27 (m, 2H), 2.20 (s, 3H), 2.19 (m, 2H), 1.98 (m, 2H); $^{13}$C NMR (126 MHz, CDCl$_3$) δ ppm 164.1, 164.5, 162.51, 162.47, 147.7 (t, J=9.6 Hz), 141.7, 138.0 (m), 132.0 (q, J=33 Hz), 128.8, 128.3, 127.4, 126.3, 124.9 (q, J=3.8 Hz), 123.7 (q, J=273 Hz), 122.8 (q, J=3.8 Hz), 111.01, 110.98, 110.84, 110.82, 109.1, 80.3 (br), 77.7, 72.0, 52.0, 46.3, 40.9, 32.6. Mass spec.: 501.14 (MH)$^+$. Accurate mass spec.: m/z 501.1974 [MH]$^+$, Δ=1.7 ppm.

Example 223

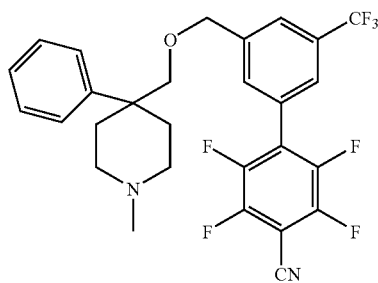 [SMILES: CN1CCC(COCc2cc(-c3c(F)c(F)c(C#N)c(F)c3F)cc(C(F)(F)F)c2)(c2ccccc2)CC1]

2,3,5,6-Tetrafluoro-3'-(((1-methyl-4-phenylpiperidin-4-yl)methoxy)methyl)-5'-(trifluoromethyl)biphenyl-4-carbonitrile. $^1$H-NMR (CDCl$_3$, 500 MHz) δ 7.55 (s, 1H), 7.50 (s, 1H), 7.36 (m, 2H), 7.25-7.32 (m, 3H), 7.13 (m, 1H), 4.46 (s, 2H), 3.47 (s, 2H), 2.57 (m, 2H), 2.26 (m, 2H), 2.19 (s, 3H), 2.18 (m, 2H), 1.98 (m, 2H). Mass spec.: 537.13 (MH)$^+$. Accurate mass spec.: m/z 537.1755 [MH]$^+$, Δ=4.1 ppm.

Example 224

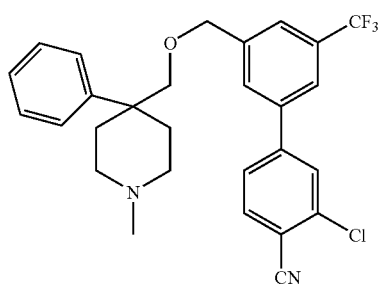 [SMILES: CN1CCC(COCc2cc(-c3ccc(C#N)c(Cl)c3)cc(C(F)(F)F)c2)(c2ccccc2)CC1]

3-Chloro-3'-(((1-methyl-4-phenylpiperidin-4-yl)methoxy)methyl)-5'-(trifluoromethyl)biphenyl-4-carbonitrile. $^1$H-NMR (CDCl$_3$, 500 MHz) δ 7.75 (d, J=8.2 Hz, 1H), 7.63 (m, 2H), 7.48 (dd, J=7.9, 1.8 Hz, 1H), 7.42 (s, 1H), 7.39 (s, 1H), 7.36 (m, 2H), 7.32 (m, 2H), 7.19 (m, 1H), 4.45 (s, 2H), 3.48 (s, 2H), 2.59 (m, 2H), 2.27 (m, 2H), 2.20 (s, 3H), 2.19 (m, 2H), 1.99 (m, 2H); $^{13}$C NMR (126 MHz, CDCl$_3$) δ ppm 145.6, 143.8, 141.4, 138.9, 137.6, 134.5, 131.8 (q, J=33 Hz), 129.0, 128.7, 128.3, 127.4, 126.2, 126.0, 124.4 (q, J=3.8 Hz), 123.8 (q, J=273 Hz), 123.0 (q, J=2.9 Hz), 115.9, 112.7, 80.1 (br), 77.7, 72.1, 52.0, 50.8, 46.3, 40.9, 32.5. Mass spec.: 499.14 (MH)$^+$. Accurate mass spec.: m/z 499.1776 [MH]$^+$, Δ=2.4 ppm.

Example 225

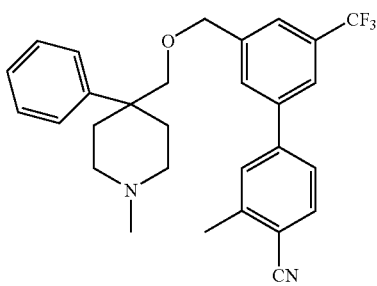 [SMILES: Cc1cc(-c2cc(COCC3(c4ccccc4)CCN(C)CC3)cc(C(F)(F)F)c2)ccc1C#N]

3-Methyl-3'-(((1-methyl-4-phenylpiperidin-4-yl)methoxy)methyl)-5'-(trifluoromethyl)biphenyl-4-carbonitrile.
$^1$H-NMR (CDCl$_3$, 500 MHz) δ 7.68 (d, J=8.2 Hz, 1H), 7.65 (s, 1H), 7.45 (s, 1H), 7.34-7.42 (m, 4H), 7.31 (m, 2H), 7.19 (m, 1H), 4.44 (s, 2H), 3.47 (s, 2H), 2.60 (m, 2H), 2.27 (m, 2H), 2.21 (s, 3H), 2.20 (m, 2H), 2.01 (m, 2H); $^{13}$C NMR (126 MHz, CDCl$_3$) δ ppm 144.0, 142.7, 140.9, 140.3, 133.1, 131.6 (q, J=33 Hz), 129.0, 128.3, 127.4, 126.2, 125.2, 124.0 (q, J=273 Hz), 123.8 (q, J=3.8 Hz), 123.0 (q, J=2.9 Hz), 118.0, 112.4, 80.0 (br), 77.7, 72.3, 52.0, 46.2, 40.9, 32.4, 20.7. Mass spec.: 479.19 (MH)$^+$. Accurate mass spec.: m/z 479.2322 [MH]$^+$, Δ=2.5 ppm.

Example 226

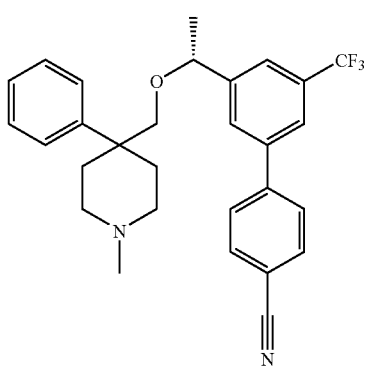 [SMILES: C[C@@H](OCC1(c2ccccc2)CCN(C)CC1)c1cc(-c2ccc(C#N)cc2)cc(C(F)(F)F)c1]

(R)-3'-(1-((1-Methyl-4-phenylpiperidin-4-yl)methoxy)ethyl)-5'-(trifluoromethyl)biphenyl-4-carbonitrile. (R)-tert-Butyl 4-((1-(4'-cyano-5-(trifluoromethyl)biphenyl-3-yl)ethoxy)methyl)-4-phenylpiperidine-1-carboxylate (300 mg, 0.53 mmol) was treated with a trifluoroacetic acid/methylene chloride mixture (1:1, 6 mL) for 1 h. The solvent was removed in vacuo and the resulting crude product dissolved in acetonitrile (5 mL), cooled to 0° C. and treated with formaldehyde (37 wt. % solution in water, 1.1 mL). The reaction was treated with sodium cyanoborohydride (163 mg, 2.58 mmol) and a few drops of acetic acid. The reaction was stirred at 0° C. for 30 min and at room temperature for 1 h. The solvent was removed in vacuo and the resulting crude mixture passed through a strong cation exchange column. After washing the column with several volumes of methanol, the product was eluted by washing the column with 2 M ammonia in methanol. The solvents were evaporated to afford 222 mg (73%). $^1$H-NMR (CDCl$_3$, 300 MHz) δ 7.71 (s, 1H), 7.68 (s, 1H), 7.62 (s, 1H), 7.53 (s, 1H), 7.51 (s, 1H), 7.21-7.35 (m, 6H), 7.09-7.14 (m, 1H), 4.27 (q, J=6.6 Hz, 1H), 3.29 (d, J=9.2 Hz, 1H), 3.24 (d, J=8.8 Hz, 1H), 2.50-2.57 (m, 2H), 2.15 (s, 3H), 1.93-2.22 (m, 6H), 1.32 (m, 3H); $^{13}$C-NMR (CDCl$_3$, 76 MHz) δ 146.5, 149.8, 140.0, 132.6, 131.4 (d, J=32.2 Hz), 128.0, 127.8, 127.7, 125.9, 123.8 (q, J=272.4 Hz), 122.8, 122.7, 122.0, 118.5, 111.6, 51.8, 50.2, 46.1, 40.1, 32.3, 31.9, 23.9. Mass spec.: 479.19 (MH)$^+$.

Example 227

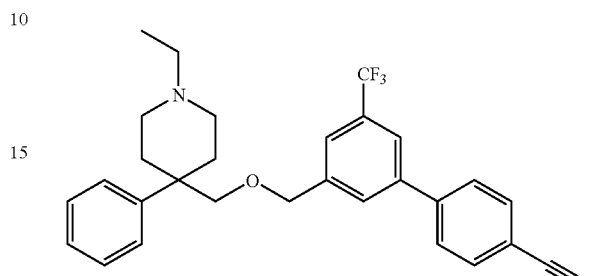

3'-(((1-Ethyl-4-phenylpiperidin-4-yl)methoxy)methyl)-5'-(trifluoromethyl)biphenyl-4-carbonitrile. 3'-(((4-phenylpiperidin-4-yl)methoxy)methyl)-5'-(trifluoromethyl)biphenyl-4-carbonitrile (25.0 mg, 0.05 mmol) and acetaldehyde (0.25 mL, 4.31 mmol) were combined in acetonitrile (2.0 mL) and cooled to 0° C. The reaction was treated with sodium cyanoborohydride (14.0 mg, 0.23 mmol) and a few drops of acetic acid. The reaction was stirred at 0° C. for 30 min and at room temperature for 1 h. The solvent was removed in vacuo and the resulting crude mixture passed through a strong cation exchange column. After washing the column with several volumes of methanol, the product was eluted by washing the column with 2 M ammonia in methanol. The solvents were evaporated to afford 17 mg (79%). $^1$H-NMR (CDCl$_3$, 500 MHz) δ 7.74-7.75 (m, 2H), 7.66 (s, 1H), 7.59-7.60 (m, 2H), 7.44 (s, 1H), 7.30-7.39 (m, 5H), 7.18-7.21 (m, 1H), 4.45 (s, 2H), 3.48 (s, 2H), 2.76 (s, 2H), 2.39-2.41 (m, 2H), 2.25-2.32 (m, 4H), 2.07-2.11 (m, 2H), 1.09 (t, J=7.0 Hz, 3H). $^{13}$C-NMR (CDCl$_3$, 126 MHz) δ 144.0, 141.0, 140.1, 132.8, 131.7 (q, J=32.6 Hz), 129.0, 128.5, 128.0, 127.4, 126.3, 124.0 (q, J=272.6 Hz), 123.9, 123.0, 118.7, 111.9, 72.2, 52.5, 49.5, 41.4, 32.0, 11.8. Mass spec.: 479.15 (MH)$^+$.

Example 228

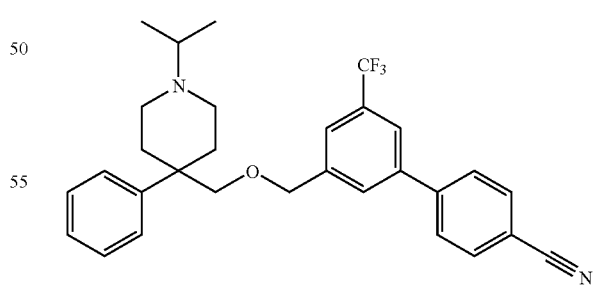

3'-(((1-Isopropyl-4-phenylpiperidin-4-yl)methoxy)methyl)-5'-(trifluoromethyl)biphenyl-4-carbonitrile. $^1$H-NMR (CDCl$_3$, 500 MHz) δ 7.75 (s, 1H), 7.74 (s, 1H), 7.66 (s, 1H), 7.60 (s, 1H), 7.58 (s, 1H), 7.36-7.43 (m, 4H), 7.29-7.32 (m, 2H), 7.16-7.19 (m, 1H), 4.44 (s, 2H), 3.48 (s, 2H), 2.58-2.60 (m, 1H), 2.25-2.32 (m, 4H), 1.97-2.02 (m, 2H), 0.99 (s, 3H), 0.97 (s, 3H). $^{13}$C-NMR (CDCl$_3$, 126 MHz) δ 144.1, 141.0, 140.1, 132.8, 131.7 (q, J=32.6 Hz), 129.1, 128.3, 128.0, 127.3, 126.1, 123.4 (q, J=272.6 Hz), 123.9, 123.0, 122.9, 118.6, 112.0, 78.0, 72.3, 54.8, 45.3, 41.3, 32.8, 32.0, 18.7. Mass spec.: 493.46 (MH)⁺. Accurate mass spec.: m/z 493.2466 [MH]⁺, Δ=0.1 ppm.

Example 229

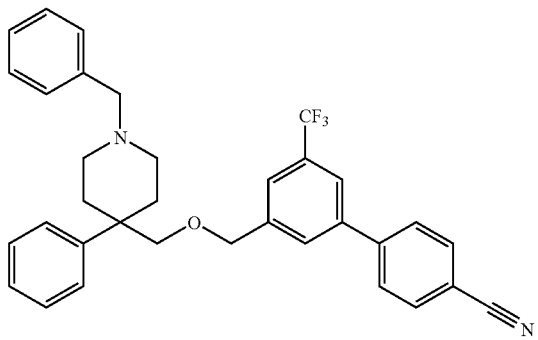 [SMILES: N#Cc1ccc(-c2cc(COCC3(c4ccccc4)CCN(Cc4ccccc4)CC3)cc(C(F)(F)F)c2)cc1]

3'-(((1-Benzyl-4-phenylpiperidin-4-yl)methoxy)methyl)-5'-(trifluoromethyl)biphenyl-4-carbonitrile. ¹H-NMR (CD₃OD, 500 MHz) δ 7.84-7.86 (m, 2H), 7.81 (s, 1H), 7.74-7.76 (m, 2H), 7.61 (s, 1H), 7.50 (s, 1H), 7.42-7.43 (m, 2H), 7.25-7.33 (m, 7H), 7.19-7.20 (m, 1H), 4.51 (s, 2H), 3.43 (s, 2H), 3.42 (s, 2H), 2.63-2.65 (m, 2H), 2.26-2.30 (m, 4H), 2.05-2.07 (m, 2H). Mass spec.: 541.23 (MH)⁺.

Example 230

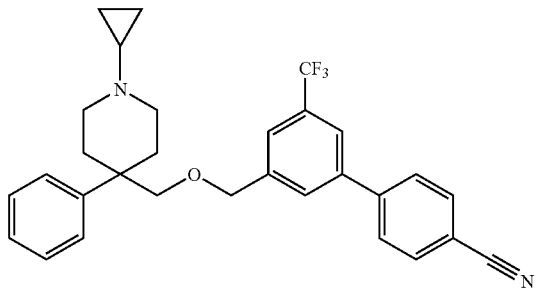 [SMILES: N#Cc1ccc(-c2cc(COCC3(c4ccccc4)CCN(C4CC4)CC3)cc(C(F)(F)F)c2)cc1]

3'-(((1-Cyclopropyl-4-phenylpiperidin-4-yl)methoxy)methyl)-5'-(trifluoromethyl)biphenyl-4-carbonitrile. A microwave tube was charged with 3'-(((4-phenylpiperidin-4-yl)methoxy)methyl)-5'-(trifluoromethyl)biphenyl-4-carbonitrile (21.5 mg, 0.05 mmol), (1-ethoxycyclopropoxy)trimethylsilane (96.5 μL, 0.47 mmol), sodium cyanoborohydride (15 mg, 0.24 mmol). The tube was flushed with nitrogen and treated with methanol (2 mL) and acetic acid (3 drops). The tube was sealed and heated at 90° C. for 1 h via microwave. After cooling, the reaction was concentrated and purified by flash chromatography on silica gel (10% methanol/methylene chloride) to afford 13.5 mg (55%) as a colorless oil. ¹H-NMR (CDCl₃, 500 MHz) δ 7.76 (s, 1H), 7.74 (s, 1H), 7.66 (s, 1H), 7.60 (s, 1H), 7.58 (s, 1H), 7.42 (s, 1H), 7.33-7.37 (m, 5H), 7.21-7.24 (m, 1H), 4.45 (s, 2H), 3.44 (s, 2H), 3.11-3.14 (m, 2H), 2.56-2.61 (m, 2H), 2.35-2.38 (m, 2H), 2.09-2.16 (m, 2H), 1.78-1.79 (m, 1H), 0.82 (m, 2H), 0.54-0.56 (m, 2H). Mass spec.: 491.44 (MH)⁺. Accurate mass spec.: m/z 491.2331 [MH]⁺, Δ=4.2 ppm.

Example 231

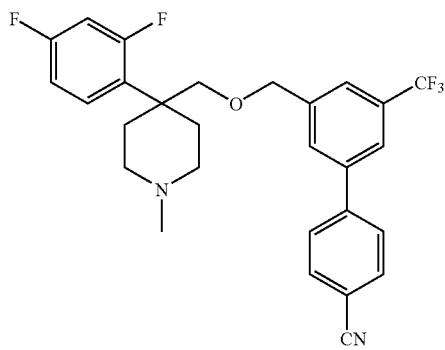 [SMILES: CN1CCC(COCc2cc(-c3ccc(C#N)cc3)cc(C(F)(F)F)c2)(c2ccc(F)cc2F)CC1]

3-(((4-(2,4-Difluorophenyl)-1-methylpiperidin-4-yl)methoxy)methyl)-5'-(trifluoromethyl)biphenyl-4-carbonitrile. Prepared by Method A. Mass Spec: 501.27 (MH)⁺. LC t_r=1.88 min (Phenomenex-Luna 4.6×50 mm S10, 10% MeOH/90% H₂O/0.1% TFA→90% MeOH/10% H₂O/0.1% TFA Gradient Time=2 min, Flow rate=4 mL/min).

Example 232

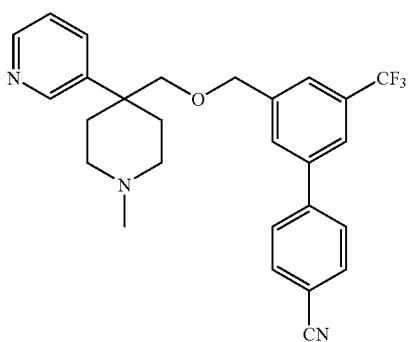 [SMILES: CN1CCC(COCc2cc(-c3ccc(C#N)cc3)cc(C(F)(F)F)c2)(c2cccnc2)CC1]

3'-(((1-Methyl-4-(pyridin-3-yl)piperidin-4-yl)methoxy)methyl)-5'-(trifluoromethyl)biphenyl-4-carbonitrile. Prepared by Method A. Mass Spec.: 466.10 (MH)⁺. LC: t_r=1.502 min (Phenomenex-Luna 4.6×50 mm S10, 10% MeOH/90% H₂O/0.1% TFA→90% MeOH/10% H₂O/0.1% TFA Gradient Time=2 min, Flow rate=4 mL/min).

Example 233

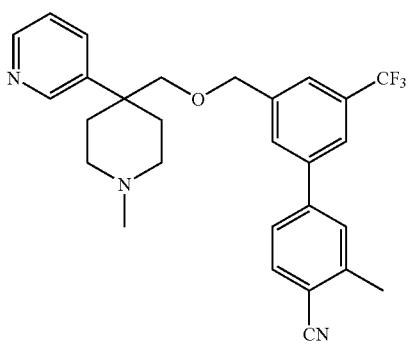 [SMILES: Cc1cc(-c2cc(COCC3(c4cccnc4)CCN(C)CC3)cc(C(F)(F)F)c2)ccc1C#N]

3-Methyl-3'-(((1-methyl-4-(pyridin-3-yl)piperidin-4-yl)methoxy)methyl)-5'-(trifluoromethyl)biphenyl-4-carbonitrile. Prepared by Method A. Mass Spec.: 480.20 (MH)⁺. LC $t_r$=2.465 min (Phenomenex-Luna 4.6×50 mm S10, 10% MeOH/90% H$_2$O/0.1% TFA→90% MeOH/10% H$_2$O/0.1% TFA Gradient Time=3 min, Flow rate=4 mL/min).

Example 234

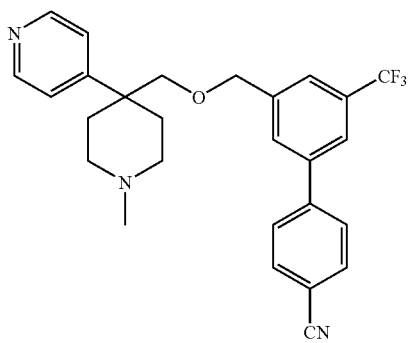 [SMILES: CN1CCC(COCc2cc(-c3ccc(C#N)cc3)cc(C(F)(F)F)c2)(c2ccncc2)CC1]

3'-(((1-Methyl-4-(pyridin-4-yl)piperidin-4-yl)methoxy)methyl)-5'-(trifluoromethyl)biphenyl-4-carbonitrile. A flask was charged with tert-butyl 4-(((4'-cyano-5-(trifluoromethyl)biphenyl-3-yl)methoxy)methyl)-4-(pyridin-4-yl)piperidine-1-carboxylate (50 mg, 0.091 mmol) and trifluoroacetic acid (1 mL, 13.0 mmol) in dichloromethane (5 mL) at 0° C. under nitrogen. After 20 min the solvent was evaporated under reduced pressure and the resulting residue dried overnight. The resulting oil was dissolved in dichloromethane (5 mL) and treated with formaldehyde (37 wt. % solution in water, 1.0 mL) at 0° C. After 20 min, the reaction was treated with sodium triacetoxyborohydride (77 mg, 0.363 mmol). The reaction was stirred at 0° C. for 30 min and at room temperature for 1 h. The solvent was removed in vacuo and the resulting residue purified via preparative HPLC. The solvent was evaporated to afford 21 mg (50%). Mass Spec: 466.10 (MH)$^+$. LC $t_r$=2.325 min (Phenomenex-Luna 4.6×50 mm S10, 10% MeOH/90% H$_2$O/0.1% TFA→90% MeOH/10% H$_2$O/0.1% TFA Gradient Time=4 min, Flow rate=4 mL/min).

Example 235

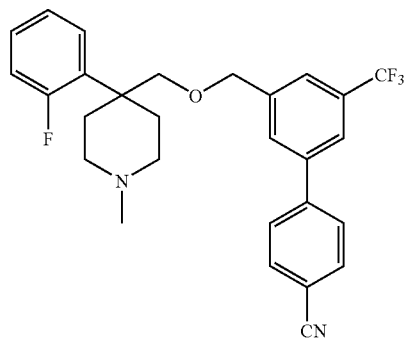 [SMILES: CN1CCC(COCc2cc(-c3ccc(C#N)cc3)cc(C(F)(F)F)c2)(c2ccccc2F)CC1]

3'-(((4-(2-fluorophenyl)-1-methylpiperidin-4-yl)methoxy)methyl)-5'-(trifluoromethyl)biphenyl-4-carbonitrile. A flask was charged with ten-butyl 4-(((4'-cyano-5-(trifluoromethyl)biphenyl-3-yl)methoxy)methyl)-4-(2-fluorophenyl)piperidine-1-carboxylate (0.125 g, 0.214 mmol) in dichloromethane (2 mL). Trifluoroacetic acid 0.5 mL was added and the mixture was allowed to stir at room temperature for 1 hr.

The reaction mixture was concentrated in vacuo. The resulting oil was dissolved in dichloromethane (3 mL) and 1 mL of a 37 wt % formaldehyde solution in water. After 5 min the reaction was treated with sodium triacetoxyborohydride (0.136 g, 0.64 mmol). The reaction was stirred at room temperature for 16 h. The reaction was diluted with 4 mL dichloromethane and the organic layer was separated, dried over Na$_2$SO$_4$ and evaporated in vacuo. The resulting residue was dissolved in methanol and loaded onto an SCX cartridge. The cartridge was washed with 5 mL methanol then eluted with 2 N NH$_3$ in methanol. The ammonia in methanol fractions were collected and evaporated in vacuo affording 0.093 g (90%) of desired N-methyl piperidine. $^1$H-NMR (CDCl$_3$, 400 MHz) δ ppm 7.73 (d, J=8.7 Hz, 2H), 7.65 (s, 1H), 7.58 (d, J=8.7 Hz, 2H), 7.41 (s, 1H), 7.35 (s, 1H), 7.32 (m, 1H), 7.16 (m, 1H), 7.09 (m, 1H), 6.91 (m, 1H), 4.46 (s, 2H), 3.69 (s, 2H), 2.57 (m, 2H), 2.37 (m, 2H), 2.24 (m, 2H), 2.21 (s, 3H), 2.00 (m, 2H). Mass spec.: 483.3 (MH)$^+$; LC $t_r$=3.228 min (Phenomenex-Luna 4.6×50 mm S10, 10% MeOH/90% H$_2$O/0.1% TFA→90% MeOH/10% H$_2$O/0.1% TFA Gradient Time=4 min, Flow rate=4 mL/min).

Example 236

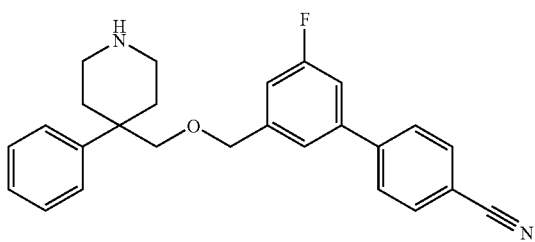

3'-Fluoro-5'-(((4-phenylpiperidin-4-yl)methoxy)methyl)biphenyl-4-carbonitrile. tert-Butyl 4-((3-bromo-5-fluorobenzyloxy)methyl)-4-phenylpiperidine-1-carboxylate (100.0 mg, 0.21 mmol), 4-cyanophenylboronic acid (93 mg, 0.63 mmol), and tetrakis(triphenylphosphine) palladium(0) (33 mg, 0.02 mmol) were combined in dry tetrahydrofuran (3 mL) in a microwave tube and sealed. After flushing with nitrogen, 0.7 mL of a 1 N potassium hydroxide aqueous solution was introduced. The mixture was heated at 120° C. for 1 h via microwave. After cooling to room temperature, the reaction mixture was concentrated and treated with a trifluoroacetic acid/methylene chloride mixture (1:1, 2 mL) for 1 h. The solvent was removed in vacuo and the resulting crude mixture passed through a strong cation exchange column. After washing the column with several volumes of methanol, the product was eluted by washing the column with 2 M ammonia in methanol and concentrated to afford 48 mg (46%). $^1$H-NMR (CDCl$_3$, 500 MHz) δ 7.72 (s, 1H), 7.70 (s, 1H), 7.57 (s, 1H), 7.56 (s, 1H), 7.31-7.38 (m, 4H), 7.19-7.22 (m, 1H), 7.11-7.13 (m, 1H), 7.08 (s, 1H), 6.84-6.86 (s, 1H), 4.40 (s, 2H), 3.45 (s, 2H), 2.89-2.93 (m, 2H), 2.73-2.78 (m, 2H), 2.17-2.20 (m, 2H), 1.88-1.94 (m, 2H). $^{13}$C-NMR (CDCl$_3$, 126 MHz) δ 163.3 (d, J=247.6 Hz), 144.2, 142.5, 141.2, 132.7, 128.4, 127.8, 127.3, 126.2, 121.3, 118.7, 114.2, 114.0, 113.1, 111.7, 80.1, 72.3, 42.7, 41.9, 33.6. Mass spec.: 401.28 (MH)$^+$. Accurate mass spec.: m/z 401.2026 [MH]$^+$, Δ=0.8 ppm.

Example 237

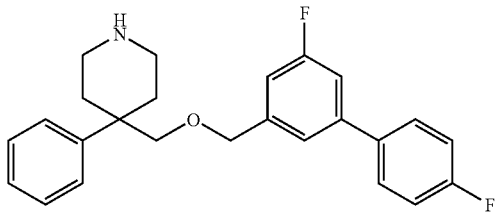 [SMILES: Fc1ccc(-c2cc(F)cc(COCC3(c4ccccc4)CCNCC3)c2)cc1]

4-(((4',5-Difluorobiphenyl-3-yl)methoxy)methyl)-4-phenylpiperidine. $^1$H-NMR (CDCl$_3$, 500 MHz) δ 8.97 (s, 1H), 7.42-7.46 (m, 2H), 7.32-7.39 (m, 4H), 7.20-7.23 (m, 1H), 7.07-7.14 (m, 3H), 7.05 (s, 1H), 6.78-6.86 (m, 1H), 4.39 (s, 2H), 3.45 (s, 2H), 2.89-2.93 (m, 2H), 2.73-2.78 (m, 2H), 2.17-2.19 (m, 2H), 1.89-1.94 (m, 2H). $^{13}$C-NMR (CDCl$_3$, 126 MHz) δ 164.1 (d, J=52.8 Hz), 162.1 (d, J=53.8 Hz), 144.3, 142.3, 142.0, 136.1, 128.8, 128.4, 127.3, 126.2, 121.2, 115.9, 115.7, 112.8, 79.9, 72.5, 42.8, 41.9, 33.6. Mass spec.: 394.3 (MH)$^+$. Accurate mass spec.: m/z 394.1978 [MH]$^+$, Δ=1.1 ppm.

Example 238

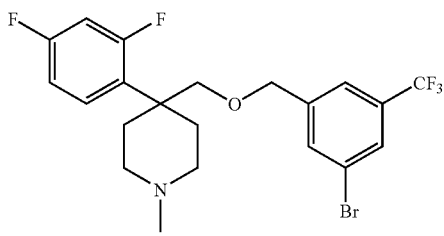 [SMILES: CN1CCC(COCc2cc(Br)cc(C(F)(F)F)c2)(c2ccc(F)cc2F)CC1]

4-((3-Bromo-5-(trifluoromethyl)benzyloxy)methyl)-4-(2,4-difluorophenyl)-1-methylpiperidine. tert-Butyl 4-((3-bromo-5-(trifluoromethyl)benzyloxy)methyl)-4-(2,4-difluorophenyl)piperidine-1-carboxylate (200 mg, 0.35 mmol) was dissolved in methanol (5 mL). Hydrochloric acid (gas) was bubbled through for 20 seconds, then removed. The reaction was allowed to stir for 20 min and the solvent evaporated. The resulting solid was dissolved in dichloromethane (2 mL) and treated with formaldehyde (37 wt. % solution in water, 1.5 mL) at 0° C. After 20 min the reaction was treated with sodium triacetoxyborohydride (297 mg, 1.4 mmol). The reaction was stirred at 0° C. for 30 min and at room temperature for 1 h. The solvent was removed in vacuo and the resulting crude mixture passed through a strong cation exchange column. After washing the column with several volumes of methanol, the product was eluted by washing the column with 2 M ammonia in methanol. The solvents were evaporated to afford 142 mg (85%). Mass Spec: 478.07 (MH)$^+$. LC t$_r$=1.885 min (Phenomenex-Luna 4.6×50 mm S10, 10% MeOH/90% H$_2$O/0.1% TFA→90% MeOH/10% H$_2$O/0.1% TFA Gradient Time=2 min, Flow rate=4 mL/min).

We claim:
1. A compound of Formula I

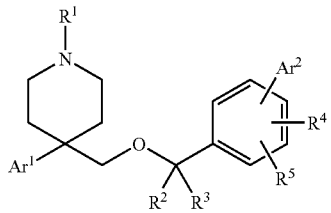

where:
R$^1$ is hydrogen, alkyl, cycloalkyl, or benzyl;
R$^2$ is hydrogen or alkyl;
R$^3$ is hydrogen or alkyl;
R$^4$ is hydrogen, alkyl, haloalkyl, hydroxy, alkoxy, haloalkoxy, cyano, or COR$^6$;
R$^5$ is hydrogen, alkyl, haloalkyl, hydroxy, alkoxy, haloalkoxy, cyano, or COR$^6$;
R$^6$ is hydroxy, alkoxy, benzyloxy, amino, alkylamino, dialkylamino, pyrrolidinyl, piperidinyl, piperazinyl, N-alkylpiperazinyl, or morpholinyl;
Ar$^1$ is phenyl or pyridinyl, and is substituted with 0-2 substituents selected from the group consisting of halo, alkyl, haloalkyl, cyano, phenyl and furanyl;
Ar$^2$ is furanyl, thienyl, pyrrolyl, isoxazolyl, isothiazolyl, pyrazolyl, oxazolyl, thiazolyl, imidazolyl, oxadiazolyl, thiadiazolyl, triazolyl, tetrazolyl, pyridinyl, pyridazinyl, pyrimidinyl, pyrazinyl, triazinyl, quinolinyl, or isoquinolinyl, and is substituted with 0-3 substituents selected from the group consisting of amino, alkylamino, dialkylamino, oxo, halo, alkyl, haloalkyl, alkoxy, alkylthio, haloalkoxy, cyano, nitro, pyrrolidinyl, piperidinyl, piperazinyl, N-alkylpiperazinyl, and morpholinyl;
or Ar$^2$ is benzodioxolyl, dibenzofuranyl, thianthrenyl, or trimethylenedioxybenzen-yl;
or a pharmaceutically acceptable salt thereof.

2. A compound of claim 1 where:
R$^1$ is hydrogen or alkyl;
R$^4$ is hydrogen, alkyl, haloalkyl, alkoxy, haloalkoxy, or cyano;
R$^5$ is hydrogen, alkyl, haloalkyl, alkoxy, haloalkoxy, or cyano;
Ar$^1$ is phenyl substituted with 0-2 substituents selected from the group consisting of halo, alkyl, haloalkyl, and cyano;
Ar$^2$ is furanyl, thienyl, pyrrolyl, isoxazolyl, isothiazolyl, pyrazolyl, oxazolyl, thiazolyl, imidazolyl, oxadiazolyl, thiadiazolyl, triazolyl, tetrazolyl, pyridinyl, pyridazinyl, pyrimidinyl, triazinyl, quinolinyl, or isoquinolinyl, and is substituted with 0-3 substituents selected from the group consisting of amino, alkylamino, dialkylamino, oxo, halo, alkyl, haloalkyl, alkoxy, alkylthio, haloalkoxy, cyano, nitro, pyrrolidinyl, piperidinyl, piperazinyl, N-alkylpiperazinyl, or morpholinyl;
or Ar$^2$ is benzodioxolyl, dibenzofuranyl or thianthrenyl.

3. A compound of claim 1 where R$^1$ is hydrogen.
4. A compound of claim 1 where R$^2$ and R$^3$ are hydrogen.
5. A compound of claim 1 where R$^2$ is methyl and R$^3$ is hydrogen.
6. A compound of claim 1 where Ar$^1$ is phenyl.
7. A compound of claim 1 where Ar$^2$ is furanyl, thienyl, pyrrolyl, isoxazolyl, isothiazolyl, pyrazolyl, oxazolyl, thiazolyl, imidazolyl, oxadiazolyl, thiadiazolyl, triazolyl, tetrazolyl, pyridinyl, pyridazinyl, pyrimidinyl, pyrazinyl, triazinyl, quinolinyl, or isoquinolinyl, and is substituted with 0-3 substituents selected from the group consisting of amino, alkylamino, dialkylamino, oxo, halo, alkyl, haloalkyl, alkoxy, alkylthio, haloalkoxy, cyano, nitro, pyrrolidinyl, piperidinyl, piperazinyl, N-alkylpiperazinyl, and morpholinyl.

8. A compound of claim 1 selected from the group consisting of

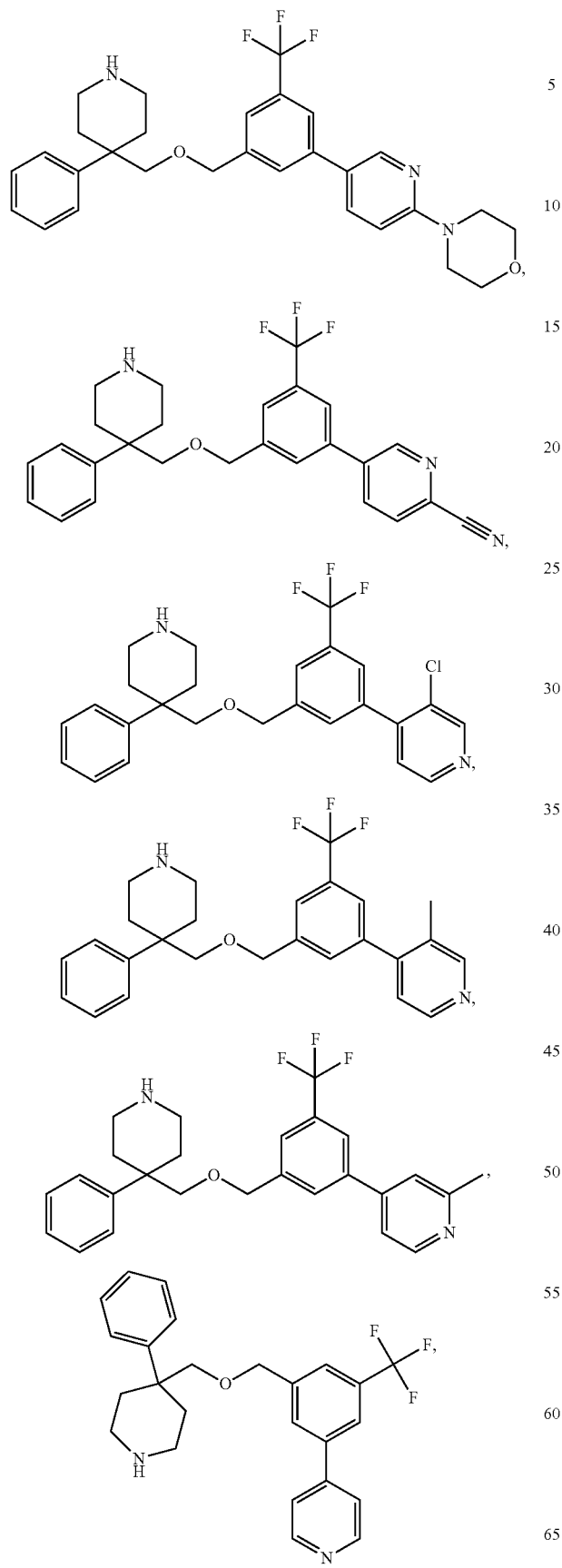
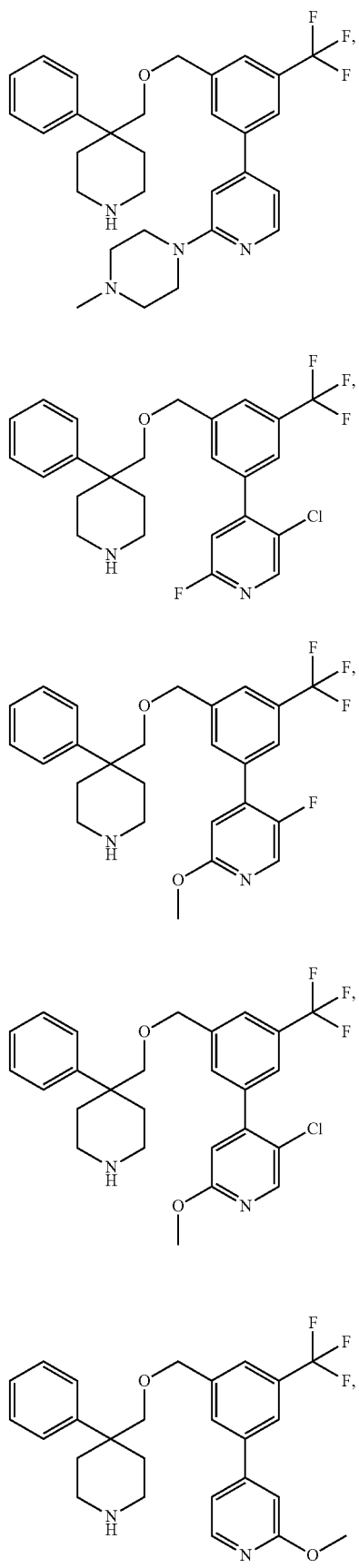

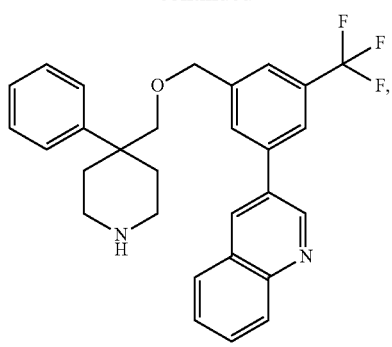
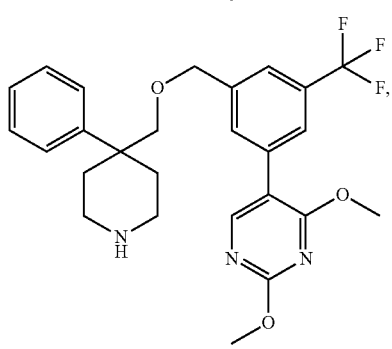
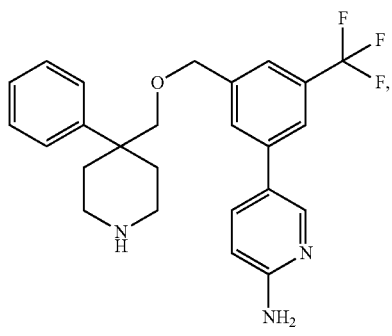
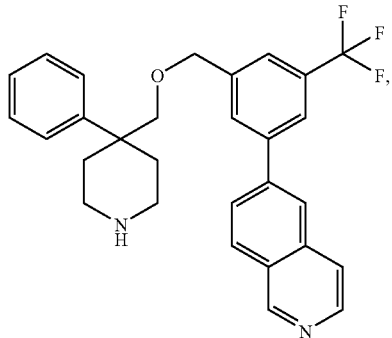
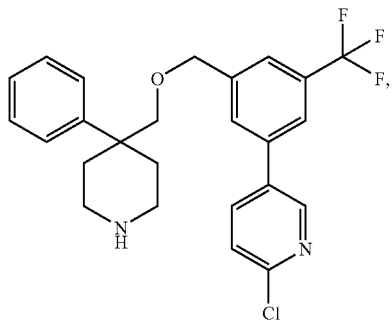
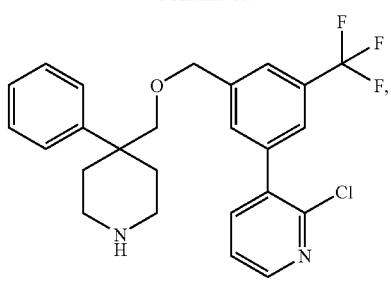
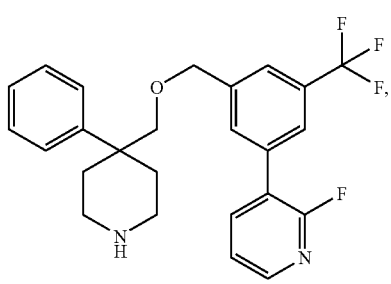
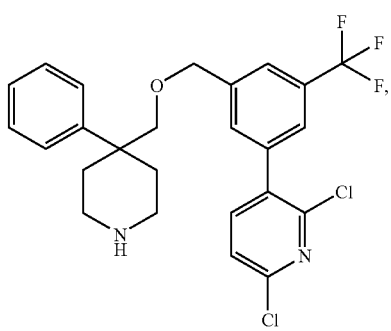
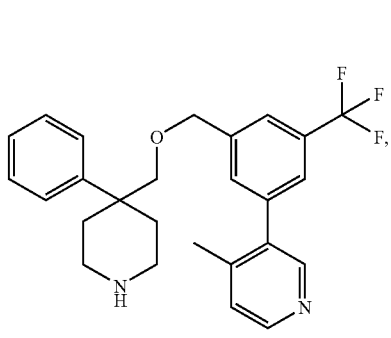
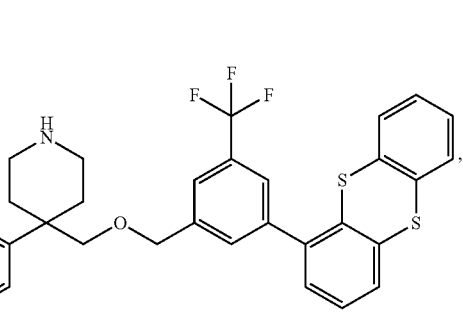

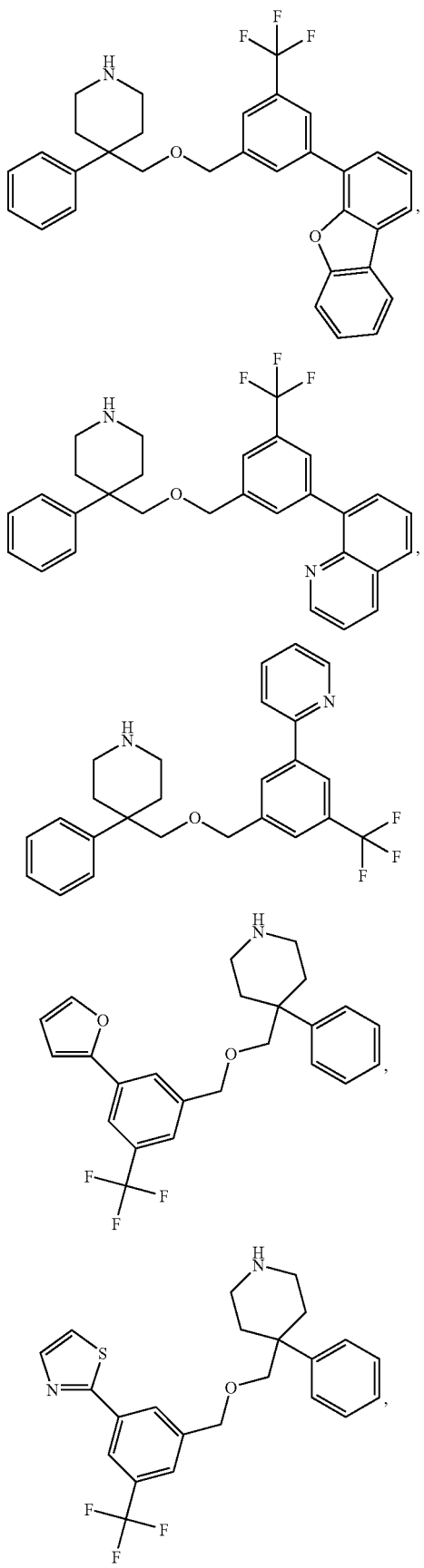
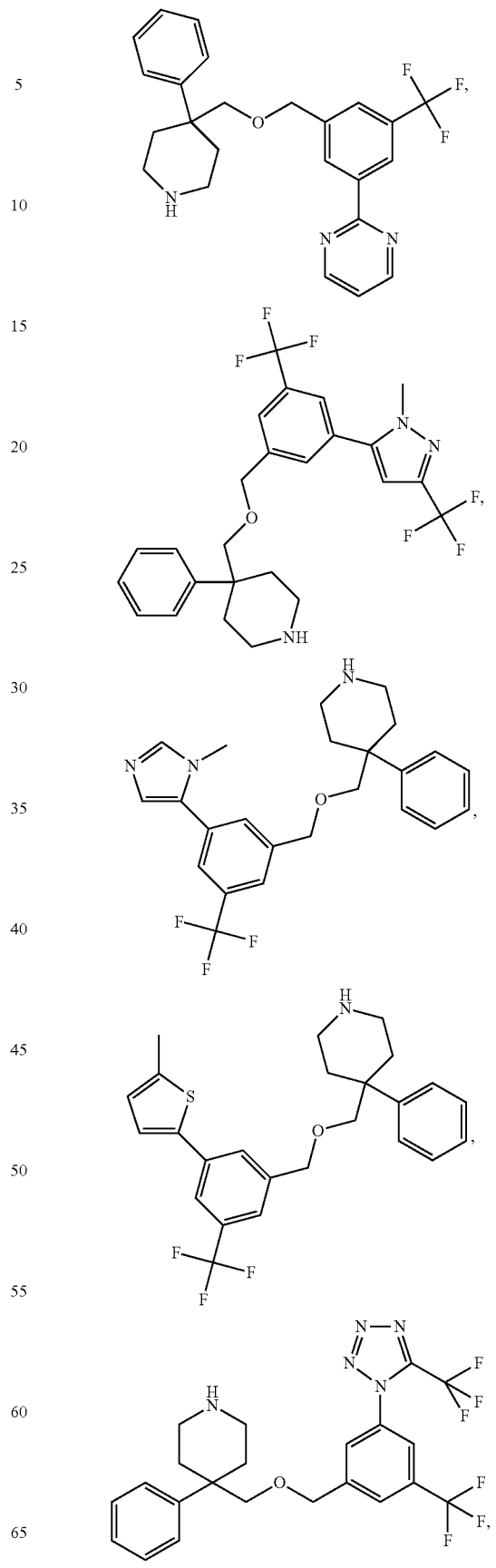

287
-continued
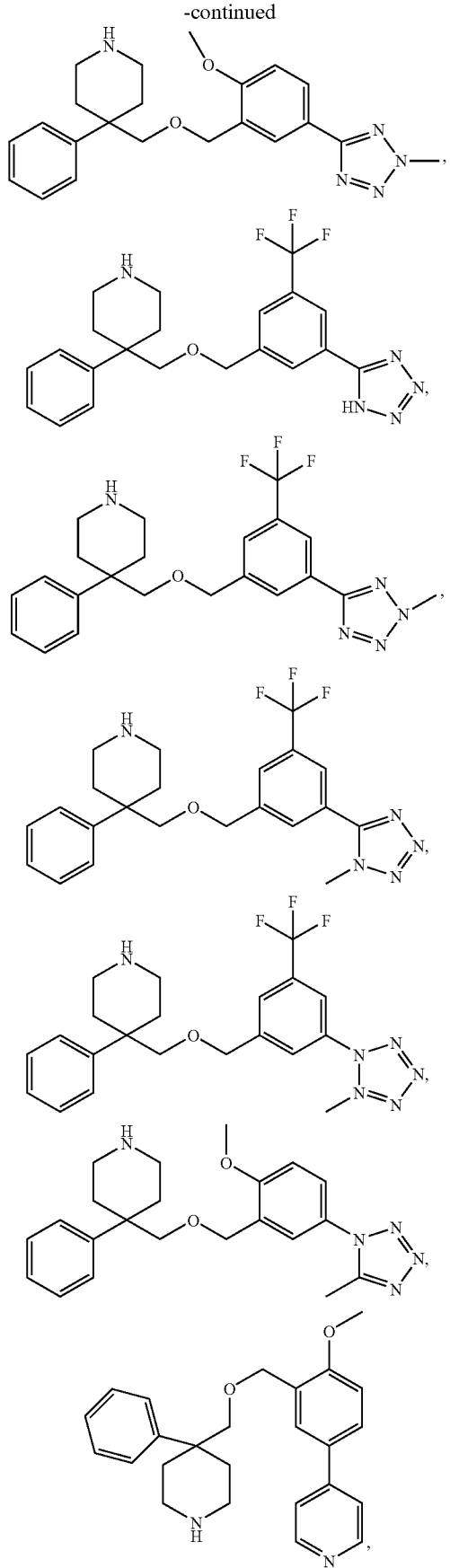
288
-continued
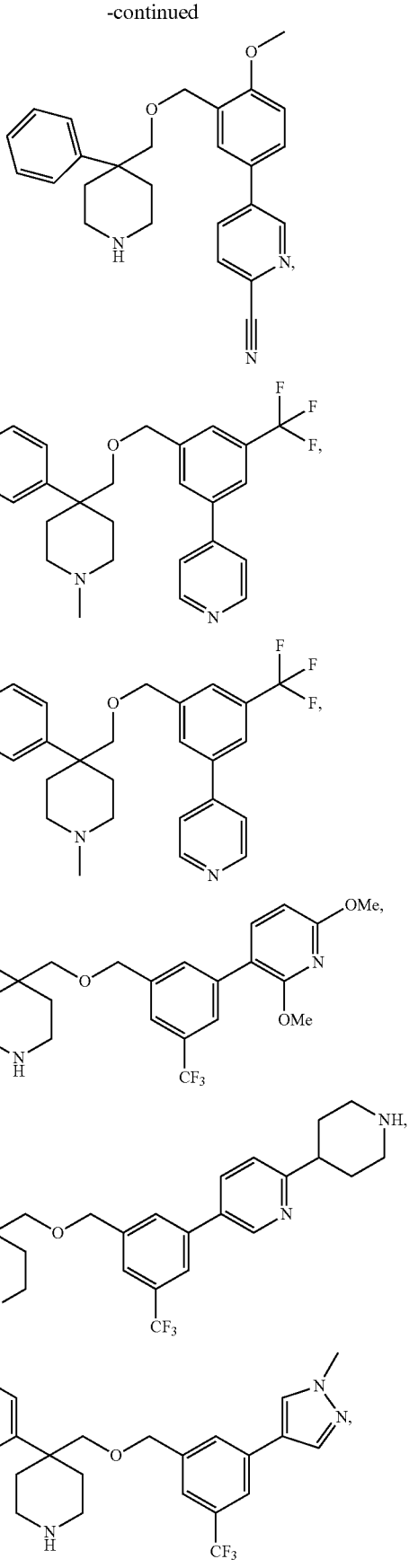

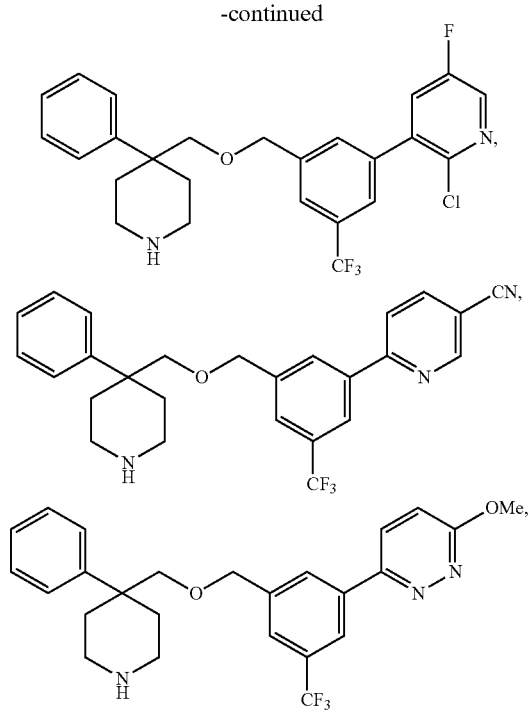
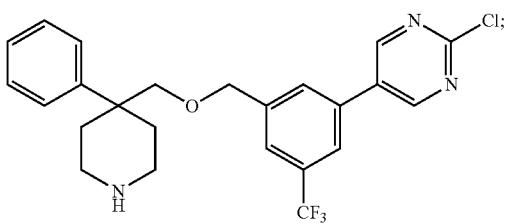
or a pharmaceutically acceptable salt thereof.
9. A composition comprising a pharmaceutically acceptable amount of a compound of claim 1 and at least one pharmaceutically acceptable carrier.
* * * * *

UNITED STATES PATENT AND TRADEMARK OFFICE
CERTIFICATE OF CORRECTION

Page 1 of 2

PATENT NO.       : 8,383,821 B2
APPLICATION NO.  : 12/618025
DATED            : February 26, 2013
INVENTOR(S)      : Andrew P. Degnan et al.

It is certified that error appears in the above-identified patent and that said Letters Patent is hereby corrected as shown below:

On the Title Page:

Item (73), Assignee, change "Bristol-Meyers Squibb Company" to -- Bristol-Myers Squibb Company --.

Item (56), References Cited, under OTHER PUBLICATIONS:
Page 2, Column 2, Wermuth, C.G. reference, change "lsosteric" to -- Isosteric --.

In the Claims:

Claim 8:
Column 285, line 35, after

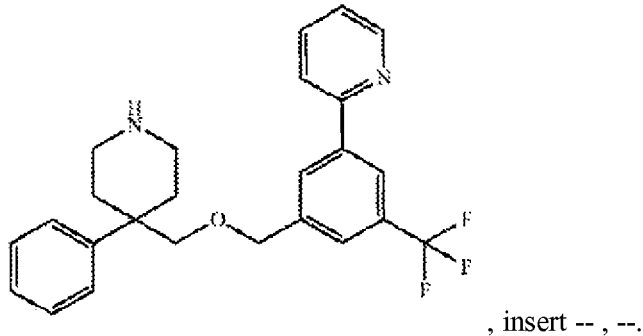

, insert -- , --.

Signed and Sealed this
Sixth Day of May, 2014

Michelle K. Lee
*Deputy Director of the United States Patent and Trademark Office*

CERTIFICATE OF CORRECTION (continued)
U.S. Pat. No. 8,383,821 B2

In the Claims:

Claim 8 (continued):

Column 288, lines 28 to 37, after

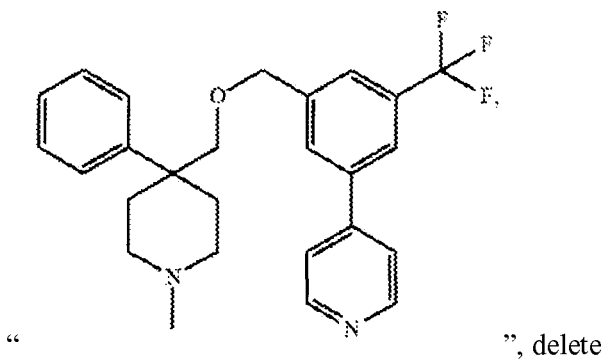 ", delete

"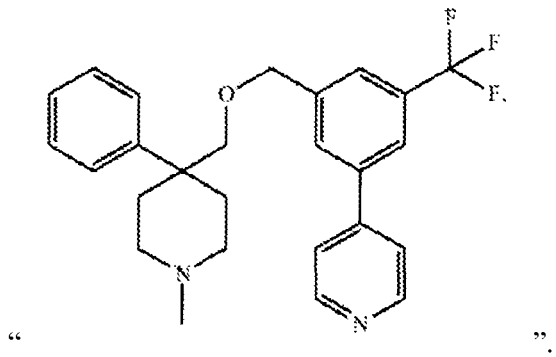".